US006677502B1

(12) United States Patent
Allen et al.

(10) Patent No.: US 6,677,502 B1
(45) Date of Patent: Jan. 13, 2004

(54) PLANT METABOLISM GENES

(75) Inventors: Stephen M. Allen, Wilmington, DE (US); Anthony J. Kinney, Wilimington, DE (US); J. Antoni Rafalski, Wilmington, DE (US); Emil M. Orozco, Jr., West Grove, PA (US); Guo-Hua Miao, Johnston, IA (US); Omolayo O. Famodu, Newark, DE (US); Jian-Ming Lee, West Caldwell, NJ (US); Karin N. Lohman, Newark, DE (US); Alan R. Rendina, Wilmington, DE (US); Hajime Sakai, Wilmington, DE (US); Zude Weng, Des Plaines, IL (US); Perry G. Caimi, Kennet Square, PA (US); Yiwen Fang, Los Angeles, CA (US); Jennie Bih-Jien Shen, Wilmington, DE (US); Ilham L. Zoughi, Wilmington, DE (US); Shawn L. Anderson, West Grove, PA (US); Jinrui Shi, Johnston, IA (US); Guihua Lu, Urbandale, IA (US); Timothy G. Helentjaris, Ankeny, IA (US); Chun Ping Li, Johnston, IA (US)

(73) Assignees: E.I. du Pont de Nemours and Company, Wilmington, DE (US); Pioneer Hi-Bred International, Des Moines, IA (US)

( * ) Notice: Subject to any disclaimer, the term of this patent is extended or adjusted under 35 U.S.C. 154(b) by 145 days.

(21) Appl. No.: 09/614,912

(22) Filed: Jul. 12, 2000

Related U.S. Application Data

(60) Provisional application No. 60/143,401, filed on Jul. 12, 1999, provisional application No. 60/143,412, filed on Jul. 12, 1999, provisional application No. 60/146,650, filed on Jul. 30, 1999, provisional application No. 60/170,906, filed on Dec. 15, 1999, provisional application No. 60/172,959, filed on Dec. 21, 1999, and provisional application No. 60/172,946, filed on Dec. 21, 1999.

(51) Int. Cl.[7] .......................... A01H 3/00; C07H 21/04; C07K 14/415; C12N 5/14; C12N 9/00

(52) U.S. Cl. .......................... 800/278; 435/6; 435/69.1; 435/183; 435/410; 435/419; 435/252.3; 435/320.1; 530/350; 530/370; 536/23.2; 536/23.6; 536/24.1; 800/295

(58) Field of Search ........................... 435/6, 69.1, 183, 435/410, 419, 252.3, 320.1; 530/350, 370; 536/23.2, 23.6, 24.1; 800/278, 295

(56) References Cited

U.S. PATENT DOCUMENTS

| | | |
|---|---|---|
| 5,689,055 A | 11/1997 | Meyerowitz et al. |
| 5,824,868 A | 10/1998 | Meyerowitz et al. |

FOREIGN PATENT DOCUMENTS

| | | |
|---|---|---|
| WO | 95/35383 | 12/1995 |

OTHER PUBLICATIONS

M. Humbelin et al., J. of Ind. Microbiol & Biotech., vol. 22:1–7, 1999, GTP cyclohydrolase II and 3,4–dihydroxy–2–butanone 4–phosphate synthase are rate–limiting enzymes in riboflavin synthesis of an industrial *Bacillus subtilis* strain used for riboflavin production.

A. Bacher et al., Methods in Enzymol. vol. 280:382–389, Biosynthesis of Riboflavin: GTP Cyclohydrolase II, Deaminase, and Reductase.

National Center for Biotechnology Information General Identifier No. 1346113, May 30, 2000, Kobayashi, M. et al., Isolation of cDNAs encoding GTP cyclohydrolase II from Arabidopsis thaliana.

Masahiko Kobayashi et al., Gene, vol. 160:303–304, 1995, Isolation of cDNAs encoding GTP cyclohydrolase II from *Arabidopsis thaliana*.

National Center for Biotechnology Information General Identifier No, 2462925, Oct. 2, 1997, Herz, S.W.

National Center For Bio Technology Information General Identifier No. 10188005, Sep. 16, 2000, Herz et al.

National Center For Biotechnology Information General Identifier No. 19552807, Nakagawa, S. Oct. 1, 2002.

Bork. Genome Research, vol. 10, 2000, p. 398–400.*

Lazar et al. Molecular and Cellular Biology, Mar. 1988, vol. 8, No. 3, p. 1247–1252.*

Burgess et al. The Journal of Cell Biology, 1990, vol. 111, p. 2129–2138.*

Broun et al. Science, Nov. 13, 1998, vol. 282, p. 131–133.*

* cited by examiner

*Primary Examiner*—Phuong T. Bui

(57) ABSTRACT

This invention relates to an isolated nucleic acid fragment encoding a GTP cyclohydrolase II/3,4-dihydroxy-2-butanone-4-phosphate synthase protein. The invention also relates to the construction of a chimeric gene encoding all or a substantial portion of the protein, in sense or antisense orientation, wherein expression of the chimeric gene results in production of altered levels of the protein in a transformed host cell.

13 Claims, No Drawings

SEQUENCE LISTING

<160> NUMBER OF SEQ ID NOS: 204

<210> SEQ ID NO 1
<211> LENGTH: 1555
<212> TYPE: DNA
<213> ORGANISM: Zea mays

<400> SEQUENCE: 1

```
cacgcacacc gcctcgactc gactcccacc tcccctgttc tcaccgtgct tgccctgttt     60

ccacctctgc tgcccatccg cctcgcttgc ccgccgtaca gtacaggcca gacagccatg    120

gtggtgctcg ccaaaccgcc tgtcgtcgac cagatcccgc tcctgcggtc cccgggcccc    180

agggacagct tctcgggagt gccggtcgtc gacctgtcca gccacggcgc ggcgcgggcg    240

atcgtcgacg cctgcgagcg cttcgggttc ttcaaggtcg tcaaccacgg cgtggccgcg    300

gccaccatgg acagggccga gtccgaggcc gtcaggttct tcgcgcaggc gcaggcggac    360

aaggaccgcg cggggccggc gtacccgttc gggtacggca gcaagcggat cgggctcaat    420

ggcgacatgg ggtggctcga gtacctcctc ctcgccgtcg acgccgcgtc gctctccgac    480

gcctgccccg tgccctccag cgccgcgttc cggagcgcgc tgaacgagta cgtcgcggcc    540

gtgcggaagg tggcggcgcg tgtgctggag gcgatggcgg agggcctggg cattgcggac    600

gcggacgcgc tgagctccat ggtgagcggc gccgggagcg accaggtgtt ccgcgtgaac    660

cactacccgc cctgccccgc gctgcagggc ctgggctgca gcaccacggg cttcggcgag    720

cacaccgacc cgcagatcat ctccgtgctc cgctccaacg gcacctccgg cctgcagatc    780

gcgctccgcg acggcgcgca gtgggtctcc gtgccctccg accgcgacgc cttcttcgtt    840

aacgtcggcg actcgttgca ggtgctgacc aacgggaggt tcaggagcgt gaagcaccgg    900

gtggtgacca acagcctcaa gtccagagtt tccttcatct acttcgcggg gccgccgctg    960

gggcagcgga tcgcgccgct gccgcaggtg ctggcggagg gagaggagag cctgtacaag   1020

gagttcacgt ggggcgagta caagaaggcc gcgtacaaga cgaggctcgg cgacaacagg   1080

ctggcccagt ttgagaagcg tagcaacatc tagctaagct agcaaggcgc gcggcccggg   1140

catgcacgcc gcgtcttcac aggacaacaa taacaaccac catgacgagc gagttacttg   1200

caagaaatga tgacaaggaa gaagaagaag aagaaggtga agacgatgat gtgaacagcc   1260

agggagcgta gtgactactc cagtagctag atttttttgt gtggtgggtg cagggtttcc   1320

gcaaagttgc taatggcctg ttctggtgct tgcggtgggg ttagttgcct atttcggtat   1380

gctggagctg gacgggcgat gagccgccgc ctgtaattag ggttaaccat gatagcatgc   1440

agcgaagcga aggggacgat cctctctggc tccgtagctt cccacgtttg cttccttgtg   1500

ctttcccttt cctggtttat atatattttc gtataaaaaa aaaaaaaaaa aaaag        1555
```

<210> SEQ ID NO 2
<211> LENGTH: 370
<212> TYPE: PRT
<213> ORGANISM: Zea mays

<400> SEQUENCE: 2

```
His Ala His Arg Leu Asp Ser Thr Pro Thr Ser Pro Val Leu Thr Val
  1               5                  10                  15

Leu Ala Leu Phe Pro Pro Leu Leu Pro Ile Arg Leu Ala Cys Pro Pro
             20                  25                  30
```

-continued

```
Tyr Ser Thr Gly Gln Thr Ala Met Val Val Leu Ala Lys Pro Pro Val
        35                  40                  45

Val Asp Gln Ile Pro Leu Leu Arg Ser Pro Gly Pro Arg Asp Ser Phe
    50                  55                  60

Ser Gly Val Pro Val Val Asp Leu Ser Ser His Gly Ala Ala Arg Ala
65                  70                  75                  80

Ile Val Asp Ala Cys Glu Arg Phe Gly Phe Phe Lys Val Val Asn His
                85                  90                  95

Gly Val Ala Ala Ala Thr Met Asp Arg Ala Glu Ser Glu Ala Val Arg
            100                 105                 110

Phe Phe Ala Gln Ala Gln Ala Asp Lys Asp Arg Ala Gly Pro Ala Tyr
        115                 120                 125

Pro Phe Gly Tyr Gly Ser Lys Arg Ile Gly Leu Asn Gly Asp Met Gly
    130                 135                 140

Trp Leu Glu Tyr Leu Leu Leu Ala Val Asp Ala Ala Ser Leu Ser Asp
145                 150                 155                 160

Ala Cys Pro Val Pro Ser Ser Ala Ala Phe Arg Ser Ala Leu Asn Glu
                165                 170                 175

Tyr Val Ala Ala Val Arg Lys Val Ala Ala Arg Val Leu Glu Ala Met
            180                 185                 190

Ala Glu Gly Leu Gly Ile Ala Asp Ala Asp Ala Leu Ser Ser Met Val
        195                 200                 205

Ser Gly Ala Gly Ser Asp Gln Val Phe Arg Val Asn His Tyr Pro Pro
    210                 215                 220

Cys Pro Ala Leu Gln Gly Leu Gly Cys Ser Thr Thr Gly Phe Gly Glu
225                 230                 235                 240

His Thr Asp Pro Gln Ile Ile Ser Val Leu Arg Ser Asn Gly Thr Ser
                245                 250                 255

Gly Leu Gln Ile Ala Leu Arg Asp Gly Ala Gln Trp Val Ser Val Pro
            260                 265                 270

Ser Asp Arg Asp Ala Phe Phe Val Asn Val Gly Asp Ser Leu Gln Val
        275                 280                 285

Leu Thr Asn Gly Arg Phe Arg Ser Val Lys His Arg Val Val Thr Asn
    290                 295                 300

Ser Leu Lys Ser Arg Val Ser Phe Ile Tyr Phe Ala Gly Pro Pro Leu
305                 310                 315                 320

Gly Gln Arg Ile Ala Pro Leu Pro Gln Val Leu Ala Glu Gly Glu Glu
                325                 330                 335

Ser Leu Tyr Lys Glu Phe Thr Trp Gly Glu Tyr Lys Lys Ala Ala Tyr
            340                 345                 350

Lys Thr Arg Leu Gly Asp Asn Arg Leu Ala Gln Phe Glu Lys Arg Ser
        355                 360                 365

Asn Ile
    370
```

<210> SEQ ID NO 3
<211> LENGTH: 1650
<212> TYPE: DNA
<213> ORGANISM: Oryza sativa

<400> SEQUENCE: 3

```
caacaccaca gcaacgcacc accggccatc aacctcctct cccctgcttc tcgctcgctc      60

tcctgccctg tttcttggag aagtgagctt aagtgagagc ctctgtccct cgcacacgct     120

attggccatg gtggttctcg ctggcccgcc cgccgtcgat cacatcccgc tgctgaggtc     180
```

-continued

```
gccggacccc ggcgacgtct tctccggcgt gccggtcgtc gacctcggca gccccggcgc    240

ggcgagggcc gtggtggacg cctgcgagcg gtacgggttc ttcaaggtcg tcaaccacgg    300

cgtggccacg gacacgatgg acaaggccga gtcggaggcc gtcaggttct tctcccagac    360

gcagcccgac aaggaccgct ccggcccggc ctacccgttc gggtacggca gcaagcggat    420

cgggttcaat ggcgacatgg ggtggctcga gtacctcctc ctcgccctcg acgacgcgtc    480

gctcgccgac gcctgcaccg tcccgtcctg cgcggtcttc cgggccgctc tgaacgagta    540

catctcgggg gtgcggaagg tggcggtgcg ggtgatggag gcgatgtcgg aggggctggg    600

cattgcgcag gcggacgcgc tgagcgcgct ggtgacggcg gaagggagcg accaggtgtt    660

ccgcgtgaac cactacccgc cgtgccgcgc gctgcagggg ctcggctgca gcgtcaccgg    720

cttcggcgag cacaccgacc cgcagctcgt ctccgtgctc cgctcaaacg gcacgtccgg    780

cctgcagatc gcgctccgcg acggccagtg ggtgtccgtg ccctccgacc gcgactcctt    840

cttcgtcaac gtcggcgact cgttgcaggt tctgaccaat gggaggttca agagcgtgaa    900

gcacagggtg gtggccaaca gcctaaagtc tagggtttcc ttcatctact ttggagggcc    960

accgttagca cagaggattg caccattgcc acagctgctg ggggagggag agcagagcct   1020

gtacaaggag ttcacatggg atgagtacaa gaaggctgcc tacaaatcaa ggcttggaga   1080

caacaggctg gcccagtttg agaagaagta gctagctaga tgcctagcaa cagaactggc   1140

cggtcaagca acaacgactt tactgcatgg cagctagcta ccttagctat gtctcacgca   1200

cacgtacggt acaccatgac cacgagaaga tgaagctgct taagagagaa aaagaaaaga   1260

aaataaaaac aggaagaaga taataacttc aagatgcaca atgtacagcc aggttggatg   1320

gatagctaga tttttctcgt gtggctaatc accgtgtgtg gtgaggtggg ctcctttcct   1380

gtttcggaat actgatcgat ggatgaacag cctccaatag ttaatgttaa ccaaatatag   1440

cacaacaaag ggttcttttt cttcctttgg ttgtttcttt tttcctcttg cctttgattt   1500

tctcgtcatg ctttctgagc attaattatg tgtgcgtgta tttcggtata cgtaacgtac   1560

ttttacctat gtgtgtatag tacgtggctt gtgttaacaa gtaaatatta tagtctctct   1620

ctttcgttaa aaaaaaaaaa aaaaaaaaaa                                     1650
```

```
<210> SEQ ID NO 4
<211> LENGTH: 368
<212> TYPE: PRT
<213> ORGANISM: Oryza sativa

<400> SEQUENCE: 4

Thr Thr Ala Thr His His Arg Pro Ser Thr Ser Ser Pro Leu Leu Leu
  1               5                  10                  15

Ala Arg Ser Pro Ala Leu Phe Leu Gly Glu Val Ser Leu Ser Glu Ser
             20                  25                  30

Leu Cys Pro Ser His Thr Leu Leu Ala Met Val Val Leu Ala Gly Pro
         35                  40                  45

Pro Ala Val Asp His Ile Pro Leu Leu Arg Ser Pro Asp Pro Gly Asp
     50                  55                  60

Val Phe Ser Gly Val Pro Val Val Asp Leu Gly Ser Pro Gly Ala Ala
 65                  70                  75                  80

Arg Ala Val Val Asp Ala Cys Glu Arg Tyr Gly Phe Phe Lys Val Val
                 85                  90                  95

Asn His Gly Val Ala Thr Asp Thr Met Asp Lys Ala Glu Ser Glu Ala
            100                 105                 110
```

-continued

```
Val Arg Phe Phe Ser Gln Thr Gln Pro Asp Lys Asp Arg Ser Gly Pro
        115                 120                 125

Ala Tyr Pro Phe Gly Tyr Gly Ser Lys Arg Ile Gly Phe Asn Gly Asp
    130                 135                 140

Met Gly Trp Leu Glu Tyr Leu Leu Leu Ala Leu Asp Asp Ala Ser Leu
145                 150                 155                 160

Ala Asp Ala Cys Thr Val Pro Ser Cys Ala Val Phe Arg Ala Ala Leu
                165                 170                 175

Asn Glu Tyr Ile Ser Gly Val Arg Lys Val Ala Val Arg Val Met Glu
            180                 185                 190

Ala Met Ser Glu Gly Leu Gly Ile Ala Gln Ala Asp Ala Leu Ser Ala
        195                 200                 205

Leu Val Thr Ala Glu Gly Ser Asp Gln Val Phe Arg Val Asn His Tyr
    210                 215                 220

Pro Pro Cys Arg Ala Leu Gln Gly Leu Gly Cys Ser Val Thr Gly Phe
225                 230                 235                 240

Gly Glu His Thr Asp Pro Gln Leu Val Ser Val Leu Arg Ser Asn Gly
                245                 250                 255

Thr Ser Gly Leu Gln Ile Ala Leu Arg Asp Gly Gln Trp Val Ser Val
            260                 265                 270

Pro Ser Asp Arg Asp Ser Phe Phe Val Asn Val Gly Asp Ser Leu Gln
        275                 280                 285

Val Leu Thr Asn Gly Arg Phe Lys Ser Val Lys His Arg Val Val Ala
    290                 295                 300

Asn Ser Leu Lys Ser Arg Val Ser Phe Ile Tyr Phe Gly Gly Pro Pro
305                 310                 315                 320

Leu Ala Gln Arg Ile Ala Pro Leu Pro Gln Leu Leu Gly Glu Gly Glu
                325                 330                 335

Gln Ser Leu Tyr Lys Glu Phe Thr Trp Asp Glu Tyr Lys Lys Ala Ala
            340                 345                 350

Tyr Lys Ser Arg Leu Gly Asp Asn Arg Leu Ala Gln Phe Glu Lys Lys
        355                 360                 365


<210> SEQ ID NO 5
<211> LENGTH: 1365
<212> TYPE: DNA
<213> ORGANISM: Glycine max

<400> SEQUENCE: 5

gcacgagctc aaagccaaac caaattttct ctctttcact tatttattga ctccccaaaa      60

gcttttcaaa tatctctgtt cctctctcac gtaccttctc cctatctttc actccacttc     120

ttaacaccac aaaacagaat aacggccgag caaacaacaa gaaaaatggt gttgttgtcc     180

aaagcaacaa cagaacaata ctcctacatt aagaactgca tgccaaccaa atttcctca      240

acaattccca tagtggacct ctccaaacct gatgcaaaga cccttatagt gaaggcttgt     300

gaggagtttg gattcttcaa agtcatcaat catggtgtct ccatggaagc tatatccgaa     360

ttggaatatg aagccttcaa attcttctct atgtcactca atgaaaagga aaaagtagga     420

cctcccaatc catttgggta tggtagcaag aaaattggac acaataggga cgttggttgg     480

attgagtacc ttcttctcaa caccaatcaa gaacacaact tctctgttta tggcaaaaac     540

cctgagaaat tcaggtgtct gttgaacagt tacatgtctt ctgtgaggaa gatggcatgt     600

gagattcttg agttgatggc agaagggttg aagattcagc aaaaggatgt gtttagcaag     660

cttctaatgg ataaacaaag tgactctatt ttcagggtga atcattaccc tgcttgtcct     720
```

-continued

```
gaaatgactc tgaatgatca gaacttgatt gggtttggag aacacacaga cccacaaatc    780

atctctctgt taagatccaa caacacttca ggccttcaga tttatcttag agatggaaat    840

tggatttcag tcccaccaga tgacaaatcc ttttttatta acgttggtga ttctcttcag    900

gttatgacaa atggaaggtt ccgaagtgtg agacacagag tgttggcaaa tgggttcaag    960

tccaggcttt caatgattta ctttggaggt ccacctttga gtgagaaaat agcaccatta   1020

tcctctctca tgaaaggaaa agaaagtcta tataaagagt ttacctggtt tgagtacaaa   1080

aaatcaatct acggttcaag attatctaaa aatagacttg aacattttga aagaattgca   1140

gcttcgtaat atatattcta gagaattgtt tgagacactt gtcaatacaa aatgggagat   1200

tacaatatgt agtttgtata ctataaatgc tttttttttt tttttttac ttttaaggtt   1260

atttatcaat cagaaggctt catagacatg ataacatatg tatccatttt gtttaaatgc   1320

tagtgaatga catctaatgt tgttatcaaa aaaaaaaaaa aaaaa                   1365
```

```
<210> SEQ ID NO 6
<211> LENGTH: 382
<212> TYPE: PRT
<213> ORGANISM: Glycine max

<400> SEQUENCE: 6

Ala Arg Ala Gln Ser Gln Thr Lys Phe Ser Leu Phe His Leu Phe Ile
  1               5                  10                  15

Asp Ser Pro Lys Ala Phe Gln Ile Ser Leu Phe Leu Ser His Val Pro
             20                  25                  30

Ser Pro Tyr Leu Ser Leu His Phe Leu Thr Pro Gln Asn Arg Ile Thr
         35                  40                  45

Ala Glu Gln Thr Thr Arg Lys Met Val Leu Leu Ser Lys Ala Thr Thr
     50                  55                  60

Glu Gln Tyr Ser Tyr Ile Lys Asn Cys Met Pro Thr Lys Phe Ser Ser
 65                  70                  75                  80

Thr Ile Pro Ile Val Asp Leu Ser Lys Pro Asp Ala Lys Thr Leu Ile
                 85                  90                  95

Val Lys Ala Cys Glu Glu Phe Gly Phe Phe Lys Val Ile Asn His Gly
            100                 105                 110

Val Ser Met Glu Ala Ile Ser Glu Leu Glu Tyr Glu Ala Phe Lys Phe
        115                 120                 125

Phe Ser Met Ser Leu Asn Glu Lys Glu Lys Val Gly Pro Pro Asn Pro
    130                 135                 140

Phe Gly Tyr Gly Ser Lys Lys Ile Gly His Asn Arg Asp Val Gly Trp
145                 150                 155                 160

Ile Glu Tyr Leu Leu Leu Asn Thr Asn Gln Glu His Asn Phe Ser Val
                165                 170                 175

Tyr Gly Lys Asn Pro Glu Lys Phe Arg Cys Leu Leu Asn Ser Tyr Met
            180                 185                 190

Ser Ser Val Arg Lys Met Ala Cys Glu Ile Leu Glu Leu Met Ala Glu
        195                 200                 205

Gly Leu Lys Ile Gln Gln Lys Asp Val Phe Ser Lys Leu Leu Met Asp
    210                 215                 220

Lys Gln Ser Asp Ser Ile Phe Arg Val Asn His Tyr Pro Ala Cys Pro
225                 230                 235                 240

Glu Met Thr Leu Asn Asp Gln Asn Leu Ile Gly Phe Gly Glu His Thr
                245                 250                 255
```

-continued

```
Asp Pro Gln Ile Ile Ser Leu Leu Arg Ser Asn Asn Thr Ser Gly Leu
            260                 265                 270

Gln Ile Tyr Leu Arg Asp Gly Asn Trp Ile Ser Val Pro Pro Asp Asp
        275                 280                 285

Lys Ser Phe Phe Ile Asn Val Gly Asp Ser Leu Gln Val Met Thr Asn
    290                 295                 300

Gly Arg Phe Arg Ser Val Arg His Arg Val Leu Ala Asn Gly Phe Lys
305                 310                 315                 320

Ser Arg Leu Ser Met Ile Tyr Phe Gly Gly Pro Pro Leu Ser Glu Lys
                325                 330                 335

Ile Ala Pro Leu Ser Ser Leu Met Lys Gly Lys Glu Ser Leu Tyr Lys
            340                 345                 350

Glu Phe Thr Trp Phe Glu Tyr Lys Lys Ser Ile Tyr Gly Ser Arg Leu
        355                 360                 365

Ser Lys Asn Arg Leu Glu His Phe Glu Arg Ile Ala Ala Ser
    370                 375                 380


<210> SEQ ID NO 7
<211> LENGTH: 1473
<212> TYPE: DNA
<213> ORGANISM: Triticum aestivum

<400> SEQUENCE: 7

gcacgagagc atctcccctg ttccgcccgc tcgcctctgc ttctttagtt ctttccagag     60

cggctctgct ctgctcctcg cctctctcga tcgcgcatac gtaccatatt tggcagccca    120

gccatggtgg ttctcgccag cacgcccgcc gtcgatcaca tcccgctcct caggtcgccc    180

gaccccgggg actacttctc cggcatgccg gtggtcgacc tctccagccc tggcgcgccg    240

cgggccatcg ccgacgcgtg cgagcgcttc gggttcttca agctcgtcaa ccacggggtg    300

cccgcggaca cgatggacag gctcgagtcg gaggccgtca ggttcttctc gctgccgcag    360

gccgacaagg accgctccgg cccggcctac ccgttcggct acggcagcaa gcgcatcggg    420

ctcaatggcg acatggggtg gctcgagtac ctgctcctgg ccgtcgactc cgcgtcgctc    480

tccggcgcct gcgccgtccc gtcctgcgcg ctcttccggg cggcgctgaa cgagtacatc    540

gcggcggtgc ggaaggtggc ggtgcgggtg atggaggcga tggcggaggg gctgggcatt    600

gcggccgtgg acgcgctgag cgggatggtg acggcggagg ggagcgacca ggtgttccgg    660

gtgaaccact acccgccgtg ccacgcgctg caggggctgg gctgcagcgc caccggcttc    720

ggcgagcaca cggacccgca gctcatctcc gtgctgcgct ccaacggcac gtccggcctg    780

cagatcgcgc tccagaacgg gcagtgggtg tccgtgccct cggaccgcga cgccttcttc    840

gtcaacgtcg gcgactcgtt gcaggtgctg accaacggga ggttcaagag cgtgaagcac    900

agggtggtgg ccaacagcct aaagtctagg gtttccatga tctactttgg agggccagcg    960

atgacacaga ggattgcacc attgccgcag ctgctgggcg cgggagagca gagcctgtac   1020

aaggacttca catggggcga gtacaagaag gctgcctaca actccaggct cggggacaac   1080

aggctggctc agttccacag gtagcatcgc ctgccgcctg ggcccgctca aggagcagct   1140

tttaccaagc cagccagcta gctagtagct agctagctgc cgtggcttat gtttcgcaca   1200

ccgtgaagac gaagatgaag atgaagagga aagctactag aaaagaaagg gaaacagagc   1260

taaaagaaga tgatttcaag acacatgtgg tagagctgcg gacgtagcta gtagatcttt   1320

ttcgtgtgcg tgtgcgcgtg tgtgtgcgtg tgcgtgtgtg ttcatagttg ctaaaactcg   1380
```

-continued

```
cctttcctat tcgggaatgc cggacgaacc atgaacagat aagttaactt gatgaatagt   1440

tagttagtgt gaaccaaaaa aaaaaaaaaa aaa                                 1473


<210> SEQ ID NO 8
<211> LENGTH: 351
<212> TYPE: PRT
<213> ORGANISM: Triticum aestivum

<400> SEQUENCE: 8

Phe Phe Pro Glu Arg Leu Cys Ser Ala Pro Arg Leu Ser Arg Ser Arg
  1               5                  10                  15

Ile Arg Thr Ile Phe Gly Ser Pro Ala Met Val Val Leu Ala Ser Thr
             20                  25                  30

Pro Ala Val Asp His Ile Pro Leu Leu Arg Ser Pro Asp Pro Gly Asp
         35                  40                  45

Tyr Phe Ser Gly Met Pro Val Val Asp Leu Ser Ser Pro Gly Ala Pro
     50                  55                  60

Arg Ala Ile Ala Asp Ala Cys Glu Arg Phe Gly Phe Phe Lys Leu Val
 65                  70                  75                  80

Asn His Gly Val Pro Ala Asp Thr Met Asp Arg Leu Glu Ser Glu Ala
                 85                  90                  95

Val Arg Phe Phe Ser Leu Pro Gln Ala Asp Lys Asp Arg Ser Gly Pro
            100                 105                 110

Ala Tyr Pro Phe Gly Tyr Gly Ser Lys Arg Ile Gly Leu Asn Gly Asp
        115                 120                 125

Met Gly Trp Leu Glu Tyr Leu Leu Leu Ala Val Asp Ser Ala Ser Leu
    130                 135                 140

Ser Gly Ala Cys Ala Val Pro Ser Cys Ala Leu Phe Arg Ala Ala Leu
145                 150                 155                 160

Asn Glu Tyr Ile Ala Ala Val Arg Lys Val Ala Val Arg Val Met Glu
                165                 170                 175

Ala Met Ala Glu Gly Leu Gly Ile Ala Ala Val Asp Ala Leu Ser Gly
            180                 185                 190

Met Val Thr Ala Glu Gly Ser Asp Gln Val Phe Arg Val Asn His Tyr
        195                 200                 205

Pro Pro Cys His Ala Leu Gln Gly Leu Gly Cys Ser Ala Thr Gly Phe
    210                 215                 220

Gly Glu His Thr Asp Pro Gln Leu Ile Ser Val Leu Arg Ser Asn Gly
225                 230                 235                 240

Thr Ser Gly Leu Gln Ile Ala Leu Gln Asn Gly Gln Trp Val Ser Val
                245                 250                 255

Pro Ser Asp Arg Asp Ala Phe Phe Val Asn Val Gly Asp Ser Leu Gln
            260                 265                 270

Val Leu Thr Asn Gly Arg Phe Lys Ser Val Lys His Arg Val Val Ala
        275                 280                 285

Asn Ser Leu Lys Ser Arg Val Ser Met Ile Tyr Phe Gly Gly Pro Ala
    290                 295                 300

Met Thr Gln Arg Ile Ala Pro Leu Pro Gln Leu Leu Gly Ala Gly Glu
305                 310                 315                 320

Gln Ser Leu Tyr Lys Asp Phe Thr Trp Gly Glu Tyr Lys Lys Ala Ala
                325                 330                 335

Tyr Asn Ser Arg Leu Gly Asp Asn Arg Leu Ala Gln Phe His Arg
            340                 345                 350
```

-continued

<210> SEQ ID NO 9
<211> LENGTH: 450
<212> TYPE: DNA
<213> ORGANISM: Zea mays
<220> FEATURE:
<221> NAME/KEY: unsure
<222> LOCATION: (439)

<400> SEQUENCE: 9

```
gactcgactc ccacctcccc tgttctcacc gtgcttgccc tgtttccacc tctgctgccc      60

atccgcctcg cttgcccgcc gtacagtaca ggccagacag ccatggtggt gctcgccaaa     120

ccgcctgtcg tcgaccagat cccgctcctg cggtccccgg gccccaggga cagcttctcg     180

ggagtgccgg tcgtcgacct gtccagccac ggcgcggcgc gggcgatcgt cgacgcctgc     240

gagcgcttcg ggttcttcaa ggtcgtcaac cacggcgtgg ccgcggccac catggacagg     300

gccgagtccg aggccgtcag gttcttcgcg caggcgcagg cggacaagga ccgcgcgggg     360

ccggcgtacc cgttcgggta cggcagcaag cggatcgggc tcaatggcga catggggtgg     420

ctcgagtacc tctcctcgnc gtcgacgccc                                      450
```

<210> SEQ ID NO 10
<211> LENGTH: 110
<212> TYPE: PRT
<213> ORGANISM: Zea mays

<400> SEQUENCE: 10

```
Met Val Val Leu Ala Lys Pro Pro Val Val Asp Gln Ile Pro Leu Leu
  1               5                  10                  15

Arg Ser Pro Gly Pro Arg Asp Ser Phe Ser Gly Val Pro Val Val Asp
             20                  25                  30

Leu Ser Ser His Gly Ala Ala Arg Ala Ile Val Asp Ala Cys Glu Arg
         35                  40                  45

Phe Gly Phe Phe Lys Val Val Asn His Gly Val Ala Ala Ala Thr Met
     50                  55                  60

Asp Arg Ala Glu Ser Glu Ala Val Arg Phe Phe Ala Gln Ala Gln Ala
 65                  70                  75                  80

Asp Lys Asp Arg Ala Gly Pro Ala Tyr Pro Phe Gly Tyr Gly Ser Lys
                 85                  90                  95

Arg Ile Gly Leu Asn Gly Asp Met Gly Trp Leu Glu Tyr Leu
            100                 105                 110
```

<210> SEQ ID NO 11
<211> LENGTH: 618
<212> TYPE: DNA
<213> ORGANISM: Oryza sativa
<220> FEATURE:
<221> NAME/KEY: unsure
<222> LOCATION: (482)
<221> NAME/KEY: unsure
<222> LOCATION: (531)
<221> NAME/KEY: unsure
<222> LOCATION: (579)
<221> NAME/KEY: unsure
<222> LOCATION: (616)

<400> SEQUENCE: 11

```
acaccacagc aacgcaccac cggccatcaa cctcctctcc cctgcttctc gctcgctctc      60

ctgccctgtt tcttggagaa gtgagcttaa gtgagagcct ctgtccctcg cacacgctat     120

tggccatggt ggttctcgct ggcccgcccg ccgtcgatca catcccgctg ctgaggtcgc     180

cggaccccgg cgacgtcttc tccggcgtgc cggtcgtcga cctcggcagc cccggcgcgg     240
```

-continued

```
cgagggccgt ggtggacgcc tgcgagcggt acgggttctt caaggtcgtc aaccacggcg    300

tggccacgga cacgatggac aaggccgatc ggaggccgtc aggttcttct cccaagacgc    360

agcccgacaa ggaccgctcc ggcccggcta ccgttcgggt acggcaacaa gcggatcggg    420

ttcaatggcg acatgggtgg tcgagtactc ctctcgccct cgacgaccgt cgctcgccga    480

cnctgcacgt cccttctgcg cgtcttccgg gccctctgaa caataatctc ngggttccga    540

agtggcgtcc ggtgatggag caattcgagg ggtgggatnc caagcgaccc ctaacccctg    600

tacgcgaagg acacantt                                                  618
```

<210> SEQ ID NO 12
<211> LENGTH: 105
<212> TYPE: PRT
<213> ORGANISM: Oryza sativa
<220> FEATURE:
<221> NAME/KEY: UNSURE
<222> LOCATION: (88)..(89)

<400> SEQUENCE: 12

```
Met Val Val Leu Ala Gly Pro Pro Ala Val Asp His Ile Pro Leu Leu
  1               5                  10                  15

Arg Ser Pro Asp Pro Gly Asp Val Phe Ser Gly Val Pro Val Val Asp
             20                  25                  30

Leu Gly Ser Pro Gly Ala Ala Arg Ala Val Val Asp Ala Cys Glu Arg
         35                  40                  45

Tyr Gly Phe Phe Lys Val Val Asn His Gly Val Ala Thr Asp Thr Met
     50                  55                  60

Asp Lys Ala Asp Arg Arg Pro Ser Gly Ser Ser Pro Lys Thr Gln Pro
 65                  70                  75                  80

Asp Lys Asp Arg Ser Gly Pro Xaa Xaa Pro Phe Gly Tyr Gly Asn Lys
                 85                  90                  95

Arg Ile Gly Phe Asn Gly Asp Met Gly
            100                 105
```

<210> SEQ ID NO 13
<211> LENGTH: 1352
<212> TYPE: DNA
<213> ORGANISM: Glycine max

<400> SEQUENCE: 13

```
ctcaaagcca aaccaaattt tctctctttc acttatttat tgactcccca aaagcttttc     60

aaatatctct gttcctctct cacgtacctt ctccctatct ttcactccac ttcttaacac    120

cacaaaacag aataacggcc gagcaaacaa caagaaaaat ggtgttgttg tccaaagcaa    180

caacagaaca atactcctac attaagaact gcatgccaac caaattttcc tcaacaattc    240

ccatagtgga cctctccaaa cctgatgcaa agacccttat agtgaaggct tgtgaggagt    300

ttggattctt caaagtcatc aatcatggtg tctccatgga agctatatcc gaattggaat    360

atgaagcctt caaattcttc tctatgtcac tcaatgaaaa ggaaaaagta ggacctccca    420

atccatttgg gtatggtagc aagaaaattg gacacaatgg ggacgttggt tggattgagt    480

accttcttct caacaccaat caagaacaca acttctctgt ttatgggaaa aaccctgaga    540

aattcaggtg tctgttgaac agttacatgt cttctgtgag gaagatggca tgtgagattc    600

ttgagttgat ggcagaaggg ttgaagattc agcaaaagga tgtgtttagc aagcttctaa    660

tggataaaca aagtgactct attttcaggg tgaatcatta ccctgcttgt cctgaaatga    720

ctctgaatga tcagaacttg attgggtttg gagaacacac agacccacaa atcatctctc    780
```

-continued

```
tgttaagatc caacaacact tcaggccttc agatttatct tagagatgga aattggattt    840

cagtcccacc agatgacaaa tcctttttta ttaacgttgg tgattctctt caggttatga    900

caaatggaag gttccgaagt gtgagacaca gagtgttggc aaatgggttc aagtccaggc    960

tttcaatgat ttactttgga ggtccacctt tgagtgagaa aatagcacca ttatcctctc   1020

tcatgaaagg aaaagaaagt ctatataaag agtttacctg gtttgagtac aaaaaatcaa   1080

tctacggttc aagattatct aaaaatagac ttgaacattt tgaaagaatt gcagcttcgt   1140

aatatatatt ctagagaatt gtttgagaca cttgtcaata caaaatggga gattacaata   1200

tgtagtttgt atactataaa tgcttttttt tttttttttt tacttttaag gttatttatc   1260

aatcaagaag gcttcataga catgataaca tatgtatcca ttttgtttaa atgctagtga   1320

atgacatcta atgttgttat caaaaaaaaa aa                                 1352
```

<210> SEQ ID NO 14
<211> LENGTH: 327
<212> TYPE: PRT
<213> ORGANISM: Glycine max

<400> SEQUENCE: 14

```
Met Val Leu Leu Ser Lys Ala Thr Thr Glu Gln Tyr Ser Tyr Ile Lys
  1               5                  10                  15

Asn Cys Met Pro Thr Lys Phe Ser Ser Thr Ile Pro Ile Val Asp Leu
            20                  25                  30

Ser Lys Pro Asp Ala Lys Thr Leu Ile Val Lys Ala Cys Glu Glu Phe
        35                  40                  45

Gly Phe Phe Lys Val Ile Asn His Gly Val Ser Met Glu Ala Ile Ser
    50                  55                  60

Glu Leu Glu Tyr Glu Ala Phe Lys Phe Phe Ser Met Ser Leu Asn Glu
 65                  70                  75                  80

Lys Glu Lys Val Gly Pro Pro Asn Pro Phe Gly Tyr Gly Ser Lys Lys
                85                  90                  95

Ile Gly His Asn Gly Asp Val Gly Trp Ile Glu Tyr Leu Leu Leu Asn
            100                 105                 110

Thr Asn Gln Glu His Asn Phe Ser Val Tyr Gly Lys Asn Pro Glu Lys
        115                 120                 125

Phe Arg Cys Leu Leu Asn Ser Tyr Met Ser Ser Val Arg Lys Met Ala
    130                 135                 140

Cys Glu Ile Leu Glu Leu Met Ala Glu Gly Leu Lys Ile Gln Gln Lys
145                 150                 155                 160

Asp Val Phe Ser Lys Leu Leu Met Asp Lys Gln Ser Asp Ser Ile Phe
                165                 170                 175

Arg Val Asn His Tyr Pro Ala Cys Pro Glu Met Thr Leu Asn Asp Gln
            180                 185                 190

Asn Leu Ile Gly Phe Gly Glu His Thr Asp Pro Gln Ile Ile Ser Leu
        195                 200                 205

Leu Arg Ser Asn Asn Thr Ser Gly Leu Gln Ile Tyr Leu Arg Asp Gly
    210                 215                 220

Asn Trp Ile Ser Val Pro Pro Asp Asp Lys Ser Phe Phe Ile Asn Val
225                 230                 235                 240

Gly Asp Ser Leu Gln Val Met Thr Asn Gly Arg Phe Arg Ser Val Arg
                245                 250                 255

His Arg Val Leu Ala Asn Gly Phe Lys Ser Arg Leu Ser Met Ile Tyr
            260                 265                 270
```

-continued

```
Phe Gly Gly Pro Pro Leu Ser Glu Lys Ile Ala Pro Leu Ser Ser Leu
        275                 280                 285

Met Lys Gly Lys Glu Ser Leu Tyr Lys Glu Phe Thr Trp Phe Glu Tyr
    290                 295                 300

Lys Lys Ser Ile Tyr Gly Ser Arg Leu Ser Lys Asn Arg Leu Glu His
305                 310                 315                 320

Phe Glu Arg Ile Ala Ala Ser
                325


<210> SEQ ID NO 15
<211> LENGTH: 595
<212> TYPE: DNA
<213> ORGANISM: Triticum aestivum
<220> FEATURE:
<221> NAME/KEY: unsure
<222> LOCATION: (451)
<221> NAME/KEY: unsure
<222> LOCATION: (467)
<221> NAME/KEY: unsure
<222> LOCATION: (486)
<221> NAME/KEY: unsure
<222> LOCATION: (506)
<221> NAME/KEY: unsure
<222> LOCATION: (510)
<221> NAME/KEY: unsure
<222> LOCATION: (559)
<221> NAME/KEY: unsure
<222> LOCATION: (564)
<221> NAME/KEY: unsure
<222> LOCATION: (571)..(572)
<221> NAME/KEY: unsure
<222> LOCATION: (578)
<221> NAME/KEY: unsure
<222> LOCATION: (582)
<221> NAME/KEY: unsure
<222> LOCATION: (591)..(592)

<400> SEQUENCE: 15

agcatctccc ctgttccgcc cgctcgcctc tgcttcttta gttctttcca gagcggctct      60

gctctgctcc tcgcctctct cgatcgcgca tacgtaccat atttggcagc ccagccatgg     120

tggttctcgc cagcacgccc gccgtcgatc acatcccgct cctcaggtcg cccgaccccg     180

gggactactt ctccggcatg ccggtggtcg acctctccag ccctggcgcg ccgcgggcca     240

tcgccgacgc gtgcgagcgc ttcgggttct tcaagctcgt caaccacggg gtgcccgcgg     300

acacgatgga caggctcgag tcggaggccg tcaggttctt ctcgctgccg caagccgaca     360

aggaccgctc cggccgggct accgttcggt acggaacaag cgcacgggct catggcgaca     420

tggggtggtc gagtacctgt ctggccgtca ntccgcgtcg tctcggngct gcgcgtccgt     480

ctgggngctc ttcgggcggg gtgaanatan acgcggggtc ggagtgcgtt cggtatgaag     540

catgcgaggg ctggaattng ctgnacctaa nngaatgnaa gngggggaac nnaat          595


<210> SEQ ID NO 16
<211> LENGTH: 86
<212> TYPE: PRT
<213> ORGANISM: Triticum aestivum

<400> SEQUENCE: 16

Met Val Val Leu Ala Ser Thr Pro Ala Val Asp His Ile Pro Leu Leu
  1               5                  10                  15

Arg Ser Pro Asp Pro Gly Asp Tyr Phe Ser Gly Met Pro Val Val Asp
             20                  25                  30

Leu Ser Ser Pro Gly Ala Pro Arg Ala Ile Ala Asp Ala Cys Glu Arg
        35                  40                  45
```

-continued

```
Phe Gly Phe Phe Lys Leu Val Asn His Gly Val Pro Ala Asp Thr Met
     50                  55                  60

Asp Arg Leu Glu Ser Glu Ala Val Arg Phe Phe Ser Leu Pro Gln Ala
 65                  70                  75                  80

Asp Lys Asp Arg Ser Gly
                 85
```

<210> SEQ ID NO 17
<211> LENGTH: 682
<212> TYPE: DNA
<213> ORGANISM: Oryza sativa

<400> SEQUENCE: 17

```
gcacgagctt acagacattc agtagaacag aagacataac atttgcaacc gaggaatgcc     60

tccttcttac tatagcataa agcgatggga atctatcttt agaggtactg tttgattgag    120

gttgtataca actaattaac actacgacaa acgtacgtat ttatagagac caaaaactat    180

gtgtaaaatt agtaatttaa tgtctgtcga ttgattgtat tgatcaatgt cgacacgtag    240

attggttacg ccctagactt cccctggaaa gcaagtctgc cacgtgttga aacaagaatg    300

tatctggagc aatatggcgc cggcagagat gtgtggatcg gtaagtcgct ttacaggctg    360

ccactcgtga acaatgatct ctatcacaac atggcaaaag ctgatttcaa gtgtttccag    420

aggcgctgcc aacttgagtg gcatggcatc aacaagtgag ctgcctcctg cctctccatc    480

cgactgatct actttaattt ggaatggaaa taaacaaaga attactacgt actacccccct    540

cctaaaatag ttgtgtttat aggattaaaa ttgtcctaaa atagtttaaa tctactttgc    600

aattttttaa actattgtct cattaattac attatattca aatttctctt ctttttaaaa    660

aaaaaaaaaa aaaaaaaaaa aa                                              682
```

<210> SEQ ID NO 18
<211> LENGTH: 72
<212> TYPE: PRT
<213> ORGANISM: Oryza sativa

<400> SEQUENCE: 18

```
Ile Gly Tyr Ala Leu Asp Phe Pro Trp Lys Ala Ser Leu Pro Arg Val
  1               5                  10                  15

Glu Thr Arg Met Tyr Leu Glu Gln Tyr Gly Ala Gly Arg Asp Val Trp
             20                  25                  30

Ile Gly Lys Ser Leu Tyr Arg Leu Pro Leu Val Asn Asn Asp Leu Tyr
         35                  40                  45

His Asn Met Ala Lys Ala Asp Phe Lys Cys Phe Gln Arg Arg Cys Gln
     50                  55                  60

Leu Glu Trp His Gly Ile Asn Lys
 65                  70
```

<210> SEQ ID NO 19
<211> LENGTH: 497
<212> TYPE: DNA
<213> ORGANISM: Oryza sativa
<220> FEATURE:
<221> NAME/KEY: unsure
<222> LOCATION: (270)
<221> NAME/KEY: unsure
<222> LOCATION: (335)
<221> NAME/KEY: unsure
<222> LOCATION: (443)
<221> NAME/KEY: unsure
<222> LOCATION: (456)

<400> SEQUENCE: 19

```
tacgacaaaa caagattacg ctcatatggc catggaggcc agtgaatacc tcgatggaat     60

cgtcaaaaag ttcaatggag gagttccctg tatctaccct ttggatgtgt acgaacgctt    120

atgggccgtc gataggctga cgaggctggg catatcaagg cacttcacaa gtgaaattga    180

ggattgctta gactacattt tcaggaactg gactccagat ggattagctc acacaaagaa    240

ctgcccggta aaggatatcg atgacacggn catgggtttc cgtctcctcc gactttacgg    300

ataccaagtc gacccatgtg tgttgaataa gttcnaaaag gatggcaagt tcttctgctt    360

gcacggggag tccaacccat cctctgtcac cccaatgtac aacacttacc gggcctccca    420

actcaaattt cctggcgatg acngtgtcct tgggcnaact gaggtgtttt gccgctcaat    480

cctccaaaga caaggag                                                   497
```

<210> SEQ ID NO 20
<211> LENGTH: 139
<212> TYPE: PRT
<213> ORGANISM: Oryza sativa
<220> FEATURE:
<221> NAME/KEY: UNSURE
<222> LOCATION: (82)
<221> NAME/KEY: UNSURE
<222> LOCATION: (104)

<400> SEQUENCE: 20

```
Met Ala Met Glu Ala Ser Glu Tyr Leu Asp Gly Ile Val Lys Lys Phe
  1               5                  10                  15

Asn Gly Gly Val Pro Cys Ile Tyr Pro Leu Asp Val Tyr Glu Arg Leu
             20                  25                  30

Trp Ala Val Asp Arg Leu Thr Arg Leu Gly Ile Ser Arg His Phe Thr
         35                  40                  45

Ser Glu Ile Glu Asp Cys Leu Asp Tyr Ile Phe Arg Asn Trp Thr Pro
     50                  55                  60

Asp Gly Leu Ala His Thr Lys Asn Cys Pro Val Lys Asp Ile Asp Asp
 65                  70                  75                  80

Thr Xaa Met Gly Phe Arg Leu Leu Arg Leu Tyr Gly Tyr Gln Val Asp
                 85                  90                  95

Pro Cys Val Leu Asn Lys Phe Xaa Lys Asp Gly Lys Phe Phe Cys Leu
            100                 105                 110

His Gly Glu Ser Asn Pro Ser Ser Val Thr Pro Met Tyr Asn Thr Tyr
        115                 120                 125

Arg Ala Ser Gln Leu Lys Phe Pro Gly Asp Asp
    130                 135
```

<210> SEQ ID NO 21
<211> LENGTH: 2543
<212> TYPE: DNA
<213> ORGANISM: Glycine max

<400> SEQUENCE: 21

```
gcacgaggcc accttccctc tttctcttct tctaaccatt tcccttttttc atcttcttct     60

tctatctctc ttcaccactt ctccaaatcc tctctgggtg ccgtgttgtc cgagactaac    120

gacaaacaag agataagatg cagagcaata tccaaaccac gaacacaaga atattcagac    180

atatttcagg gtagtctagc aacgttaaag tttcgtgaga ttaatgtgga agatgacata    240

gaagaggagc aagacatcgg gaaggttttt gtggcaaatg agatcaagaa gagagtggac    300

actatcaaat caatattggg ttccatggaa gatggagaga taacagtatc tgcttatgac    360
```

-continued

```
actgcttggg ttgctctgat agaagatgtt catggaagtg gtgctcctca atttccatcg    420

agtctagaat ggatagcgaa aaatcaacac cctgatggtt catggggtga taaggaatta    480

ttctcagccc atgatcggat tattaacacg ttggcttgtg ttattgcatt aaaatcatgg    540

catatgcacc ctgaaaagtg tgagaaagga atgacatttt ttaaggagaa tcttaaccag    600

cttcagaatg agaatgtgga gcatatgcca attgggtttg aagtagcttt tccatcactt    660

cttgacatgg ctcgtggctt gaacattgaa gtgccggaca attccccaat cctgaacaaa    720

atcttcgcaa tgagaaacgt aaaactcaca agaataccaa aagcgatgat gcataaagtg    780

cccacaagtc tgcttcatag cttggaaggg atgtcaggcc ttgactggaa agagcttcta    840

aaactgcagt ctcaagacgg gtccttcttg ttttctccgt cctccactgc ctttgctctc    900

atgcaaacta aagaccaaaa ttgccacaat tacttgaata aagtggtcaa gaggttcaat    960

gggggagttc cgaacgtgta cccagtggat ttgttcgaac atatttgggt ggttgatagg   1020

cttgaacgcc tcggaatatc tcagtatttt cagcaagaga tcaaggactg tttgagttat   1080

gttcacagat attggactga aaagggtatt tgttgggcaa gaaattcaaa tgttcaagac   1140

attgatgaca cggcaatggg tttcagatta ctaagattac acggctatca agtttcagcc   1200

gatgtgttca agaactttga gagaaatggt gaatttttct gcttcacggg gcagactaca   1260

caagccgtga caggaatgtt taatctatat agggccacac aagtaatgtt cccgggagag   1320

aaaattcttg agcatgggaa gcatttctct gccaaatttt tgagggataa gagagcagca   1380

aatgagctag tacataaatg gatcataatg aagaacctgg cagaagaggt tgcgtacgct   1440

ttggacgtac catggtatgc aagcctacct cgagtggaga caagattcta cattgatcaa   1500

tacggtggtg agagtgacgt gtggataggc aaaacccttt acaggatggc ctatgtgaac   1560

aacaataact atctcgagct tgctaaatta gattacaaca attgccaggc actgcatcta   1620

atagagtggg ggagaattca gaagtggtac tcagaatcta ggttgggaga gtttggattg   1680

aacagaagaa ctcttctgtt ggcctatttt ctggcagcag caagcatatt tgagcctgaa   1740

aagtctcatg tgagactagc gtgggccaaa accagtgtct tacttgagac cataacatcc   1800

tatgttagtg atgcagaaat gaggaaagat ttcatgaaaa aattcagtga ctgcattaac   1860

aggcgagact actccatggg ctggaggttg aacaggaaca gaataggaca tggactggct   1920

gaggctttgg ttgccaccat agatcaaatc tcgtgggata tactcgtgtc tcacggtcac   1980

gaaattggat atcacatgca tcgcagttgg gaaaagtggc tttcaagttg gcatcgcgaa   2040

ggagacaaat gtgaaggaca agctgagctt ttggcgcaga taataaacct atgtgacggg   2100

cattggattt ccgaggatca agtgttcgat ccacaatatc agagtctcct tcaactcact   2160

aacacactct gcaatagact ccgttgccac caaaaggaca aggaactcga gagcggcaac   2220

tgcggcacga atgtaaacag catgatcacc caagaagaag agtcaaaaat gcaagaactc   2280

gtgcaattgg tgtaccaaaa atctccaact ggcattgatt tcaatatcaa gaatactttc   2340

ctcacagtgg ccaagagttt ttactataca gctttctgtg attcaaggac cgtcaacttc   2400

catattgcca aagttctgtt tgataaagtc gtttaaatca aattttattt cttgaataga   2460

tattagactc caccatatca ttgtgaatat tatccctctg taatgataaa aagaaaggaa   2520

aacaaaaaaa aaaaaaaaaa aaa                                            2543
```

<210> SEQ ID NO 22
<211> LENGTH: 811
<212> TYPE: PRT
<213> ORGANISM: Glycine max -continued

<400> SEQUENCE: 22

```
Ala Arg Gly His Leu Pro Ser Phe Ser Ser Ser Asn His Phe Pro Phe
  1               5                  10                  15

Ser Ser Ser Ser Ser Ile Ser Leu His His Phe Ser Lys Ser Ser Leu
             20                  25                  30

Gly Ala Val Leu Ser Glu Thr Asn Asp Lys Gln Glu Ile Arg Cys Arg
         35                  40                  45

Ala Ile Ser Lys Pro Arg Thr Gln Glu Tyr Ser Asp Ile Phe Gln Gly
     50                  55                  60

Ser Leu Ala Thr Leu Lys Phe Arg Glu Ile Asn Val Glu Asp Asp Ile
 65                  70                  75                  80

Glu Glu Glu Gln Asp Ile Gly Lys Val Phe Val Ala Asn Glu Ile Lys
                 85                  90                  95

Lys Arg Val Asp Thr Ile Lys Ser Ile Leu Gly Ser Met Glu Asp Gly
            100                 105                 110

Glu Ile Thr Val Ser Ala Tyr Asp Thr Ala Trp Val Ala Leu Ile Glu
        115                 120                 125

Asp Val His Gly Ser Gly Ala Pro Gln Phe Pro Ser Ser Leu Glu Trp
    130                 135                 140

Ile Ala Lys Asn Gln His Pro Asp Gly Ser Trp Gly Asp Lys Glu Leu
145                 150                 155                 160

Phe Ser Ala His Asp Arg Ile Ile Asn Thr Leu Ala Cys Val Ile Ala
                165                 170                 175

Leu Lys Ser Trp His Met His Pro Glu Lys Cys Glu Lys Gly Met Thr
            180                 185                 190

Phe Phe Lys Glu Asn Leu Asn Gln Leu Gln Asn Glu Asn Val Glu His
        195                 200                 205

Met Pro Ile Gly Phe Glu Val Ala Phe Pro Ser Leu Leu Asp Met Ala
    210                 215                 220

Arg Gly Leu Asn Ile Glu Val Pro Asp Asn Ser Pro Ile Leu Asn Lys
225                 230                 235                 240

Ile Phe Ala Met Arg Asn Val Lys Leu Thr Arg Ile Pro Lys Ala Met
                245                 250                 255

Met His Lys Val Pro Thr Ser Leu Leu His Ser Leu Glu Gly Met Ser
            260                 265                 270

Gly Leu Asp Trp Lys Glu Leu Leu Lys Leu Gln Ser Gln Asp Gly Ser
        275                 280                 285

Phe Leu Phe Ser Pro Ser Ser Thr Ala Phe Ala Leu Met Gln Thr Lys
    290                 295                 300

Asp Gln Asn Cys His Asn Tyr Leu Asn Lys Val Val Lys Arg Phe Asn
305                 310                 315                 320

Gly Gly Val Pro Asn Val Tyr Pro Val Asp Leu Phe Glu His Ile Trp
                325                 330                 335

Val Val Asp Arg Leu Glu Arg Leu Gly Ile Ser Gln Tyr Phe Gln Gln
            340                 345                 350

Glu Ile Lys Asp Cys Leu Ser Tyr Val His Arg Tyr Trp Thr Glu Lys
        355                 360                 365

Gly Ile Cys Trp Ala Arg Asn Ser Asn Val Gln Asp Ile Asp Asp Thr
    370                 375                 380

Ala Met Gly Phe Arg Leu Leu Arg Leu His Gly Tyr Gln Val Ser Ala
385                 390                 395                 400

Asp Val Phe Lys Asn Phe Glu Arg Asn Gly Glu Phe Phe Cys Phe Thr
                405                 410                 415
```

-continued

```
Gly Gln Thr Thr Gln Ala Val Thr Gly Met Phe Asn Leu Tyr Arg Ala
            420                 425                 430

Thr Gln Val Met Phe Pro Gly Glu Lys Ile Leu Glu His Gly Lys His
        435                 440                 445

Phe Ser Ala Lys Phe Leu Arg Asp Lys Arg Ala Ala Asn Glu Leu Val
    450                 455                 460

His Lys Trp Ile Ile Met Lys Asn Leu Ala Glu Glu Val Ala Tyr Ala
465                 470                 475                 480

Leu Asp Val Pro Trp Tyr Ala Ser Leu Pro Arg Val Glu Thr Arg Phe
                485                 490                 495

Tyr Ile Asp Gln Tyr Gly Gly Glu Ser Asp Val Trp Ile Gly Lys Thr
            500                 505                 510

Leu Tyr Arg Met Ala Tyr Val Asn Asn Asn Asn Tyr Leu Glu Leu Ala
        515                 520                 525

Lys Leu Asp Tyr Asn Asn Cys Gln Ala Leu His Leu Ile Glu Trp Gly
    530                 535                 540

Arg Ile Gln Lys Trp Tyr Ser Glu Ser Arg Leu Gly Glu Phe Gly Leu
545                 550                 555                 560

Asn Arg Arg Thr Leu Leu Leu Ala Tyr Phe Leu Ala Ala Ala Ser Ile
                565                 570                 575

Phe Glu Pro Glu Lys Ser His Val Arg Leu Ala Trp Ala Lys Thr Ser
            580                 585                 590

Val Leu Leu Glu Thr Ile Thr Ser Tyr Val Ser Asp Ala Glu Met Arg
        595                 600                 605

Lys Asp Phe Met Lys Lys Phe Ser Asp Cys Ile Asn Arg Arg Asp Tyr
    610                 615                 620

Ser Met Gly Trp Arg Leu Asn Arg Asn Arg Ile Gly His Gly Leu Ala
625                 630                 635                 640

Glu Ala Leu Val Ala Thr Ile Asp Gln Ile Ser Trp Asp Ile Leu Val
                645                 650                 655

Ser His Gly His Glu Ile Gly Tyr His Met His Arg Ser Trp Glu Lys
            660                 665                 670

Trp Leu Ser Ser Trp His Arg Glu Gly Asp Lys Cys Glu Gly Gln Ala
        675                 680                 685

Glu Leu Leu Ala Gln Ile Ile Asn Leu Cys Asp Gly His Trp Ile Ser
    690                 695                 700

Glu Asp Gln Val Phe Asp Pro Gln Tyr Gln Ser Leu Leu Gln Leu Thr
705                 710                 715                 720

Asn Thr Leu Cys Asn Arg Leu Arg Cys His Gln Lys Asp Lys Glu Leu
                725                 730                 735

Glu Ser Gly Asn Cys Gly Thr Asn Val Asn Ser Met Ile Thr Gln Glu
            740                 745                 750

Glu Glu Ser Lys Met Gln Glu Leu Val Gln Leu Val Tyr Gln Lys Ser
        755                 760                 765

Pro Thr Gly Ile Asp Phe Asn Ile Lys Asn Thr Phe Leu Thr Val Ala
    770                 775                 780

Lys Ser Phe Tyr Tyr Thr Ala Phe Cys Asp Ser Arg Thr Val Asn Phe
785                 790                 795                 800

His Ile Ala Lys Val Leu Phe Asp Lys Val Val
                805                 810
```

<210> SEQ ID NO 23
<211> LENGTH: 2403
<212> TYPE: DNA

<213> ORGANISM: Zea mays
<220> FEATURE:
<221> NAME/KEY: unsure
<222> LOCATION: (1049)

<400> SEQUENCE: 23

```
ccacgcgtcc gctgcagaac cagcaggatg atggatcttg gggtgtcagc caatctgact      60
catcggtcag caaggatgtt ctcctatcca cgttggcatg tgttcttgcg ttgaagagat     120
ggaatgttgg cagagagaac atttggagag gactgcattt catcgggagg aatttctctg     180
ttgctatgga cgagcagttc acttctccta taggtttcaa cttcaccttt cctggtttgc     240
ttagcctcgg cattgatatg ggtttagaat ttcctgtaag acaaattgat gtctgtggca     300
ttcttcaccg ccgggagatg gaattgaaaa ggctggctgt ggatagttct tttggaagaa     360
aagcatatat ggcttttatc ccagaaggat tcggaaatat gctggactgg gatcaagtta     420
tgaagtttca gaggaagaat ggatcattgt tcagcactcc ttccacaact gctgttgcat     480
taatccacaa atacaacgac caagcccttc aatacctaaa tttgcttgtc aatgaatttg     540
gcagtgcagt accagcaatg tatccttcaa gggtacattg tcagctttca atggtggacg     600
cgcttgaaaa aatgggaatt tctcagcgct ttgtcagtga aatagaaagc atcctggaca     660
tggcatacaa ttgctggtta cagaatgatg aggaactcat gatggacata gcaacatttg     720
caatggcatt tcgccttttg aggatgaatg gttacgatgt ttcctcagat gagctgtctc     780
acgttgctgg agcttccact ttccatgatt cactacaagg atatttaaat gatacaaaat     840
ccctactgga attgtacaag acctcaaaag tcaccttatc agaaaacgat ctgatcttag     900
atcgcatagg ttcctggtct ggcaacttat tgaaggataa gatgtgctgt agtaaggtgc     960
aaaagactcg atttttggag agatgctgca aacaaaattt aaattctcat tttcaccttg    1020
gaggttcagt ttatgtctgt gttttgtgnt ttcagatcga gtatgctgtt aattttccct    1080
tgtattccac actggagcgt ctagaacaca agagaaacat cgaacatttt gatgcttggg    1140
gttctctgat gctaacaaca aaatcctcat cttttcgtat caatcaagaa ttcctagctt    1200
tggcagtcga agatttcagt ttctctcaac gtgtttaccg ggatgaactt cggcatcttg    1260
atagttgggt gaaggagaac aagctggacc agctacaatt tgctcggcag aaactgacat    1320
attgctatct gtctgctgct gctaccgtat tttcttctga attgtctgac gctcgcattt    1380
catgggccaa aaatggtgtc ctcacaactg tggttgatga cttcttcgat gttggtggat    1440
caaaagaaga attagaaaac ctgatagcac tagttgagaa atggcatggg caccatgcag    1500
ttgagttcta ttcggaacag gtgaaaatag tattttctgc tatttataca acagtgaacc    1560
atcttggagc aatggcttct gcagcacaag gccgtgatct tacaaaccac ctagtagaaa    1620
tatggctgga tttgttaaga tctatgatgg tcgaggcaga atggcagaga tgccaatatg    1680
taccaacagt tgaagaatac atgacaaatg ctgttgtctc atttgcactg ggcccaattg    1740
tgctcccagc attgtatttt gtagggcaag agctattaga gcatgctgtc aaagatgaag    1800
agtacgataa attatttagg ctagtgagca cttgcgggag gctcctcaat gactaccaaa    1860
gtttagagag ggaaggcaac caggggaagc tgaatagtgt ttctctactt gtgctccaca    1920
gtggtggttc tatgtccata gaagccgcta aaaaggcaat gcagaagtcc atagacgtgt    1980
ctaggagaga cttgctaaga ttggttctca ggaaagaaag tgctgttcct aggccatgca    2040
aggagctctt ctggaagatg tgtaagatac ttcacctgtt ttactctcag aatgatggat    2100
ttagctcccc aaaggaaatg gtcagtgcag tgaatgctgt tatcaacgag ccactcaaag    2160
```

-continued

```
tccaaaacag tactacgttt ttgtctagtt catcaaggta gcgaggatat catgtaattt   2220

atcctgttca tatggatcag aagcaacagc agcaagctta agatatttgt aagtttgtga   2280

ctgggctgct gtggatctgt gaagctacaa ctttgctgta tgtggatcaa ggtattagga   2340

agatctggtt cacatattga taacataatg gataaaccat aacgttaaaa aaaaaaaaaa   2400

aag                                                                 2403


<210> SEQ ID NO 24
<211> LENGTH: 732
<212> TYPE: PRT
<213> ORGANISM: Zea mays
<220> FEATURE:
<221> NAME/KEY: UNSURE
<222> LOCATION: (349)

<400> SEQUENCE: 24

Thr Arg Pro Leu Gln Asn Gln Gln Asp Asp Gly Ser Trp Gly Val Ser
  1               5                  10                  15

Gln Ser Asp Ser Ser Val Ser Lys Asp Val Leu Leu Ser Thr Leu Ala
             20                  25                  30

Cys Val Leu Ala Leu Lys Arg Trp Asn Val Gly Arg Glu Asn Ile Trp
         35                  40                  45

Arg Gly Leu His Phe Ile Gly Arg Asn Phe Ser Val Ala Met Asp Glu
     50                  55                  60

Gln Phe Thr Ser Pro Ile Gly Phe Asn Phe Thr Phe Pro Gly Leu Leu
 65                  70                  75                  80

Ser Leu Gly Ile Asp Met Gly Leu Glu Phe Pro Val Arg Gln Ile Asp
                 85                  90                  95

Val Cys Gly Ile Leu His Arg Arg Glu Met Glu Leu Lys Arg Leu Ala
            100                 105                 110

Val Asp Ser Ser Phe Gly Arg Lys Ala Tyr Met Ala Phe Ile Pro Glu
        115                 120                 125

Gly Phe Gly Asn Met Leu Asp Trp Asp Gln Val Met Lys Phe Gln Arg
    130                 135                 140

Lys Asn Gly Ser Leu Phe Ser Thr Pro Ser Thr Thr Ala Val Ala Leu
145                 150                 155                 160

Ile His Lys Tyr Asn Asp Gln Ala Leu Gln Tyr Leu Asn Leu Leu Val
                165                 170                 175

Asn Glu Phe Gly Ser Ala Val Pro Ala Met Tyr Pro Ser Arg Val His
            180                 185                 190

Cys Gln Leu Ser Met Val Asp Ala Leu Glu Lys Met Gly Ile Ser Gln
        195                 200                 205

Arg Phe Val Ser Glu Ile Glu Ser Ile Leu Asp Met Ala Tyr Asn Cys
    210                 215                 220

Trp Leu Gln Asn Asp Glu Glu Leu Met Met Asp Ile Ala Thr Phe Ala
225                 230                 235                 240

Met Ala Phe Arg Leu Leu Arg Met Asn Gly Tyr Asp Val Ser Ser Asp
                245                 250                 255

Glu Leu Ser His Val Ala Gly Ala Ser Thr Phe His Asp Ser Leu Gln
            260                 265                 270

Gly Tyr Leu Asn Asp Thr Lys Ser Leu Leu Glu Leu Tyr Lys Thr Ser
        275                 280                 285

Lys Val Thr Leu Ser Glu Asn Asp Leu Ile Leu Asp Arg Ile Gly Ser
    290                 295                 300
```

-continued

```
Trp Ser Gly Asn Leu Leu Lys Asp Lys Met Cys Cys Ser Lys Val Gln
305                 310                 315                 320

Lys Thr Arg Phe Leu Glu Arg Cys Cys Lys Gln Asn Leu Asn Ser His
                325                 330                 335

Phe His Leu Gly Gly Ser Val Tyr Val Cys Val Leu Xaa Phe Gln Ile
            340                 345                 350

Glu Tyr Ala Val Asn Phe Pro Leu Tyr Ser Thr Leu Glu Arg Leu Glu
        355                 360                 365

His Lys Arg Asn Ile Glu His Phe Asp Ala Trp Gly Ser Leu Met Leu
    370                 375                 380

Thr Thr Lys Ser Ser Ser Phe Arg Ile Asn Gln Glu Phe Leu Ala Leu
385                 390                 395                 400

Ala Val Glu Asp Phe Ser Phe Ser Gln Arg Val Tyr Arg Asp Glu Leu
                405                 410                 415

Arg His Leu Asp Ser Trp Val Lys Glu Asn Lys Leu Asp Gln Leu Gln
            420                 425                 430

Phe Ala Arg Gln Lys Leu Thr Tyr Cys Tyr Leu Ser Ala Ala Ala Thr
        435                 440                 445

Val Phe Ser Ser Glu Leu Ser Asp Ala Arg Ile Ser Trp Ala Lys Asn
    450                 455                 460

Gly Val Leu Thr Thr Val Val Asp Asp Phe Phe Asp Val Gly Gly Ser
465                 470                 475                 480

Lys Glu Glu Leu Glu Asn Leu Ile Ala Leu Val Glu Lys Trp His Gly
                485                 490                 495

His His Ala Val Glu Phe Tyr Ser Glu Gln Val Lys Ile Val Phe Ser
            500                 505                 510

Ala Ile Tyr Thr Thr Val Asn His Leu Gly Ala Met Ala Ser Ala Ala
        515                 520                 525

Gln Gly Arg Asp Leu Thr Asn His Leu Val Glu Ile Trp Leu Asp Leu
    530                 535                 540

Leu Arg Ser Met Met Val Glu Ala Glu Trp Gln Arg Cys Gln Tyr Val
545                 550                 555                 560

Pro Thr Val Glu Glu Tyr Met Thr Asn Ala Val Val Ser Phe Ala Leu
                565                 570                 575

Gly Pro Ile Val Leu Pro Ala Leu Tyr Phe Val Gly Gln Glu Leu Leu
            580                 585                 590

Glu His Ala Val Lys Asp Glu Glu Tyr Asp Lys Leu Phe Arg Leu Val
        595                 600                 605

Ser Thr Cys Gly Arg Leu Leu Asn Asp Tyr Gln Ser Leu Glu Arg Glu
    610                 615                 620

Gly Asn Gln Gly Lys Leu Asn Ser Val Ser Leu Leu Val Leu His Ser
625                 630                 635                 640

Gly Gly Ser Met Ser Ile Glu Ala Ala Lys Lys Ala Met Gln Lys Ser
                645                 650                 655

Ile Asp Val Ser Arg Arg Asp Leu Leu Arg Leu Val Leu Arg Lys Glu
            660                 665                 670

Ser Ala Val Pro Arg Pro Cys Lys Glu Leu Phe Trp Lys Met Cys Lys
        675                 680                 685

Ile Leu His Leu Phe Tyr Ser Gln Asn Asp Gly Phe Ser Ser Pro Lys
    690                 695                 700
```

-continued

```
Glu Met Val Ser Ala Val Asn Ala Val Ile Asn Glu Pro Leu Lys Val
705                 710                 715                 720

Gln Asn Ser Thr Thr Phe Leu Ser Ser Ser Ser Arg
                725                 730


<210> SEQ ID NO 25
<211> LENGTH: 468
<212> TYPE: DNA
<213> ORGANISM: Oryza sativa
<220> FEATURE:
<221> NAME/KEY: unsure
<222> LOCATION: (435)
<221> NAME/KEY: unsure
<222> LOCATION: (448)

<400> SEQUENCE: 25

cttaagtttc ccttctacac cacactggac cgtctagatc acaagaggaa cattgaacgt      60

tttgatgcaa aggattccca gatgttaaag acggaatact tgcttcctca tgccaatcaa     120

gatattctag ctttggctgt tgaagatttc agtagttctc aatctatata ccaggatgaa     180

cttaattatc ttgagtgttg ggtgaaagat gaaaagctcg atcagctgcc atttgcacgc     240

cagaagttga catattgcta cctttctgct gctgctacca tattccccg tgaattgtct     300

gaagcccgca ttgcatgggc taaaaatggt gtacctgaca actgttgttg atgacttctt     360

tgatcttggg ggatcaaaag aagaactaag aaaacctcat tgctttagtt gagaagtggg     420

atggacatca aagangagtt ctactcanaa caagtaagaa tagttttt                  468


<210> SEQ ID NO 26
<211> LENGTH: 140
<212> TYPE: PRT
<213> ORGANISM: Oryza sativa
<220> FEATURE:
<221> NAME/KEY: UNSURE
<222> LOCATION: (34)
<221> NAME/KEY: UNSURE
<222> LOCATION: (112)
<221> NAME/KEY: UNSURE
<222> LOCATION: (130)

<400> SEQUENCE: 26

Leu Lys Phe Pro Phe Tyr Thr Thr Leu Asp Arg Leu Asp His Lys Arg
  1               5                  10                  15

Asn Ile Glu Arg Phe Asp Ala Lys Asp Ser Gln Met Leu Lys Thr Glu
             20                  25                  30

Tyr Xaa Leu Pro His Ala Asn Gln Asp Ile Leu Ala Leu Ala Val Glu
         35                  40                  45

Asp Phe Ser Ser Ser Gln Ser Ile Tyr Gln Asp Glu Leu Asn Tyr Leu
     50                  55                  60

Glu Cys Trp Val Lys Asp Glu Lys Leu Asp Gln Leu Pro Phe Ala Arg
 65                  70                  75                  80

Gln Lys Leu Thr Tyr Cys Tyr Leu Ser Ala Ala Ala Thr Ile Phe Pro
                 85                  90                  95

Arg Glu Leu Ser Glu Ala Arg Ile Ala Trp Ala Lys Asn Gly Val Xaa
            100                 105                 110

Thr Thr Val Val Asp Asp Phe Phe Asp Leu Gly Gly Ser Lys Glu Glu
        115                 120                 125

Leu Xaa Asn Leu Ile Ala Leu Val Glu Lys Trp Asp
    130                 135                 140
```

<210> SEQ ID NO 27
<211> LENGTH: 531
<212> TYPE: DNA
<213> ORGANISM: Triticum aestivum

<400> SEQUENCE: 27

```
gctgctgcaa ccatatccgc tcatgaattc tctgatgctc gcattgcatg tgcgaaagct     60

attgcactcg tacttgttac tgatgacttc tttgatgttg gagcatccaa ggaagaacaa    120

gaaaacctca tagcattagt agagaagtgg gatcaccatc acaaagttga gttctactcc    180

gagcaagtag aagtagtatt ttctgctttt tataccacag ttaatcagct tggagaaatg    240

gcttccgcag tacaaaactg cgatgttaca aagcacttgg atgaaacatg gctacattac    300

atgaggtctg tggcaaccga ggcaaaatgg caacggaatc aatatgtgcc aacagttgag    360

gaatacatga cagacgcgct tacctcatac gggatgggcc cgattatgct cacatcactg    420

tattttgtcc aaaacaaact tatgaagcac attatcaaag accggagtac agtgagttgc    480

ttagactaat gggtacatgt ggccgtctct tgaatgatac caaggcttgg a             531
```

<210> SEQ ID NO 28
<211> LENGTH: 177
<212> TYPE: PRT
<213> ORGANISM: Triticum aestivum
<220> FEATURE:
<221> NAME/KEY: UNSURE
<222> LOCATION: (153)..(154)..(155)

<400> SEQUENCE: 28

```
Ala Ala Ala Thr Ile Ser Ala His Glu Phe Ser Asp Ala Arg Ile Ala
  1               5                  10                  15

Cys Ala Lys Ala Ile Ala Leu Val Leu Val Thr Asp Asp Phe Phe Asp
             20                  25                  30

Val Gly Ala Ser Lys Glu Glu Gln Glu Asn Leu Ile Ala Leu Val Glu
         35                  40                  45

Lys Trp Asp His His His Lys Val Glu Phe Tyr Ser Glu Gln Val Glu
     50                  55                  60

Val Val Phe Ser Ala Phe Tyr Thr Thr Val Asn Gln Leu Gly Glu Met
 65                  70                  75                  80

Ala Ser Ala Val Gln Asn Cys Asp Val Thr Lys His Leu Asp Glu Thr
                 85                  90                  95

Trp Leu His Tyr Met Arg Ser Val Ala Thr Glu Ala Lys Trp Gln Arg
            100                 105                 110

Asn Gln Tyr Val Pro Thr Val Glu Glu Tyr Met Thr Asp Ala Leu Thr
        115                 120                 125

Ser Tyr Gly Met Gly Pro Ile Met Leu Thr Ser Leu Tyr Phe Val Gln
    130                 135                 140

Asn Lys Leu Met Lys His Ile Ile Xaa Xaa Xaa Glu Tyr Ser Glu Leu
145                 150                 155                 160

Leu Arg Leu Met Gly Thr Cys Gly Arg Leu Leu Asn Asp Thr Lys Ala
                165                 170                 175

Trp
```

<210> SEQ ID NO 29
<211> LENGTH: 476
<212> TYPE: DNA
<213> ORGANISM: Oryza sativa -continued

```
<400> SEQUENCE: 29

cttacagaca ttcagtagaa cagaagacat aacatttgca accgaggaat gcctccttct     60

tactatagca taaagcgatg ggaatctatc tttagaggta ctgtttgatt gaggttgtat    120

acaactaatt aacactacga caaacgtacg tatttataga gaccaaaaac tatgtgtaaa    180

attaagtaat ttaatgtctg tcgattgatt gtattgatca atgtcgacac gtagattggt    240

tacgccctag acttcccctg gaaagcaagt ctgccacgtg ttgaaacaag aatgtatctg    300

gagcaatatg gcgccggcag agatgtgtgg atcggtaagt cgctttacag gtaaaagcac    360

ggtaattaac caacaattgt gaaatactct ctcctttatc atgtcatcat cctcaaatat    420

actgggcgta cacggtccta aacctttctg gaaggctggc actccgtgaa caaagg        476


<210> SEQ ID NO 30
<211> LENGTH: 48
<212> TYPE: PRT
<213> ORGANISM: Oryza sativa
<220> FEATURE:
<221> NAME/KEY: UNSURE
<222> LOCATION: (9)

<400> SEQUENCE: 30

Ile Val Leu Ile Asn Val Asp Thr Xaa Ile Gly Tyr Ala Leu Asp Phe
  1               5                  10                  15

Pro Trp Lys Ala Ser Leu Pro Arg Val Glu Thr Arg Met Tyr Leu Glu
             20                  25                  30

Gln Tyr Gly Ala Gly Arg Asp Val Trp Ile Gly Lys Ser Leu Tyr Arg
         35                  40                  45


<210> SEQ ID NO 31
<211> LENGTH: 518
<212> TYPE: DNA
<213> ORGANISM: Glycine max
<220> FEATURE:
<221> NAME/KEY: unsure
<222> LOCATION: (245)
<221> NAME/KEY: unsure
<222> LOCATION: (406)
<221> NAME/KEY: unsure
<222> LOCATION: (427)
<221> NAME/KEY: unsure
<222> LOCATION: (461)
<221> NAME/KEY: unsure
<222> LOCATION: (466)
<221> NAME/KEY: unsure
<222> LOCATION: (492)
<221> NAME/KEY: unsure
<222> LOCATION: (512)

<400> SEQUENCE: 31

gccaccttcc ctctttctct tcttctaacc atttcccttt ttcatcttct tcttctatct     60

ctcttcacca cttctccaaa tcctctctgg gtgccgtgtt gtccgagact aacgacaaac    120

aagagataag atgcagagca atatccaaac cacgaacaca agaatattca gacatatttc    180

agggtagtct agcaacgtta aagtttcgtg agattaatgt ggaagatgac atagaagagg    240

agcangacat cgggaaggtt tttgtggcaa atgagatcaa gaagagagtg gacactatca    300

aatcaatatt gggttccatg gaagatggag agataacagt atctgcttat gacactgctt    360

gggttgctct gatagaagat gttcaaggga agtggtgctc ctcaanttca accgagtcta    420

gaatggntaa gcgaaaaaat caacaccctg gatgggtcaa nggggngata agggaattat    480

cccaagccca angttcgggt tttttaaaac gntgggtt                            518
```

<210> SEQ ID NO 32
<211> LENGTH: 127
<212> TYPE: PRT
<213> ORGANISM: Glycine max
<220> FEATURE:
<221> NAME/KEY: UNSURE
<222> LOCATION: (81)

<400> SEQUENCE: 32

```
His Leu Pro Ser Phe Ser Ser Ser Asn His Phe Pro Phe Ser Ser Ser
  1               5                  10                  15

Ser Ser Ile Ser Leu His His Phe Ser Lys Ser Ser Leu Gly Ala Val
             20                  25                  30

Leu Ser Glu Thr Asn Asp Lys Gln Glu Ile Arg Cys Arg Ala Ile Ser
         35                  40                  45

Lys Pro Arg Thr Gln Glu Tyr Ser Asp Ile Phe Gln Gly Ser Leu Ala
     50                  55                  60

Thr Leu Lys Phe Arg Glu Ile Asn Val Glu Asp Asp Ile Glu Glu Glu
 65                  70                  75                  80

Xaa Asp Ile Gly Lys Val Phe Val Ala Asn Glu Ile Lys Lys Arg Val
                 85                  90                  95

Asp Thr Ile Lys Ser Ile Leu Gly Ser Met Glu Asp Gly Glu Ile Thr
            100                 105                 110

Val Ser Ala Tyr Asp Thr Ala Trp Val Ala Leu Ile Glu Asp Val
        115                 120                 125
```

<210> SEQ ID NO 33
<211> LENGTH: 1157
<212> TYPE: DNA
<213> ORGANISM: Zea mays
<220> FEATURE:
<221> NAME/KEY: unsure
<222> LOCATION: (40)
<221> NAME/KEY: unsure
<222> LOCATION: (44)
<221> NAME/KEY: unsure
<222> LOCATION: (60)
<221> NAME/KEY: unsure
<222> LOCATION: (64)
<221> NAME/KEY: unsure
<222> LOCATION: (712)
<221> NAME/KEY: unsure
<222> LOCATION: (721)
<221> NAME/KEY: unsure
<222> LOCATION: (723)
<221> NAME/KEY: unsure
<222> LOCATION: (732)
<221> NAME/KEY: unsure
<222> LOCATION: (738)
<221> NAME/KEY: unsure
<222> LOCATION: (757)
<221> NAME/KEY: unsure
<222> LOCATION: (763)
<221> NAME/KEY: unsure
<222> LOCATION: (782)
<221> NAME/KEY: unsure
<222> LOCATION: (809)
<221> NAME/KEY: unsure
<222> LOCATION: (813)
<221> NAME/KEY: unsure
<222> LOCATION: (824)
<221> NAME/KEY: unsure
<222> LOCATION: (826)..(827)
<221> NAME/KEY: unsure
<222> LOCATION: (849)..(850)
<221> NAME/KEY: unsure
<222> LOCATION: (858)
<221> NAME/KEY: unsure
<222> LOCATION: (863)
<221> NAME/KEY: unsure
<222> LOCATION: (872)
<221> NAME/KEY: unsure
<222> LOCATION: (874)
<221> NAME/KEY: unsure
<222> LOCATION: (888)
<221> NAME/KEY: unsure
<222> LOCATION: (930)..(931)
<221> NAME/KEY: unsure
<222> LOCATION: (938)
<221> NAME/KEY: unsure
<222> LOCATION: (942)
<221> NAME/KEY: unsure
<222> LOCATION: (961)
<221> NAME/KEY: unsure
<222> LOCATION: (967)
<221> NAME/KEY: unsure
<222> LOCATION: (971)
<221> NAME/KEY: unsure
<222> LOCATION: (981)
<221> NAME/KEY: unsure
<222> LOCATION: (988)..(989)
<221> NAME/KEY: unsure
<222> LOCATION: (993)
<221> NAME/KEY: unsure
<222> LOCATION: (999)
<221> NAME/KEY: unsure
<222> LOCATION: (1024)
<221> NAME/KEY: unsure
<222> LOCATION: (1028)
<221> NAME/KEY: unsure
<222> LOCATION: (1031)
<221> NAME/KEY: unsure
<222> LOCATION: (1035)
<221> NAME/KEY: unsure
<222> LOCATION: (1040)
<221> NAME/KEY: unsure
<222> LOCATION: (1049)..(1050)
<221> NAME/KEY: unsure
<222> LOCATION: (1068)
<221> NAME/KEY: unsure
<222> LOCATION: (1089)
<221> NAME/KEY: unsure
<222> LOCATION: (1105)..(1106)
<221> NAME/KEY: unsure
<222> LOCATION: (1121)
<221> NAME/KEY: unsure
<222> LOCATION: (1124)
<221> NAME/KEY: unsure
<222> LOCATION: (1131)
<221> NAME/KEY: unsure
<222> LOCATION: (1136)..(1137)
<221> NAME/KEY: unsure
<222> LOCATION: (1155)

<400> SEQUENCE: 33
atgcaaaacc aacaagataa tggatcttgg ggtgtcagcn gggnctgact catcggtcan 60
caangatgtt ctcctatcca cgttggcatg tgttcttgcg ttgaagagat ggaatgttgg 120
cagagagaac atttggagag gactgcattt catcgggagg aatttctctg ttgctatgga 180
cgagcagttc acttctccta taggtttcaa cttcaccttt cctggtttgc ttagcctcgg 240
cattgatatg ggtttagaat ttcctgtaag acaaattgat gtctgtggca ttcttcaccg 300
ccgggagatg gaattgaaaa ggctggctgt ggatagttct tttggaagaa aagcatatat 360
ggcttttatc ccagaaggat tcggaaatat gctggactgg gatcaagtta tgaagtttca 420
gaggaagaat ggatcattgt tcagcactcc ttccacaact gctgttgcat taatccacaa 480
atacaacgac caagcccttc aatacctaaa tttgcttgtc aatgaatttg gcagtgcagt 540
accagcaatg tatccttcaa gggtacattg tcagctttca atggtggacg cgcttgaaaa 600
aatgggaatt tctcagcgct ttgtcagtga aataaaaaac atcctggaca tggcatacaa 660
ttgctggtta cagaaagatg aggaaatcat gatggacata gcaacatttg cnatggcatt 720

-continued

```
ncnccttttg angatgantg gttacaatgt ttcctcngat ganctgtctc acgttgctgg    780

ancttccact ttccatgaat cactacaang atntttaaat gatncnnaat ccctactgga    840

attgtacann acctcaanag tcnccttatc ananaacgat ctgatctnag atcgcatagg    900

ttcctggtct ggcgacttat tgaacgatan natgtgcngt tntaaggtgc aaaaagactc    960

nattttngga nagatggact ntgctgtnna ttntccctnt gtattccccc ctgggaccgt   1020

ctanaacncc naganaaacn tccaacatnn tgatgcttgg ggttctcnga tgctcacaaa   1080

ccaaatccnc atcttttcgt atccnncccc acaaatccct nccnttggcc nctccnnaaa   1140

ttccccccttt ccccnca                                                 1157


<210> SEQ ID NO 34
<211> LENGTH: 259
<212> TYPE: PRT
<213> ORGANISM: Zea mays
<220> FEATURE:
<221> NAME/KEY: UNSURE
<222> LOCATION: (217)..(218)
<221> NAME/KEY: UNSURE
<222> LOCATION: (221)
<221> NAME/KEY: UNSURE
<222> LOCATION: (223)
<221> NAME/KEY: UNSURE
<222> LOCATION: (231)
<221> NAME/KEY: UNSURE
<222> LOCATION: (238)
<221> NAME/KEY: UNSURE
<222> LOCATION: (247)..(248)
<221> NAME/KEY: UNSURE
<222> LOCATION: (252)..(253)

<400> SEQUENCE: 34

Leu Leu Ser Thr Leu Ala Cys Val Leu Ala Leu Lys Arg Trp Asn Val
  1               5                  10                  15

Gly Arg Glu Asn Ile Trp Arg Gly Leu His Phe Ile Gly Arg Asn Phe
             20                  25                  30

Ser Val Ala Met Asp Glu Gln Phe Thr Ser Pro Ile Gly Phe Asn Phe
         35                  40                  45

Thr Phe Pro Gly Leu Leu Ser Leu Gly Ile Asp Met Gly Leu Glu Phe
     50                  55                  60

Pro Val Arg Gln Ile Asp Val Cys Gly Ile Leu His Arg Arg Glu Met
 65                  70                  75                  80

Glu Leu Lys Arg Leu Ala Val Asp Ser Ser Phe Gly Arg Lys Ala Tyr
                 85                  90                  95

Met Ala Phe Ile Pro Glu Gly Phe Gly Asn Met Leu Asp Trp Asp Gln
            100                 105                 110

Val Met Lys Phe Gln Arg Lys Asn Gly Ser Leu Phe Ser Thr Pro Ser
        115                 120                 125

Thr Thr Ala Val Ala Leu Ile His Lys Tyr Asn Asp Gln Ala Leu Gln
    130                 135                 140

Tyr Leu Asn Leu Leu Val Asn Glu Phe Gly Ser Ala Val Pro Ala Met
145                 150                 155                 160

Tyr Pro Ser Arg Val His Cys Gln Leu Ser Met Val Asp Ala Leu Glu
                165                 170                 175

Lys Met Gly Ile Ser Gln Arg Phe Val Ser Glu Ile Lys Asn Ile Leu
            180                 185                 190

Asp Met Ala Tyr Asn Cys Trp Leu Gln Lys Asp Glu Glu Ile Met Met
        195                 200                 205
```

-continued

```
Asp Ile Ala Thr Phe Ala Met Ala Xaa Xaa Leu Leu Xaa Met Xaa Gly
    210                 215                 220

Tyr Asn Val Ser Ser Asp Xaa Leu Ser His Val Ala Gly Xaa Ser Thr
225                 230                 235                 240

Phe His Glu Ser Leu Gln Xaa Xaa Leu Asn Asp Xaa Xaa Ser Leu Leu
                245                 250                 255

Glu Leu Tyr


<210> SEQ ID NO 35
<211> LENGTH: 1436
<212> TYPE: DNA
<213> ORGANISM: Zea mays

<400> SEQUENCE: 35

ccacgcgtcc gagcagttgc agttgcagcg gcctcctcct ctgcttcctc cctcctcctc     60

ctcaccatgg tgctggctgc gcacgatccc cctccccttg tgttcgacgc tgcccgcctg    120

agcggcctct ccgacatccc gcagcagttc atctggccgg cggacgagag ccccaccccg    180

gactccgccg aggagctggc cgtgccgctc atcgacctct ccggggacgc cgccgaggtg    240

gtccggcagg tccggcgcgc ctgcgacctg cacggcttct tccaggtggt ggggcacggc    300

atcgacgcgg cgctgacggc ggaggcccac cgctgcatgg acgccttctt cacgctgccg    360

ctcccggaca agcagcgcgc gcagcgccgc caggggggaca gctgcggcta cgccagcagc    420

ttcacgggcc ggttcgcgtc caagctgccc tggaaggaga cgctgtcgtt ccgctacacc    480

gacgacgacg acggcgacaa gtccaaggac gtcgtggcgt cctacttcgt ggacaagctg    540

ggcgaggggt accggcacca cggggaggtg tacgggcgct actgctctga gatgagccgt    600

ctgtcgctgg agctcatgga ggtgctaggc gagagcctgg gcgtgggccg gcgccacttc    660

cggcgcttct tccaggggaa cgactccatc atgcgcctca actactaccc gccgtgccag    720

cggccctacg acacgctggg cacggggccg cattgcgacc ccacgtcgct caccatcctg    780

caccaggacg acgtgggcgg actccaggtg ttcgacgccg ccacgctcgc gtggcgctcc    840

atcaggcccc gcccgggcgc cttcgtcgtc aacatcggcg acaccttcat ggcgctctcc    900

aacgggcgct acaggagctg cctccaccgc gccgtcgtca acagccgggt ggcacgccgc    960

tcgctcgcct tcttcctgtg cccggagatg gacaaggtgg tcaggccgcc caaggagctg   1020

gtggacgacg ccaacccgag ggcgtacccg gacttcacgt ggaggacgct gctggacttc   1080

accatgaggc actacaggtc ggacatgagg acgctcgagg ccttctccaa ctggctcagc   1140

accagtagca atggcggaca gcacctgctg gagaagaagt aggcatgcta tttgggtatg   1200

gaagatggtg gatgtaagca aacaaagcca aattaagcag agtaggttaa ttaaggttgg   1260

ctgatgatcc atttagggaa ggagctgatc tccctgactc cctcctccaa ttttctcaac   1320

caaatttata tagtataata ataataataa aatagcaagt aatagttgta tcgtattatt   1380

attaattaat ttattagctg gtaggcaagt agtattaaaa aaaaaaaaaa aaaaag       1436


<210> SEQ ID NO 36
<211> LENGTH: 393
<212> TYPE: PRT
<213> ORGANISM: Zea mays

<400> SEQUENCE: 36

Pro Arg Val Arg Ala Val Ala Val Ala Ala Ala Ser Ser Ser Ala Ser
  1               5                  10                  15
```

-continued

```
Ser Leu Leu Leu Leu Thr Met Val Leu Ala Ala His Asp Pro Pro Pro
            20                  25                  30

Leu Val Phe Asp Ala Ala Arg Leu Ser Gly Leu Ser Asp Ile Pro Gln
        35                  40                  45

Gln Phe Ile Trp Pro Ala Asp Glu Ser Pro Thr Pro Asp Ser Ala Glu
    50                  55                  60

Glu Leu Ala Val Pro Leu Ile Asp Leu Ser Gly Asp Ala Ala Glu Val
65                  70                  75                  80

Val Arg Gln Val Arg Arg Ala Cys Asp Leu His Gly Phe Phe Gln Val
                85                  90                  95

Val Gly His Gly Ile Asp Ala Ala Leu Thr Ala Glu Ala His Arg Cys
            100                 105                 110

Met Asp Ala Phe Phe Thr Leu Pro Leu Pro Asp Lys Gln Arg Ala Gln
        115                 120                 125

Arg Arg Gln Gly Asp Ser Cys Gly Tyr Ala Ser Ser Phe Thr Gly Arg
    130                 135                 140

Phe Ala Ser Lys Leu Pro Trp Lys Glu Thr Leu Ser Phe Arg Tyr Thr
145                 150                 155                 160

Asp Asp Asp Asp Gly Asp Lys Ser Lys Asp Val Val Ala Ser Tyr Phe
                165                 170                 175

Val Asp Lys Leu Gly Glu Gly Tyr Arg His His Gly Glu Val Tyr Gly
            180                 185                 190

Arg Tyr Cys Ser Glu Met Ser Arg Leu Ser Leu Glu Leu Met Glu Val
        195                 200                 205

Leu Gly Glu Ser Leu Gly Val Gly Arg Arg His Phe Arg Arg Phe Phe
    210                 215                 220

Gln Gly Asn Asp Ser Ile Met Arg Leu Asn Tyr Tyr Pro Pro Cys Gln
225                 230                 235                 240

Arg Pro Tyr Asp Thr Leu Gly Thr Gly Pro His Cys Asp Pro Thr Ser
                245                 250                 255

Leu Thr Ile Leu His Gln Asp Asp Val Gly Gly Leu Gln Val Phe Asp
            260                 265                 270

Ala Ala Thr Leu Ala Trp Arg Ser Ile Arg Pro Arg Pro Gly Ala Phe
        275                 280                 285

Val Val Asn Ile Gly Asp Thr Phe Met Ala Leu Ser Asn Gly Arg Tyr
    290                 295                 300

Arg Ser Cys Leu His Arg Ala Val Val Asn Ser Arg Val Ala Arg Arg
305                 310                 315                 320

Ser Leu Ala Phe Phe Leu Cys Pro Glu Met Asp Lys Val Val Arg Pro
                325                 330                 335

Pro Lys Glu Leu Val Asp Asp Ala Asn Pro Arg Ala Tyr Pro Asp Phe
            340                 345                 350

Thr Trp Arg Thr Leu Leu Asp Phe Thr Met Arg His Tyr Arg Ser Asp
        355                 360                 365

Met Arg Thr Leu Glu Ala Phe Ser Asn Trp Leu Ser Thr Ser Ser Asn
    370                 375                 380

Gly Gly Gln His Leu Leu Glu Lys Lys
385                 390
```

<210> SEQ ID NO 37
<211> LENGTH: 1361
<212> TYPE: DNA
<213> ORGANISM: Oryza sativa

<400> SEQUENCE: 37

```
gcacgagggc agccgtggtg ttcgacgcgg cgatcctgag caagcaggag gcgatcccgg      60
cgcagttcgt ctggccggcc gacgaggcgc cggcggcgga cgacggcgtg gtggaggaga     120
tcgccatccc cgtcgtcgac ctggccgcgt tcctcgccag cggcggcatt gggcgcgacg     180
tggcggaggc gtgcgagcgg cacgggttct tccaggtggt gaaccacggc gtcgacccgg     240
cgctgctcgc cgaggcgtac cgctgctgtg acgcgttcta cgcgcggccg ctcgccgaga     300
agcagcgcgc gcggcgccgc cccggcgaga accacggcta cgcgagcagc ttcacggggc     360
ggttcgactg caagctgccg tggaaggaga ccatgtcgtt caactgctcc gccgcgccgg     420
ggaacgcgcg catggtcgcc gactatttcg tcgacgccct cggcgaggaa taccgccaca     480
tgggggaggt gtaccaggag tactgcgacg tgatgacgcg gctggcgctg gacgtgacgg     540
aggtgctcgc ggtggcgctc gggctcggcc gcggcgagct ccgcggcttc ttcgccgacg     600
gcgacccggt gatgcggctg aaccactacc cgccgtgccg gcagccgcac ctgacgctgg     660
gcacgggccc gcaccgcgac ccgacgtcgc tgacgctgct ccaccaggac gacgtcggcg     720
gcctgcaggt gctccccgac gacgccgcgg cggcggcggg cgggtggcgc gccgtgcgcc     780
cgcgcgccga cgcgttcgtc gtcaacatcg gcgacacgtt cgcggcgctc accaacgggc     840
gccacgccag ctgcctccac cgcgccgtgg tgaacggccg cgtcgcgcgc aggtcgctca     900
ccttcttcct caacccgcgc ctcgaccgcg tcgtgtcgcc gccgccggcg ctcgtcgacg     960
ccgcgcaccc gcgcgcgttc ccggacttca cgtggcgcga gttcctcgag ttcacgcaga    1020
ggcactaccg gtcggacacc aacaccatgg acgccttcgt cgcctggatc aagcaaagga    1080
atggctatga aagcctcgac aagtactaga cagatgggat gagaagatca ggtcatcaag    1140
attcaagagt tgatggacga ataaaccaga gtttctactc gatcgatcgc cattttcgtg    1200
tttatttgtt tttaagatat atatagcgtg cattgcaaca tgcatgtttt aaataaggga    1260
acatgtcagt gaatttgaaa aaggtttaaa ttgtatatat attgcaatct ctttcgtatt    1320
gttcgagaaa aaaaaaaaaa aaaaaaaaaa aaaaaaaaaa a                        1361
```

<210> SEQ ID NO 38
<211> LENGTH: 368
<212> TYPE: PRT
<213> ORGANISM: Oryza sativa

<400> SEQUENCE: 38

```
Thr Arg Ala Ala Val Val Phe Asp Ala Ala Ile Leu Ser Lys Gln Glu
  1               5                  10                  15

Ala Ile Pro Ala Gln Phe Val Trp Pro Ala Asp Glu Ala Pro Ala Ala
             20                  25                  30

Asp Asp Gly Val Val Glu Glu Ile Ala Ile Pro Val Val Asp Leu Ala
         35                  40                  45

Ala Phe Leu Ala Ser Gly Gly Ile Gly Arg Asp Val Ala Glu Ala Cys
     50                  55                  60

Glu Arg His Gly Phe Phe Gln Val Val Asn His Gly Val Asp Pro Ala
 65                  70                  75                  80

Leu Leu Ala Glu Ala Tyr Arg Cys Cys Asp Ala Phe Tyr Ala Arg Pro
                 85                  90                  95

Leu Ala Glu Lys Gln Arg Ala Arg Arg Arg Pro Gly Glu Asn His Gly
            100                 105                 110

Tyr Ala Ser Ser Phe Thr Gly Arg Phe Asp Cys Lys Leu Pro Trp Lys
        115                 120                 125
```

-continued

```
Glu Thr Met Ser Phe Asn Cys Ser Ala Ala Pro Gly Asn Ala Arg Met
    130                 135                 140

Val Ala Asp Tyr Phe Val Asp Ala Leu Gly Glu Glu Tyr Arg His Met
145                 150                 155                 160

Gly Glu Val Tyr Gln Glu Tyr Cys Asp Val Met Thr Arg Leu Ala Leu
                165                 170                 175

Asp Val Thr Glu Val Leu Ala Val Ala Leu Gly Leu Gly Arg Gly Glu
            180                 185                 190

Leu Arg Gly Phe Phe Ala Asp Gly Asp Pro Val Met Arg Leu Asn His
        195                 200                 205

Tyr Pro Pro Cys Arg Gln Pro His Leu Thr Leu Gly Thr Gly Pro His
    210                 215                 220

Arg Asp Pro Thr Ser Leu Thr Leu Leu His Gln Asp Asp Val Gly Gly
225                 230                 235                 240

Leu Gln Val Leu Pro Asp Asp Ala Ala Ala Ala Ala Gly Gly Trp Arg
                245                 250                 255

Ala Val Arg Pro Arg Ala Asp Ala Phe Val Val Asn Ile Gly Asp Thr
            260                 265                 270

Phe Ala Ala Leu Thr Asn Gly Arg His Ala Ser Cys Leu His Arg Ala
        275                 280                 285

Val Val Asn Gly Arg Val Ala Arg Arg Ser Leu Thr Phe Phe Leu Asn
    290                 295                 300

Pro Arg Leu Asp Arg Val Val Ser Pro Pro Pro Ala Leu Val Asp Ala
305                 310                 315                 320

Ala His Pro Arg Ala Phe Pro Asp Phe Thr Trp Arg Glu Phe Leu Glu
                325                 330                 335

Phe Thr Gln Arg His Tyr Arg Ser Asp Thr Asn Thr Met Asp Ala Phe
            340                 345                 350

Val Ala Trp Ile Lys Gln Arg Asn Gly Tyr Glu Ser Leu Asp Lys Tyr
        355                 360                 365


<210> SEQ ID NO 39
<211> LENGTH: 1270
<212> TYPE: DNA
<213> ORGANISM: Glycine max

<400> SEQUENCE: 39

gcacgagata gcaagctcat agctcaagct cataagctca tagatgattt cttctgcatg      60

caactctcac agaagcagaa ggctcagaga aagattggag aacattgtgg ctatgctaat     120

agcttcattg gaagattctc ctccaaactt ccttggaagg aaacactttc tttccattat     180

tctgcagata aatccagaaa aactgtggag gattatttcc ttaatgtcat gggggaagat     240

ttcaagcaat ttgggagtgt gttccaagaa tactgtgaag ccatgagcaa actctctctt     300

gggataatgg agcttctggg gatgagccta ggagttggca gggaatgttt cagagatttc     360

ttcgaaggaa atgagtcggt tatgaggttg aattactacc caccatgcca aaaacctgag     420

ttagctttag gaactggacc tcattgtgac cctacatccc taaccattct ccaccaagat     480

caagtcgagg gcctccaagt ctttgttgat ggaagatggt actctgtcgc tcctaaagaa     540

gatgctttcg ttgtcaatat tggcgacaca tttatggctc tatcgaatgg gatgttcaag     600

agttgcttgc atagagcagt tgtaaacaac aaaattgtga gaaaatcact tgctttcttc     660

ctatgtccaa atagagacaa agtggtcacc cctccaaaag atctaatcag ctacgaaaat     720

tcaagaacat acccagattt cacatggcca agccttcttg aatttacaca gaaacactac     780
```

-continued

```
agatctgaca caaaaacact tgatgctttc tcgagatggc tactagaaaa aaacaatccg    840

aacaggggtg cccccacaaa tgttccatgg ccaacaaaat ctataaactg agctttaact    900

tgcatctgct tgaatgagga agatatgaca tcatataaag tgaaaaagag ggtgcttttg    960

gtgggtcgac ttgtgaagaa aaagataaca gaaacatcaa aaagggaagg gctaatcatc   1020

agtaattagt tgtggtgtta gtgttgggag aatcctatat ggtgcaaatg gaagaagaac   1080

tgaggccata ttctttggaa taaagagagt tgatttgtgt agtgaagtta ttcgatgttg   1140

tcactactta tgcattatta gttgtcttga actatgttgt agttatgtga tatgcatgta   1200

tgtagaactt ttaattaatt aataataaac tgcattgcat tttctgtcat caaaaaaaaa   1260

aaaaaaaaaa                                                          1270
```

```
<210> SEQ ID NO 40
<211> LENGTH: 296
<212> TYPE: PRT
<213> ORGANISM: Glycine max

<400> SEQUENCE: 40

Ala Arg Asp Ser Lys Leu Ile Ala Gln Ala His Lys Leu Ile Asp Asp
  1               5                  10                  15

Phe Phe Cys Met Gln Leu Ser Gln Lys Gln Lys Ala Gln Arg Lys Ile
             20                  25                  30

Gly Glu His Cys Gly Tyr Ala Asn Ser Phe Ile Gly Arg Phe Ser Ser
         35                  40                  45

Lys Leu Pro Trp Lys Glu Thr Leu Ser Phe His Tyr Ser Ala Asp Lys
     50                  55                  60

Ser Arg Lys Thr Val Glu Asp Tyr Phe Leu Asn Val Met Gly Glu Asp
 65                  70                  75                  80

Phe Lys Gln Phe Gly Ser Val Phe Gln Glu Tyr Cys Glu Ala Met Ser
                 85                  90                  95

Lys Leu Ser Leu Gly Ile Met Glu Leu Leu Gly Met Ser Leu Gly Val
            100                 105                 110

Gly Arg Glu Cys Phe Arg Asp Phe Phe Glu Gly Asn Glu Ser Val Met
        115                 120                 125

Arg Leu Asn Tyr Tyr Pro Pro Cys Gln Lys Pro Glu Leu Ala Leu Gly
    130                 135                 140

Thr Gly Pro His Cys Asp Pro Thr Ser Leu Thr Ile Leu His Gln Asp
145                 150                 155                 160

Gln Val Glu Gly Leu Gln Val Phe Val Asp Gly Arg Trp Tyr Ser Val
                165                 170                 175

Ala Pro Lys Glu Asp Ala Phe Val Val Asn Ile Gly Asp Thr Phe Met
            180                 185                 190

Ala Leu Ser Asn Gly Met Phe Lys Ser Cys Leu His Arg Ala Val Val
        195                 200                 205

Asn Asn Lys Ile Val Arg Lys Ser Leu Ala Phe Phe Leu Cys Pro Asn
    210                 215                 220

Arg Asp Lys Val Val Thr Pro Pro Lys Asp Leu Ile Ser Tyr Glu Asn
225                 230                 235                 240

Ser Arg Thr Tyr Pro Asp Phe Thr Trp Pro Ser Leu Leu Glu Phe Thr
                245                 250                 255

Gln Lys His Tyr Arg Ser Asp Thr Lys Thr Leu Asp Ala Phe Ser Arg
            260                 265                 270
```

-continued

```
Trp Leu Leu Glu Lys Asn Asn Pro Asn Arg Gly Ala Pro Thr Asn Val
        275                 280                 285

Pro Trp Pro Thr Lys Ser Ile Asn
    290                 295
```

<210> SEQ ID NO 41
<211> LENGTH: 634
<212> TYPE: DNA
<213> ORGANISM: Zea mays

<400> SEQUENCE: 41

```
gcacgagcct gaccatcctg taccaggacg acgtcggggg gctcgacgtc cggcggcgct     60

ccgacggcga gtgggtccgc gtcaggcccg tgcccgactc gttcatcatc aacgtcggcg    120

acctcatcca ggtgtggagc aacgacaggt acgagagcgc ggagcaccgg gtgtcggtga    180

actcggcgag ggagaggttc tccatgccct acttcttcaa cccggcgacc tacaccatgg    240

tggagccggt ggaggagctg gtgagcaagg acgatccgcc caggtacgac gcctacaact    300

ggggcgactt cttcagcacc aggaagaaca gcaacttcaa gaagctcaac gtggagaaca    360

ttcagatcgc gcatttcaag aagagcctcg tcctcgccta actactgcta ctgctaggat    420

ccatgccatt gccatgtcgt cttcagattc agagcacgcc atgtcgtcgc tagcttcgtg    480

gtagaacaaa taatgatgtg cgtgctgtgt gtaagcatgg atatggatgt gaatatgtaa    540

tatgatgagc actcctactt tggtatgttt gggaataaca gacttgtgtt ggtctggttc    600

aaaaaaaaaa aaaaaaaaaa aaaaaaaaaa aaaa                                634
```

<210> SEQ ID NO 42
<211> LENGTH: 132
<212> TYPE: PRT
<213> ORGANISM: Zea mays

<400> SEQUENCE: 42

```
Thr Ser Leu Thr Ile Leu Tyr Gln Asp Asp Val Gly Gly Leu Asp Val
  1               5                  10                  15

Arg Arg Arg Ser Asp Gly Glu Trp Val Arg Val Arg Pro Val Pro Asp
             20                  25                  30

Ser Phe Ile Ile Asn Val Gly Asp Leu Ile Gln Val Trp Ser Asn Asp
         35                  40                  45

Arg Tyr Glu Ser Ala Glu His Arg Val Ser Val Asn Ser Ala Arg Glu
     50                  55                  60

Arg Phe Ser Met Pro Tyr Phe Phe Asn Pro Ala Thr Tyr Thr Met Val
 65                  70                  75                  80

Glu Pro Val Glu Glu Leu Val Ser Lys Asp Asp Pro Pro Arg Tyr Asp
                 85                  90                  95

Ala Tyr Asn Trp Gly Asp Phe Phe Ser Thr Arg Lys Asn Ser Asn Phe
            100                 105                 110

Lys Lys Leu Asn Val Glu Asn Ile Gln Ile Ala His Phe Lys Lys Ser
        115                 120                 125

Leu Val Leu Ala
    130
```

<210> SEQ ID NO 43
<211> LENGTH: 1066
<212> TYPE: DNA
<213> ORGANISM: Glycine max -continued

<400> SEQUENCE: 43

```
gcacgagctc cacctcagtc acattattcc cttagacttt tcttcagccc ttagcttacc      60

tgattctcac gcatggcctc actgtcaacc caatgatgat gcatcatcat catcatcatc     120

atcatccata cccatcatag acctcatgga tcccaatgct atggacctca taggccatgc     180

atgtgagaag tggggtgctt tccaattgaa gaaccatggc atacctttttg gtgtcattga     240

agatgttgaa gaagaggcta aaagactttt tgctcttccc actgaacaga agttgaaggc     300

tcttcgatct cccggtggtg ccactgggta tggcagagca aggatttcac cgttcttccc     360

aaagtttatg tggcacgaag gattcaccat cattggctct ccctctcacg atgccaaaaa     420

gatatggcct aatgattatg cacgcttttg tgatttgatg gagaattatg agaagcaaat     480

gaaggttcta gcggatagac taacagagat gatattcaac ttaatggaca taagtgagga     540

aaaaagaaag tgggttggtg caagcaacat aagtgaagct gttcagttaa atttctaccc     600

aagttgtccc gagccaaacc gagccatggg cttagcccct cacaccgaca cttctctctt     660

cacaattctt caccaaagtc aaatcactgg tcttcaaatc ttcaaggaag gaaaagggtg     720

ggttcctgtg caccctcacc ctaataccct ggtcgtgcac acaggcgatc tcttgcacat     780

catttccaac gcaaggtttc gctgtgcact tcaccgcgta acggtgaata ggacatggga     840

acgttactct gtggcttatt tctattctcc accgatggat tatgtagttt ctcctttggt     900

tcactctgtt gctcgttttc gtgatgtgac tgtgaaggag tatattggga ttaaggctaa     960

gaattttgga gaagcattgt cctttattag tacttgaaac tatgtatgta tcttatgatt    1020

ttgttatatg tattaattcc ttaaataaaa aaaaaaaaaa aaaaaa                   1066
```

<210> SEQ ID NO 44
<211> LENGTH: 331
<212> TYPE: PRT
<213> ORGANISM: Glycine max

<400> SEQUENCE: 44

```
His Glu Leu His Leu Ser His Ile Ile Pro Leu Asp Phe Ser Ser Ala
  1               5                  10                  15

Leu Ser Leu Pro Asp Ser His Ala Trp Pro His Cys Gln Pro Asn Asp
             20                  25                  30

Asp Ala Ser Ser Ser Ser Ser Ser Ser Ser Ile Pro Ile Ile Asp Leu
         35                  40                  45

Met Asp Pro Asn Ala Met Asp Leu Ile Gly His Ala Cys Glu Lys Trp
     50                  55                  60

Gly Ala Phe Gln Leu Lys Asn His Gly Ile Pro Phe Gly Val Ile Glu
 65                  70                  75                  80

Asp Val Glu Glu Glu Ala Lys Arg Leu Phe Ala Leu Pro Thr Glu Gln
                 85                  90                  95

Lys Leu Lys Ala Leu Arg Ser Pro Gly Gly Ala Thr Gly Tyr Gly Arg
            100                 105                 110

Ala Arg Ile Ser Pro Phe Phe Pro Lys Phe Met Trp His Glu Gly Phe
        115                 120                 125

Thr Ile Ile Gly Ser Pro Ser His Asp Ala Lys Lys Ile Trp Pro Asn
    130                 135                 140

Asp Tyr Ala Arg Phe Cys Asp Leu Met Glu Asn Tyr Glu Lys Gln Met
145                 150                 155                 160

Lys Val Leu Ala Asp Arg Leu Thr Glu Met Ile Phe Asn Leu Met Asp
                165                 170                 175
```

-continued

Ile Ser Glu Glu Lys Arg Lys Trp Val Gly Ala Ser Asn Ile Ser Glu
180 185 190

Ala Val Gln Leu Asn Phe Tyr Pro Ser Cys Pro Glu Pro Asn Arg Ala
195 200 205

Met Gly Leu Ala Pro His Thr Asp Thr Ser Leu Phe Thr Ile Leu His
210 215 220

Gln Ser Gln Ile Thr Gly Leu Gln Ile Phe Lys Glu Gly Lys Gly Trp
225 230 235 240

Val Pro Val His Pro His Pro Asn Thr Leu Val Val His Thr Gly Asp
245 250 255

Leu Leu His Ile Ile Ser Asn Ala Arg Phe Arg Cys Ala Leu His Arg
260 265 270

Val Thr Val Asn Arg Thr Trp Glu Arg Tyr Ser Val Ala Tyr Phe Tyr
275 280 285

Ser Pro Pro Met Asp Tyr Val Val Ser Pro Leu Val His Ser Val Ala
290 295 300

Arg Phe Arg Asp Val Thr Val Lys Glu Tyr Ile Gly Ile Lys Ala Lys
305 310 315 320

Asn Phe Gly Glu Ala Leu Ser Phe Ile Ser Thr
325 330

<210> SEQ ID NO 45
<211> LENGTH: 790
<212> TYPE: DNA
<213> ORGANISM: Triticum aestivum

<400> SEQUENCE: 45
gcacgagggg aaccccgcct tctgcgacac gatcgcgtcc gcggccaaga acgtgtggga 60
gctgcagcgc accgtggaga cgatgatcct ggagggcctg ggcgtcggcg aggagcacat 120
cggcgcgcat ctggacacgc tcgcccacag cgtccggctg tcgcgctacg ggcccccgcc 180
ggacgcggag accagcatgt ccctgcaggc gcaccgcgac gacagcatca tgacggcgat 240
cgtgcagcac ggcgtggagg gcctcgaggt gcaggctcag gacgggatct ggctcacggt 300
gccgcctgag ccggacttgt tcaccttcgt cgccggcgag ctgttcacgg tcgtgactaa 360
cgggagggtg ccgggttgct tccaccgcgt gaggacgccg agcaaccgcg agcgcctgtc 420
ggcgctgttc ggctgcccgg ggaaggacgg cgtccttctg ggcgccattg acgagctcgt 480
cgacgacgaa caccctctgc tgtaccgtcc ctgcaccaac gacggctaca caacgttccg 540
gcactcggac gaagggcgca aggccagtga tccattgaag gccttctgtg ggtggagaa 600 agatgatcgc cgttcgtaag tcaagctcac ttcacctcac cattctgaag tcgtcaagct 660
ccgttctcca caccattctg aagccgacat tgctaggtta cccatgtaat gattgcgacg 720
ccattctgaa gtcctattgc tactgaactt tactcaaaaa aaaaaaaaaa aaaaaaaaaa 780
aaaaaaaaaa 790

<210> SEQ ID NO 46
<211> LENGTH: 205
<212> TYPE: PRT
<213> ORGANISM: Triticum aestivum

<400> SEQUENCE: 46

His Glu Gly Asn Pro Ala Phe Cys Asp Thr Ile Ala Ser Ala Ala Lys
1 5 10 15

Asn Val Trp Glu Leu Gln Arg Thr Val Glu Thr Met Ile Leu Glu Gly
20 25 30

-continued

```
Leu Gly Val Gly Glu Glu His Ile Gly Ala His Leu Asp Thr Leu Ala
        35                  40                  45

His Ser Val Arg Leu Ser Arg Tyr Gly Pro Pro Pro Asp Ala Glu Thr
    50                  55                  60

Ser Met Ser Leu Gln Ala His Arg Asp Asp Ser Ile Met Thr Ala Ile
 65                 70                  75                  80

Val Gln His Gly Val Glu Gly Leu Glu Val Gln Ala Gln Asp Gly Ile
                85                  90                  95

Trp Leu Thr Val Pro Pro Glu Pro Asp Leu Phe Thr Phe Val Ala Gly
            100                 105                 110

Glu Leu Phe Thr Val Val Thr Asn Gly Arg Val Pro Gly Cys Phe His
        115                 120                 125

Arg Val Arg Thr Pro Ser Asn Arg Glu Arg Leu Ser Ala Leu Phe Gly
    130                 135                 140

Cys Pro Gly Lys Asp Gly Val Leu Leu Gly Ala Ile Asp Glu Leu Val
145                 150                 155                 160

Asp Asp Glu His Pro Leu Leu Tyr Arg Pro Cys Thr Asn Asp Gly Tyr
                165                 170                 175

Thr Thr Phe Arg His Ser Asp Glu Gly Arg Lys Ala Ser Asp Pro Leu
            180                 185                 190

Lys Ala Phe Cys Gly Val Glu Lys Asp Asp Arg Arg Ser
        195                 200                 205
```

<210> SEQ ID NO 47
<211> LENGTH: 445
<212> TYPE: DNA
<213> ORGANISM: Triticum aestivum
<220> FEATURE:
<221> NAME/KEY: unsure
<222> LOCATION: (445)

<400> SEQUENCE: 47

```
ctcgtgccga attcggcacg aggccctcac cattctcctc atggaccccc acgtctccgg     60

cctgcaggtc ctcaaggacg gcgcccagtg gatcgccgtt gacccccggc ccaacgccct    120

cgtcgtcaac ctaggcgacc agttgcaggc gctgagcaac ggcgcgtaca agagcgtctg    180

gcaccgcgcg gtggtcaatg cggcgcggga gcgcctgtcg gtggcatctt tcctgtgccc    240

gtgcaacagc gcggtgatcg gcccggtggc caagctcgtc ggcgacgggg acgagcccgt    300

gtaccgcagc tacacctacg acgagtacta caagaagttc tggagcagga acctggacca    360

aggaccattg cctggagctc ttcacgggtc agaaagtgat ccgtgtgcac aagcttgcct    420

catccacgac gcaacattac tcaan                                          445
```

<210> SEQ ID NO 48
<211> LENGTH: 110
<212> TYPE: PRT
<213> ORGANISM: Triticum aestivum

<400> SEQUENCE: 48

```
Leu Thr Ile Leu Leu Met Asp Pro His Val Ser Gly Leu Gln Val Leu
  1               5                  10                  15

Lys Asp Gly Ala Gln Trp Ile Ala Val Asp Pro Arg Pro Asn Ala Leu
            20                  25                  30

Val Val Asn Leu Gly Asp Gln Leu Gln Ala Leu Ser Asn Gly Ala Tyr
        35                  40                  45

Lys Ser Val Trp His Arg Ala Val Val Asn Ala Ala Arg Glu Arg Leu
    50                  55                  60
```

-continued

```
Ser Val Ala Ser Phe Leu Cys Pro Cys Asn Ser Ala Val Ile Gly Pro
 65                  70                  75                  80

Val Ala Lys Leu Val Gly Asp Gly Asp Glu Pro Val Tyr Arg Ser Tyr
                 85                  90                  95

Thr Tyr Asp Glu Tyr Tyr Lys Lys Phe Trp Ser Arg Asn Leu
            100                 105                 110
```

```
<210> SEQ ID NO 49
<211> LENGTH: 1431
<212> TYPE: DNA
<213> ORGANISM: Zea mays
<220> FEATURE:
<221> NAME/KEY: unsure
<222> LOCATION: (1309)
<221> NAME/KEY: unsure
<222> LOCATION: (1339)
<221> NAME/KEY: unsure
<222> LOCATION: (1351)
<221> NAME/KEY: unsure
<222> LOCATION: (1402)
<221> NAME/KEY: unsure
<222> LOCATION: (1429)

<400> SEQUENCE: 49

gagcagtttc agttgcagcg gcctcctcct ctgcttcctc cctcctcctc ctcaccatgg     60

tgctggctgc gcacgatccc cctccccttg tgttcgacgc tgcccgcctg agcggcctct    120

ccgacatccc gcagcagttc atctggccgg cggacgagag ccccaccccg gactccgccg    180

aggagctggc cgtgccgctc atcgacctct ccggggaagc cgccgaggtg gtccggcagg    240

tccggcgcgc ctgcgacctg cacggcttct tccaggtggt ggggcacggc atcgacgcgg    300

cgctgacggc ggaggcccac cgctgcatgg acgccttctt cacgctgccg ctcccggaca    360

agcagcgcgc gcagcgccgt caggggggaca gctgcggcta cgccagcagc ttcacgggcc    420

ggttcgcgtc caagctgccc tggaaggaga cgctgtcgtt ccggtacacc gacgacgacg    480

acggcgacaa gtccaaggac gtcgtggcgt cctacttcgt ggacaagctg ggcgaggggt    540

accggcacca cggggaggtg tacgggcgct actgctctga gatgagccgt ctgtcgctgg    600

agctcatgga ggtgctaggc gagagcctgg gcgtgggccg gcgccacttc cggcgcttct    660

tccaggggaa cgactccatc atgcgcctca actactaccc gccgtgccag cggccctacg    720

acacgctggg cacggggccg cattgcgacc ccacgtcgct caccatcctg caccaggacg    780

acgtgggcgg actccaggtg ttcgacgccg ccacgctcgc gtggcgctcc atcaggcccc    840

gcccgggcgc cttcgtcgtc aacatcggcg acaccttcat ggcgctctcc aacgggcgct    900

acaggagctg cctccaccgc gccgtcgtca acagccgggt ggcacgccgc tcgctcgcct    960

tcttcctgtg cccggagatg gacaaggtgg tcaggccgcc caaggagctg gtggacgacg   1020

ccaacccgag ggcgtacccg gacttcacgt ggaggacgct gctggacttc accatgaggc   1080

actacaggtc ggacatgagg acgctcgagg ccttctccaa ctggctcagc accagtagca   1140

atggcggaca gcacctgctg gagaagaagt aggatgctat ttgggtatgg aagatggtgg   1200

atgtaagcaa acaaagccaa attaagcaga gtaggttaat taagggttgg ctgatgatca   1260

attaagggaa aggagctgat ttccctgact ccctcctcca aattttcanc aaattaatat   1320

ataatatata taaatacant aatagttgta nctattataa taataattta ctgagcagta   1380

tattaataca tttttacaag gntattcatt tggttaaaaa aaaaaaaanc a            1431
```

```
<210> SEQ ID NO 50
<211> LENGTH: 371
<212> TYPE: PRT
<213> ORGANISM: Zea mays

<400> SEQUENCE: 50

Met Val Leu Ala Ala His Asp Pro Pro Pro Leu Val Phe Asp Ala Ala
  1               5                  10                  15

Arg Leu Ser Gly Leu Ser Asp Ile Pro Gln Gln Phe Ile Trp Pro Ala
            20                  25                  30

Asp Glu Ser Pro Thr Pro Asp Ser Ala Glu Glu Leu Ala Val Pro Leu
        35                  40                  45

Ile Asp Leu Ser Gly Glu Ala Ala Glu Val Val Arg Gln Val Arg Arg
    50                  55                  60

Ala Cys Asp Leu His Gly Phe Phe Gln Val Val Gly His Gly Ile Asp
 65                  70                  75                  80

Ala Ala Leu Thr Ala Glu Ala His Arg Cys Met Asp Ala Phe Phe Thr
                 85                  90                  95

Leu Pro Leu Pro Asp Lys Gln Arg Ala Gln Arg Arg Gln Gly Asp Ser
            100                 105                 110

Cys Gly Tyr Ala Ser Ser Phe Thr Gly Arg Phe Ala Ser Lys Leu Pro
        115                 120                 125

Trp Lys Glu Thr Leu Ser Phe Arg Tyr Thr Asp Asp Asp Asp Gly Asp
    130                 135                 140

Lys Ser Lys Asp Val Val Ala Ser Tyr Phe Val Asp Lys Leu Gly Glu
145                 150                 155                 160

Gly Tyr Arg His His Gly Glu Val Tyr Gly Arg Tyr Cys Ser Glu Met
                165                 170                 175

Ser Arg Leu Ser Leu Glu Leu Met Glu Val Leu Gly Glu Ser Leu Gly
            180                 185                 190

Val Gly Arg Arg His Phe Arg Arg Phe Phe Gln Gly Asn Asp Ser Ile
        195                 200                 205

Met Arg Leu Asn Tyr Tyr Pro Pro Cys Gln Arg Pro Tyr Asp Thr Leu
    210                 215                 220

Gly Thr Gly Pro His Cys Asp Pro Thr Ser Leu Thr Ile Leu His Gln
225                 230                 235                 240

Asp Asp Val Gly Gly Leu Gln Val Phe Asp Ala Ala Thr Leu Ala Trp
                245                 250                 255

Arg Ser Ile Arg Pro Arg Pro Gly Ala Phe Val Val Asn Ile Gly Asp
            260                 265                 270

Thr Phe Met Ala Leu Ser Asn Gly Arg Tyr Arg Ser Cys Leu His Arg
        275                 280                 285

Ala Val Val Asn Ser Arg Val Ala Arg Arg Ser Leu Ala Phe Phe Leu
    290                 295                 300

Cys Pro Glu Met Asp Lys Val Val Arg Pro Pro Lys Glu Leu Val Asp
305                 310                 315                 320

Asp Ala Asn Pro Arg Ala Tyr Pro Asp Phe Thr Trp Arg Thr Leu Leu
                325                 330                 335

Asp Phe Thr Met Arg His Tyr Arg Ser Asp Met Arg Thr Leu Glu Ala
            340                 345                 350

Phe Ser Asn Trp Leu Ser Thr Ser Ser Asn Gly Gly Gln His Leu Leu
        355                 360                 365

Glu Lys Lys
    370
```

-continued

```
<210> SEQ ID NO 51
<211> LENGTH: 432
<212> TYPE: DNA
<213> ORGANISM: Oryza sativa
<220> FEATURE:
<221> NAME/KEY: unsure
<222> LOCATION: (33)
<221> NAME/KEY: unsure
<222> LOCATION: (342)

<400> SEQUENCE: 51

ggcagccgtg gtgttcgacg cggcgatcct gancaagcag gaggcgatcc cggcgcagtt     60

cgtctggccg gccgacgagg cgccggcggc ggacgacggc gtggtggagg agatcgccat    120

ccccgtcgtc gacctggccg cgttcctcgc cagcggcggc attgggcgcg acgtggcgga    180

ggcgtgcgag cggcacgggt tcttccaggt ggtgaaccac ggcgtcgacc cggcgctgct    240

cgccgaggcg taccgctgct gtgacgcgtt ctacgcgcgg ccgctcgccg agaagcagcg    300

cgcgcggcgc cgccccggcg agaaccacgg ctacgcgagc ancttcacgg ggcggttccg    360

actgcaagct ggcccgtgga aagagaccat gtcgttcaac tggctccgcc cgcgcccggg    420

ggaaccccgc aa                                                        432


<210> SEQ ID NO 52
<211> LENGTH: 132
<212> TYPE: PRT
<213> ORGANISM: Oryza sativa
<220> FEATURE:
<221> NAME/KEY: UNSURE
<222> LOCATION: (11)
<221> NAME/KEY: UNSURE
<222> LOCATION: (114)

<400> SEQUENCE: 52

Ala Ala Val Val Phe Asp Ala Ala Ile Leu Xaa Lys Gln Glu Ala Ile
  1               5                  10                  15

Pro Ala Gln Phe Val Trp Pro Ala Asp Glu Ala Pro Ala Ala Asp Asp
             20                  25                  30

Gly Val Val Glu Glu Ile Ala Ile Pro Val Val Asp Leu Ala Ala Phe
         35                  40                  45

Leu Ala Ser Gly Gly Ile Gly Arg Asp Val Ala Glu Ala Cys Glu Arg
     50                  55                  60

His Gly Phe Phe Gln Val Val Asn His Gly Val Asp Pro Ala Leu Leu
 65                  70                  75                  80

Ala Glu Ala Tyr Arg Cys Cys Asp Ala Phe Tyr Ala Arg Pro Leu Ala
                 85                  90                  95

Glu Lys Gln Arg Ala Arg Arg Arg Pro Gly Glu Asn His Gly Tyr Ala
            100                 105                 110

Ser Xaa Phe Thr Gly Arg Phe Arg Leu Gln Ala Gly Pro Trp Lys Glu
        115                 120                 125

Thr Met Ser Phe
    130


<210> SEQ ID NO 53
<211> LENGTH: 522
<212> TYPE: DNA
<213> ORGANISM: Glycine max
<220> FEATURE:
<221> NAME/KEY: unsure
<222> LOCATION: (30)
<221> NAME/KEY: unsure
<222> LOCATION: (341)
<221> NAME/KEY: unsure
```

```
<222> LOCATION: (445)
<221> NAME/KEY: unsure
<222> LOCATION: (450)
<221> NAME/KEY: unsure
<222> LOCATION: (484)
<221> NAME/KEY: unsure
<222> LOCATION: (521)

<400> SEQUENCE: 53

gagatagcaa gctcatagct caagctcatn aagctcatag atgatttctt ctgcatgcaa     60

ctctcacaga agcagaaggc tcagagaaag attggagaac attgtggcta tgctaatagc    120

ttcattggaa gattctcctc caaacttcct tggaaggaaa cacttctttc cattattctg    180

cagataaatc cagaaaaact gtggaggatt atttccttaa tgtcatgggg gaagatttca    240

agcaatttgg gagtgtgttc caagaatact gtgaagccat gagcaaactc tctcttggga    300

taatggagct tctggggatg agcctaggag ttggcaggga ngtttcagag atttcttcga    360

aggaaatgag tcggttatga ggttgaatta ctacccacca tgccaaaaac ctgagttagc    420

tttaggaact ggacctcatt gtgancctan atccctaacc attctccacc aagatcaagt    480

cgangggctc caagtctttg ttgaagggaa gatggtaccc nt                       522


<210> SEQ ID NO 54
<211> LENGTH: 169
<212> TYPE: PRT
<213> ORGANISM: Glycine max
<220> FEATURE:
<221> NAME/KEY: UNSURE
<222> LOCATION: (148)
<221> NAME/KEY: UNSURE
<222> LOCATION: (150)
<221> NAME/KEY: UNSURE
<222> LOCATION: (161)

<400> SEQUENCE: 54

Asp Ser Lys Leu Ile Ala Gln Ala His Lys Leu Ile Asp Asp Phe Phe
  1               5                  10                  15

Cys Met Gln Leu Ser Gln Lys Gln Lys Ala Gln Arg Lys Ile Gly Glu
             20                  25                  30

His Cys Gly Tyr Ala Asn Ser Phe Ile Gly Arg Phe Ser Ser Lys Leu
         35                  40                  45

Pro Trp Lys Glu Thr Leu Ser Phe His Tyr Ser Ala Asp Lys Ser Arg
     50                  55                  60

Lys Thr Val Glu Asp Tyr Phe Leu Asn Val Met Gly Glu Asp Phe Lys
 65                  70                  75                  80

Gln Phe Gly Ser Val Phe Gln Glu Tyr Cys Glu Ala Met Ser Lys Leu
                 85                  90                  95

Ser Leu Gly Ile Met Glu Leu Leu Gly Met Ser Leu Gly Val Gly Gln
            100                 105                 110

Glu Cys Phe Arg Asp Phe Phe Glu Gly Asn Glu Ser Val Met Arg Leu
        115                 120                 125

Asn Tyr Tyr Pro Pro Cys Gln Lys Pro Glu Leu Ala Leu Gly Thr Gly
    130                 135                 140

Pro His Cys Xaa Pro Xaa Ser Leu Thr Ile Leu His Gln Asp Gln Val
145                 150                 155                 160

Xaa Gly Leu Gln Val Phe Val Glu Gly
                165
```

-continued

<210> SEQ ID NO 55
<211> LENGTH: 490
<212> TYPE: DNA
<213> ORGANISM: Zea mays
<220> FEATURE:
<221> NAME/KEY: unsure
<222> LOCATION: (394)
<221> NAME/KEY: unsure
<222> LOCATION: (399)
<221> NAME/KEY: unsure
<222> LOCATION: (427)
<221> NAME/KEY: unsure
<222> LOCATION: (432)
<221> NAME/KEY: unsure
<222> LOCATION: (445)
<221> NAME/KEY: unsure
<222> LOCATION: (448)..(449)
<221> NAME/KEY: unsure
<222> LOCATION: (455)
<221> NAME/KEY: unsure
<222> LOCATION: (460)
<221> NAME/KEY: unsure
<222> LOCATION: (475)

<400> SEQUENCE: 55

```
cctgaccatc ctgtaccagg acgacgtcgg ggggctcgac gtccggcggc gctccgacgg     60

cgagtgggtc cgcgtcaggc ccgtgcccga ctcgttcatc atcaacgtcg gcgacctcat    120

ccaggtgtgg agcaacgaca ggtacgagag cgcggacacc gggtgtcggt gaactcggcg    180

agggagaggt tctccatgcc ctacttcttc aacccggcga cctacaccat ggtggagccg    240

gtggaggagc tggtgagcaa ggacgatccg cccaggtacg acgcctacaa ctggggcgac    300

ttcttcagca ccaggaagaa cagcaacttc aagaagtcaa cgtggagaca ttcagatcgc    360

gcatttcaag aagagctcgt ctcgctaact actntactnt agatccatgc attgcatgcg    420

gctcaantag anacgcatgt gtccnacnng tgganaaaan atatggcgtc cttgnacatg    480

aatgattaaa                                                           490
```

<210> SEQ ID NO 56
<211> LENGTH: 50
<212> TYPE: PRT
<213> ORGANISM: Zea mays

<400> SEQUENCE: 56

```
Leu Thr Ile Leu Tyr Gln Asp Asp Val Gly Gly Leu Asp Val Arg Arg
  1               5                  10                  15

Arg Ser Asp Gly Glu Trp Val Arg Val Arg Pro Val Pro Asp Ser Phe
             20                  25                  30

Ile Ile Asn Val Gly Asp Leu Ile Gln Val Trp Ser Asn Asp Arg Tyr
         35                  40                  45

Glu Ser
     50
```

<210> SEQ ID NO 57
<211> LENGTH: 536
<212> TYPE: DNA
<213> ORGANISM: Glycine max
<220> FEATURE:
<221> NAME/KEY: unsure
<222> LOCATION: (291)
<221> NAME/KEY: unsure
<222> LOCATION: (394)
<221> NAME/KEY: unsure
<222> LOCATION: (401)
<221> NAME/KEY: unsure
<222> LOCATION: (406)
<221> NAME/KEY: unsure
<222> LOCATION: (436)
<221> NAME/KEY: unsure
<222> LOCATION: (439)
<221> NAME/KEY: unsure
<222> LOCATION: (457)
<221> NAME/KEY: unsure
<222> LOCATION: (482)
<221> NAME/KEY: unsure
<222> LOCATION: (493)
<221> NAME/KEY: unsure
<222> LOCATION: (508)
<221> NAME/KEY: unsure
<222> LOCATION: (522)

<400> SEQUENCE: 57
aattaaaaat gaacactact ctctctgaag cctacaaagc acaccctctc cacctccgtg 60
acattattcc cttagacttt tcttcagccc atagcttacc tgattctcac gcatggtctc 120
actctcaacc caacgatgat gattatgtct cattcaatga tgatgcatca tcatcatcat 180
tcatacccat catagacctc atggatccaa atgccatgga acaaataggc catgcatgtg 240
agaaatgggg tgctttccaa ttgaagaacc atgggcatac ccttttgtgt nattgaagat 300
gtagaagaag aggctaaaag gctctttgct cttcccactg aacagaagtt gaagggctct 360
tcgatctcct ggtggtgcga ggggtatggc agancaagga nttcancgtt cttcccaaag 420
ttcagtgggc aagaanggnt taccatcatt gggtctncct ctcatgatgg ccaaaaagat 480
antggcctaa cgnatcatgc aagggttngg gaattggatg gnagattaag gaaaaa 536

<210> SEQ ID NO 58
<211> LENGTH: 148
<212> TYPE: PRT
<213> ORGANISM: Glycine max
<220> FEATURE:
<221> NAME/KEY: UNSURE
<222> LOCATION: (90)
<221> NAME/KEY: UNSURE
<222> LOCATION: (129)
<221> NAME/KEY: UNSURE
<222> LOCATION: (131)
<221> NAME/KEY: UNSURE
<222> LOCATION: (133)
<221> NAME/KEY: UNSURE
<222> LOCATION: (143)..(144)

<400> SEQUENCE: 58

Met Asn Thr Thr Leu Ser Glu Ala Tyr Lys Ala His Pro Leu His Leu
1 5 10 15

Arg Asp Ile Ile Pro Leu Asp Phe Ser Ser Ala His Ser Leu Pro Asp
20 25 30

Ser His Ala Trp Ser His Ser Gln Pro Asn Asp Asp Asp Tyr Val Ser
35 40 45

Phe Asn Asp Asp Ala Ser Ser Ser Ser Phe Ile Pro Ile Ile Asp Leu
50 55 60

Met Asp Pro Asn Ala Met Glu Gln Ile Gly His Ala Cys Glu Lys Trp
65 70 75 80

Gly Ala Phe Gln Leu Lys Asn His Gly Xaa Pro Phe Cys Val Ile Glu
85 90 95

Asp Val Glu Glu Glu Ala Lys Arg Leu Phe Ala Leu Pro Thr Glu Gln
100 105 110

Lys Leu Lys Gly Ser Ser Ile Ser Trp Trp Cys Glu Gly Tyr Gly Arg
115 120 125

-continued

```
Xaa Arg Xaa Ser Xaa Phe Phe Pro Lys Phe Ser Gly Gln Glu Xaa Xaa
    130                 135                 140

Thr Ile Ile Gly
145


<210> SEQ ID NO 59
<211> LENGTH: 459
<212> TYPE: DNA
<213> ORGANISM: Triticum aestivum
<220> FEATURE:
<221> NAME/KEY: unsure
<222> LOCATION: (378)
<221> NAME/KEY: unsure
<222> LOCATION: (422)

<400> SEQUENCE: 59

gggaaccccg ccttctgcga cacgatcgcg tccgcggcca agaacgtgtg ggagctgcag      60

cgcaccgtgg agacgatgat cctggagggc ctgggcgtcg gcgaggagca catcggcgcg     120

catctggaca cgctcgccca cagcgtccgg ctgtcgcgct acgggccccc gccggacgcg     180

gagaccagca tgtccctgca ggcgcaccgc gacgacagca tcatgacggc gatcgtgcag     240

cacggcgtgg agggcctcga ggtgcaggct caggacggga tctggctcac ggtgccgcct     300

gagccggact tgttcacctt cgtcgccggc gagctgttca cggtcgtgac taacgggagg     360

gtgccgggtt gcttcaancg cgtgaggacc cgagcaaccg cgagcgcctg tcggcgcttt     420

cngctgcccg gggaaggacg gcgtccttct gggcgcaat                            459


<210> SEQ ID NO 60
<211> LENGTH: 129
<212> TYPE: PRT
<213> ORGANISM: Triticum aestivum
<220> FEATURE:
<221> NAME/KEY: UNSURE
<222> LOCATION: (122)

<400> SEQUENCE: 60

Phe Cys Asp Thr Ile Ala Ser Ala Ala Lys Asn Val Trp Glu Leu Gln
  1               5                  10                  15

Arg Thr Val Glu Thr Met Ile Leu Glu Gly Leu Gly Val Gly Glu Glu
             20                  25                  30

His Ile Gly Ala His Leu Asp Thr Leu Ala His Ser Val Arg Leu Ser
         35                  40                  45

Arg Tyr Gly Pro Pro Pro Asp Ala Glu Thr Ser Met Ser Leu Gln Ala
     50                  55                  60

His Arg Asp Asp Ser Ile Met Thr Ala Ile Val Gln His Gly Val Glu
 65                  70                  75                  80

Gly Leu Glu Val Gln Ala Gln Asp Gly Ile Trp Leu Thr Val Pro Pro
                 85                  90                  95

Glu Pro Asp Leu Phe Thr Phe Val Ala Gly Glu Leu Phe Thr Val Val
            100                 105                 110

Thr Asn Gly Arg Val Pro Gly Cys Phe Xaa Arg Val Arg Thr Arg Ala
        115                 120                 125

Thr


<210> SEQ ID NO 61
<211> LENGTH: 1209
<212> TYPE: DNA
<213> ORGANISM: Zea mays
```

<400> SEQUENCE: 61

```
gcacgaggaa acagtgtttg ctggtaaaaa gaaagaaaaa agaagctgaa agtgttttca     60
ggcagatgcc tacatttttc tctctatcct agttgtaaca tatgattgaa agtgatgtac    120
ttaatatggt tgcaagaatc atattaatac ctatggctgg ttatgtacac gcctcttcgg    180
tgttcttatg tgctgttgct ggtgatcctt gagatattga ttgccatgct agcaaatttt    240
atctgttgca ggtataggag gaaaagagac aggctaattg aacgcgcttc tgttgcacgc    300
ttgcctttga aatggggcaa tgtccatgcc tattgctaca aatctgttat tgatggcatt    360
gagcatattg ccatggtgaa aggtgatatt ggtgacggcc aagacatttt ggtgagggtg    420
cactctgagt gcctcacagg cgacattttt ggatccgcaa gatgtgattg tggcgaccag    480
cttgcgatgg caatggagat gattgagaag actaatacac cccttccagc cttctccgtg    540
gacatgaagg aaggggtatt ggtctgggcc acaagcttcg tgcttataac ttacaggatg    600
atgggcgtga tactgtggaa gctaacgagg aacttggtct tcctgtggac tcacgggaat    660
atgggattgg cgcacagata ttgcgggatc taggagtccg ttcaatgaag ctgatgacta    720
ataaccctgc gaaatatagt ggtctcaagg gctatggatt gagcattgcg ggcagggtgc    780
ccttgattac gccaattacc agtgagaacc gtaggtacct ggagactaaa agaacaaaga    840
tgggacatgt atatgggttg gccaatgcgc aggccaacca agcaaatggc agccagagca    900
cagaagagaa tcattaggcc cccaagcatg tttccattat tattccagca atccagcttg    960
gtgtggtggc acaaaagagt gatatgattc ttcgtttggg gagttcctga aatcttctcc   1020
cccgatattt ccgtagattc tttcgcaaaa aagccgatat ttcggtagat cgatttgttc   1080
ttcaattgta actgtaggtt tcaaggtggc taatgaacgg taggtttcaa gatggcccgt   1140
aatgatatac acggagtttg tcgtcaaaaa aaaaaaaaaa aaaaaaaaaa aaaaaaaaaa   1200
aaaaaaaaa                                                           1209
```

<210> SEQ ID NO 62
<211> LENGTH: 250
<212> TYPE: PRT
<213> ORGANISM: Zea mays
<220> FEATURE:
<221> NAME/KEY: UNSURE
<222> LOCATION: (123)

<400> SEQUENCE: 62

```
Met Tyr Thr Pro Leu Arg Cys Ser Tyr Val Leu Leu Leu Val Ile Leu
  1               5                  10                  15

Glu Ile Leu Ile Ala Met Leu Ala Asn Phe Ile Cys Cys Arg Tyr Arg
             20                  25                  30

Arg Lys Arg Asp Arg Leu Ile Glu Arg Ala Ser Val Ala Arg Leu Pro
         35                  40                  45

Leu Lys Trp Gly Asn Val His Ala Tyr Cys Tyr Lys Ser Val Ile Asp
     50                  55                  60

Gly Ile Glu His Ile Ala Met Val Lys Gly Asp Ile Gly Asp Gly Gln
 65                  70                  75                  80

Asp Ile Leu Val Arg Val His Ser Glu Cys Leu Thr Gly Asp Ile Phe
                 85                  90                  95

Gly Ser Ala Arg Cys Asp Cys Gly Asp Gln Leu Ala Met Ala Met Glu
            100                 105                 110

Met Ile Glu Lys Thr Asn Thr Pro Leu Pro Xaa Leu Arg Gly His Glu
        115                 120                 125
```

-continued

```
Gly Arg Gly Ile Gly Leu Gly His Lys Leu Arg Ala Tyr Asn Leu Gln
    130                 135                 140

Asp Asp Gly Arg Asp Thr Val Glu Ala Asn Glu Glu Leu Gly Leu Pro
145                 150                 155                 160

Val Asp Ser Arg Glu Tyr Gly Ile Gly Ala Gln Ile Leu Arg Asp Leu
                165                 170                 175

Gly Val Arg Ser Met Lys Leu Met Thr Asn Asn Pro Ala Lys Tyr Ser
            180                 185                 190

Gly Leu Lys Gly Tyr Gly Leu Ser Ile Ala Gly Arg Val Pro Leu Ile
        195                 200                 205

Thr Pro Ile Thr Ser Glu Asn Arg Arg Tyr Leu Glu Thr Lys Arg Thr
    210                 215                 220

Lys Met Gly His Val Tyr Gly Leu Ala Asn Ala Gln Ala Asn Gln Ala
225                 230                 235                 240

Asn Gly Ser Gln Ser Thr Glu Glu Asn His
                245                 250
```

<210> SEQ ID NO 63
<211> LENGTH: 1454
<212> TYPE: DNA
<213> ORGANISM: Zea mays

<400> SEQUENCE: 63

```
gcacgaggat cttagtacga gtgcattcgg agtgcctaac tggggacata tttggatcag     60

cgagatgcga ttatgggaat taacttgctc tggcaatgac catgattgag aaaactggcc    120

ggggtgtagt agtctatctt cgtggccatg agggtagggg tattgggctg ggtcacaagc    180

ttcaagcata caacttacaa gatgatgggc gcgatactgt cgaggcaaac ttggagctag    240

ggctgcctgc tgactcgcgg gagtacggta taggtgcaca gatattacgc catcttggtg    300

ccaggaccat gcggctgatg actaacaacc ctgccaagta cactggactc aagggctatg    360

gtttaagtgt ccttggtaga gtgccattgc taacaccgat aaccaccgag aataggcgct    420

atatggaaac aaagcgattg aagatggggc atgtttatgg aagccgctcc agtaatcatg    480

caaacggcag tggcttggct ggtgctggcg agagagagga gcaggatcag aatgacagtg    540

ctggcgtgca agagcgaact ccagaagctt gagtgcctaa ctctgcgttc cttagagctg    600

ctccaatggg agtcttaaaa agagatgcat cttaaaatat agggctccat ggcaaaaaaa    660

tcactccaac ggggacctca ttttacaaaa actcaggaaa caaatttggg ctccggtctc    720

attggtccca aatgtaggac ttgaaactat cggccctatt ctcgttccca cgccccccacg   780

accttcggtc ttttcctgtt gcattcgttc tcaagccgtc tctcccacaa accaaaccct    840

ctgcctgtcg agaagcattg gcgagatgga tggacggcca ccgccttttc ctcgttcacg    900

gccaacaggt tggcctcgtt gaacttccat ggagatggca ctagatgtga tagggagatc    960

atcagctgtg tcttctccgc cagatttgcg caggcctcct gtggccgtgg ctgcagagcg   1020

aaggcctgca agtatgtctg caacttccca acagacacaa ggacaagcgt cttggcatcg   1080

aatcgctgca gaccatgccg atcggagttt atcagtggca ccgatgatgt atcaagatcc   1140

attgtcaatg attgatgact ataggtaata acctttctgt tgagattagt agtcgattat   1200

atttgctcat gaattcaatc gatggtgatc tgggatctcc atggttgaga aattgaagtc   1260

aaggcctggt gaggttactt gtactggtag gtgctgatag atgtagtgct caccgatgct   1320

tgtgaattga attattggtt ctgaaaatat cctcacttca accatgcata cgagattatg   1380
```

-continued

```
agtaaatgtg aattccataa aaaaaaaaaa aaaaaaaaaa aaaaaaaaaa aaaaaaaaaa   1440

aaaaaaaaaa aaaa                                                     1454


<210> SEQ ID NO 64
<211> LENGTH: 189
<212> TYPE: PRT
<213> ORGANISM: Zea mays
<220> FEATURE:
<221> NAME/KEY: UNSURE
<222> LOCATION: (27)

<400> SEQUENCE: 64

Thr Arg Ile Leu Val Arg Val His Ser Glu Cys Leu Thr Gly Asp Ile
  1               5                  10                  15

Phe Gly Ser Ala Arg Cys Asp Tyr Gly Asn Xaa Leu Ala Leu Ala Met
             20                  25                  30

Thr Met Ile Glu Lys Thr Gly Arg Gly Val Val Val Tyr Leu Arg Gly
         35                  40                  45

His Glu Gly Arg Gly Ile Gly Leu Gly His Lys Leu Gln Ala Tyr Asn
     50                  55                  60

Leu Gln Asp Asp Gly Arg Asp Thr Val Glu Ala Asn Leu Glu Leu Gly
 65                  70                  75                  80

Leu Pro Ala Asp Ser Arg Glu Tyr Gly Ile Gly Ala Gln Ile Leu Arg
                 85                  90                  95

His Leu Gly Ala Arg Thr Met Arg Leu Met Thr Asn Asn Pro Ala Lys
            100                 105                 110

Tyr Thr Gly Leu Lys Gly Tyr Gly Leu Ser Val Leu Gly Arg Val Pro
        115                 120                 125

Leu Leu Thr Pro Ile Thr Thr Glu Asn Arg Arg Tyr Met Glu Thr Lys
    130                 135                 140

Arg Leu Lys Met Gly His Val Tyr Gly Ser Arg Ser Ser Asn His Ala
145                 150                 155                 160

Asn Gly Ser Gly Leu Ala Gly Ala Gly Glu Arg Glu Glu Gln Asp Gln
                165                 170                 175

Asn Asp Ser Ala Gly Val Gln Glu Arg Thr Pro Glu Ala
            180                 185


<210> SEQ ID NO 65
<211> LENGTH: 1788
<212> TYPE: DNA
<213> ORGANISM: Zea mays

<400> SEQUENCE: 65

ccacgcgtcc gccaaatgga ccgtgttctt ctgagctccc acttgccatc tcacgctcat     60

gcaaacacga ggttgcagca gggtcctggt ggcctcaaca gtataggatt tgcagtcata    120

aaaaagggat gcttgaagtt aagatgttac gcgatcggcg atgaactcgg tggtccaggg    180

cgctttagta agcatttcat cgagaacagt aatggacctg ttttccaggg actcgatgcg    240

tctgctggtt cttttagaac tgtcggtgct gaaatcactc aggacactgg agatttcttt    300

gtcagtgacg cagagggtga tccagacaaa cctaccgatg ggttctcctc gatcgaccag    360

gctataggtg ctttgcgtga agggaagttt gttattgctg tagatgatga gaacggcgac    420

aacgaaggcg accttgtgat ggcggccact ctagtggacc agaagtcagt cgcattcatg    480

atcaggaatg gctctgggat tatctcggta ggcatggagg aggaggacct gactagactg    540

atgattccga tgatgtcccc tatcacagaa atcgaagata tcacggctgc tgcttccacg    600
```

-continued

```
gtgacagtgg atgccagggt tggcatatct acgggtgtgt cggctgcaga cagggcgaag    660

accatcctca ctctagcctc ctctgactcc aagcccagtg atctgaggag accaggccac    720

atattccccc tcaagtaccg gaacgggggc gtgctgaaga gagctggcca cacagaagcg    780

tcggtggatc tggttgcgtt ggcaggtctc cgtcctgtgt ccgttctctc caccgtcatg    840

gaccccaggg acggttcgat ggcaggcgta acggttctcc agcagatggc tatggagcat    900

gacataccca tcgtttcgat tgctgatctc atccggtata ggagaaagcg ggagaagctg    960

gtggagctga ttgctgtgtc tcgcttgccg acgaaatggg gcctcttccg agcctactgc   1020

taccagtcca ggctcgatgg aaccgagcac atcgctgttg tgaagggcga tatcggcgac   1080

ggcgaagagg tcctggtgag ggtgcactcg gagtgcctga cgggggacat cctcggctca   1140

gcccgctgcg actgcggcaa ccagctggag ctggcgatgc agctgatcga gaaggccggc   1200

cgtggcgtgc tcgtgtacct ccgcggccac gagggccgcg gcattggcct gggccagaag   1260

ctccgcgcct acaacctcca ggacgagggc cacgacaccg tcgaggccaa cgtcgagctc   1320

ggcctcgccg tggacgcccg cgagtacggc atcggcgccc agatactccg tgacatcggc   1380

gtgcgcacga tgcggctgat gaccaacaac cccgccaagt tcatcgggct caagggctac   1440

gggctcgccg tggtggggag ggtgccggtg atctctccca tcaccaagga gaaccagaag   1500

tacctcgaga ccaagcgcac caagatgggc cacgtctacg gctccgatct cccgggaagc   1560

ctgccggagt tcgccaaccc acaagaggcc cccacagaac aagacgacga cgataaccaa   1620

aactgataaa aaaactatac ggtgtcgttt ttttaggaaa agataccaat ataaccacaa   1680

attcttgtat tccactgaga acgagtattg cagagtattt atttatcaac tgcaaaatta   1740

ttaagtataa tagagataca aacttttatc aaaaaaaaaa aaaaaaag                1788


<210> SEQ ID NO 66
<211> LENGTH: 541
<212> TYPE: PRT
<213> ORGANISM: Zea mays

<400> SEQUENCE: 66

Pro Arg Val Arg Gln Met Asp Arg Val Leu Leu Ser Ser His Leu Pro
  1               5                  10                  15

Ser His Ala His Ala Asn Thr Arg Leu Gln Gln Gly Pro Gly Gly Leu
             20                  25                  30

Asn Ser Ile Gly Phe Ala Val Ile Lys Lys Gly Cys Leu Lys Leu Arg
         35                  40                  45

Cys Tyr Ala Ile Gly Asp Glu Leu Gly Gly Pro Gly Arg Phe Ser Lys
     50                  55                  60

His Phe Ile Glu Asn Ser Asn Gly Pro Val Phe Gln Gly Leu Asp Ala
 65                  70                  75                  80

Ser Ala Gly Ser Phe Arg Thr Val Gly Ala Glu Ile Thr Gln Asp Thr
                 85                  90                  95

Gly Asp Phe Phe Val Ser Asp Ala Glu Gly Asp Pro Asp Lys Pro Thr
            100                 105                 110

Asp Gly Phe Ser Ser Ile Asp Gln Ala Ile Gly Ala Leu Arg Glu Gly
        115                 120                 125

Lys Phe Val Ile Ala Val Asp Asp Glu Asn Gly Asp Asn Glu Gly Asp
    130                 135                 140

Leu Val Met Ala Ala Thr Leu Val Asp Gln Lys Ser Val Ala Phe Met
145                 150                 155                 160
```

-continued

```
Ile Arg Asn Gly Ser Gly Ile Ile Ser Val Gly Met Glu Glu Glu Asp
                165                 170                 175

Leu Thr Arg Leu Met Ile Pro Met Met Ser Pro Ile Thr Glu Ile Glu
            180                 185                 190

Asp Ile Thr Ala Ala Ala Ser Thr Val Thr Val Asp Ala Arg Val Gly
        195                 200                 205

Ile Ser Thr Gly Val Ser Ala Ala Asp Arg Ala Lys Thr Ile Leu Thr
    210                 215                 220

Leu Ala Ser Ser Asp Ser Lys Pro Ser Asp Leu Arg Arg Pro Gly His
225                 230                 235                 240

Ile Phe Pro Leu Lys Tyr Arg Asn Gly Gly Val Leu Lys Arg Ala Gly
                245                 250                 255

His Thr Glu Ala Ser Val Asp Leu Val Ala Leu Ala Gly Leu Arg Pro
            260                 265                 270

Val Ser Val Leu Ser Thr Val Met Asp Pro Arg Asp Gly Ser Met Ala
        275                 280                 285

Gly Val Thr Val Leu Gln Gln Met Ala Met Glu His Asp Ile Pro Ile
    290                 295                 300

Val Ser Ile Ala Asp Leu Ile Arg Tyr Arg Arg Lys Arg Glu Lys Leu
305                 310                 315                 320

Val Glu Leu Ile Ala Val Ser Arg Leu Pro Thr Lys Trp Gly Leu Phe
                325                 330                 335

Arg Ala Tyr Cys Tyr Gln Ser Arg Leu Asp Gly Thr Glu His Ile Ala
            340                 345                 350

Val Val Lys Gly Asp Ile Gly Asp Gly Glu Glu Val Leu Val Arg Val
        355                 360                 365

His Ser Glu Cys Leu Thr Gly Asp Ile Leu Gly Ser Ala Arg Cys Asp
    370                 375                 380

Cys Gly Asn Gln Leu Glu Leu Ala Met Gln Leu Ile Glu Lys Ala Gly
385                 390                 395                 400

Arg Gly Val Leu Val Tyr Leu Arg Gly His Glu Gly Arg Gly Ile Gly
                405                 410                 415

Leu Gly Gln Lys Leu Arg Ala Tyr Asn Leu Gln Asp Glu Gly His Asp
            420                 425                 430

Thr Val Glu Ala Asn Val Glu Leu Gly Leu Ala Val Asp Ala Arg Glu
        435                 440                 445

Tyr Gly Ile Gly Ala Gln Ile Leu Arg Asp Ile Gly Val Arg Thr Met
    450                 455                 460

Arg Leu Met Thr Asn Asn Pro Ala Lys Phe Ile Gly Leu Lys Gly Tyr
465                 470                 475                 480

Gly Leu Ala Val Val Gly Arg Val Pro Val Ile Ser Pro Ile Thr Lys
                485                 490                 495

Glu Asn Gln Lys Tyr Leu Glu Thr Lys Arg Thr Lys Met Gly His Val
            500                 505                 510

Tyr Gly Ser Asp Leu Pro Gly Ser Leu Pro Glu Phe Ala Asn Pro Gln
        515                 520                 525

Glu Ala Pro Thr Glu Gln Asp Asp Asp Asp Asn Gln Asn
    530                 535                 540
```

<210> SEQ ID NO 67
<211> LENGTH: 1239
<212> TYPE: DNA
<213> ORGANISM: Oryza sativa

<400> SEQUENCE: 67

```
gcacgagctt acacctgact ctaagcctga agacttcaat cggcctggtc atattttccc     60
tctgaaatac agagagggtg gtgttctgaa acgagctgga catactgaag catctgtaga    120
tcttgctatg ttagctgggt tacctcctgc tgcggtctta tgtgagattg tggatgagga    180
tgggtccatg gctcgcctac caaagctgcg cgtgtttgct gaaagggaga atttgaagat    240
tgtatccatt gctgacttga ttagatatag gagaaaaaga gacaggctag ttgaacgttc    300
atctgttgca cgcttacctt tgagatgggg taatgtccgc gcttactgct acagatctgt    360
tattgatggg atagagcata ttgcaatggt gaaaggggag attggagatg gtcaaggcgt    420
tttagtgagg gtgcactccg aatgcctcac aggggacatt tttggatcag caagatgtga    480
ttgtggtgat cagcttgcca tggcaatgga gatgattgag aaggctggaa ggggtgtact    540
agtttatctt cgtggacatg aagggagggg tattggtctc ggtcacaagc tccgtgctta    600
taacctgcaa gatgacgggc gcgacactgt ggaggctaat gaagacctag gactgcctgt    660
ggattcacgg gaatatggca ttggtgcaca gatattacgt gatctggggg tccgttcaat    720
gaagttgatg actaataacc cagcaaagta tggtggtctc aagggttatg gattgagcat    780
tgtgggcagg gttcccttgg taactccaat cacctcagag aatcggagat acctggaaac    840
aaagagaaca aagatggggc atgtatatgg attggccaat ggccaagcta gccatcagac    900
gggcagcaat ggtgccaaag gggagcatta ggccaatcgg actcaggttc acattctaat    960
ccacgacaat cttatgtgat ggagtttgtc aaattatgct acaacatatg ttcgtggtga   1020
accaattttt ttttagctga cagtaggttg aaagatgggc gtaataaaag tatcccttta   1080
tttgttgtaa tccacagcca cacaactggg ttattactgt aaatatatac acacacataa   1140
actgctccct agcgggtaca gactccagcc ttacctgaat tgagaagact ggcgataaaa   1200
atatcgactg agatccaagg caaaaaaaaa aaaaaaaaa                          1239
```

<210> SEQ ID NO 68
<211> LENGTH: 309
<212> TYPE: PRT
<213> ORGANISM: Oryza sativa

<400> SEQUENCE: 68

```
His Glu Leu Thr Pro Asp Ser Lys Pro Glu Asp Phe Asn Arg Pro Gly
  1               5                  10                  15

His Ile Phe Pro Leu Lys Tyr Arg Glu Gly Gly Val Leu Lys Arg Ala
             20                  25                  30

Gly His Thr Glu Ala Ser Val Asp Leu Ala Met Leu Ala Gly Leu Pro
         35                  40                  45

Pro Ala Ala Val Leu Cys Glu Ile Val Asp Glu Asp Gly Ser Met Ala
     50                  55                  60

Arg Leu Pro Lys Leu Arg Val Phe Ala Glu Arg Glu Asn Leu Lys Ile
 65                  70                  75                  80

Val Ser Ile Ala Asp Leu Ile Arg Tyr Arg Arg Lys Arg Asp Arg Leu
                 85                  90                  95

Val Glu Arg Ser Ser Val Ala Arg Leu Pro Leu Arg Trp Gly Asn Val
            100                 105                 110

Arg Ala Tyr Cys Tyr Arg Ser Val Ile Asp Gly Ile Glu His Ile Ala
        115                 120                 125

Met Val Lys Gly Glu Ile Gly Asp Gly Gln Gly Val Leu Val Arg Val
    130                 135                 140
```

-continued

His Ser Glu Cys Leu Thr Gly Asp Ile Phe Gly Ser Ala Arg Cys Asp
145 150 155 160

Cys Gly Asp Gln Leu Ala Met Ala Met Glu Met Ile Glu Lys Ala Gly
165 170 175

Arg Gly Val Leu Val Tyr Leu Arg Gly His Glu Gly Arg Gly Ile Gly
180 185 190

Leu Gly His Lys Leu Arg Ala Tyr Asn Leu Gln Asp Asp Gly Arg Asp
195 200 205

Thr Val Glu Ala Asn Glu Asp Leu Gly Leu Pro Val Asp Ser Arg Glu
210 215 220

Tyr Gly Ile Gly Ala Gln Ile Leu Arg Asp Leu Gly Val Arg Ser Met
225 230 235 240

Lys Leu Met Thr Asn Asn Pro Ala Lys Tyr Gly Gly Leu Lys Gly Tyr
245 250 255

Gly Leu Ser Ile Val Gly Arg Val Pro Leu Val Thr Pro Ile Thr Ser
260 265 270

Glu Asn Arg Arg Tyr Leu Glu Thr Lys Arg Thr Lys Met Gly His Val
275 280 285

Tyr Gly Leu Ala Asn Gly Gln Ala Ser His Gln Thr Gly Ser Asn Gly
290 295 300

Ala Lys Gly Glu His
305

<210> SEQ ID NO 69
<211> LENGTH: 1636
<212> TYPE: DNA
<213> ORGANISM: Oryza sativa

<400> SEQUENCE: 69
acgtcgccat ggcctaccat acgacatacc aagattacgc tcatatggcc atggaggcca 60
gtgaatgatc ctttaaagga aagcaataat ggacctgttt tgcaaggatt caatggatct 120
agtgcttcct ttcggactgt tggtgctaaa atcactcagg aaactggtga tttctttgtt 180
agcgatgcag agggtgaccc agacaaacca actgatggtt tttcctctat tgatgaggct 240
ataggcgcat tgcatgaagg aaagtttgtt attgctgtag atgatgaaag cggtgataat 300
gaaggggatc ttgtcatggc agctacgctg gcagacccag aatctattgc attcatgatc 360
aggaatggtt ctgggatcat ctcagtgggc atgaaggaag aggacttaac aagattgatg 420
attcctatga tgtctccaat tgcagaaatt gaggatattt cagctgctgc ttccacagta 480
acagtggatg ccagagtggg catatcaacc ggcgtctcgg ctgcagatag ggcaaaaacg 540
atttttactc tagcctcccc tgattctaag ccaactgacc tcagaagacc aggccatata 600
ttccctctaa aataccgaaa cggtggtgtg ctaaaaagag ctggacatac tgaggcatcc 660
gtcgatcttg tcgcgttggc tggcttgcgc cctgtgtctg tcctgtcaac cgtcatcaac 720
ccagtggatg gttcaatggc aggaatgcca gtgctgaaac agatggcttt ggagcatgat 780
atcccaattg tttcaatcgc tgatctcatc cggtatagaa ggaagaggga gaagctggtg 840
gaactgattg ctgtatctcg tttgccgacg aaatggggcc ttttccgagc ttactgctac 900
caatccaagc ttgatggaac cgagcacatt gctgttgcaa agggcgacat cggcgacggc 960
gaggacgtct tggtgagggt ccattccgag tgcctgaccg gcgacatcct cggctccgcc 1020
cgctgcgact gcggcaacca gctggacctg gcgatgcagc tcatcgacaa ggccggccgc 1080
ggcgtcctcg tctacctccg cggccacgag ggccgcggca tcggcctcgg ccagaagctc 1140

-continued

```
cgcgcctaca acctccagga cgacggccac gacaccgtcc aggccaacgt cgagctcggc   1200

ctcgccgtcg actcccgcga gtacggcatc ggcgcccaga ttctgcggga catgggggtg   1260

cgcacgatgc ggctgatgac gaacaacccg gcaaagttcg tcgggctcaa gggctacggg   1320

ctcgccgtcg tcggcagggt tccggtgatc tcccccatca ccaaggagaa ccagaggtac   1380

ctcgagacga agcgcaccaa gatgggccat gtctacggct ccgacctccc cggcaacgtc   1440

ccggaggaat tcctcaaccc ggacgacatc gccggagacc aagacgaaga cgacacccac   1500

aactgaatgc aacaacaaaa ttcacaacca cagattctcc acatctcatt ttgtgatcaa   1560

attgcatctc aaactgcacc gatcttgtta tactagtaac aaatcttgat ttggaaccaa   1620

aaaaaaaaaa aaaaaa                                                   1636
```

<210> SEQ ID NO 70
<211> LENGTH: 501
<212> TYPE: PRT
<213> ORGANISM: Oryza sativa

<400> SEQUENCE: 70

```
Thr Ser Pro Trp Pro Thr Ile Arg His Thr Lys Ile Thr Leu Ile Trp
  1               5                  10                  15

Pro Trp Arg Pro Val Asn Asp Pro Leu Lys Glu Ser Asn Asn Gly Pro
             20                  25                  30

Val Leu Gln Gly Phe Asn Gly Ser Ser Ala Ser Phe Arg Thr Val Gly
         35                  40                  45

Ala Lys Ile Thr Gln Glu Thr Gly Asp Phe Phe Val Ser Asp Ala Glu
     50                  55                  60

Gly Asp Pro Asp Lys Pro Thr Asp Gly Phe Ser Ser Ile Asp Glu Ala
 65                  70                  75                  80

Ile Gly Ala Leu His Glu Gly Lys Phe Val Ile Ala Val Asp Asp Glu
                 85                  90                  95

Ser Gly Asp Asn Glu Gly Asp Leu Val Met Ala Ala Thr Leu Ala Asp
            100                 105                 110

Pro Glu Ser Ile Ala Phe Met Ile Arg Asn Gly Ser Gly Ile Ile Ser
        115                 120                 125

Val Gly Met Lys Glu Glu Asp Leu Thr Arg Leu Met Ile Pro Met Met
    130                 135                 140

Ser Pro Ile Ala Glu Ile Glu Asp Ile Ser Ala Ala Ala Ser Thr Val
145                 150                 155                 160

Thr Val Asp Ala Arg Val Gly Ile Ser Thr Gly Val Ser Ala Ala Asp
                165                 170                 175

Arg Ala Lys Thr Ile Phe Thr Leu Ala Ser Pro Asp Ser Lys Pro Thr
            180                 185                 190

Asp Leu Arg Arg Pro Gly His Ile Phe Pro Leu Lys Tyr Arg Asn Gly
        195                 200                 205

Gly Val Leu Lys Arg Ala Gly His Thr Glu Ala Ser Val Asp Leu Val
    210                 215                 220

Ala Leu Ala Gly Leu Arg Pro Val Ser Val Leu Ser Thr Val Ile Asn
225                 230                 235                 240

Pro Val Asp Gly Ser Met Ala Gly Met Pro Val Leu Lys Gln Met Ala
                245                 250                 255

Leu Glu His Asp Ile Pro Ile Val Ser Ile Ala Asp Leu Ile Arg Tyr
            260                 265                 270

Arg Arg Lys Arg Glu Lys Leu Val Glu Leu Ile Ala Val Ser Arg Leu
        275                 280                 285
```

-continued

```
Pro Thr Lys Trp Gly Leu Phe Arg Ala Tyr Cys Tyr Gln Ser Lys Leu
    290                 295                 300

Asp Gly Thr Glu His Ile Ala Val Ala Lys Gly Asp Ile Gly Asp Gly
305                 310                 315                 320

Glu Asp Val Leu Val Arg Val His Ser Glu Cys Leu Thr Gly Asp Ile
                325                 330                 335

Leu Gly Ser Ala Arg Cys Asp Cys Gly Asn Gln Leu Asp Leu Ala Met
            340                 345                 350

Gln Leu Ile Asp Lys Ala Gly Arg Gly Val Leu Val Tyr Leu Arg Gly
        355                 360                 365

His Glu Gly Arg Gly Ile Gly Leu Gly Gln Lys Leu Arg Ala Tyr Asn
    370                 375                 380

Leu Gln Asp Asp Gly His Asp Thr Val Gln Ala Asn Val Glu Leu Gly
385                 390                 395                 400

Leu Ala Val Asp Ser Arg Glu Tyr Gly Ile Gly Ala Gln Ile Leu Arg
                405                 410                 415

Asp Met Gly Val Arg Thr Met Arg Leu Met Thr Asn Asn Pro Ala Lys
            420                 425                 430

Phe Val Gly Leu Lys Gly Tyr Gly Leu Ala Val Val Gly Arg Val Pro
        435                 440                 445

Val Ile Ser Pro Ile Thr Lys Glu Asn Gln Arg Tyr Leu Glu Thr Lys
    450                 455                 460

Arg Thr Lys Met Gly His Val Tyr Gly Ser Asp Leu Pro Gly Asn Val
465                 470                 475                 480

Pro Glu Glu Phe Leu Asn Pro Asp Asp Ile Ala Gly Asp Gln Asp Glu
                485                 490                 495

Asp Asp Thr His Asn
            500
```

<210> SEQ ID NO 71
<211> LENGTH: 2079
<212> TYPE: DNA
<213> ORGANISM: Glycine max

<400> SEQUENCE: 71

```
gcacgagatt cattcattga caaaacaaaa caatggcttc tttcaatctc tcttattctt     60

cctcaccagc cctctcacgt ccccgggcaa gcaaacactt caaattcttc aatgatgtgc    120

cttttgtccg aatgaattct aaatttccct caagtgataa tgcttttggg agaatcaaag    180

ctatgttgat ctctggaggg ggtgaactac tttcccatcc aaatggcaat gacattgtga    240

taggtacaaa tctggttgga gatgaatctg ttcaaattga ggtacagcct aatggaacac    300

tggcagatga cacagggcta acaagcaatg ttttctctat ggacaacaat gaatttgatt    360

cggacagccc ctcagcaggt tttgcttcca ttcctgaggc aattgaagac attcgccagg    420

gaaagatggt agtggttgtg gacgatgaag atcgagaaaa tgaaggagac ttgataatgg    480

cagcacagtt ggcaacaccc gaggcaatgg cttttattgt aaagcatgga actggtatag    540

tttgtgtaag catgaaagag gaagatctgg atagattgga acttcctttg atggtgaaca    600

gtaaggacaa tgatgagaaa ctttgtacgg cattcactgt gacagtggat gctaaacatg    660

gtacaaccac tggggtgtca gctcacgata gggcaacaac agtcttggcc cttgcgtcta    720

gagattctac tccaggcgat ttcaatcgcc cgggccatat tttcccacta aaatacaggg    780

aaggtggtgt cttgaagaga gccggacata cagaagcttc tgttgatctt gctgtacttg    840

ctggtttgga tccagtggca gttctgtgtg agattgtaga tgatgatggt tccatggcta    900
```

-continued

```
gactgccaaa gcttcgccag tttgcagagc atgaaaattt gaaaattgta tctattgctg    960
acttaataag atatagaaga aaaagggata agttagtgga tcgctcttct gctgcacaga   1020
tacctacaat gtggggacca ttcacagctt actgttacag atcactttta gacgggattg   1080
agcatattgc aatggttaag ggtgacattg gagatggaca agatgttctt gtgagagtac   1140
actcagagtg tctgacagga gacatatttg gatctgccag atgtgactgc ggaaatcagc   1200
ttgcacttgc aatgcaacag attgaggctg ctggtaaggg tgtgctggta tatctccgtg   1260
gacacgaagg aaggggtatt ggattgggcc acaagcttcg tgcttataac ctacaggatg   1320
atggacgaga tactgttgaa gccaatgagg aattgggatt gccagttgac tccagggagt   1380
atggcattgg tgcacagatg ttgagggact tgggtgtacg atctatgaag ctgatgacaa   1440
acaatccggc aaaatatatt gggctcaaag gttatggttt gacagtttcg ggtaggatcc   1500
cattgttaac tcttatcact tcggagaaca agagatattt agagaccaaa cgtgtgaaaa   1560
tgggtcacat atatggcacg gaatttaacg gccgattgag cactcatgac agtggtaatg   1620
gtaatgccac caggattgag gactctaatg ctgttactgg cttataaaca tccttttttt   1680
aactagataa tatggaagaa ctagatttcc atggtgcaga tgaatacata aagttataaa   1740
gttatagaaa ccatttttct tattcatttg tctgataaac ttcagctcta ctaaactata   1800
ggctctaccg aacaccattc atcttgatta ttgaaacata gtgccatgac aagggcattg   1860
ctatttcagg gttatttttt ctttggtgcc ttttagaggt tcatcatttc tagactctgg   1920
aaatcattag ccgatttaaa cctagtttct tcattctttt ttatccaatt acccatgcat   1980
cacagttgcc tcaataatgc atgatagaaa agttatatga tttgtagctc cacaatttat   2040
aataaataaa ttccttttgt aaaaaaaaaa aaaaaaaaa                          2079
```

```
<210> SEQ ID NO 72
<211> LENGTH: 544
<212> TYPE: PRT
<213> ORGANISM: Glycine max

<400> SEQUENCE: 72

Met Ala Ser Phe Asn Leu Ser Tyr Ser Ser Ser Pro Ala Leu Ser Arg
  1               5                  10                  15

Pro Arg Ala Ser Lys His Phe Lys Phe Phe Asn Asp Val Pro Phe Val
             20                  25                  30

Arg Met Asn Ser Lys Phe Pro Ser Ser Asp Asn Ala Phe Gly Arg Ile
         35                  40                  45

Lys Ala Met Leu Ile Ser Gly Gly Gly Glu Leu Leu Ser His Pro Asn
     50                  55                  60

Gly Asn Asp Ile Val Ile Gly Thr Asn Leu Val Gly Asp Glu Ser Val
 65                  70                  75                  80

Gln Ile Glu Val Gln Pro Asn Gly Thr Leu Ala Asp Asp Thr Gly Leu
                 85                  90                  95

Thr Ser Asn Val Phe Ser Met Asp Asn Asn Glu Phe Asp Ser Asp Ser
            100                 105                 110

Pro Ser Ala Gly Phe Ala Ser Ile Pro Glu Ala Ile Glu Asp Ile Arg
        115                 120                 125

Gln Gly Lys Met Val Val Val Val Asp Asp Glu Asp Arg Glu Asn Glu
    130                 135                 140

Gly Asp Leu Ile Met Ala Ala Gln Leu Ala Thr Pro Glu Ala Met Ala
145                 150                 155                 160
```

-continued

```
Phe Ile Val Lys His Gly Thr Gly Ile Val Cys Val Ser Met Lys Glu
                165                 170                 175

Glu Asp Leu Asp Arg Leu Glu Leu Pro Leu Met Val Asn Ser Lys Asp
            180                 185                 190

Asn Asp Glu Lys Leu Cys Thr Ala Phe Thr Val Thr Val Asp Ala Lys
        195                 200                 205

His Gly Thr Thr Thr Gly Val Ser Ala His Asp Arg Ala Thr Thr Val
    210                 215                 220

Leu Ala Leu Ala Ser Arg Asp Ser Thr Pro Gly Asp Phe Asn Arg Pro
225                 230                 235                 240

Gly His Ile Phe Pro Leu Lys Tyr Arg Glu Gly Gly Val Leu Lys Arg
                245                 250                 255

Ala Gly His Thr Glu Ala Ser Val Asp Leu Ala Val Leu Ala Gly Leu
            260                 265                 270

Asp Pro Val Ala Val Leu Cys Glu Ile Val Asp Asp Asp Gly Ser Met
        275                 280                 285

Ala Arg Leu Pro Lys Leu Arg Gln Phe Ala Glu His Glu Asn Leu Lys
    290                 295                 300

Ile Val Ser Ile Ala Asp Leu Ile Arg Tyr Arg Arg Lys Arg Asp Lys
305                 310                 315                 320

Leu Val Asp Arg Ser Ser Ala Ala Gln Ile Pro Thr Met Trp Gly Pro
                325                 330                 335

Phe Thr Ala Tyr Cys Tyr Arg Ser Leu Leu Asp Gly Ile Glu His Ile
            340                 345                 350

Ala Met Val Lys Gly Asp Ile Gly Asp Gly Gln Asp Val Leu Val Arg
        355                 360                 365

Val His Ser Glu Cys Leu Thr Gly Asp Ile Phe Gly Ser Ala Arg Cys
    370                 375                 380

Asp Cys Gly Asn Gln Leu Ala Leu Ala Met Gln Gln Ile Glu Ala Ala
385                 390                 395                 400

Gly Lys Gly Val Leu Val Tyr Leu Arg Gly His Glu Gly Arg Gly Ile
                405                 410                 415

Gly Leu Gly His Lys Leu Arg Ala Tyr Asn Leu Gln Asp Asp Gly Arg
            420                 425                 430

Asp Thr Val Glu Ala Asn Glu Glu Leu Gly Leu Pro Val Asp Ser Arg
        435                 440                 445

Glu Tyr Gly Ile Gly Ala Gln Met Leu Arg Asp Leu Gly Val Arg Ser
    450                 455                 460

Met Lys Leu Met Thr Asn Asn Pro Ala Lys Tyr Ile Gly Leu Lys Gly
465                 470                 475                 480

Tyr Gly Leu Thr Val Ser Gly Arg Ile Pro Leu Leu Thr Leu Ile Thr
                485                 490                 495

Ser Glu Asn Lys Arg Tyr Leu Glu Thr Lys Arg Val Lys Met Gly His
            500                 505                 510

Ile Tyr Gly Thr Glu Phe Asn Gly Arg Leu Ser Thr His Asp Ser Gly
        515                 520                 525

Asn Gly Asn Ala Thr Arg Ile Glu Asp Ser Asn Ala Val Thr Gly Leu
    530                 535                 540


<210> SEQ ID NO 73
<211> LENGTH: 934
<212> TYPE: DNA
<213> ORGANISM: Triticum aestivum
```

<400> SEQUENCE: 73

```
gcacgagatc tgtcctttca accatcatcg acccgaagga cggctcgatg gcatcaacac     60

aagcgctgaa acagatggct ttggagcatg atgtcccgat tgtttcgatc gctgatctca    120

tccggtacag gaggaaaagg gagaagctgg tggaattgat cgctgtatct cgtttgccta    180

ctaaatgggg cctattccgt gcttactgct accaatccaa gctggatgga actgagcaca    240

tcgctgttgc aaagggtgat attggcgatg gagaagacgt gctggtgagg gtgcattcag    300

agtgcctgac cggcgacatc ctcggctccg cccgctgcga ctgtggcgag cagctggacc    360

tggcgatgca gctgatcgag aaggccggcc gcggcgtcct cgtgtaccta cgcggacatg    420

aaggccgagg catcgggctc ggccagaagc tccgcgccta caacctgcag gaccaaggca    480

gcgacacggt ggaggccaac gtcgagctcg gcctcgccat cgactcccgc gagtacggca    540

tcggtgccca gattctcagg gacattggcg tgcgcacgat gcggctgatg acgaacaacc    600

cggccaaatt cgtggggctc aaggggtacg ggctcgcggt ggtgggccgg gtcccggtga    660

tctcgccgat cacaaaggag aaccagaaat acctcgagac caagaggacc aagatggggc    720

acctctacgg ctccgacctc cccggcggcc tcctcaagga attcctcaac cctacggaag    780

acaacgccac gaactaatta tacacccacc acacgatcca cggatcattt ggtttctttt    840

aacttcattt ctttctgata tacaacgatc gaacgagaat tgagacgaaa tattgcaacc    900

aatctgtagc gattccaaaa aaaaaaaaaa aaaa                                934
```

<210> SEQ ID NO 74
<211> LENGTH: 264
<212> TYPE: PRT
<213> ORGANISM: Triticum aestivum

<400> SEQUENCE: 74

```
Thr Arg Ser Val Leu Ser Thr Ile Ile Asp Pro Lys Asp Gly Ser Met
  1               5                  10                  15

Ala Ser Thr Gln Ala Leu Lys Gln Met Ala Leu Glu His Asp Val Pro
             20                  25                  30

Ile Val Ser Ile Ala Asp Leu Ile Arg Tyr Arg Arg Lys Arg Glu Lys
         35                  40                  45

Leu Val Glu Leu Ile Ala Val Ser Arg Leu Pro Thr Lys Trp Gly Leu
     50                  55                  60

Phe Arg Ala Tyr Cys Tyr Gln Ser Lys Leu Asp Gly Thr Glu His Ile
 65                  70                  75                  80

Ala Val Ala Lys Gly Asp Ile Gly Asp Gly Glu Asp Val Leu Val Arg
                 85                  90                  95

Val His Ser Glu Cys Leu Thr Gly Asp Ile Leu Gly Ser Ala Arg Cys
            100                 105                 110

Asp Cys Gly Glu Gln Leu Asp Leu Ala Met Gln Leu Ile Glu Lys Ala
        115                 120                 125

Gly Arg Gly Val Leu Val Tyr Leu Arg Gly His Glu Gly Arg Gly Ile
    130                 135                 140

Gly Leu Gly Gln Lys Leu Arg Ala Tyr Asn Leu Gln Asp Gln Gly Ser
145                 150                 155                 160

Asp Thr Val Glu Ala Asn Val Glu Leu Gly Leu Ala Ile Asp Ser Arg
                165                 170                 175

Glu Tyr Gly Ile Gly Ala Gln Ile Leu Arg Asp Ile Gly Val Arg Thr
            180                 185                 190
```

-continued

```
Met Arg Leu Met Thr Asn Asn Pro Ala Lys Phe Val Gly Leu Lys Gly
        195                 200                 205

Tyr Gly Leu Ala Val Val Gly Arg Val Pro Val Ile Ser Pro Ile Thr
    210                 215                 220

Lys Glu Asn Gln Lys Tyr Leu Glu Thr Lys Arg Thr Lys Met Gly His
225                 230                 235                 240

Leu Tyr Gly Ser Asp Leu Pro Gly Gly Leu Leu Lys Glu Phe Leu Asn
                245                 250                 255

Pro Thr Glu Asp Asn Ala Thr Asn
            260
```

<210> SEQ ID NO 75
<211> LENGTH: 970
<212> TYPE: DNA
<213> ORGANISM: Zea mays

<400> SEQUENCE: 75

```
gcacgagggc atccaaaggg attgagaagc tccaaggtgc tgggataagt gtgagggtgg     60

gtgtggagga agcgttatgc cgcaaactaa acgaggctta tatccatcgt atgctcaccg    120

ggaaggcttt tgcaactctg agagctacac tctcaatgaa tggaatcatc acgaaccaga    180

ttgggaaggg agctgatcag tcaggtgggt actactcgca gctgatgaaa gaatacgacg    240

gagtcataat ttcaagcgac ctggccaaga tgtcggcctt acctttgtcg cgtgaagccg    300

gcacaaacca acctctctgt atcatcatag cacagggtga aagctcccgg ctacacatcc    360

catctctcag ccaagagcat gcatccaggg ccatagtcct tgccgatagt ccggtcactg    420

tggagccagc aggagtggaa gttgcagttt ttcgtcagat agacctggag tctattctcc    480

agcttcttgc gcagcgaggg ctctgcagcg tgctggtgga cttcagagag gccggcgaaa    540

gcttcgcgtc gcttctgaac gacttccagg aggacaagct ggtgcagaag gtcgtcgttg    600

aggtcctgcc cttttggctc gcgagcgacg ggctcagcaa cctggcattt ggtggcagcc    660

aatcgttccc gttgaagaac ttggagctca gggatgtgaa tgggagtgtg ctgctggaag    720

gctatgtgta atagcctctc ttctgtcgga gattggcatt gtttgttttc cctcgtgtaa    780

acagatagcc ctgtaatata cttgcagagc cgcccacgag ccatgtgggg ttttgctttt    840

ttatatatat agttgaaaat caatgccatg cgtccttcat tttgctgaca tggaactgct    900

gcccggtgat actccctgtc tgcaaatcaa tgcaaatgtc ttattaaaaa aaaaaaaaaa    960

aaaaaaaaaa                                                           970
```

<210> SEQ ID NO 76
<211> LENGTH: 242
<212> TYPE: PRT
<213> ORGANISM: Zea mays

<400> SEQUENCE: 76

```
Thr Arg Ala Ser Lys Gly Ile Glu Lys Leu Gln Gly Ala Gly Ile Ser
  1               5                  10                  15

Val Arg Val Gly Val Glu Glu Ala Leu Cys Arg Lys Leu Asn Glu Ala
             20                  25                  30

Tyr Ile His Arg Met Leu Thr Gly Lys Ala Phe Ala Thr Leu Arg Ala
         35                  40                  45

Thr Leu Ser Met Asn Gly Ile Ile Thr Asn Gln Ile Gly Lys Gly Ala
     50                  55                  60

Asp Gln Ser Gly Gly Tyr Tyr Ser Gln Leu Met Lys Glu Tyr Asp Gly
 65                  70                  75                  80
```

-continued

```
Val Ile Ile Ser Ser Asp Leu Ala Lys Met Ser Ala Leu Pro Leu Ser
                85                  90                  95

Arg Glu Ala Gly Thr Asn Gln Pro Leu Cys Ile Ile Ile Ala Gln Gly
            100                 105                 110

Glu Ser Ser Arg Leu His Ile Pro Ser Leu Ser Gln Glu His Ala Ser
        115                 120                 125

Arg Ala Ile Val Leu Ala Asp Ser Pro Val Thr Val Glu Pro Ala Gly
    130                 135                 140

Val Glu Val Ala Val Phe Arg Gln Ile Asp Leu Glu Ser Ile Leu Gln
145                 150                 155                 160

Leu Leu Ala Gln Arg Gly Leu Cys Ser Val Leu Val Asp Phe Arg Glu
                165                 170                 175

Ala Gly Glu Ser Phe Ala Ser Leu Leu Asn Asp Phe Gln Glu Asp Lys
            180                 185                 190

Leu Val Gln Lys Val Val Val Glu Val Leu Pro Phe Trp Leu Ala Ser
        195                 200                 205

Asp Gly Leu Ser Asn Leu Ala Phe Gly Gly Ser Gln Ser Phe Pro Leu
    210                 215                 220

Lys Asn Leu Glu Leu Arg Asp Val Asn Gly Ser Val Leu Leu Glu Gly
225                 230                 235                 240

Tyr Val
```

<210> SEQ ID NO 77
<211> LENGTH: 1445
<212> TYPE: DNA
<213> ORGANISM: Oryza sativa

<400> SEQUENCE: 77

```
gcacgaggtt ctaacctcct ctgcgcgacg gacatggcct cctcgctcgt ctcgcgcacc     60

cacctcactc cgcgccccgc cgccgccgcc tcgacggcct ctccttgcag cgcccgcttc    120

gcggtccggc ggcgccgtgg cctcgtcggc ggtgtgcggt gccaggcgca ggcgagcgac    180

atggacggcc actacatgcg gcggtgcgtg gagctggcgc gcaaggcggc cggacacacc    240

agccctaacc ccatggtcgg ctgtgtcgtt gtccgcgacg gccgcgtcgt cggcgaggga    300

ttccatccca aagccggcca gccccacgcc gaggtgtttg ctctgagaga tgctggggat    360

ttagcagaga atgcaacagc ctatgtgagc ttagagccct gcaaccatta cgggcggaca    420

cctccctgca ctgaagcact catcaatgcc aaagttaaag atgttgtggt ggggatgact    480

gacccaaatc ctattgtggc atccaagggg attgaaaggc tcagaagcgc cgggatagat    540

gtgaggttgt gcgtggatga agaagcgtca tgccgcaagc taaatgaggc ttacatccat    600

cgcatgctta ctgggaaggc ctttgcaact ttaagaacta cactctcgat gaatggagtt    660

gtcatcaatc agattgggag tggagctgat caaccagaag gatactactc gcagttattg    720

aaagaatacg atggagtaat aatttcaagc aattttgcca agacaaatac cttgcctgta    780

tcccgtgaag ctggtgcgaa gcagcctctt tatatcatca tagcgcagtg cgaaaattcc    840

caattaaaca ttccgtttct caaagaagag cgtgcagccg aggcagtagt tctgtcggat    900

agtcctatca ctgtggagcc agcaggagtt gatgttttag tccttgatca gatgaacctg    960

gatgccattc ttcaacttct tgcacaacga gggctatgta gtgtgctggt ggatttcagg   1020

gaggctggag gaggcattgc atcacttctg aacaattttc aggatgacaa gctggtacag   1080

aaggttgttg tggagctcct gcctgtctgg gcggtcagca aagggccgag cgacctggcg   1140

tttggtggga gccagtcatt tccactgaag gatgtggagc acagtgaggt aaatggatcc   1200
```

-continued

```
gtgctgcttc agggctatgt gtaacaaact tttttggttc gaggttgatc ctgccctgag   1260

tagcgctgca tatttttacc tctcactctc tctcgttctg gctctggtaa actgtccgtc   1320

atgtaaactt acctgaatct gcagtcaatg cggtggtgct cctagacagg gatctggttc   1380

ttctgatttt tacagtatca tgcaataaat ctatgagaga actgcgaaaa aaaaaaaaaa   1440

aaaaa                                                               1445


<210> SEQ ID NO 78
<211> LENGTH: 407
<212> TYPE: PRT
<213> ORGANISM: Oryza sativa

<400> SEQUENCE: 78

Ala Arg Gly Ser Asn Leu Leu Cys Ala Thr Asp Met Ala Ser Ser Leu
  1               5                  10                  15

Val Ser Arg Thr His Leu Thr Pro Arg Pro Ala Ala Ala Ala Ser Thr
            20                  25                  30

Ala Ser Pro Cys Ser Ala Arg Phe Ala Val Arg Arg Arg Arg Gly Leu
        35                  40                  45

Val Gly Gly Val Arg Cys Gln Ala Gln Ala Ser Asp Met Asp Gly His
    50                  55                  60

Tyr Met Arg Arg Cys Val Glu Leu Ala Arg Lys Ala Ala Gly His Thr
 65                  70                  75                  80

Ser Pro Asn Pro Met Val Gly Cys Val Val Val Arg Asp Gly Arg Val
                85                  90                  95

Val Gly Glu Gly Phe His Pro Lys Ala Gly Gln Pro His Ala Glu Val
            100                 105                 110

Phe Ala Leu Arg Asp Ala Gly Asp Leu Ala Glu Asn Ala Thr Ala Tyr
        115                 120                 125

Val Ser Leu Glu Pro Cys Asn His Tyr Gly Arg Thr Pro Pro Cys Thr
    130                 135                 140

Glu Ala Leu Ile Asn Ala Lys Val Lys Asp Val Val Val Gly Met Thr
145                 150                 155                 160

Asp Pro Asn Pro Ile Val Ala Ser Lys Gly Ile Glu Arg Leu Arg Ser
                165                 170                 175

Ala Gly Ile Asp Val Arg Leu Cys Val Asp Glu Glu Ala Ser Cys Arg
            180                 185                 190

Lys Leu Asn Glu Ala Tyr Ile His Arg Met Leu Thr Gly Lys Ala Phe
        195                 200                 205

Ala Thr Leu Arg Thr Thr Leu Ser Met Asn Gly Val Val Ile Asn Gln
    210                 215                 220

Ile Gly Ser Gly Ala Asp Gln Pro Glu Gly Tyr Tyr Ser Gln Leu Leu
225                 230                 235                 240

Lys Glu Tyr Asp Gly Val Ile Ile Ser Ser Asn Phe Ala Lys Thr Asn
                245                 250                 255

Thr Leu Pro Val Ser Arg Glu Ala Gly Ala Lys Gln Pro Leu Tyr Ile
            260                 265                 270

Ile Ile Ala Gln Cys Glu Asn Ser Gln Leu Asn Ile Pro Phe Leu Lys
        275                 280                 285

Glu Glu Arg Ala Ala Glu Ala Val Val Leu Ser Asp Ser Pro Ile Thr
    290                 295                 300

Val Glu Pro Ala Gly Val Asp Val Leu Val Leu Asp Gln Met Asn Leu
305                 310                 315                 320
```

-continued

```
Asp Ala Ile Leu Gln Leu Leu Ala Gln Arg Gly Leu Cys Ser Val Leu
                325                 330                 335

Val Asp Phe Arg Glu Ala Gly Gly Gly Ile Ala Ser Leu Leu Asn Asn
            340                 345                 350

Phe Gln Asp Asp Lys Leu Val Gln Lys Val Val Val Glu Leu Leu Pro
        355                 360                 365

Val Trp Ala Val Ser Lys Gly Pro Ser Asp Leu Ala Phe Gly Gly Ser
    370                 375                 380

Gln Ser Phe Pro Leu Lys Asp Val Glu His Ser Glu Val Asn Gly Ser
385                 390                 395                 400

Val Leu Leu Gln Gly Tyr Val
                405


<210> SEQ ID NO 79
<211> LENGTH: 866
<212> TYPE: DNA
<213> ORGANISM: Triticum aestivum

<400> SEQUENCE: 79

cccggcgact gctacgggga cagcaccgcc gtctcctccc tcgtgcagtc aggaattaca     60

agagttgtgg tgggtcttag acatcccttg aagcacttga gagggaaagc gattcaatca    120

ttgcgaagtg aaggcattca ggtcgatatt gtgggggaag atctccagag caaattgttc    180

aaggaagcct ttacttcatg cctcatcgta aatgctccat tactttaccg agctgccttt    240

cgtgttccat tctctgttct gaagtatgct atgactgcag atggaaaaat tgcagctagt    300

agtgggcatg cgtcttgggt aagcggcaga gcatccagag gccgagtatt tgaattgcgt    360

ggaagaagtg atgctgttat agttggtggg aatacagttc gccgtgatga tcctcgatta    420

actgcaaggc atgtgaaggg gcatgttcca gtgcgcattg taatgtcaca aacttgtaac    480

cttcctgaag aagcaaattt atggaatgtt catgaggcct atacaatagt tgcaacacaa    540

agaggtgctc ggagagattt ccaaaagaag cttgctatga agggtgttga agtagtggaa    600

tttgacatgc taaatcctag agatgttatg tcatattgtt atgatcgtgg ttacctttct    660

gtattatggg agtgcggtgg gaccctatca gctgctgcta tatctgcaag agttattcac    720

aaggtttatg cattctgtgc tccaaaaata atcggtggag taactgctcc aacaccagta    780

ggtgacctag ggatgaatca aatgactcag gcgattgatt taattgatgt ttcacatgag    840

catgtcacgg tcaatctgcc tcgtgc                                          866


<210> SEQ ID NO 80
<211> LENGTH: 288
<212> TYPE: PRT
<213> ORGANISM: Triticum aestivum

<400> SEQUENCE: 80

Pro Gly Asp Cys Tyr Gly Asp Ser Thr Ala Val Ser Ser Leu Val Gln
  1               5                  10                  15

Ser Gly Ile Thr Arg Val Val Val Gly Leu Arg His Pro Leu Lys His
            20                  25                  30

Leu Arg Gly Lys Ala Ile Gln Ser Leu Arg Ser Glu Gly Ile Gln Val
        35                  40                  45

Asp Ile Val Gly Glu Asp Leu Gln Ser Lys Leu Phe Lys Glu Ala Phe
     50                  55                  60

Thr Ser Cys Leu Ile Val Asn Ala Pro Leu Leu Tyr Arg Ala Ala Phe
 65                  70                  75                  80
```

-continued

```
Arg Val Pro Phe Ser Val Leu Lys Tyr Ala Met Thr Ala Asp Gly Lys
                85                  90                  95

Ile Ala Ala Ser Ser Gly His Ala Ser Trp Val Ser Gly Arg Ala Ser
            100                 105                 110

Arg Gly Arg Val Phe Glu Leu Arg Gly Arg Ser Asp Ala Val Ile Val
        115                 120                 125

Gly Gly Asn Thr Val Arg Arg Asp Asp Pro Arg Leu Thr Ala Arg His
    130                 135                 140

Val Lys Gly His Val Pro Val Arg Ile Val Met Ser Gln Thr Cys Asn
145                 150                 155                 160

Leu Pro Glu Glu Ala Asn Leu Trp Asn Val His Glu Ala Tyr Thr Ile
                165                 170                 175

Val Ala Thr Gln Arg Gly Ala Arg Arg Asp Phe Gln Lys Lys Leu Ala
            180                 185                 190

Met Lys Gly Val Glu Val Val Glu Phe Asp Met Leu Asn Pro Arg Asp
        195                 200                 205

Val Met Ser Tyr Cys Tyr Asp Arg Gly Tyr Leu Ser Val Leu Trp Glu
    210                 215                 220

Cys Gly Gly Thr Leu Ser Ala Ala Ala Ile Ser Ala Arg Val Ile His
225                 230                 235                 240

Lys Val Tyr Ala Phe Cys Ala Pro Lys Ile Ile Gly Gly Val Thr Ala
                245                 250                 255

Pro Thr Pro Val Gly Asp Leu Gly Met Asn Gln Met Thr Gln Ala Ile
            260                 265                 270

Asp Leu Ile Asp Val Ser His Glu His Val Thr Val Asn Leu Pro Arg
        275                 280                 285
```

<210> SEQ ID NO 81
<211> LENGTH: 1251
<212> TYPE: DNA
<213> ORGANISM: Oryza sativa

<400> SEQUENCE: 81

```
gcacgagctt acaagaggac ttaacaagat tgatgattcc tatgatgtct ccaattgcag     60

aaattgagga tatttcagct gctgcttcca cagtaacagt ggatgccaga gtgggcatat    120

caaccggcgt ctcggctgca gatagggcaa aaacgatttt tactctagcc tcccctgatt    180

ctaagccaac tgacctcaga agaccaggcc atatattccc tctaaaatac cgaaacggtg    240

gtgtgctaaa aagagctgga catactgagg catccgtcga tcttgtcgcg ttggctggct    300

tgcgccctgt gtctgtcctg tcaaccgtca tcaacccagt ggatggttca atggcaggaa    360

tgccagtgct gaaacagatg gctttggagc atgatatccc aattgtttca atcgctgatc    420

tcatccggta tagaaggaag agggagaagc tggtggaact gattgctgta tctcgtttgc    480

cgacgaaatg ggccttttc cgagcttact gctaccaatc caagcttgat ggaaccgagc    540

acattgctgt tgcaaagggc gacatcggcg acggcgagga cgtcttggtg agggtccatt    600

ccgagtgcct gaccggcgac atcctcggct ccgcccgctg cgactgcggc aaccagctgg    660

acctggcgat gcagctcatc gacaaggccg gccgcggcgt cctcgtctac ctccgcggcc    720

acgagggccg cggcatcggc ctcggccaga agctccgcgc ctacaacctc caggacgacg    780

gccacgacac cgtccaggcc aacgtcgagc tcggcctcgc cgtcgactcc cgcgagtacg    840

gcatcggcgc ccagattctg cgggacatgg gggtgcgcac gatgcggctg atgacgaaca    900

acccggcaaa gttcgtcggg ctcaagggct acgggctcgc cgtcgtcggc agggttccgg    960
```

-continued

```
tgatctcccc catcaccaag gagaaccaga ggtacctcga gacgaagcgc accaagatgg   1020

gccatgtcta cggctccgac ctccccggca acgtcccgga ggaattcctc aacccggacg   1080

acatcgccgg agaccaagac gaagacgaca cccacaactg aatgcaacaa caaaattcac   1140

aaccacagat tctccacatc tcattttgtg atcaaattgc atctcaaact gcaccgatct   1200

tgttatacta gtaacaaatc ttgatttgga accaaaaaaa aaaaaaaaaa a            1251
```

```
<210> SEQ ID NO 82
<211> LENGTH: 372
<212> TYPE: PRT
<213> ORGANISM: Oryza sativa

<400> SEQUENCE: 82

Thr Ser Leu Gln Glu Asp Leu Thr Arg Leu Met Ile Pro Met Met Ser
  1               5                  10                  15

Pro Ile Ala Glu Ile Glu Asp Ile Ser Ala Ala Ala Ser Thr Val Thr
             20                  25                  30

Val Asp Ala Arg Val Gly Ile Ser Thr Gly Val Ser Ala Ala Asp Arg
         35                  40                  45

Ala Lys Thr Ile Phe Thr Leu Ala Ser Pro Asp Ser Lys Pro Thr Asp
     50                  55                  60

Leu Arg Arg Pro Gly His Ile Phe Pro Leu Lys Tyr Arg Asn Gly Gly
 65                  70                  75                  80

Val Leu Lys Arg Ala Gly His Thr Glu Ala Ser Val Asp Leu Val Ala
                 85                  90                  95

Leu Ala Gly Leu Arg Pro Val Ser Val Leu Ser Thr Val Ile Asn Pro
            100                 105                 110

Val Asp Gly Ser Met Ala Gly Met Pro Val Leu Lys Gln Met Ala Leu
        115                 120                 125

Glu His Asp Ile Pro Ile Val Ser Ile Ala Asp Leu Ile Arg Tyr Arg
    130                 135                 140

Arg Lys Arg Glu Lys Leu Val Glu Leu Ile Ala Val Ser Arg Leu Pro
145                 150                 155                 160

Thr Lys Trp Gly Leu Phe Arg Ala Tyr Cys Tyr Gln Ser Lys Leu Asp
                165                 170                 175

Gly Thr Glu His Ile Ala Val Ala Lys Gly Asp Ile Gly Asp Gly Glu
            180                 185                 190

Asp Val Leu Val Arg Val His Ser Glu Cys Leu Thr Gly Asp Ile Leu
        195                 200                 205

Gly Ser Ala Arg Cys Asp Cys Gly Asn Gln Leu Asp Leu Ala Met Gln
    210                 215                 220

Leu Ile Asp Lys Ala Gly Arg Gly Val Leu Val Tyr Leu Arg Gly His
225                 230                 235                 240

Glu Gly Arg Gly Ile Gly Leu Gly Gln Lys Leu Arg Ala Tyr Asn Leu
                245                 250                 255

Gln Asp Asp Gly His Asp Thr Val Gln Ala Asn Val Glu Leu Gly Leu
            260                 265                 270

Ala Val Asp Ser Arg Glu Tyr Gly Ile Gly Ala Gln Ile Leu Arg Asp
        275                 280                 285

Met Gly Val Arg Thr Met Arg Leu Met Thr Asn Asn Pro Ala Lys Phe
    290                 295                 300

Val Gly Leu Lys Gly Tyr Gly Leu Ala Val Val Gly Arg Val Pro Val
305                 310                 315                 320
```

-continued

```
Ile Ser Pro Ile Thr Lys Glu Asn Gln Arg Tyr Leu Glu Thr Lys Arg
                325                 330                 335

Thr Lys Met Gly His Val Tyr Gly Ser Asp Leu Pro Gly Asn Val Pro
            340                 345                 350

Glu Glu Phe Leu Asn Pro Asp Asp Ile Ala Gly Asp Gln Asp Glu Asp
        355                 360                 365

Asp Thr His Asn
    370


<210> SEQ ID NO 83
<211> LENGTH: 475
<212> TYPE: DNA
<213> ORGANISM: Zea mays
<220> FEATURE:
<221> NAME/KEY: unsure
<222> LOCATION: (140)
<221> NAME/KEY: unsure
<222> LOCATION: (404)
<221> NAME/KEY: unsure
<222> LOCATION: (450)
<221> NAME/KEY: unsure
<222> LOCATION: (460)
<221> NAME/KEY: unsure
<222> LOCATION: (463)

<400> SEQUENCE: 83

gcaaggtgaa ccaggagacg cgcggtagat acatagtagc tgcaagtaca ttaattcgca      60

ctgaagatta ccaaaaccaa tggctgcgcg gtgcagcggc ggctgcgacg ggcgcgagga     120

cagcgccgtg gaggcctggn tgcagtggca gaaggtgagc gacttcctga tcggggcgtc     180

ctacatgtcc atcccgctgg aactgctgca cttcgccacc tgcgccgacc tcgcgccgct     240

gcggtgggtg ctcctccagt tcggcgcctt catcgtgctc tgggctcgtc caactcgtcg     300

catttcacta cgcccgccgg atcgcgccgc ttctgccggc agtatggtgg ccaacttgtg     360

actgtaatcg gtgctgaaat acacaagacc gacgagtggc attnagacta cctactgcgc     420

gtatgtacaa aagcaagttt agcggtcggn taaagacaan canttgtatg aaatg          475


<210> SEQ ID NO 84
<211> LENGTH: 67
<212> TYPE: PRT
<213> ORGANISM: Zea mays
<220> FEATURE:
<221> NAME/KEY: UNSURE
<222> LOCATION: (21)

<400> SEQUENCE: 84

Met Ala Ala Arg Cys Ser Gly Gly Cys Asp Gly Arg Glu Asp Ser Ala
  1               5                  10                  15

Val Glu Ala Trp Xaa Gln Trp Gln Lys Val Ser Asp Phe Leu Ile Gly
             20                  25                  30

Ala Ser Tyr Met Ser Ile Pro Leu Glu Leu Leu His Phe Ala Thr Cys
         35                  40                  45

Ala Asp Leu Ala Pro Leu Arg Trp Val Leu Leu Gln Phe Gly Ala Phe
     50                  55                  60

Ile Val Leu
 65


<210> SEQ ID NO 85
<211> LENGTH: 2463
<212> TYPE: DNA
<213> ORGANISM: Zea mays
```

<400> SEQUENCE: 85

```
ccacgcgtcc gcgtctggtg aatgcaggag cgtcggcacc cgcagcgtgg aatcgacgac     60
gggcgcctcc agtcggttca gaaatgcgca aatgcgcgtc tgaatgaagc ctggttggag    120
gtggtagagc cgatggtggt gggaacggca ctgctgcgcg gggtttcctc cgcgtggatc    180
ctcctgttcc tctcctccct gctcctctcg ccgtcagcgg cgtctgtcga tttcggccac    240
tgcggcggct gcgacgacgc cgacgacggc gccctctcca gcacctataa catcctgcaa    300
tgccagaagg tcagcgactt cctcatcgcc gcggcctact tctccatccc gctcgagctg    360
ctctacttcg ccacctgctc cgacctcttc cccctcaaat ggatcgtgct gcagttcggc    420
gccttcatcg tgctctgcgg cctcacgcac ctcatcactg tgttcaccta cgagccgcac    480
tccttccacc tcgtactcgc ccttaccgtc gccaagttcc tgacggcact ggtctccttc    540
gcgacggcca tcaccctgct gacgctgata ccacagctcc tgagggtgaa ggtcagggaa    600
aacttcctga tgaacaaggc gcgtgagctg gaccgggagg tggggaggat gaaaaggaaa    660
gaagaggcga gctggcatgt gcgcatgctc acacaggaga tccgcaagtc gctcgacaga    720
cataccatct tgtacaccac catggttgag ctctcgaagg cactggaact gcagaattgt    780
gctgtctgga tgcctgatga gaccaggagc acgatgatct taacacatca gctgagggaa    840
agggatataa tggacccaca gaaacactcg attcctattg atgatccgga tgttcaagaa    900
ataaaggcaa ccaaggatgc aaaagttctt ggcccagatt cggcgctagg ggtttctagc    960
cgaagcaagc atgaagcagg gcctgtggct gcaataagga tgccgatgtt aagggtgtca   1020
aatttcaaag gagggactcc ggaagtgatg cagacgagct atgctatctt ggttctggtt   1080
ttgcctaatg atggttcatt agggtggggt cgaagagagt tggagattgt tgaggtagtt   1140
gctgaccaag ttgcagtcgc tctgtcacat gctgcactcc tagaggagtc tcagctgatg   1200
cgagagaagc ttgccgagca gcatagggac ttgctgcagg caaaggatga agccatgagg   1260
gcaggggacg ctaggaattc cttccagact gcaatgtacg atggaatgcg aaggccaatg   1320
cactcaatcc ttggtctcgt ctcaatgatg caacaggaga gcatgaatcc agagcaaagg   1380
cttgtgatgg atgccattgc caagacaagc agtgttgcat ccacactgat gaacgatgtg   1440
atgcaaacat cgacaatgaa ctgtgagcac ttgtctttgg tcaggaggcc gttcaacctt   1500
cattccttca ttaaagaagt tgttggagtg gtcagatgtc taactggttg caagggtgtg   1560
gagtttgagt ttcaagtgga gaattctttg ccagaaagga tcattggtga tgagaagaga   1620
gtcttccata ttgtcctgca catggtaggc actctaacag accgatgtaa tgctggctgt   1680
atctcattat atgtaaatgt ccataatgag gttgaagata ggcataatca tgactggatg   1740
ctgcgaagag caaacttctc tgggggctat gtatgtgtga aatttgagat taggattaga   1800
aaatcaaagg gctatctgtt gagttcatca agcagtcaga taagtcaggg atccaaaccc   1860
aacaattctg agatggggct tagcttcaat atgtgcaaga agattgtgca gatgatgaat   1920
ggcaatattt ggtcagtatc agattctaaa agcatcggag aaactatcat gctagtcctc   1980
cagttccagt tggaacctgt gactccggtc tctggagcgt cctcagattt gtacagatca   2040
tccgcaattc ccaactttaa tgggctcaga gtcctccttg cggacagcga ctgcaccaac   2100
cgagctgtaa ctcacaggct cctagagaag cttggttgcc gagtcctttc ggtcgcttct   2160
ggcgtccaat gcatcagctc cttcgctgcg gagtcgtcct tccagctggt ggttcttgat   2220
cttgacatgc agacgatgga tggattcgaa gtagcccgcg cgatcaggaa gttcagtagc   2280
aatagttggc tgccgttgat tattgcccta gcagcaagaa tcgacgacaa catccgggat   2340
```

-continued cgttgccaga ggtcaggagt aaatggcctg atccagaaac cggtcacatt agccgcgctg 2400
ggagatgaac tgtatagagt ccttcagaac aattaaaaga gcctgacggt tctcatttct 2460
ttc 2463

<210> SEQ ID NO 86
<211> LENGTH: 804
<212> TYPE: PRT
<213> ORGANISM: Zea mays

<400> SEQUENCE: 86

Met Gln Glu Arg Arg His Pro Gln Arg Gly Ile Asp Asp Gly Arg Leu
1 5 10 15

Gln Ser Val Gln Lys Cys Ala Asn Ala Arg Leu Asn Glu Ala Trp Leu
20 25 30

Glu Val Val Glu Pro Met Val Val Gly Thr Ala Leu Leu Arg Gly Val
35 40 45

Ser Ser Ala Trp Ile Leu Leu Phe Leu Ser Ser Leu Leu Leu Ser Pro
50 55 60

Ser Ala Ala Ser Val Asp Phe Gly His Cys Gly Gly Cys Asp Asp Ala
65 70 75 80

Asp Asp Gly Ala Leu Ser Ser Thr Tyr Asn Ile Leu Gln Cys Gln Lys
85 90 95

Val Ser Asp Phe Leu Ile Ala Ala Ala Tyr Phe Ser Ile Pro Leu Glu
100 105 110

Leu Leu Tyr Phe Ala Thr Cys Ser Asp Leu Phe Pro Leu Lys Trp Ile
115 120 125

Val Leu Gln Phe Gly Ala Phe Ile Val Leu Cys Gly Leu Thr His Leu
130 135 140

Ile Thr Val Phe Thr Tyr Glu Pro His Ser Phe His Leu Val Leu Ala
145 150 155 160

Leu Thr Val Ala Lys Phe Leu Thr Ala Leu Val Ser Phe Ala Thr Ala
165 170 175

Ile Thr Leu Leu Thr Leu Ile Pro Gln Leu Leu Arg Val Lys Val Arg
180 185 190

Glu Asn Phe Leu Met Asn Lys Ala Arg Glu Leu Asp Arg Glu Val Gly
195 200 205

Arg Met Lys Arg Lys Glu Glu Ala Ser Trp His Val Arg Met Leu Thr
210 215 220

Gln Glu Ile Arg Lys Ser Leu Asp Arg His Thr Ile Leu Tyr Thr Thr
225 230 235 240

Met Val Glu Leu Ser Lys Ala Leu Glu Leu Gln Asn Cys Ala Val Trp
245 250 255

Met Pro Asp Glu Thr Arg Ser Thr Met Ile Leu Thr His Gln Leu Arg
260 265 270

Glu Arg Asp Ile Met Asp Pro Gln Lys His Ser Ile Pro Ile Asp Asp
275 280 285

Pro Asp Val Gln Glu Ile Lys Ala Thr Lys Asp Ala Lys Val Leu Gly
290 295 300

Pro Asp Ser Ala Leu Gly Val Ser Ser Arg Ser Lys His Glu Ala Gly
305 310 315 320

Pro Val Ala Ala Ile Arg Met Pro Met Leu Arg Val Ser Asn Phe Lys
325 330 335

Gly Gly Thr Pro Glu Val Met Gln Thr Ser Tyr Ala Ile Leu Val Leu
340 345 350

-continued

```
Val Leu Pro Asn Asp Gly Ser Leu Gly Trp Gly Arg Arg Glu Leu Glu
        355                 360                 365

Ile Val Glu Val Val Ala Asp Gln Val Ala Val Ala Leu Ser His Ala
    370                 375                 380

Ala Leu Leu Glu Glu Ser Gln Leu Met Arg Glu Lys Leu Ala Glu Gln
385                 390                 395                 400

His Arg Asp Leu Leu Gln Ala Lys Asp Glu Ala Met Arg Ala Gly Asp
                405                 410                 415

Ala Arg Asn Ser Phe Gln Thr Ala Met Tyr Asp Gly Met Arg Arg Pro
            420                 425                 430

Met His Ser Ile Leu Gly Leu Val Ser Met Met Gln Gln Glu Ser Met
        435                 440                 445

Asn Pro Glu Gln Arg Leu Val Met Asp Ala Ile Ala Lys Thr Ser Ser
    450                 455                 460

Val Ala Ser Thr Leu Met Asn Asp Val Met Gln Thr Ser Thr Met Asn
465                 470                 475                 480

Cys Glu His Leu Ser Leu Val Arg Arg Pro Phe Asn Leu His Ser Phe
                485                 490                 495

Ile Lys Glu Val Val Gly Val Val Arg Cys Leu Thr Gly Cys Lys Gly
            500                 505                 510

Val Glu Phe Glu Phe Gln Val Glu Asn Ser Leu Pro Glu Arg Ile Ile
        515                 520                 525

Gly Asp Glu Lys Arg Val Phe His Ile Val Leu His Met Val Gly Thr
    530                 535                 540

Leu Thr Asp Arg Cys Asn Ala Gly Cys Ile Ser Leu Tyr Val Asn Val
545                 550                 555                 560

His Asn Glu Val Glu Asp Arg His Asn His Asp Trp Met Leu Arg Arg
                565                 570                 575

Ala Asn Phe Ser Gly Gly Tyr Val Cys Val Lys Phe Glu Ile Arg Ile
            580                 585                 590

Arg Lys Ser Lys Gly Tyr Leu Leu Ser Ser Ser Ser Ser Gln Ile Ser
        595                 600                 605

Gln Gly Ser Lys Pro Asn Asn Ser Glu Met Gly Leu Ser Phe Asn Met
    610                 615                 620

Cys Lys Lys Ile Val Gln Met Met Asn Gly Asn Ile Trp Ser Val Ser
625                 630                 635                 640

Asp Ser Lys Ser Ile Gly Glu Thr Ile Met Leu Val Leu Gln Phe Gln
                645                 650                 655

Leu Glu Pro Val Thr Pro Val Ser Gly Ala Ser Ser Asp Leu Tyr Arg
            660                 665                 670

Ser Ser Ala Ile Pro Asn Phe Asn Gly Leu Arg Val Leu Leu Ala Asp
        675                 680                 685

Ser Asp Cys Thr Asn Arg Ala Val Thr His Arg Leu Leu Glu Lys Leu
    690                 695                 700

Gly Cys Arg Val Leu Ser Val Ala Ser Gly Val Gln Cys Ile Ser Ser
705                 710                 715                 720

Phe Ala Ala Glu Ser Ser Phe Gln Leu Val Val Leu Asp Leu Asp Met
                725                 730                 735

Gln Thr Met Asp Gly Phe Glu Val Ala Arg Ala Ile Arg Lys Phe Ser
            740                 745                 750

Ser Asn Ser Trp Leu Pro Leu Ile Ile Ala Leu Ala Ala Arg Ile Asp
        755                 760                 765
```

-continued

```
Asp Asn Ile Arg Asp Arg Cys Gln Arg Ser Gly Val Asn Gly Leu Ile
    770                 775                 780

Gln Lys Pro Val Thr Leu Ala Ala Leu Gly Asp Glu Leu Tyr Arg Val
785                 790                 795                 800

Leu Gln Asn Asn


<210> SEQ ID NO 87
<211> LENGTH: 2308
<212> TYPE: DNA
<213> ORGANISM: Zea mays

<400> SEQUENCE: 87

ccacgcgtcc gctttctccc gttcaccccg cgtgcacgct ctttcccttc ctcgtgccga     60

cgaccgggcg accgccgcgc cccggcccgc gccccttgt ctcgggccac tcgccggcaa    120

cgagcagcca ccaggaaatg ttgtgaggac tgatgcaata actaagcttg ctggatggac    180

ggatgtgatt gcatcgagcc actatggcct accgatgatc tccttgtcaa gtatcagtac    240

atctcagact tcttcatagc cctagcgtac ttctctattc cgttggagct catatatttc    300

gtgaagaagt cgtccttctt cccgtacaga tgggtcttga tccagtttgg tgcgtttata    360

gttctctgtg ggcaacccca tctgataaac ctgtggacgt tcaccacaca tacaaagacc    420

gttgcgatgg tcatgaccat agcaaaggtt tctacagcag ttgtgtcctg tgcaactgct    480

ttgatgcttg ttcatatcat ccccgactta ttgagcgtga aaactagaga gttgttcctg    540

aagaataaag ctgaagagct tgacagagag atgggactga taaggacgca ggaggagacc    600

ggtagacatg ttaggatgct tacacatgaa atcagaagta ctcttgacag gcatacgatt    660

ttgaagacta ctcttgttga gctaggaagg accttgggtc tggaggaatg tgcattgtgg    720

atgccatctc gaagtggttc aagccttcag ctttctcata ctttgcacca ccagattact    780

gttggatcat cggtgccaat taatcttcct gtcatcaatc aagtgttcag tagcaaccgg    840

gcaattataa taccccacac atctcctttg gcgcggattc gacctcttac agggcgatat    900

gttccaccag aagtggctgc agtccgtgta cctcttctcc acctttcaaa cttccaaata    960

aatgattggc ctgagctttc agcaaaaagc tttgcaatca tggttttgat gcttccatct   1020

gatagtgcaa gaaaatggca tgtacatgaa ttggagctgg ttgaggtcgt tgctgatcag   1080

gtagcagttg cactatctca tgcggctatt cttgaagagt ccatgcgagc acgtgattta   1140

ctaatggagc agaatgttgc cctggattta gctcgaagag aggctgagat ggctatccgt   1200

gctcgcaatg atttcctagc tgttatgaat cacgaaatga gaacacccat gaatgcaata   1260

atagcccttt cctccttgct tttggaaact gaacttactc ctgagcagcg tctaatggtg   1320

gaaacagtac tgaaaagcag caatctgtta gcaacactca tcaatgatgt gctagatctt   1380

tccaaactcg aggatggaag ccttgaactg gagattaaag cattcaatct tcatgctgtt   1440

ttcaaagaag tgatgggttt cattaaacca attgcatcta tcaagaggct atctgtatcg   1500

gttatgttgg caccagattt gccgttatgt gccattggtg atgaaaagag actcatgcaa   1560

actattctga acatctctgg caacgctgta aagtttacca aggagggaca catcacactt   1620

gtagcttcca ttgtgaaggc tgactctttg agagagttca gaaccccaga atttcatcca   1680

actgcaagtg atgaccattt ctatttgaaa gttcaggtaa aagatacagg ctgtggaatt   1740

ggtccacagg atctacctca tgtatttaca aagtttgctc atcctcaaag cggaggaaac   1800

cgagggttta atggtagtgg tcttggcctt gccatatgca agaggtttgt tagtctcatg   1860

ggagggcaca tctggattga cagcgaagga accggaagag gttgcaccgc aacattcgtc   1920
```

-continued

```
gtcaagctcg gcgtgtgtga caacacaaac acctaccagc agcagctgat ccctctagta   1980

tggccaagca gtgcagactc cgatttgcgt gctccgaaag cgcttccgga cgggagagga   2040

tctacaccct tgaaatcccg gtaccaaagg agcgtatgag cctagtgtaa atgattgacg   2100

gcatagtgcc aagtagggga ccgattagtg ccaccgtcta attttgtttg taaccctgtc   2160

atagcaggca tatgatgtac aaatactgta aagcaaatgg agactgcggc cgtgtatctg   2220

ggtggcaacg ctgacttgct gcattgagtg gtatatacat atgctaccag cggattgaat   2280

tgcttaaaaa aaaaaaaaaa aaaaaaag                                      2308


<210> SEQ ID NO 88
<211> LENGTH: 634
<212> TYPE: PRT
<213> ORGANISM: Zea mays

<400> SEQUENCE: 88

Met Asp Gly Cys Asp Cys Ile Glu Pro Leu Trp Pro Thr Asp Asp Leu
  1               5                  10                  15

Leu Val Lys Tyr Gln Tyr Ile Ser Asp Phe Phe Ile Ala Leu Ala Tyr
             20                  25                  30

Phe Ser Ile Pro Leu Glu Leu Ile Tyr Phe Val Lys Lys Ser Ser Phe
         35                  40                  45

Phe Pro Tyr Arg Trp Val Leu Ile Gln Phe Gly Ala Phe Ile Val Leu
     50                  55                  60

Cys Gly Ala Thr His Leu Ile Asn Leu Trp Thr Phe Thr Thr His Thr
 65                  70                  75                  80

Lys Thr Val Ala Met Val Met Thr Ile Ala Lys Val Ser Thr Ala Val
                 85                  90                  95

Val Ser Cys Ala Thr Ala Leu Met Leu Val His Ile Ile Pro Asp Leu
            100                 105                 110

Leu Ser Val Lys Thr Arg Glu Leu Phe Leu Lys Asn Lys Ala Glu Glu
        115                 120                 125

Leu Asp Arg Glu Met Gly Leu Ile Arg Thr Gln Glu Glu Thr Gly Arg
    130                 135                 140

His Val Arg Met Leu Thr His Glu Ile Arg Ser Thr Leu Asp Arg His
145                 150                 155                 160

Thr Ile Leu Lys Thr Thr Leu Val Glu Leu Gly Arg Thr Leu Gly Leu
                165                 170                 175

Glu Glu Cys Ala Leu Trp Met Pro Ser Arg Ser Gly Ser Ser Leu Gln
            180                 185                 190

Leu Ser His Thr Leu His His Gln Ile Thr Val Gly Ser Ser Val Pro
        195                 200                 205

Ile Asn Leu Pro Val Ile Asn Gln Val Phe Ser Ser Asn Arg Ala Ile
    210                 215                 220

Ile Ile Pro His Thr Ser Pro Leu Ala Arg Ile Arg Pro Leu Thr Gly
225                 230                 235                 240

Arg Tyr Val Pro Pro Glu Val Ala Ala Val Arg Val Pro Leu Leu His
                245                 250                 255

Leu Ser Asn Phe Gln Ile Asn Asp Trp Pro Glu Leu Ser Ala Lys Ser
            260                 265                 270

Phe Ala Ile Met Val Leu Met Leu Pro Ser Asp Ser Ala Arg Lys Trp
        275                 280                 285

His Val His Glu Leu Glu Leu Val Glu Val Val Ala Asp Gln Val Ala
    290                 295                 300
```

-continued

```
Val Ala Leu Ser His Ala Ala Ile Leu Glu Glu Ser Met Arg Ala Arg
305                 310                 315                 320

Asp Leu Leu Met Glu Gln Asn Val Ala Leu Asp Leu Ala Arg Arg Glu
                325                 330                 335

Ala Glu Met Ala Ile Arg Ala Arg Asn Asp Phe Leu Ala Val Met Asn
            340                 345                 350

His Glu Met Arg Thr Pro Met Asn Ala Ile Ile Ala Leu Ser Ser Leu
        355                 360                 365

Leu Leu Glu Thr Glu Leu Thr Pro Glu Gln Arg Leu Met Val Glu Thr
    370                 375                 380

Val Leu Lys Ser Ser Asn Leu Leu Ala Thr Leu Ile Asn Asp Val Leu
385                 390                 395                 400

Asp Leu Ser Lys Leu Glu Asp Gly Ser Leu Glu Leu Glu Ile Lys Ala
                405                 410                 415

Phe Asn Leu His Ala Val Phe Lys Glu Val Met Gly Phe Ile Lys Pro
            420                 425                 430

Ile Ala Ser Ile Lys Arg Leu Ser Val Ser Val Met Leu Ala Pro Asp
        435                 440                 445

Leu Pro Leu Cys Ala Ile Gly Asp Glu Lys Arg Leu Met Gln Thr Ile
    450                 455                 460

Leu Asn Ile Ser Gly Asn Ala Val Lys Phe Thr Lys Glu Gly His Ile
465                 470                 475                 480

Thr Leu Val Ala Ser Ile Val Lys Ala Asp Ser Leu Arg Glu Phe Arg
                485                 490                 495

Thr Pro Glu Phe His Pro Thr Ala Ser Asp Asp His Phe Tyr Leu Lys
            500                 505                 510

Val Gln Val Lys Asp Thr Gly Cys Gly Ile Gly Pro Gln Asp Leu Pro
        515                 520                 525

His Val Phe Thr Lys Phe Ala His Pro Gln Ser Gly Gly Asn Arg Gly
    530                 535                 540

Phe Asn Gly Ser Gly Leu Gly Leu Ala Ile Cys Lys Arg Phe Val Ser
545                 550                 555                 560

Leu Met Gly Gly His Ile Trp Ile Asp Ser Glu Gly Thr Gly Arg Gly
                565                 570                 575

Cys Thr Ala Thr Phe Val Val Lys Leu Gly Val Cys Asp Asn Thr Asn
            580                 585                 590

Thr Tyr Gln Gln Gln Leu Ile Pro Leu Val Trp Pro Ser Ser Ala Asp
        595                 600                 605

Ser Asp Leu Arg Ala Pro Lys Ala Leu Pro Asp Gly Arg Gly Ser Thr
    610                 615                 620

Pro Leu Lys Ser Arg Tyr Gln Arg Ser Val
625                 630
```

<210> SEQ ID NO 89
<211> LENGTH: 2593
<212> TYPE: DNA
<213> ORGANISM: Oryza sativa

<400> SEQUENCE: 89

```
gcacgagctt acaattgcat tgagccgctc tggcaggcgg atgatctcct tgtaaagtat     60

cagtacatat ctgacttctt tattgcgctc gcttacttct cgatcccttt ggagctcata    120

tatttcgtta agaagtcagc attcttccct taccgatggg tgcttataca attcggcgca    180

ttcattgttc tttgtggggc aacccacctg ataaatttgt ggacttttgc catatatacc    240
```

-continued

```
aagactatag ctgtggtact gacagtggcg aaagcagcga cagcggttgt ttcgtgcatc    300
acagctttga tgcttgtgca tataattcct gatttgttga atgtgaagtt gagagagaga    360
tttctgaagg ataaggctga tgagcttgat agagagatgg ggattataag aacacaagag    420
gagacaggaa gacatgtcca catgctgacc catgagataa gaagcacact tgacaggcac    480
accattctgc gaactacgct cgtcgagctg ggaaggactc ttgttttagc ggagtgtgcc    540
ctgtggatgc caacacgctc tggatcggcc cttcagctct ctcatacgat atataacagc    600
gcagcaattg gatcagttgt tcctatcaac cttcccattg tcagtaaggt ttttaatagt    660
aaccgtgtag taaaaattcc gcatacctcc ccgttagctt cgataacggc tgacaaaagc    720
agacagtgca agagaatggc ggccgcatga acgggagctt gttgaagtcg ttgctgatca    780
ggtagcggtc gcattgtctc atgctgccat tttggaagag tccatgcggg cccgtgatct    840
actaatggag caaaacattg ctcttgatgc agcacgtcgg gaggcagaaa tggctatttg    900
tgcccgtaat gattttcttg ctgtaatgaa ccatgaaatg cggactccta tgcgagcaat    960
cgtttctttg tcctctctcc ttttagaaac aaatcttagt gctgaacaac gcctaatggt   1020
tgagactata ctaaagagta gcgatcttct ggcaactctt acgaatgatg ttttggacgt   1080
ttcaaagctt gagaatggga gtcttgagct ggaaattgca ccttttaatt tgcattccac   1140
ctttacagat gtggttaatt tgattaagcc agtagcagcg tgcaagaggc tctcggttat   1200
ggtcactttg gcaccagagt tacctctaca tgctattggt gatcaaaagc gattgatgca   1260
aataatccta aatgttgccg ggaactccat taagttcaca aaggagggtc atgtttcgat   1320
tacagcttct atggccagac cagatgcttt gagaggtcca catgaacctg actaccatcc   1380
agttgtctct gatggattct tttacctggc tgttcaggta aaagacacag gctgcggaat   1440
cagccctcag gatatgcccc acacattcag aaagtttgca caccctgaaa acgcaggcaa   1500
atggaacagt ggcagtggat tggggctggc cctttccaga agatttgtca gtctaatgga   1560
aggtaacatc tggctcgaga gcgaaggcgt cgggaagggc tgtaccgcga tgttctttgt   1620
gaaacttggc atgcctgaga aaccaaatgc aaacctccga agaatggcgc cgcaccctct   1680
acagccaaac caaggagctg gaggccctga tgccctcagt atatccataa tggacagcaa   1740
cccgagggtt cctcgggttc gctaccaatc aagcgtatga gaagcaccga tgatgccatc   1800
gccatgccaa ggcagagcat ccgacccagt tttgccatca cagtttacag ctccatttgc   1860
agctctcttt ttgatgtatg gatggtagat gttgttcttg tccatcagtg gaggtacctt   1920
gggcatgctg gtataagttt cattggcatt cttgaatctt gatttcagtt gtgagggtga   1980
ttgggtggtc ttaagtggtg acaattgtga aagctgatgt agtgatcttt tgcagctctc   2040
tttttgatgt atggatggta gatgttgttc ttgtccatca gtagaggtac cttttgggca   2100
tgatggtata agtttcattg gcattcttga ttgcagttgt gagggcgatt gggtgatctt   2160
aagtggtgac aattgggaaa gctgatgtag tgatctgttg tctgcacgag tctgaagtta   2220
ctgggaagtg ccaatttact gcaagtgaca gtgaacatga aggtctatgg ccatcttaca   2280
tctctgatac cctgagctat agaagagctt ggacgaacgt gtttattttt cttacttttt   2340
tttccctaga ttagggctac aacctggaag ggatcgatct actagctgat tgcagtatca   2400
tttgtacttt ttgttttttt tttctgaaat aagagtatca gtggtaattg taagcgttac   2460
tgcagtgctt tataagcaca agcaaattat catcaaatca aattatagaa aaatctagtg   2520
aattaaaaag agctcaataa gatgaaccta caagcgaagt gtttactgct caaaaaaaaa   2580
aaaaaaaaaa aaa                                                      2593
```

-continued

```
<210> SEQ ID NO 90
<211> LENGTH: 592
<212> TYPE: PRT
<213> ORGANISM: Oryza sativa
<220> FEATURE:
<221> NAME/KEY: UNSURE
<222> LOCATION: (236)..(237)..(238)..(239)

<400> SEQUENCE: 90

Ala Arg Ala Tyr Asn Cys Ile Glu Pro Leu Trp Gln Ala Asp Asp Leu
  1               5                  10                  15

Leu Val Lys Tyr Gln Tyr Ile Ser Asp Phe Phe Ile Ala Leu Ala Tyr
             20                  25                  30

Phe Ser Ile Pro Leu Glu Leu Ile Tyr Phe Val Lys Lys Ser Ala Phe
         35                  40                  45

Phe Pro Tyr Arg Trp Val Leu Ile Gln Phe Gly Ala Phe Ile Val Leu
     50                  55                  60

Cys Gly Ala Thr His Leu Ile Asn Leu Trp Thr Phe Ala Ile Tyr Thr
 65                  70                  75                  80

Lys Thr Ile Ala Val Val Leu Thr Val Ala Lys Ala Ala Thr Ala Val
                 85                  90                  95

Val Ser Cys Ile Thr Ala Leu Met Leu Val His Ile Ile Pro Asp Leu
            100                 105                 110

Leu Asn Val Lys Leu Arg Glu Arg Phe Leu Lys Asp Lys Ala Asp Glu
        115                 120                 125

Leu Asp Arg Glu Met Gly Ile Ile Arg Thr Gln Glu Glu Thr Gly Arg
    130                 135                 140

His Val His Met Leu Thr His Glu Ile Arg Ser Thr Leu Asp Arg His
145                 150                 155                 160

Thr Ile Leu Arg Thr Thr Leu Val Glu Leu Gly Arg Thr Leu Val Leu
                165                 170                 175

Ala Glu Cys Ala Leu Trp Met Pro Thr Arg Ser Gly Ser Ala Leu Gln
            180                 185                 190

Leu Ser His Thr Ile Tyr Asn Ser Ala Ala Ile Gly Ser Val Val Pro
        195                 200                 205

Ile Asn Leu Pro Ile Val Ser Lys Val Phe Asn Ser Asn Arg Val Val
    210                 215                 220

Lys Ile Pro His Thr Ser Pro Leu Ala Ser Ile Xaa Xaa Xaa Xaa Ala
225                 230                 235                 240

Asp Ser Ala Arg Glu Trp Arg Pro His Glu Arg Glu Leu Val Glu Val
                245                 250                 255

Val Ala Asp Gln Val Ala Val Ala Leu Ser His Ala Ala Ile Leu Glu
            260                 265                 270

Glu Ser Met Arg Ala Arg Asp Leu Leu Met Glu Gln Asn Ile Ala Leu
        275                 280                 285

Asp Ala Ala Arg Arg Glu Ala Glu Met Ala Ile Cys Ala Arg Asn Asp
    290                 295                 300

Phe Leu Ala Val Met Asn His Glu Met Arg Thr Pro Met Arg Ala Ile
305                 310                 315                 320

Val Ser Leu Ser Ser Leu Leu Leu Glu Thr Asn Leu Ser Ala Glu Gln
                325                 330                 335

Arg Leu Met Val Glu Thr Ile Leu Lys Ser Ser Asp Leu Leu Ala Thr
            340                 345                 350

Leu Thr Asn Asp Val Leu Asp Val Ser Lys Leu Glu Asn Gly Ser Leu
        355                 360                 365
```

```
Glu Leu Glu Ile Ala Pro Phe Asn Leu His Ser Thr Phe Thr Asp Val
    370                 375                 380

Val Asn Leu Ile Lys Pro Val Ala Ala Cys Lys Arg Leu Ser Val Met
385                 390                 395                 400

Val Thr Leu Ala Pro Glu Leu Pro Leu His Ala Ile Gly Asp Gln Lys
                405                 410                 415

Arg Leu Met Gln Ile Ile Leu Asn Val Ala Gly Asn Ser Ile Lys Phe
            420                 425                 430

Thr Lys Glu Gly His Val Ser Ile Thr Ala Ser Met Ala Arg Pro Asp
        435                 440                 445

Ala Leu Arg Gly Pro His Glu Pro Asp Tyr His Pro Val Val Ser Asp
    450                 455                 460

Gly Phe Phe Tyr Leu Ala Val Gln Val Lys Asp Thr Gly Cys Gly Ile
465                 470                 475                 480

Ser Pro Gln Asp Met Pro His Thr Phe Arg Lys Phe Ala His Pro Glu
                485                 490                 495

Asn Ala Gly Lys Trp Asn Ser Gly Ser Gly Leu Gly Leu Ala Leu Ser
            500                 505                 510

Arg Arg Phe Val Ser Leu Met Glu Gly Asn Ile Trp Leu Glu Ser Glu
        515                 520                 525

Gly Val Gly Lys Gly Cys Thr Ala Met Phe Phe Val Lys Leu Gly Met
    530                 535                 540

Pro Glu Lys Pro Asn Ala Asn Leu Arg Arg Met Ala Pro His Pro Leu
545                 550                 555                 560

Gln Pro Asn Gln Gly Ala Gly Gly Pro Asp Ala Leu Ser Ile Ser Ile
                565                 570                 575

Met Asp Ser Asn Pro Arg Val Pro Arg Val Arg Tyr Gln Ser Ser Val
            580                 585                 590


<210> SEQ ID NO 91
<211> LENGTH: 2311
<212> TYPE: DNA
<213> ORGANISM: Glycine max

<400> SEQUENCE: 91

gcacgagtgt cttcacctaa ccaaatgggc gcctccacca cctgatccac ctctgtttct     60

tcttcctttc atccgttcat acgggggtta gatgatggag tcctgtgatt gtatagatac    120

gcagtatccg ccggatgaac ttcttgtgaa gtatcagtat atctcggatg tgctaattgc    180

tcttgcgtat ttttcgattc cggtggagct catctatttt gttcagaagt ctgctttctt    240

tccgtataga tgggtgctta tgcagtttgg tgcctttatt gttctctgtg gagcaactca    300

tttcataaac ctgtggacat tctctccgca ctctaagtct gttgctgttg tcatgacgat    360

tgccaaagtt tcgtgtgcta ttgtgtcatg tgcgacggca ctgatgcttg tacacattat    420

tcccgatctg ttgagtgtca agaggcgcga atcgatcctc aagaacaagg ctgaagagct    480

tgacagagag atgggactta ttcttactca ggaagagacg ggaagacatg ttagaatgtt    540

gactcatgaa attaggagca cacttgacag gcatacaatt ttaaagacta ctcttgtgga    600

gctggggagg actttgggct tggaggagtg tgcattatgg atgccttcga gaagtggtct    660

gaatctgcaa ctttcccata ctttaaccta tcatgtgcaa gttgggtcta cggtgcaaac    720

aaacaatcct attgtcaatg aagttttcaa cagccctcaa gctatgcgga taccacccac    780

ctgtccattg gccaggatca gacctcttgt gggaagatat gtgcccccctg aagttgttgc    840

tgttcgggtg ccgcttttga atctgtcaaa ttttcaaatt aacgattggc ctgatatttc    900
```

```
agcaaagagc tatgcaatca tggttctcat cctccctact gacagtgtta gaaaatggcg    960

agaccatgag ttggaacttg ttgatgttgt tgcagatcag gtagcagttg ccctttcaca   1020

tgctgctatt ttggaggagt ctatgcgtgc ccgtgatcaa ctcatggagc agaatgttgc   1080

tttagattta gcccggcgag aggcagagat ggcaattcat gctcgcaatg attttcttgc   1140

tgtcatgaat catgaaatga ggacaccaat gcatgcaatt atagcattgt catcacttct   1200

cttggagact gaactgacgc cagagcaaag ggttatgata gagacagtgt tgaagagtag   1260

taatgttttg gcaacactca ttaatgatgt tctagatctt tctcgacttg aagatggtag   1320

cctcgaatta gaaatgggaa aattcaacct ccatggagtt ttgggagaga ttgttgaact   1380

gataaaacca atagcatccg tgaaaaagtt acctatcacc ttaattctgt ctcctgatct   1440

gcctactcat gccattggtg atgaaaagcg gcttacacaa actcttttga atgtcgtggg   1500

taatgctgtc aaattcacta aggagggcta tgtttctgta agagtatcag ttgcaaaacc   1560

agaatcttca caggattggc gacctccaga gttttatcca gcatctagtg atggccattt   1620

ctacattcga gtccaggtta aggactctgg atgtgggatt ctcccacaag atattccgca   1680

tctctttacc aagtttgccc agtctcggag tggaccagct cgacctagca gtggtgcagg   1740

tcttgggctt gccatttgta aaagatttgt aaacctcatg ggaggccaca tatggattga   1800

gagtgagggc cttgacaaag gaagcacagc tacatttata gtcaaacttg ggatttgtgg   1860

caatccagat ccatccgatc atcaagctgc aaacagaagc caagcatata gtggaagtgg   1920

tggcctcgct agatttaaac ccttcatcac agatgaaaac gacactggtt tttctactag   1980

acgcaatcaa agaagtttct aatatccaag acaccaaaat tgcatacctc tcaatcacag   2040

tcgacaagat ggagtaaacc tcctactttc attttgcatg tgctaaattg tataatttgc   2100

agtttgcggc tgtagaatag gattactatg tcaggcatat ttctaacaaa caggttttat   2160

gcgaactcct gttgtattaa ctggaataca atacaacaaa acaaagttga gagacgatct   2220

gttacttaat ttgacttgta gtatatattg tcagtggcaa aaaaaaaaaa aaaaaaaaaa   2280

aaaaaaaaaa aaaaaaaaaa aaaaaaaaaa a                                  2311
```

<210> SEQ ID NO 92
<211> LENGTH: 636
<212> TYPE: PRT
<213> ORGANISM: Glycine max

<400> SEQUENCE: 92

```
Met Met Glu Ser Cys Asp Cys Ile Asp Thr Gln Tyr Pro Pro Asp Glu
  1               5                  10                  15

Leu Leu Val Lys Tyr Gln Tyr Ile Ser Asp Val Leu Ile Ala Leu Ala
             20                  25                  30

Tyr Phe Ser Ile Pro Val Glu Leu Ile Tyr Phe Val Gln Lys Ser Ala
         35                  40                  45

Phe Phe Pro Tyr Arg Trp Val Leu Met Gln Phe Gly Ala Phe Ile Val
     50                  55                  60

Leu Cys Gly Ala Thr His Phe Ile Asn Leu Trp Thr Phe Ser Pro His
 65                  70                  75                  80

Ser Lys Ser Val Ala Val Val Met Thr Ile Ala Lys Val Ser Cys Ala
                 85                  90                  95

Ile Val Ser Cys Ala Thr Ala Leu Met Leu Val His Ile Ile Pro Asp
            100                 105                 110

Leu Leu Ser Val Lys Arg Arg Glu Ser Ile Leu Lys Asn Lys Ala Glu
        115                 120                 125
```

-continued

```
Glu Leu Asp Arg Glu Met Gly Leu Ile Leu Thr Gln Glu Glu Thr Gly
    130                 135                 140

Arg His Val Arg Met Leu Thr His Glu Ile Arg Ser Thr Leu Asp Arg
145                 150                 155                 160

His Thr Ile Leu Lys Thr Thr Leu Val Glu Leu Gly Arg Thr Leu Gly
                165                 170                 175

Leu Glu Glu Cys Ala Leu Trp Met Pro Ser Arg Ser Gly Leu Asn Leu
            180                 185                 190

Gln Leu Ser His Thr Leu Thr Tyr His Val Gln Val Gly Ser Thr Val
        195                 200                 205

Gln Thr Asn Asn Pro Ile Val Asn Glu Val Phe Asn Ser Pro Gln Ala
    210                 215                 220

Met Arg Ile Pro Pro Thr Cys Pro Leu Ala Arg Ile Arg Pro Leu Val
225                 230                 235                 240

Gly Arg Tyr Val Pro Pro Glu Val Val Ala Val Arg Val Pro Leu Leu
                245                 250                 255

Asn Leu Ser Asn Phe Gln Ile Asn Asp Trp Pro Asp Ile Ser Ala Lys
            260                 265                 270

Ser Tyr Ala Ile Met Val Leu Ile Leu Pro Thr Asp Ser Val Arg Lys
        275                 280                 285

Trp Arg Asp His Glu Leu Glu Leu Val Asp Val Val Ala Asp Gln Val
    290                 295                 300

Ala Val Ala Leu Ser His Ala Ala Ile Leu Glu Glu Ser Met Arg Ala
305                 310                 315                 320

Arg Asp Gln Leu Met Glu Gln Asn Val Ala Leu Asp Leu Ala Arg Arg
                325                 330                 335

Glu Ala Glu Met Ala Ile His Ala Arg Asn Asp Phe Leu Ala Val Met
            340                 345                 350

Asn His Glu Met Arg Thr Pro Met His Ala Ile Ile Ala Leu Ser Ser
        355                 360                 365

Leu Leu Leu Glu Thr Glu Leu Thr Pro Glu Gln Arg Val Met Ile Glu
    370                 375                 380

Thr Val Leu Lys Ser Ser Asn Val Leu Ala Thr Leu Ile Asn Asp Val
385                 390                 395                 400

Leu Asp Leu Ser Arg Leu Glu Asp Gly Ser Leu Glu Leu Glu Met Gly
                405                 410                 415

Lys Phe Asn Leu His Gly Val Leu Gly Glu Ile Val Glu Leu Ile Lys
            420                 425                 430

Pro Ile Ala Ser Val Lys Lys Leu Pro Ile Thr Leu Ile Leu Ser Pro
        435                 440                 445

Asp Leu Pro Thr His Ala Ile Gly Asp Glu Lys Arg Leu Thr Gln Thr
    450                 455                 460

Leu Leu Asn Val Val Gly Asn Ala Val Lys Phe Thr Lys Glu Gly Tyr
465                 470                 475                 480

Val Ser Val Arg Val Ser Val Ala Lys Pro Glu Ser Ser Gln Asp Trp
                485                 490                 495

Arg Pro Pro Glu Phe Tyr Pro Ala Ser Ser Asp Gly His Phe Tyr Ile
            500                 505                 510

Arg Val Gln Val Lys Asp Ser Gly Cys Gly Ile Leu Pro Gln Asp Ile
        515                 520                 525

Pro His Leu Phe Thr Lys Phe Ala Gln Ser Arg Ser Gly Pro Ala Arg
    530                 535                 540
```

-continued

```
Pro Ser Ser Gly Ala Gly Leu Gly Leu Ala Ile Cys Lys Arg Phe Val
545                 550                 555                 560

Asn Leu Met Gly Gly His Ile Trp Ile Glu Ser Glu Gly Leu Asp Lys
                565                 570                 575

Gly Ser Thr Ala Thr Phe Ile Val Lys Leu Gly Ile Cys Gly Asn Pro
            580                 585                 590

Asp Pro Ser Asp His Gln Ala Ala Asn Arg Ser Gln Ala Tyr Ser Gly
        595                 600                 605

Ser Gly Gly Leu Ala Arg Phe Lys Pro Phe Ile Thr Asp Glu Asn Asp
    610                 615                 620

Thr Gly Phe Ser Thr Arg Arg Asn Gln Arg Ser Phe
625                 630                 635


<210> SEQ ID NO 93
<211> LENGTH: 756
<212> TYPE: DNA
<213> ORGANISM: Glycine max

<400> SEQUENCE: 93

tttttttttt tttttttttt tttttttttt tttttttttt tttttttttt tttttttgtt      60

gttggttatg gtgctttctg tttatgccaa cgatgtggaa tattcacagt gcaattgtga     120

tgaggaaggg ctttggagca tccacagcgt gctggtttgt cagaaagtga gtgacttttt     180

cattgccatt gcatattttt ccatacccct tgagcttctt tactttgtga gctgctccaa     240

tgtccccttt aaattggtct tccttcaatt cattgccttc atagttctct gtggattgac     300

ccatttgctc aatgcctata cttactatgg ccctcactcc ttccagttgt ttctttccct     360

tactgttgct aagttcctca ctgctcttgt ttcttgtgcc actgcaattt cctttcccac     420

actcattcct cttttgctga aaatcaaagt gagggagcta tttttgaggc agaatgtgtt     480

ggaattgggc caagaggttg ggatgatgaa gaaacagaag gaagctagtt ggcatgttag     540

gatgctcact tgtgagatta ggaaatctct ggataagcat accatcttgt ataccacact     600

tgttgagctt tccaaggcat tggatttgca caattgtgca gtatggatgc ctgatgagga     660

taggagagaa atgcatttga ctcatgagtt gaaaccaagc tcagcgagga gttttcacaa     720

ttctattgct atcagtgatc ctgatgtgtc tcgtgc                               756


<210> SEQ ID NO 94
<211> LENGTH: 233
<212> TYPE: PRT
<213> ORGANISM: Glycine max

<400> SEQUENCE: 94

Leu Leu Leu Val Met Val Leu Ser Val Tyr Ala Asn Asp Val Glu Tyr
  1               5                  10                  15

Ser Gln Cys Asn Cys Asp Glu Glu Gly Leu Trp Ser Ile His Ser Val
            20                  25                  30

Leu Val Cys Gln Lys Val Ser Asp Phe Phe Ile Ala Ile Ala Tyr Phe
        35                  40                  45

Ser Ile Pro Leu Glu Leu Leu Tyr Phe Val Ser Cys Ser Asn Val Pro
    50                  55                  60

Phe Lys Leu Val Phe Leu Gln Phe Ile Ala Phe Ile Val Leu Cys Gly
 65                  70                  75                  80

Leu Thr His Leu Leu Asn Ala Tyr Thr Tyr Tyr Gly Pro His Ser Phe
                 85                  90                  95
```

-continued

```
Gln Leu Phe Leu Ser Leu Thr Val Ala Lys Phe Leu Thr Ala Leu Val
            100                 105                 110

Ser Cys Ala Thr Ala Ile Ser Phe Pro Thr Leu Ile Pro Leu Leu Leu
        115                 120                 125

Lys Ile Lys Val Arg Glu Leu Phe Leu Arg Gln Asn Val Leu Glu Leu
    130                 135                 140

Gly Gln Glu Val Gly Met Met Lys Lys Gln Lys Glu Ala Ser Trp His
145                 150                 155                 160

Val Arg Met Leu Thr Cys Glu Ile Arg Lys Ser Leu Asp Lys His Thr
                165                 170                 175

Ile Leu Tyr Thr Thr Leu Val Glu Leu Ser Lys Ala Leu Asp Leu His
            180                 185                 190

Asn Cys Ala Val Trp Met Pro Asp Glu Asp Arg Arg Glu Met His Leu
        195                 200                 205

Thr His Glu Leu Lys Pro Ser Ser Ala Arg Ser Phe His Asn Ser Ile
    210                 215                 220

Ala Ile Ser Asp Pro Asp Val Ser Arg
225                 230


<210> SEQ ID NO 95
<211> LENGTH: 1603
<212> TYPE: DNA
<213> ORGANISM: Triticum aestivum

<400> SEQUENCE: 95

gcacgaggtt cgtcgccctt ttgccaacct ctccttccct ccctccttcc tttacccccct     60

ctccatctag ctgccgtcgc catgccaccg ccctgccgca cccaacacca actccggtgc    120

tcgccccaca agcagggaac aagtacaggc caggaagaca agtaaacaac aacgacactc    180

tatagttagg catccaggct ccagattaac taaatggagg gctgtgcctg catcgagcag    240

ttccggcgaa ctgacgagct cctcatcaag taccagtaca tctcggactt cttcatagcc    300

ctcgcctact tctccatccc actcgagctg atctacttcg ccaagaagtc gggatccttc    360

ccctacagat gggtgctcct ccagttcagc gccttcattg tcctctgcgg ggccacccac    420

ctcataaacc tctggacctt caccaagcac acccagaccg tcgacatcgt catgacggta    480

accaaggtca ccacggccgt cgtttcctgc gcgacggccc tcacgctcat ccatatcata    540

cctgatttgt tgggtgtcaa gacgagggag ttgttcctca agaagaaggc cgacgagctc    600

gacagggaga tgagcctcat gcggtcgcag gaggacaccg ggaggcatgt caggatgctc    660

atccatgaga tcaggagcac gcttgacagg cacaccatcc tcaagactac tctggttgag    720

ctcgggagga cgctgggtct ggaggaatgt gctttctgga tgccgtcgag gagcggttcg    780

agccttgagc taactcatac catgcgccac cacatcccca cgggctcttc tgtggagatt    840

aatctccctg ttgtcaacca agtcttaagt accaaccgtg cgatcatagt gccacatact    900

tctcctttgg cgaggatcca ccctgttcaa gggcggcatg tcccacccga ggtggctgct    960

gtgagagttc ctctgctgca tctttcaaac tttcatcccg agcttttggc gaaaagctac   1020

gcaattatgg ttttgatgct cccatctgat agtgtgagga aatggcttgc tcatgaactc   1080

gagctcatcg aggtcgtcgc caatcaggta gctgttgccc tctctcaagc ggaaattctt   1140

gaagaatcaa tgcgagcacg tgatctactg acggagcaaa atgtcgccct ggatttagct   1200

ctgcgggagg ctgaaatggc aatacatgct cgcaatgtca acagggtggg ggttgaactt   1260

gtggggcctg aggacgcaga caacgtcgct accatcaact catctgcttc tgcagccaag   1320
```

-continued

```
gtgcacaacg ccgagccatg atcgacgcgt ctaccccaac ttcgcccgac actgagatgc   1380

gtcacttcta cccaccaaga agtacgcctt gatccaaatc gtactctcta gttgcctttg   1440

cttgcaccct ataggtgccc caaaggccca aaccgtttcc tttgctgctg ctgcgacagc   1500

actatctatc tgaacctatg tagtttaaat ttggccctgc tgtgtgcaat ctatctggat   1560

ttgtgctaag ttatgctatt tatctaaaaa aaaaaaaaaa aaa                     1603
```

```
<210> SEQ ID NO 96
<211> LENGTH: 375
<212> TYPE: PRT
<213> ORGANISM: Triticum aestivum

<400> SEQUENCE: 96

Met Glu Gly Cys Ala Cys Ile Glu Gln Phe Arg Arg Thr Asp Glu Leu
  1               5                  10                  15

Leu Ile Lys Tyr Gln Tyr Ile Ser Asp Phe Phe Ile Ala Leu Ala Tyr
             20                  25                  30

Phe Ser Ile Pro Leu Glu Leu Ile Tyr Phe Ala Lys Lys Ser Gly Ser
         35                  40                  45

Phe Pro Tyr Arg Trp Val Leu Leu Gln Phe Ser Ala Phe Ile Val Leu
     50                  55                  60

Cys Gly Ala Thr His Leu Ile Asn Leu Trp Thr Phe Thr Lys His Thr
 65                  70                  75                  80

Gln Thr Val Asp Ile Val Met Thr Val Thr Lys Val Thr Thr Ala Val
                 85                  90                  95

Val Ser Cys Ala Thr Ala Leu Thr Leu Ile His Ile Ile Pro Asp Leu
            100                 105                 110

Leu Gly Val Lys Thr Arg Glu Leu Phe Leu Lys Lys Lys Ala Asp Glu
        115                 120                 125

Leu Asp Arg Glu Met Ser Leu Met Arg Ser Gln Glu Asp Thr Gly Arg
    130                 135                 140

His Val Arg Met Leu Ile His Glu Ile Arg Ser Thr Leu Asp Arg His
145                 150                 155                 160

Thr Ile Leu Lys Thr Thr Leu Val Glu Leu Gly Arg Thr Leu Gly Leu
                165                 170                 175

Glu Glu Cys Ala Phe Trp Met Pro Ser Arg Ser Gly Ser Ser Leu Glu
            180                 185                 190

Leu Thr His Thr Met Arg His His Ile Pro Thr Gly Ser Ser Val Glu
        195                 200                 205

Ile Asn Leu Pro Val Val Asn Gln Val Leu Ser Thr Asn Arg Ala Ile
    210                 215                 220

Ile Val Pro His Thr Ser Pro Leu Ala Arg Ile His Pro Val Gln Gly
225                 230                 235                 240

Arg His Val Pro Pro Glu Val Ala Ala Val Arg Val Pro Leu Leu His
                245                 250                 255

Leu Ser Asn Phe His Pro Glu Leu Leu Ala Lys Ser Tyr Ala Ile Met
            260                 265                 270

Val Leu Met Leu Pro Ser Asp Ser Val Arg Lys Trp Leu Ala His Glu
        275                 280                 285

Leu Glu Leu Ile Glu Val Val Ala Asn Gln Val Ala Val Ala Leu Ser
    290                 295                 300

Gln Ala Glu Ile Leu Glu Glu Ser Met Arg Ala Arg Asp Leu Leu Thr
305                 310                 315                 320
```

-continued

```
Glu Gln Asn Val Ala Leu Asp Leu Ala Leu Arg Glu Ala Glu Met Ala
            325                 330                 335

Ile His Ala Arg Asn Val Asn Arg Val Gly Val Glu Leu Val Gly Pro
            340                 345                 350

Glu Asp Ala Asp Asn Val Ala Thr Ile Asn Ser Ser Ala Ser Ala Ala
        355                 360                 365

Lys Val His Asn Ala Glu Pro
    370                 375


<210> SEQ ID NO 97
<211> LENGTH: 491
<212> TYPE: DNA
<213> ORGANISM: Zea mays
<220> FEATURE:
<221> NAME/KEY: unsure
<222> LOCATION: (418)
<221> NAME/KEY: unsure
<222> LOCATION: (428)
<221> NAME/KEY: unsure
<222> LOCATION: (446)
<221> NAME/KEY: unsure
<222> LOCATION: (476)
<221> NAME/KEY: unsure
<222> LOCATION: (491)

<400> SEQUENCE: 97

gcgtctggtg aatgcaggag cgtcggcacc cgcagcgtgg aatcgacgac gggcgcctcc      60

agtcggttca gaaatgcgca aatgcgcgtc tgaatgaagc ctggttggag gtggtagagc     120

cgatggtggt gggaacggca ctgctgcgcg gggtttctcc gcgtggatcc tcctgttcct     180

ctcctccctg ctcctctcgc cgtcagcggc gtctgtcgat ttcggccact gcggcggctg     240

cgacgacgcc gacgacggcg ccctctccag cacctataac atcctgcaat gccagaaggt     300

cagcgacttc ctcatcgccg cggctacttc tccatcccgc tcgagctgtc tacttcgcca     360

cctgctccga cctcttcccc ctcaaatgga tcgtgctgca gttcggcgcc ttcatcgngc     420

tctgcggnct acgcacctca tactgngtca cctacgagcc gacttcttca acttgnactt     480

ggccttaccg n                                                          491


<210> SEQ ID NO 98
<211> LENGTH: 89
<212> TYPE: PRT
<213> ORGANISM: Zea mays
<220> FEATURE:
<221> NAME/KEY: UNSURE
<222> LOCATION: (53)
<221> NAME/KEY: UNSURE
<222> LOCATION: (62)
<221> NAME/KEY: UNSURE
<222> LOCATION: (70)
<221> NAME/KEY: UNSURE
<222> LOCATION: (85)

<400> SEQUENCE: 98

Ile Leu Leu Phe Leu Ser Ser Leu Leu Leu Ser Pro Ser Ala Ala Ser
  1               5                  10                  15

Val Asp Phe Gly His Cys Gly Gly Cys Asp Asp Ala Asp Asp Gly Ala
             20                  25                  30

Leu Ser Ser Thr Tyr Asn Ile Leu Gln Cys Gln Lys Val Ser Asp Phe
         35                  40                  45

Leu Ile Ala Ala Xaa Tyr Phe Ser Ile Pro Leu Glu Leu Xaa Tyr Phe
     50                  55                  60
```

-continued

```
Ala Thr Cys Ser Asp Xaa Phe Pro Leu Lys Trp Ile Val Leu Gln Phe
 65                  70                  75                  80

Gly Ala Phe Ile Xaa Leu Cys Gly Leu
                85


<210> SEQ ID NO 99
<211> LENGTH: 2403
<212> TYPE: DNA
<213> ORGANISM: Zea mays

<400> SEQUENCE: 99

gctttctccc gttcaccccg cgtgcacgct ctttcccttc ctcgtgccga cgaccgggcg     60

accgccgcgc cccggcccgc gccccccttgt ctcgggccac tcgccggcaa cgagcagcca    120

ccaggaaatg ttgtgaggac tgatgcaata actaagcttg ctggatggac ggatgtgatt    180

gcatcgagcc actatggcct accgatgatc tccttgtcaa gtatcagtac atctcagact    240

tcttcatagc cctagcgtac ttctctattc cgttggagct catatatttc gtgaagaagt    300

cgtccttctt cccgtacaga tgggtcttga tccagtttgg tgcgtttata gttctytgtg    360

gggcaaccca tctgataaac ctgtggacgt tcaccacaca tacaaagacc gttgcgatgg    420

tcatgaccat agcaaaggtt tctacagcag ttgtgtcctg tgcaactgct ttgatgcttg    480

ttcatatcat ccccgactta ttgagcgtga aaactagaga gttgttcctg aagaataaag    540

ctgaagagct tgacagagag atgggactga taaggacgca ggaggagacc ggtagacatg    600

ttaggatgct tacacatgaa atcagaagta ctcttgacag gcatatgatt ttgaagacta    660

ctcttgttga gctaggaagg accttgggtc tggaagaatg tgcattgtgg atgccatctc    720

gaagtggttc aagccttcag ctttctcata ctttgcacca ccagattact gttggatcat    780

cggtgccaat taatcttcct gtcatcaatc aagtgttcag tagcaaccgg gcaattataa    840

taccccacac atctcctttg gcgcggattc gacctcttac agggcgatat gttccaccag    900

aagtggctgc agtccgtgta cctcttctcc acctttcaaa cttccaaata aatgattggc    960

ctgagctttc ggcaaaaagc tttgcaatca tggttttgat gcttccatct gatagtgcaa   1020

gaaaatggca tgtacatgaa ttggagctgg ttgaggttgt tgctgatcag gtagcagttg   1080

cactatctca tgcggctatt cttgaagagt ccatgcgagc acgtgattta ctaatggagc   1140

agaatgttgc cctggattta gctcgaagag aggctgagat ggctatccgt gctcgcaatg   1200

atttcctagc tgttatgaat cacgaaatga gaacacccat gaatgcaata atagcccttt   1260

cctccttgct tttggaaact gagcttactc ctgagcagcg tctaatggtg gaaacagtac   1320

tgaaaagcag caatttgtta gcaacactca tcaatgatgt tctggatctt tccaaactcg   1380

aggatggaag ccttgaactg gagattaaag cattcaatct tcatgctgtt ttcaaagaag   1440

tgatgggttt cattaaacca attgcatcta tcaagaggct atctgtatcg gttatgttgg   1500

caccagatct gccgttatgt gcaattggtg atgaaaagag actcatgcaa actattctga   1560

acatctctgg caatgctgta aagtttacca aggagggaca catcacgctt gtagcttcca   1620

ttgtgaaggc tgactctttg agagagttca gaaccccaga atttcatcca actgcaagtg   1680

atgaacattt ctatttgaaa gttcaggtaa aagatacagg ctgtggagtt agtcctcagg   1740

atctacctca tgtattcaca aagtttgctc atcctcaaag tggaggaaac cgagggttta   1800

atggtagtgg tcttggcctt gccatatgca agaggtttgt tagtcttatg ggagggcaca   1860

tctggatcga cagcgaagga accggaagag gttgcaccgc aacattcgtc atcaagctcg   1920

gcgtgtgtga caacacaaac acctaccagc agcagctggt tcctctagtc tggccaagca   1980
```

-continued

```
gtgcagactc caatttgtct gctccgaaag tgctgcccga cgggagagga tctgtttccc   2040

tgaaatctcg gtaccaaaga agcgtatgag ctcagtgtaa atgattgacg gcatagtgcc   2100

aagtagggga tcgattagtg ccattgtcta attttgtttg taacccagtc atagcaacat   2160

atagtgtaca aataatgtaa agccaatgga gactgcagct gtgtatctgg gtagcaacgc   2220

tgacttgctg cattgagtag tatgtcctac cagcggattg aattgcttgt tctggggtgt   2280

gcggcgcgcg ccccgttgat tgttctgttg taacttgtaa tcccatatta atcgtgtaat   2340

atgaaattca atgcaaatac acggtcaaaa aaaaaaaaaa aaaaaaaaaa aaaaaaaaaa   2400

aaa                                                                 2403
```

```
<210> SEQ ID NO 100
<211> LENGTH: 634
<212> TYPE: PRT
<213> ORGANISM: Zea mays

<400> SEQUENCE: 100

Met Asp Gly Cys Asp Cys Ile Glu Pro Leu Trp Pro Thr Asp Asp Leu
  1               5                  10                  15

Leu Val Lys Tyr Gln Tyr Ile Ser Asp Phe Phe Ile Ala Leu Ala Tyr
             20                  25                  30

Phe Ser Ile Pro Leu Glu Leu Ile Tyr Phe Val Lys Lys Ser Ser Phe
         35                  40                  45

Phe Pro Tyr Arg Trp Val Leu Ile Gln Phe Gly Ala Phe Ile Val Leu
     50                  55                  60

Cys Gly Ala Thr His Leu Ile Asn Leu Trp Thr Phe Thr Thr His Thr
 65                  70                  75                  80

Lys Thr Val Ala Met Val Met Thr Ile Ala Lys Val Ser Thr Ala Val
                 85                  90                  95

Val Ser Cys Ala Thr Ala Leu Met Leu Val His Ile Ile Pro Asp Leu
            100                 105                 110

Leu Ser Val Lys Thr Arg Glu Leu Phe Leu Lys Asn Lys Ala Glu Glu
        115                 120                 125

Leu Asp Arg Glu Met Gly Leu Ile Arg Thr Gln Glu Glu Thr Gly Arg
    130                 135                 140

His Val Arg Met Leu Thr His Glu Ile Arg Ser Thr Leu Asp Arg His
145                 150                 155                 160

Met Ile Leu Lys Thr Thr Leu Val Glu Leu Gly Arg Thr Leu Gly Leu
                165                 170                 175

Glu Glu Cys Ala Leu Trp Met Pro Ser Arg Ser Gly Ser Ser Leu Gln
            180                 185                 190

Leu Ser His Thr Leu His His Gln Ile Thr Val Gly Ser Ser Val Pro
        195                 200                 205

Ile Asn Leu Pro Val Ile Asn Gln Val Phe Ser Ser Asn Arg Ala Ile
    210                 215                 220

Ile Ile Pro His Thr Ser Pro Leu Ala Arg Ile Arg Pro Leu Thr Gly
225                 230                 235                 240

Arg Tyr Val Pro Pro Glu Val Ala Ala Val Arg Val Pro Leu Leu His
                245                 250                 255

Leu Ser Asn Phe Gln Ile Asn Asp Trp Pro Glu Leu Ser Ala Lys Ser
            260                 265                 270

Phe Ala Ile Met Val Leu Met Leu Pro Ser Asp Ser Ala Arg Lys Trp
        275                 280                 285
```

-continued

```
His Val His Glu Leu Glu Leu Val Glu Val Val Ala Asp Gln Val Ala
    290                 295                 300

Val Ala Leu Ser His Ala Ala Ile Leu Glu Glu Ser Met Arg Ala Arg
305                 310                 315                 320

Asp Leu Leu Met Glu Gln Asn Val Ala Leu Asp Leu Ala Arg Arg Glu
                325                 330                 335

Ala Glu Met Ala Ile Arg Ala Arg Asn Asp Phe Leu Ala Val Met Asn
            340                 345                 350

His Glu Met Arg Thr Pro Met Asn Ala Ile Ile Ala Leu Ser Ser Leu
        355                 360                 365

Leu Leu Glu Thr Glu Leu Thr Pro Glu Gln Arg Leu Met Val Glu Thr
    370                 375                 380

Val Leu Lys Ser Ser Asn Leu Leu Ala Thr Leu Ile Asn Asp Val Leu
385                 390                 395                 400

Asp Leu Ser Lys Leu Glu Asp Gly Ser Leu Glu Leu Glu Ile Lys Ala
                405                 410                 415

Phe Asn Leu His Ala Val Phe Lys Glu Val Met Gly Phe Ile Lys Pro
            420                 425                 430

Ile Ala Ser Ile Lys Arg Leu Ser Val Ser Val Met Leu Ala Pro Asp
        435                 440                 445

Leu Pro Leu Cys Ala Ile Gly Asp Glu Lys Arg Leu Met Gln Thr Ile
    450                 455                 460

Leu Asn Ile Ser Gly Asn Ala Val Lys Phe Thr Lys Glu Gly His Ile
465                 470                 475                 480

Thr Leu Val Ala Ser Ile Val Lys Ala Asp Ser Leu Arg Glu Phe Arg
                485                 490                 495

Thr Pro Glu Phe His Pro Thr Ala Ser Asp Glu His Phe Tyr Leu Lys
            500                 505                 510

Val Gln Val Lys Asp Thr Gly Cys Gly Val Ser Pro Gln Asp Leu Pro
        515                 520                 525

His Val Phe Thr Lys Phe Ala His Pro Gln Ser Gly Gly Asn Arg Gly
    530                 535                 540

Phe Asn Gly Ser Gly Leu Gly Leu Ala Ile Cys Lys Arg Phe Val Ser
545                 550                 555                 560

Leu Met Gly Gly His Ile Trp Ile Asp Ser Glu Gly Thr Gly Arg Gly
                565                 570                 575

Cys Thr Ala Thr Phe Val Ile Lys Leu Gly Val Cys Asp Asn Thr Asn
            580                 585                 590

Thr Tyr Gln Gln Gln Leu Val Pro Leu Val Trp Pro Ser Ser Ala Asp
        595                 600                 605

Ser Asn Leu Ser Ala Pro Lys Val Leu Pro Asp Gly Arg Gly Ser Val
    610                 615                 620

Ser Leu Lys Ser Arg Tyr Gln Arg Ser Val
625                 630
```

<210> SEQ ID NO 101
<211> LENGTH: 530
<212> TYPE: DNA
<213> ORGANISM: Oryza sativa
<220> FEATURE:
<221> NAME/KEY: unsure
<222> LOCATION: (271)
<221> NAME/KEY: unsure
<222> LOCATION: (378)
<221> NAME/KEY: unsure
<222> LOCATION: (382)

-continued

<221> NAME/KEY: unsure
<222> LOCATION: (384)
<221> NAME/KEY: unsure
<222> LOCATION: (399)
<221> NAME/KEY: unsure
<222> LOCATION: (403)
<221> NAME/KEY: unsure
<222> LOCATION: (414)
<221> NAME/KEY: unsure
<222> LOCATION: (428)
<221> NAME/KEY: unsure
<222> LOCATION: (443)
<221> NAME/KEY: unsure
<222> LOCATION: (448)
<221> NAME/KEY: unsure
<222> LOCATION: (453)
<221> NAME/KEY: unsure
<222> LOCATION: (462)
<221> NAME/KEY: unsure
<222> LOCATION: (480)
<221> NAME/KEY: unsure
<222> LOCATION: (497)
<221> NAME/KEY: unsure
<222> LOCATION: (505)
<221> NAME/KEY: unsure
<222> LOCATION: (516)
<221> NAME/KEY: unsure
<222> LOCATION: (518)
<221> NAME/KEY: unsure
<222> LOCATION: (521)

<400> SEQUENCE: 101
cttacaattg cattgagccg ctctggcagg cggatgatct ccttgtaaag tatcagtaca 60
tatctgactt ctttattgcg ctcgcttact tctcgatccc tttggagctc atatatttcg 120
ttaagaagtc agcattcttc ccttaccgat gggtgcttat acaattcggc gcattcattg 180
ttctttgtgg ggcaacccac ctgataaatt tgtggacttt tgccatatat accaagacta 240
tagctgtggg tactgacagt ggcgaaagca ncgacagcgg ttgtttcgtg catcacagct 300
ttgatgcttg tgcatataat tcctgatttg ttgaatggtg aaggtttcaa gaagaagaag 360
aattttctga aagggatnag gntngatgaa gcttgatanc aanaaaatgg ggantataac 420
gaacacantg aaggagacag ggnaggantt gtncacatgc tngacccatg aagataagan 480
ggcacaactt gacaggncac aacanttcct gccgananta ngcccggccg 530

<210> SEQ ID NO 102
<211> LENGTH: 110
<212> TYPE: PRT
<213> ORGANISM: Oryza sativa
<220> FEATURE:
<221> NAME/KEY: UNSURE
<222> LOCATION: (81)
<221> NAME/KEY: UNSURE
<222> LOCATION: (89)

<400> SEQUENCE: 102

```
Asn Cys Ile Glu Pro Leu Trp Gln Ala Asp Asp Leu Leu Val Lys Tyr
  1               5                  10                  15

Gln Tyr Ile Ser Asp Phe Phe Ile Ala Leu Ala Tyr Phe Ser Ile Pro
             20                  25                  30

Leu Glu Leu Ile Tyr Phe Val Lys Lys Ser Ala Phe Phe Pro Tyr Arg
         35                  40                  45

Trp Val Leu Ile Gln Phe Gly Ala Phe Ile Val Leu Cys Gly Ala Thr
     50                  55                  60

His Leu Ile Asn Leu Trp Thr Phe Ala Ile Tyr Thr Lys Thr Ile Ala
 65                  70                  75                  80
```

-continued

```
Xaa Val Leu Thr Val Ala Lys Ala Xaa Thr Ala Val Val Ser Cys Ile
                 85                  90                  95

Thr Ala Leu Met Leu Val His Ile Ile Pro Asp Leu Leu Asn
            100                 105                 110


<210> SEQ ID NO 103
<211> LENGTH: 463
<212> TYPE: DNA
<213> ORGANISM: Glycine max
<220> FEATURE:
<221> NAME/KEY: unsure
<222> LOCATION: (447)..(448)

<400> SEQUENCE: 103

tgtcttcacc taaccaaatg ggcgcctcca ccacctgatc cacctctgtt tcttcttcct     60

ttcatccgtt catacggggg ttagatgatg gagtcctgtg attgtataga tacgcagtat    120

ccgccggatg aacttcttgt gaagtatcag tatatctcgg atgtgctaat tgctcttgcg    180

tatttttcga ttccggtgga gctcatctat tttgttcaga agtctgcttt ctttccgtat    240

agatgggtgc ttatgcagtt tggtgccttt attgttctct gtggagcaac tcatttcata    300

aacctgtgga cattctctcc gcactctaag tctgttgctg ttgtcatgac gaatgccaaa    360

agtttcgtgt gctattgtgt catgtgcgac ggcactgatg cttgtacaca ttattcccga    420

tttgttgagt gtcaagaggc gcgaatnnat tctcaaaaaa caa                      463


<210> SEQ ID NO 104
<211> LENGTH: 126
<212> TYPE: PRT
<213> ORGANISM: Glycine max
<220> FEATURE:
<221> NAME/KEY: UNSURE
<222> LOCATION: (93)
<221> NAME/KEY: UNSURE
<222> LOCATION: (121)

<400> SEQUENCE: 104

Met Met Glu Ser Cys Asp Cys Ile Asp Thr Gln Tyr Pro Pro Asp Glu
  1               5                  10                  15

Leu Leu Val Lys Tyr Gln Tyr Ile Ser Asp Val Leu Ile Ala Leu Ala
             20                  25                  30

Tyr Phe Ser Ile Pro Val Glu Leu Ile Tyr Phe Val Gln Lys Ser Ala
         35                  40                  45

Phe Phe Pro Tyr Arg Trp Val Leu Met Gln Phe Gly Ala Phe Ile Val
     50                  55                  60

Leu Cys Gly Ala Thr His Phe Ile Asn Leu Trp Thr Phe Ser Pro His
 65                  70                  75                  80

Ser Lys Ser Val Ala Val Val Met Thr Asn Ala Lys Xaa Ser Cys Ala
                 85                  90                  95

Ile Val Ser Cys Ala Thr Ala Leu Met Leu Val His Ile Ile Pro Asp
            100                 105                 110

Leu Leu Ser Val Lys Arg Arg Glu Xaa Ile Leu Lys Lys Gln
        115                 120                 125


<210> SEQ ID NO 105
<211> LENGTH: 484
<212> TYPE: DNA
<213> ORGANISM: Glycine max
<220> FEATURE:
<221> NAME/KEY: unsure
<222> LOCATION: (10)
```

<221> NAME/KEY: unsure
<222> LOCATION: (67)

<400> SEQUENCE: 105

```
ttcatttccn ttcatagttc tcttgtggat tgacccattt gctcaatgcc tatacttact     60

atgcccntca ctccttccca gttgtttctt tcccttactg ttgctaagtt cctcactgct    120

cttgtttctt gtgccactgc aatttccttt cccacactca ttcctctttt gctgaaaatc    180

aaagtgaggg agctattttt gaggcagaat gtgttggaat tgggccaaga ggttgggatg    240

atgaagaaac agaaggaagc tagttggcat gttaggatgc tcacttgtga gattaggaaa    300

tctctggata agcataccat cttgtatacc acacttgttg agctttccaa ggcattggat    360

ttgcacaatt gtgcagtatg gatgcctgat gaggatagga gagaaatgca tttgactcat    420

gagttgaaac caagctcagc gaggagtttt cacaattcta ttgctatcag tgatcctgat    480

gtgt                                                                 484
```

<210> SEQ ID NO 106
<211> LENGTH: 153
<212> TYPE: PRT
<213> ORGANISM: Glycine max
<220> FEATURE:
<221> NAME/KEY: UNSURE
<222> LOCATION: (13)
<221> NAME/KEY: UNSURE
<222> LOCATION: (15)

<400> SEQUENCE: 106

```
Cys Gly Leu Thr His Leu Leu Asn Ala Tyr Thr Tyr Xaa Pro Xaa Thr
  1               5                  10                  15

Pro Ser Gln Leu Phe Leu Ser Leu Thr Val Ala Lys Phe Leu Thr Ala
             20                  25                  30

Leu Val Ser Cys Ala Thr Ala Ile Ser Phe Pro Thr Leu Ile Pro Leu
         35                  40                  45

Leu Leu Lys Ile Lys Val Arg Glu Leu Phe Leu Arg Gln Asn Val Leu
     50                  55                  60

Glu Leu Gly Gln Glu Val Gly Met Met Lys Lys Gln Lys Glu Ala Ser
 65                  70                  75                  80

Trp His Val Arg Met Leu Thr Cys Glu Ile Arg Lys Ser Leu Asp Lys
                 85                  90                  95

His Thr Ile Leu Tyr Thr Thr Leu Val Glu Leu Ser Lys Ala Leu Asp
            100                 105                 110

Leu His Asn Cys Ala Val Trp Met Pro Asp Glu Asp Arg Arg Glu Met
        115                 120                 125

His Leu Thr His Glu Leu Lys Pro Ser Ser Ala Arg Ser Phe His Asn
    130                 135                 140

Ser Ile Ala Ile Ser Asp Pro Asp Val
145                 150
```

<210> SEQ ID NO 107
<211> LENGTH: 419
<212> TYPE: DNA
<213> ORGANISM: Triticum aestivum
<220> FEATURE:
<221> NAME/KEY: unsure
<222> LOCATION: (390)
<221> NAME/KEY: unsure
<222> LOCATION: (419)

<400> SEQUENCE: 107

```
gttcgtcgcc cttttgccaa cctctccttc cctccctcct tcctttaccc cctctccatc      60

tagctgccgt cgccatgcca ccgccctgcc gcacccaaca ccaactccgg tgctcgcccc     120

acaagcaggg aacaagtaca ggccaggaag acaagtaaac aacaacgaca ctctatagtt     180

aggcatccag gctccagatt aactaaatgg agggctgtgc ctgcatcgaa gcagttccgg     240

cgaaactgac gaagctcctc atcaagtacc aagttaacat ctcggacttc ttcatagccc     300

tcgcctactt ctccatccca ctcgaagctg atctacttcg ccaaagaaag tcgggatcct     360

tcccctacag atgggtgctc ctccaagttn aagcggcttc attgtcctct ggcgggggn      419
```

<210> SEQ ID NO 108
<211> LENGTH: 62
<212> TYPE: PRT
<213> ORGANISM: Triticum aestivum
<220> FEATURE:
<221> NAME/KEY: UNSURE
<222> LOCATION: (41)
<221> NAME/KEY: UNSURE
<222> LOCATION: (49)
<221> NAME/KEY: UNSURE
<222> LOCATION: (61)

<400> SEQUENCE: 108

```
Met Glu Gly Cys Ala Cys Ile Glu Ala Val Pro Ala Lys Leu Thr Lys
  1               5                  10                  15

Leu Leu Ile Lys Tyr Gln Val Asn Ile Ser Asp Phe Phe Ile Ala Leu
             20                  25                  30

Ala Tyr Phe Ser Ile Pro Leu Glu Xaa Ile Tyr Phe Ala Lys Glu Ser
         35                  40                  45

Xaa Ser Phe Pro Tyr Arg Trp Val Leu Leu Gln Val Xaa Ala
     50                  55                  60
```

<210> SEQ ID NO 109
<211> LENGTH: 1100
<212> TYPE: DNA
<213> ORGANISM: Zea mays

<400> SEQUENCE: 109

```
ggcactagca gcagcatcca agactgttga ttgtctaaaa atggtgcata gtttgcatgc      60

aatttttctt gttgctggag acaataacat accgataata tatcaagttc atcgggcacg     120

tgatggatcc agctttgcca caagaaaagt ggaggcaaag cagaagggcc tagttgtatt     180

caccttgatt gcttctttcc agaaggaaga agtgggtttt gagcatcagg ctgcaatcat     240

gcctgatgtt cctccgccag aacagctcct taatctggag gagatacgtg aaagacggct     300

tactgatcca cgcttcccat cccaatatag gaacttggca gctaaaaaaa agtttattcc     360

ttggcccata gaaatgagat tttgtgaagg ttcagcgtct caacataaac caagcttaaa     420

ctactggttt agagctcgag ggaaactctc agacgaccaa gctctacaca gatgtgttgt     480

agcatatgct tcggatctac tattttctgg ggtgagcctt aaccctcatc gggagaaggg     540

tttgaagaca tactgcctca gtcttgacca ttccatctgg ttccacaaac ctgtgaaggc     600

tgacgaatgg atgctgtatg tgatcgagag cccatctgcg cacggtggtc gcggtttcgt     660

caccggacgc atgttcaaca ggcaaggaga gcttatcatg tcgctgaccc aagaggcatt     720

gattcgaagg gagaagccgc gaggaccaaa tccgaggccg aagctttgag gcacctgaca     780

gcctctgcag tcgactgtag aggatcccaa ccgagctttg agaggcgcac catcctttct     840
```

-continued

```
tctaatttgg tttagatatt tatgaattca caaacaaaaa tatagaatat caagcagtat    900

aaaagatctc aagtcaaacc taacattttt tttcatttct ccggatgatt tctatttgtt    960

ttggtgtgtg tgtggttgga ggggtattgg aagcggaagc ggaggcggag ggtttgatac   1020

tttaggctat ttcctgcagc ttactttcat tatacgaaca gtatatatac atatttaaac   1080

ttcaaaaaaa aaaaaaaaaa                                               1100


<210> SEQ ID NO 110
<211> LENGTH: 255
<212> TYPE: PRT
<213> ORGANISM: Zea mays

<400> SEQUENCE: 110

Ala Leu Ala Ala Ala Ser Lys Thr Val Asp Cys Leu Lys Met Val His
  1               5                  10                  15

Ser Leu His Ala Ile Phe Leu Val Ala Gly Asp Asn Asn Ile Pro Ile
             20                  25                  30

Ile Tyr Gln Val His Arg Ala Arg Asp Gly Ser Ser Phe Ala Thr Arg
         35                  40                  45

Lys Val Glu Ala Lys Gln Lys Gly Leu Val Val Phe Thr Leu Ile Ala
     50                  55                  60

Ser Phe Gln Lys Glu Glu Val Gly Phe Glu His Gln Ala Ala Ile Met
 65                  70                  75                  80

Pro Asp Val Pro Pro Pro Glu Gln Leu Leu Asn Leu Glu Glu Ile Arg
                 85                  90                  95

Glu Arg Arg Leu Thr Asp Pro Arg Phe Pro Ser Gln Tyr Arg Asn Leu
            100                 105                 110

Ala Ala Lys Lys Lys Phe Ile Pro Trp Pro Ile Glu Met Arg Phe Cys
        115                 120                 125

Glu Gly Ser Ala Ser Gln His Lys Pro Ser Leu Asn Tyr Trp Phe Arg
    130                 135                 140

Ala Arg Gly Lys Leu Ser Asp Asp Gln Ala Leu His Arg Cys Val Val
145                 150                 155                 160

Ala Tyr Ala Ser Asp Leu Leu Phe Ser Gly Val Ser Leu Asn Pro His
                165                 170                 175

Arg Glu Lys Gly Leu Lys Thr Tyr Cys Leu Ser Leu Asp His Ser Ile
            180                 185                 190

Trp Phe His Lys Pro Val Lys Ala Asp Glu Trp Met Leu Tyr Val Ile
        195                 200                 205

Glu Ser Pro Ser Ala His Gly Gly Arg Gly Phe Val Thr Gly Arg Met
    210                 215                 220

Phe Asn Arg Gln Gly Glu Leu Ile Met Ser Leu Thr Gln Glu Ala Leu
225                 230                 235                 240

Ile Arg Arg Glu Lys Pro Arg Gly Pro Asn Pro Arg Pro Lys Leu
                245                 250                 255


<210> SEQ ID NO 111
<211> LENGTH: 1414
<212> TYPE: DNA
<213> ORGANISM: Oryza sativa

<400> SEQUENCE: 111

gcacgagtgg tacgttattg cagtatcaaa ggttccttgt tcatgtttct atttttaata     60

acagtataag ctgatggtgt ccctactgta ataataaata tcttctggct tcagcttatt    120

gttagtatcc tattttgcag ctgacctgct tcgtattgcc aaatcaatat ggacacttgt    180
```

-continued

```
tgcaaccaaa gaccatttgg agtgcagaag agacacctga gaaccattct ttgctagaac    240

aaattttgca cttagagcca ttggaggtcg atatcttccg tgggtttact ttgccaggag    300

ctccgacttt taggcaagtt tttggaggac agttgatagg acaggcacta gcagcagcat    360

ccaagaccgt tgactgccta aaagcggtgc acagtttgca cgcaattttc cttatcgcag    420

gagacaagaa tttgccaata atatatcagg ttcatcgggc gcgcgatgga acaagctttg    480

ccaccagaaa agtggaggca aagcaaaagg gccttgtcat tttcaccttg attgcttcat    540

tccagaaaga cgaattaggg tttgagcatc aagctgcaat catgcctgat gttcctcctc    600

cagaagagct cctgaatctg gaagagatac gggaaagaag acttactgat cctcgcttcc    660

caatgcaata taggaactca gctgccaaga aaaagttcgt accttggccc atagaaatga    720

ggttttgtga agattcagca tctcaacata aaccaagctt aaattattgg tttagagcca    780

gaggaaaact ttctgatgat ccagcactgc ataggtgtgt tgtagcatat gcttcggatc    840

tactatattc tggtgtcagc ctaaatcctc atagggagaa gggtctgaag acatactcac    900

tcagtcttga tcactcgatt tggttccaca agcctgtgaa agctgatgat tggcttttat    960

atgtgatcga cagcccatct gcacacggtg ggcggggttt tgttacaggg cgaatgttca   1020

accgacaagg agagctcgtc atgtcgttga cccaagaggc gctgattagg agggcgaaga   1080

cgccaggaca accgtcacaa accccaaggc caaagctttg agaggtgcag aagagcagta   1140

ttatcgtttc atttttggca ctttcacagt tattttcctt ttcaatggaa gtctataaca   1200

cgtagacgtg aagccgaagt atagcatact gcatatatgt agcaagaaaa aacgatggta   1260

aaactggttc tgtaattcac gaacagctta ctgacatacc acgtatgtat tggatcggga   1320

aaaataagcg aagaacttgg tatcgctttt tttttatctc aataaagcct tcaattgttt   1380

caaaaaaaaa aaaaaaaaaa aaaaaaaaaa aaaa                               1414
```

```
<210> SEQ ID NO 112
<211> LENGTH: 331
<212> TYPE: PRT
<213> ORGANISM: Oryza sativa

<400> SEQUENCE: 112

Tyr Pro Ile Leu Gln Leu Thr Cys Phe Val Leu Pro Asn Gln Tyr Gly
  1               5                  10                  15

His Leu Leu Gln Pro Lys Thr Ile Trp Ser Ala Glu Glu Thr Pro Glu
             20                  25                  30

Asn His Ser Leu Leu Glu Gln Ile Leu His Leu Glu Pro Leu Glu Val
         35                  40                  45

Asp Ile Phe Arg Gly Phe Thr Leu Pro Gly Ala Pro Thr Phe Arg Gln
     50                  55                  60

Val Phe Gly Gly Gln Leu Ile Gly Gln Ala Leu Ala Ala Ala Ser Lys
 65                  70                  75                  80

Thr Val Asp Cys Leu Lys Ala Val His Ser Leu His Ala Ile Phe Leu
                 85                  90                  95

Ile Ala Gly Asp Lys Asn Leu Pro Ile Ile Tyr Gln Val His Arg Ala
            100                 105                 110

Arg Asp Gly Thr Ser Phe Ala Thr Arg Lys Val Glu Ala Lys Gln Lys
        115                 120                 125

Gly Leu Val Ile Phe Thr Leu Ile Ala Ser Phe Gln Lys Asp Glu Leu
    130                 135                 140

Gly Phe Glu His Gln Ala Ala Ile Met Pro Asp Val Pro Pro Pro Glu
145                 150                 155                 160
```

-continued

```
Glu Leu Leu Asn Leu Glu Glu Ile Arg Glu Arg Arg Leu Thr Asp Pro
                165                 170                 175

Arg Phe Pro Met Gln Tyr Arg Asn Ser Ala Ala Lys Lys Lys Phe Val
            180                 185                 190

Pro Trp Pro Ile Glu Met Arg Phe Cys Glu Asp Ser Ala Ser Gln His
        195                 200                 205

Lys Pro Ser Leu Asn Tyr Trp Phe Arg Ala Arg Gly Lys Leu Ser Asp
    210                 215                 220

Asp Pro Ala Leu His Arg Cys Val Val Ala Tyr Ala Ser Asp Leu Leu
225                 230                 235                 240

Tyr Ser Gly Val Ser Leu Asn Pro His Arg Glu Lys Gly Leu Lys Thr
                245                 250                 255

Tyr Ser Leu Ser Leu Asp His Ser Ile Trp Phe His Lys Pro Val Lys
            260                 265                 270

Ala Asp Asp Trp Leu Leu Tyr Val Ile Asp Ser Pro Ser Ala His Gly
        275                 280                 285

Gly Arg Gly Phe Val Thr Gly Arg Met Phe Asn Arg Gln Gly Glu Leu
    290                 295                 300

Val Met Ser Leu Thr Gln Glu Ala Leu Ile Arg Arg Ala Lys Thr Pro
305                 310                 315                 320

Gly Gln Pro Ser Gln Thr Pro Arg Pro Lys Leu
                325                 330
```

<210> SEQ ID NO 113
<211> LENGTH: 530
<212> TYPE: DNA
<213> ORGANISM: Glycine max
<220> FEATURE:
<221> NAME/KEY: unsure
<222> LOCATION: (437)
<221> NAME/KEY: unsure
<222> LOCATION: (450)
<221> NAME/KEY: unsure
<222> LOCATION: (483)
<221> NAME/KEY: unsure
<222> LOCATION: (486)
<221> NAME/KEY: unsure
<222> LOCATION: (488)
<221> NAME/KEY: unsure
<222> LOCATION: (503)
<221> NAME/KEY: unsure
<222> LOCATION: (529)

<400> SEQUENCE: 113

```
gtattgttca tcctatagca actgtttttg tttgctgtga cagctatcat gcttggtgct     60

gccccatgag cactcagcat tgctgcagcc aaagtctatc tggagtgcag aaaaatctca    120

tgatacatgc tcacttgtgg agcatatatt gcatttggaa cctatagaga catcttccga    180

ggaatcactc ctacagatgc tccaacattt gggaaggtat ttggtggaca aatagttgga    240

caggcactgg ctgcggcatc aaaatctgtt gattgtctta aagttgttca tagcttgcat    300

gtctattttc ttccttgggg gggattttaa catacccatt atatatcaag ttaaagcgtc    360

tccgtgatgg gaagagtttt gctactaagg aaagtgggtg caattcaaaa gggaaatgtc    420

aaaatcactt tgctggnttc aattcacaan ggaagaagta gggttcaaca accaaggaag    480

tgnccnancc aacaatccct ggntccaaga taccgggaaa ggggactanc               530
```

<210> SEQ ID NO 114
<211> LENGTH: 87
<212> TYPE: PRT
<213> ORGANISM: Glycine max -continued

```
<220> FEATURE:
<221> NAME/KEY: UNSURE
<222> LOCATION: (64)

<400> SEQUENCE: 114

Met Leu Thr Cys Gly Ala Tyr Ile Ala Phe Gly Thr Tyr Arg Asp Ile
  1               5                  10                  15

Phe Arg Gly Ile Thr Pro Thr Asp Ala Pro Thr Phe Gly Lys Val Phe
             20                  25                  30

Gly Gly Gln Ile Val Gly Gln Ala Leu Ala Ala Ala Ser Lys Ser Val
         35                  40                  45

Asp Cys Leu Lys Val Val His Ser Leu His Val Tyr Phe Leu Pro Xaa
     50                  55                  60

Gly Ile Leu Thr Tyr Pro Leu Tyr Ile Lys Leu Lys Arg Leu Arg Asp
 65                  70                  75                  80

Gly Lys Ser Phe Ala Thr Lys
                 85


<210> SEQ ID NO 115
<211> LENGTH: 1225
<212> TYPE: DNA
<213> ORGANISM: Glycine max

<400> SEQUENCE: 115

gcacgaggtt tgtcaaacac agttcaccag gcagatgttg ttgctttgtc taagctcaca      60

tgcttagtgc ttccccatgt gcactcaaca ctgctgcagc caaagtctat ctggagagca     120

gaaaattctc tcgagacatg ctcacctgtg gagaatatat tgcatttgga gccccttgag     180

taataccctg gaattcagcc ttaaattaaa gcattttttt attctctttg gaaggtagat     240

atcttccaag gagttaccct tccagatgct ccaagatttg gaaaggtgtt tggggggcag     300

atgattggac aggcactggc tgcagcttca aaatctgttg actgtcttaa ggttgttcat     360

agtttgcatg cctattttat tcttgcgggg gatttaaaca tgccaattac atatcaaatt     420

caccgtctcc gtgatggaaa gagcttcgct tcaaggaaag tggatggaat tcaaaaggga     480

aatgtcatat tcactctgat ggcttcattt caaaaagaag aatcagggat ggtccaccaa     540

gaagtagcta taccatctgt ccctgctcca gataagcttc tgccgatgga agagctacgg     600

gagagacgtc ttactgaccc tcgtttacca ataacctatc ggaacaaagt agctacatct     660

caattcatcc catggcccat agagatacga ttatgtgaat atgaaactgc aacaaatatg     720

acaaaatctc ctcccagttt gagatactgg tttagagcca agggaaaact ttcagatgat     780

caagccttgc ataggtgtgt ggtggcatat gcttcagatc taatatttct tcaagtaagt     840

ttgaatcccc accgtgagaa gggtttcagg acacgttctg ttagtctgga ccactctatg     900

tggtttcacc gatccgtaaa agctgatgaa tgggtgctat ttgcgatctt tactcctagt     960

gcccatagtg cacgtgtctt tgtcaccggc caaatgttca atcagaaggg agagcttctt    1020

gtatcattgg ttcaagaagg actagccagg aaaattaatc ccggaaattc agccattaaa    1080

tctatgttat gaactgctga aaaatgcaca gattagcatg tatccatttt atagttttat    1140

ttttaaaaaa ttccatgtat ccatcaccat aacatcttag tatctaaatt atatatgtaa    1200

atttttgtat tgctctaaaa aaaaa                                          1225


<210> SEQ ID NO 116
<211> LENGTH: 295
<212> TYPE: PRT
<213> ORGANISM: Glycine max
```

<400> SEQUENCE: 116

```
Ile Lys Ala Phe Phe Tyr Ser Leu Trp Lys Val Asp Ile Phe Gln Gly
  1               5                  10                  15

Val Thr Leu Pro Asp Ala Pro Arg Phe Gly Lys Val Phe Gly Gly Gln
             20                  25                  30

Met Ile Gly Gln Ala Leu Ala Ala Ala Ser Lys Ser Val Asp Cys Leu
         35                  40                  45

Lys Val Val His Ser Leu His Ala Tyr Phe Ile Leu Ala Gly Asp Leu
     50                  55                  60

Asn Met Pro Ile Thr Tyr Gln Ile His Arg Leu Arg Asp Gly Lys Ser
 65                  70                  75                  80

Phe Ala Ser Arg Lys Val Asp Gly Ile Gln Lys Gly Asn Val Ile Phe
                 85                  90                  95

Thr Leu Met Ala Ser Phe Gln Lys Glu Glu Ser Gly Met Val His Gln
            100                 105                 110

Glu Val Ala Ile Pro Ser Val Pro Ala Pro Asp Lys Leu Leu Pro Met
        115                 120                 125

Glu Glu Leu Arg Glu Arg Arg Leu Thr Asp Pro Arg Leu Pro Ile Thr
    130                 135                 140

Tyr Arg Asn Lys Val Ala Thr Ser Gln Phe Ile Pro Trp Pro Ile Glu
145                 150                 155                 160

Ile Arg Leu Cys Glu Tyr Glu Thr Ala Thr Asn Met Thr Lys Ser Pro
                165                 170                 175

Pro Ser Leu Arg Tyr Trp Phe Arg Ala Lys Gly Lys Leu Ser Asp Asp
            180                 185                 190

Gln Ala Leu His Arg Cys Val Val Ala Tyr Ala Ser Asp Leu Ile Phe
        195                 200                 205

Leu Gln Val Ser Leu Asn Pro His Arg Glu Lys Gly Phe Arg Thr Arg
    210                 215                 220

Ser Val Ser Leu Asp His Ser Met Trp Phe His Arg Ser Val Lys Ala
225                 230                 235                 240

Asp Glu Trp Val Leu Phe Ala Ile Phe Thr Pro Ser Ala His Ser Ala
                245                 250                 255

Arg Val Phe Val Thr Gly Gln Met Phe Asn Gln Lys Gly Glu Leu Leu
            260                 265                 270

Val Ser Leu Val Gln Glu Gly Leu Ala Arg Lys Ile Asn Pro Gly Asn
        275                 280                 285

Ser Ala Ile Lys Ser Met Leu
    290                 295
```

<210> SEQ ID NO 117
<211> LENGTH: 1756
<212> TYPE: DNA
<213> ORGANISM: Glycine max

<400> SEQUENCE: 117

```
gtaagttcac catgctgatg ttgtagcttt gacaaagcta tcatgcttgg tgctgcccca      60

tgagcactca gcattgctgc agccaaagtc tatttggagt gcagaaaaat ctcatgatac     120

atgctcactt gtggagcata tattgcattt ggaccctata gaggtagaca tcttccgagg     180

aatcactcct ccagatgctc caacatttgg gaaggtattt ggtggacaaa tagttggaca     240

ggcactggct gcagcatcaa aatctgttga ttgtcgtaaa gttgttcata gcttgcatgt     300

ctattttctt cttgtggggg attttaacat acccattata tatcaagtta agcgtctccg     360
```

-continued

```
tgatgggaag agttttgcta caaggaaagt ggatgcaatt caaaagggaa atgtcatatt    420
cactttgttg gcttcatttc ataaggaaga agtagggttt caccaccagg aagtgtctat    480
cccatcagtc cctgctccag atacgctttt atcgttggaa gagcttcggg agcaacgtct    540
tactgaccct cgtcttccaa gaacttaccg gaacaaggtt gctacaattg aattcattcc    600
ctggcccata gagatacggt tctgtgaacc taaaatttca acaaatcaga ccaaatctcc    660
tcctagtttg agatactggt ttagagcaag gggaaaactt tcagatgatc aagccttgca    720
taggtgtgtg gtagcatata catcagatct aatcttcctt caagtgagtt tgaaccccaa    780
ccgtaggaag ggaaggaagg ctcgtgctgt gagtctggac cactccatgt ggtttcacag    840
acctttaaga gctgatgatt ggatactatt tgtgatcttt agtcctactg ccaataatgc    900
ccgcggctat gtcactggcc aaatgttcaa tcagaaggga gagcatcttg tgtctgtggt    960
tcaagaaggt gtaatgaggg aagttatttc tgctaagtca gccatcaaat ctaatctatg   1020
aatagctaaa aatgcactga aacttgtgtt ctttttagtt ttgtcttctt ttgttttcct   1080
tctatagtga atgatcgggt gaaccataca ataggtggtg caccactata tcaccatcat   1140
atagtgcacc tttattttta atcaacggtt caaaattgtg attgacaagt aattgatgtg   1200
ttagatttat ttacaattaa ctagttttaa aatttacaaa ttggtccttt tgttgtcgcg   1260
tttgtaccat ctcctacaaa gattcacgcc tctgtcggct cttccatcac cacgagccct   1320
gatctctgct ggcatccgca acaaccatgg ctcatctctt catttcaaaa gttatagctt   1380
tacttcatca atcactatac aaccagaatt gccaattcaa atgtaagaaa aatatacttt   1440
tttttatgga caaatgatac atataacatt acctaccagt atagtcttgc ttcctaagtc   1500
ttgggagaag acaaatgatg aattctgggt ttgttttggg tccttatgct ttcaaaaaca   1560
cgttgaacac gaattgttat ttatttggat tacactaaac gtgctctaac atgtaacgca   1620
aatacaaata ttcccagagt cattgaaatg ttattctagt ggaaagaact tgactatcca   1680
tatttggagg aaattaattt taagcccaaa ataatacgag atatgttaca caaaaaaaaa   1740
aaaaaaaaaa aaaaaa                                                   1756
```

<210> SEQ ID NO 118
<211> LENGTH: 338
<212> TYPE: PRT
<213> ORGANISM: Glycine max

<400> SEQUENCE: 118

```
Val His His Ala Asp Val Val Ala Leu Thr Lys Leu Ser Cys Leu Val
  1               5                  10                  15

Leu Pro His Glu His Ser Ala Leu Leu Gln Pro Lys Ser Ile Trp Ser
             20                  25                  30

Ala Glu Lys Ser His Asp Thr Cys Ser Leu Val Glu His Ile Leu His
         35                  40                  45

Leu Asp Pro Ile Glu Val Asp Ile Phe Arg Gly Ile Thr Pro Pro Asp
     50                  55                  60

Ala Pro Thr Phe Gly Lys Val Phe Gly Gly Gln Ile Val Gly Gln Ala
 65                  70                  75                  80

Leu Ala Ala Ala Ser Lys Ser Val Asp Cys Arg Lys Val Val His Ser
                 85                  90                  95

Leu His Val Tyr Phe Leu Leu Val Gly Asp Phe Asn Ile Pro Ile Ile
            100                 105                 110

Tyr Gln Val Lys Arg Leu Arg Asp Gly Lys Ser Phe Ala Thr Arg Lys
        115                 120                 125
```

-continued

```
Val Asp Ala Ile Gln Lys Gly Asn Val Ile Phe Thr Leu Leu Ala Ser
    130                 135                 140

Phe His Lys Glu Glu Val Gly Phe His His Gln Glu Val Ser Ile Pro
145                 150                 155                 160

Ser Val Pro Ala Pro Asp Thr Leu Leu Ser Leu Glu Glu Leu Arg Glu
                165                 170                 175

Gln Arg Leu Thr Asp Pro Arg Leu Pro Arg Thr Tyr Arg Asn Lys Val
            180                 185                 190

Ala Thr Ile Glu Phe Ile Pro Trp Pro Ile Glu Ile Arg Phe Cys Glu
        195                 200                 205

Pro Lys Ile Ser Thr Asn Gln Thr Lys Ser Pro Pro Ser Leu Arg Tyr
    210                 215                 220

Trp Phe Arg Ala Arg Gly Lys Leu Ser Asp Asp Gln Ala Leu His Arg
225                 230                 235                 240

Cys Val Val Ala Tyr Thr Ser Asp Leu Ile Phe Leu Gln Val Ser Leu
                245                 250                 255

Asn Pro Asn Arg Arg Lys Gly Arg Lys Ala Arg Ala Val Ser Leu Asp
            260                 265                 270

His Ser Met Trp Phe His Arg Pro Leu Arg Ala Asp Asp Trp Ile Leu
        275                 280                 285

Phe Val Ile Phe Ser Pro Thr Ala Asn Asn Ala Arg Gly Tyr Val Thr
    290                 295                 300

Gly Gln Met Phe Asn Gln Lys Gly Glu His Leu Val Ser Val Val Gln
305                 310                 315                 320

Glu Gly Val Met Arg Glu Val Ile Ser Ala Lys Ser Ala Ile Lys Ser
                325                 330                 335

Asn Leu


<210> SEQ ID NO 119
<211> LENGTH: 1083
<212> TYPE: DNA
<213> ORGANISM: Zea mays
<220> FEATURE:
<221> NAME/KEY: unsure
<222> LOCATION: (986)
<221> NAME/KEY: unsure
<222> LOCATION: (1014)
<221> NAME/KEY: unsure
<222> LOCATION: (1017)
<221> NAME/KEY: unsure
<222> LOCATION: (1019)
<221> NAME/KEY: unsure
<222> LOCATION: (1022)

<400> SEQUENCE: 119

gcacgagaga ctgttgattg tctaaaaatg gtgcatagtt tgcatgcaat ttttcttgtt      60

gctggagaca ataacatacc gataatatat caagttcatc gggcacgtga tggatccagc     120

tttgccacaa gaaaagtgga ggcaaagcag aagggcctag ttgtattcac cttgattgct     180

tctttccaga aggaagaagt gggttttgag catcaggctg caatcatgcc tgatgttcct     240

ccgccagaac agctccttaa tctggaggag atacgtgaaa gacggcttac tgatccacgc     300

ttcccatccc aatataggaa cttggcagct aaaaaaaagt ttattccttg gcccatagaa     360

atgagatttt gtgaaggttc agcgtctcaa cataaaccaa gcttaaacta ctggtttaga     420

gctcgaggga aactctcaga cgaccaagct ctacacagat gtgttgtagc atatgcttcg     480

gatctactat tttctggggt gagccttaac cctcatcggg agaagggttt gaagacatac     540

tgcctcagtc ttgaccattc catctggttc cacaaacctg tgaaggctga cgaatggatg     600
```

-continued

```
ctgtatgtga tcgagagccc atctgcgcac ggtggtcgcg gtttcgtcac cggacgcatg     660

ttcaacaggc aaggagagct tatcatgtcg ctgacccaag aggcattgat tcgaagggag     720

aagccgcgag gaccaaatcc gaggccgaag ctttgaggca cctgacagcc tctgcagtcg     780

actgtagagg atcccaaccg agctttgaga ggcgcaccat cctttcttct aatttggttt     840

agatatttat gaattcacaa acaaaaatat agaatatcaa gcagtataaa agatctcaag     900

tcaaacctaa catttttttt tcatttctcc ggatgatttc tatttgtttt ggtgtgtgtg     960

tggttggagg ggtattggaa gcggangcgg aggcggaggg tttgatactt tagnctntnt    1020

cntgcagctt actaattctc gtacacatat ttaaatttca ttatacgaac agtatatata    1080

caa                                                                  1083
```

```
<210> SEQ ID NO 120
<211> LENGTH: 251
<212> TYPE: PRT
<213> ORGANISM: Zea mays

<400> SEQUENCE: 120

Ala Arg Glu Thr Val Asp Cys Leu Lys Met Val His Ser Leu His Ala
  1               5                  10                  15

Ile Phe Leu Val Ala Gly Asp Asn Asn Ile Pro Ile Ile Tyr Gln Val
             20                  25                  30

His Arg Ala Arg Asp Gly Ser Ser Phe Ala Thr Arg Lys Val Glu Ala
         35                  40                  45

Lys Gln Lys Gly Leu Val Val Phe Thr Leu Ile Ala Ser Phe Gln Lys
     50                  55                  60

Glu Glu Val Gly Phe Glu His Gln Ala Ala Ile Met Pro Asp Val Pro
 65                  70                  75                  80

Pro Pro Glu Gln Leu Leu Asn Leu Glu Glu Ile Arg Glu Arg Arg Leu
                 85                  90                  95

Thr Asp Pro Arg Phe Pro Ser Gln Tyr Arg Asn Leu Ala Ala Lys Lys
            100                 105                 110

Lys Phe Ile Pro Trp Pro Ile Glu Met Arg Phe Cys Glu Gly Ser Ala
        115                 120                 125

Ser Gln His Lys Pro Ser Leu Asn Tyr Trp Phe Arg Ala Arg Gly Lys
    130                 135                 140

Leu Ser Asp Asp Gln Ala Leu His Arg Cys Val Val Ala Tyr Ala Ser
145                 150                 155                 160

Asp Leu Leu Phe Ser Gly Val Ser Leu Asn Pro His Arg Glu Lys Gly
                165                 170                 175

Leu Lys Thr Tyr Cys Leu Ser Leu Asp His Ser Ile Trp Phe His Lys
            180                 185                 190

Pro Val Lys Ala Asp Glu Trp Met Leu Tyr Val Ile Glu Ser Pro Ser
        195                 200                 205

Ala His Gly Gly Arg Gly Phe Val Thr Gly Arg Met Phe Asn Arg Gln
    210                 215                 220

Gly Glu Leu Ile Met Ser Leu Thr Gln Glu Ala Leu Ile Arg Arg Glu
225                 230                 235                 240

Lys Pro Arg Gly Pro Asn Pro Arg Pro Lys Leu
                245                 250


<210> SEQ ID NO 121
<211> LENGTH: 1312
<212> TYPE: DNA
<213> ORGANISM: Oryza sativa
```

-continued

<220> FEATURE:
<221> NAME/KEY: unsure
<222> LOCATION: (1197)
<221> NAME/KEY: unsure
<222> LOCATION: (1216)
<221> NAME/KEY: unsure
<222> LOCATION: (1234)

<400> SEQUENCE: 121
tggtacgtta ttgcagtatc aaaggttcct tgttcatgtt tctattttta ataacagtat 60
aagctgatgg tgtccctact gtaataataa atatcttctg gcttcagctt attgttagta 120
tcctattttg cagctgacct gcttcgtatt gccaaatcaa tatggacact tgttgcaacc 180
aaagaccatt tggagtgcag aagagacacc tgagaaccat tctttgctag aacaaatttt 240
gcacttagag ccattggagg tcgatatctt ccgtgggttt actttgccaa ggagctccac 300
ttttaggcaa gtttttggag gacagttgat aggacaggca ctagcagcag catccaagac 360
cgttgactgc ctaaaagcgg tgcacagttt gcacgcaatt ttccttatcg caggagacaa 420
gaatttgcca ataatatatc aggttcatcg ggcgcgcgat ggaacaagct ttgccaccag 480
aaaagtggag gcaaagcaaa agggccttgt cattttcacc ttgattgctt cattccagaa 540
agacgaatta gggtttgagc atcaagctgc aatcatgcct gatgttcctc ctccagaaga 600
gctcctgaat ctggaagaca tacaggaaag aagacttact gatcctcgct taccagcata 660
taggaactca gctgccaaga aaaagttcgt accttggccc atagaaatga ggttttgtga 720
agattcagca tctcaacata aaccaagctt aaattattgg tttagagcca gaggaaaact 780
ttctgatgat ccagcactgc ataggtgtgt tgtagcatat gcttcggatc tactatattc 840
tggtgtcagc ctaaatcctc atagggagaa gggtctgaag acatactcac tcagtcttga 900
tcactcgatt tggttccaca agcctgtgaa agctgatgat tggcttttat atgtgatcga 960
cagcccatct gcacacggtg ggcggggttt tgttacaggg cgaatgttca accgacaagg 1020
agagctcgtc atgtcgttga cccaagaggc gctgattagg agggcgaaga cgccaggaca 1080
accgtcacaa accccaaggc caaagctttg agaggtgcag aagagcagta ttatcgtttc 1140
atttttggca ctttcacaag ttattttcct tttcaatgga aagtctataa cacgtanacg 1200
tgaagccgaa gtatancata ctgcatatat gtancaagaa aaaacgatgg taaaactggt 1260
tctgttattc acgaacaact tactggacat accaacgtat gtatggatcg gg 1312

<210> SEQ ID NO 122
<211> LENGTH: 330
<212> TYPE: PRT
<213> ORGANISM: Oryza sativa

<400> SEQUENCE: 122

Tyr Pro Ile Leu Gln Leu Thr Cys Phe Val Leu Pro Asn Gln Tyr Gly
1 5 10 15

His Leu Leu Gln Pro Lys Thr Ile Trp Ser Ala Glu Glu Thr Pro Glu
20 25 30

Asn His Ser Leu Leu Glu Gln Ile Leu His Leu Glu Pro Leu Glu Val
35 40 45

Asp Ile Phe Arg Gly Phe Thr Leu Pro Arg Ser Ser Thr Phe Arg Gln
50 55 60

Val Phe Gly Gly Gln Leu Ile Gly Gln Ala Leu Ala Ala Ala Ser Lys
65 70 75 80

Thr Val Asp Cys Leu Lys Ala Val His Ser Leu His Ala Ile Phe Leu
85 90 95

-continued

```
Ile Ala Gly Asp Lys Asn Leu Pro Ile Ile Tyr Gln Val His Arg Ala
            100                 105                 110

Arg Asp Gly Thr Ser Phe Ala Thr Arg Lys Val Glu Ala Lys Gln Lys
        115                 120                 125

Gly Leu Val Ile Phe Thr Leu Ile Ala Ser Phe Gln Lys Asp Glu Leu
    130                 135                 140

Gly Phe Glu His Gln Ala Ala Ile Met Pro Asp Val Pro Pro Pro Glu
145                 150                 155                 160

Glu Leu Leu Asn Leu Glu Asp Ile Gln Glu Arg Arg Leu Thr Asp Pro
                165                 170                 175

Arg Leu Pro Ala Tyr Arg Asn Ser Ala Ala Lys Lys Lys Phe Val Pro
            180                 185                 190

Trp Pro Ile Glu Met Arg Phe Cys Glu Asp Ser Ala Ser Gln His Lys
        195                 200                 205

Pro Ser Leu Asn Tyr Trp Phe Arg Ala Arg Gly Lys Leu Ser Asp Asp
    210                 215                 220

Pro Ala Leu His Arg Cys Val Val Ala Tyr Ala Ser Asp Leu Leu Tyr
225                 230                 235                 240

Ser Gly Val Ser Leu Asn Pro His Arg Glu Lys Gly Leu Lys Thr Tyr
                245                 250                 255

Ser Leu Ser Leu Asp His Ser Ile Trp Phe His Lys Pro Val Lys Ala
            260                 265                 270

Asp Asp Trp Leu Leu Tyr Val Ile Asp Ser Pro Ser Ala His Gly Gly
        275                 280                 285

Arg Gly Phe Val Thr Gly Arg Met Phe Asn Arg Gln Gly Glu Leu Val
    290                 295                 300

Met Ser Leu Thr Gln Glu Ala Leu Ile Arg Arg Ala Lys Thr Pro Gly
305                 310                 315                 320

Gln Pro Ser Gln Thr Pro Arg Pro Lys Leu
                325                 330
```

```
<210> SEQ ID NO 123
<211> LENGTH: 627
<212> TYPE: DNA
<213> ORGANISM: Glycine max
<220> FEATURE:
<221> NAME/KEY: unsure
<222> LOCATION: (507)..(508)
<221> NAME/KEY: unsure
<222> LOCATION: (512)
<221> NAME/KEY: unsure
<222> LOCATION: (542)
<221> NAME/KEY: unsure
<222> LOCATION: (545)
<221> NAME/KEY: unsure
<222> LOCATION: (553)
<221> NAME/KEY: unsure
<222> LOCATION: (570)
<221> NAME/KEY: unsure
<222> LOCATION: (577)
<221> NAME/KEY: unsure
<222> LOCATION: (580)

<400> SEQUENCE: 123

gtttgtcaaa cacagttcac caggcagatg ttgttgcttt gtctaagctc acatgcttag     60

tgcttcccca tgtgcactca acactgctgc agccaaagtc tatctggaga gcagaaaatt    120

ctctcgagac atgctcacct gtggagaata tattgcattt ggagcccctt gagtaatacc    180

ctggaattca gccttaaatt aaagcatttt tttattctct ttggaaggta gatatcttcc    240

aaggagttac ccttccagat gctccaagat ttggaaaggt gtttgggggg cagatgattg    300
```

-continued

```
gacaggcact ggctgcagct tcaaaatctg ttgactgtct taaggttgtt caaagtttgc    360

atgcctattt tattcttgcg ggggatttaa acatgccaat tacatatcag attcaccgtc    420

tccgtgatgg aaagagcttc gcttcacgga aagtggatgg aattcaaaag ggaaatgtca    480

tattcactct gatggcttca tttcaannag angaatcagg gatggcccac caagaagtaa    540

cnatnccatc tgnccctgct ccaagataan cttctgncgn tgggagaggc tacgggagag    600

acgtcttact ggacccctcg tttacca                                        627
```

<210> SEQ ID NO 124
<211> LENGTH: 123
<212> TYPE: PRT
<213> ORGANISM: Glycine max
<220> FEATURE:
<221> NAME/KEY: UNSURE
<222> LOCATION: (104)..(105)
<221> NAME/KEY: UNSURE
<222> LOCATION: (116)
<221> NAME/KEY: UNSURE
<222> LOCATION: (119)

<400> SEQUENCE: 124

```
Ile Lys Ala Phe Phe Tyr Ser Leu Trp Lys Val Asp Ile Phe Gln Gly
  1               5                  10                  15

Val Thr Leu Pro Asp Ala Pro Arg Phe Gly Lys Val Phe Gly Gly Gln
             20                  25                  30

Met Ile Gly Gln Ala Leu Ala Ala Ala Ser Lys Ser Val Asp Cys Leu
         35                  40                  45

Lys Val Val Gln Ser Leu His Ala Tyr Phe Ile Leu Ala Gly Asp Leu
     50                  55                  60

Asn Met Pro Ile Thr Tyr Gln Ile His Arg Leu Arg Asp Gly Lys Ser
 65                  70                  75                  80

Phe Ala Ser Arg Lys Val Asp Gly Ile Gln Lys Gly Asn Val Ile Phe
                 85                  90                  95

Thr Leu Met Ala Ser Phe Gln Xaa Xaa Glu Ser Gly Met Ala His Gln
            100                 105                 110

Glu Val Thr Xaa Pro Ser Xaa Pro Ala Pro Arg
        115                 120
```

<210> SEQ ID NO 125
<211> LENGTH: 477
<212> TYPE: DNA
<213> ORGANISM: Glycine max
<220> FEATURE:
<221> NAME/KEY: unsure
<222> LOCATION: (428)
<221> NAME/KEY: unsure
<222> LOCATION: (460)
<221> NAME/KEY: unsure
<222> LOCATION: (469)
<221> NAME/KEY: unsure
<222> LOCATION: (471)
<221> NAME/KEY: unsure
<222> LOCATION: (477)

<400> SEQUENCE: 125

```
ccatgctgat gttgtagctt tgacaaagct atcatgcttg gtgctgcccc atgagcactc     60

agcattgctg cagccaaagt ctatttggag tgcagaaaaa tctcatgata catgctcact    120

tgtggagcat atattgcatt tggaccctat agaggtagac atcttccgag gaatcactcc    180

tccagatgct ccaacatttg ggaaggtatt tggtggacaa atagttggac aggcactggc    240

tgcagcatca aaatctgttg attgtcgtaa agttgttcat agcttgcatg tctattttct    300
```

-continued

```
tcttgtgggg gattttaaca tacccattat atatcaagtt aagcgtctcc gtgatgggaa    360

gagttttgct acaaggaaag tggatgcaat tcaaaaggga aatgtcatat tcactttgtt    420

ggcttcantt cataaaggaa gaagtagggt tcaccaccan gaagtgtcna nccatcn       477


<210> SEQ ID NO 126
<211> LENGTH: 158
<212> TYPE: PRT
<213> ORGANISM: Glycine max
<220> FEATURE:
<221> NAME/KEY: UNSURE
<222> LOCATION: (143)
<221> NAME/KEY: UNSURE
<222> LOCATION: (153)
<221> NAME/KEY: UNSURE
<222> LOCATION: (157)

<400> SEQUENCE: 126

His Ala Asp Val Val Ala Leu Thr Lys Leu Ser Cys Leu Val Leu Pro
  1               5                  10                  15

His Glu His Ser Ala Leu Leu Gln Pro Lys Ser Ile Trp Ser Ala Glu
             20                  25                  30

Lys Ser His Asp Thr Cys Ser Leu Val Glu His Ile Leu His Leu Asp
         35                  40                  45

Pro Ile Glu Val Asp Ile Phe Arg Gly Ile Thr Pro Pro Asp Ala Pro
     50                  55                  60

Thr Phe Gly Lys Val Phe Gly Gly Gln Ile Val Gly Gln Ala Leu Ala
 65                  70                  75                  80

Ala Ala Ser Lys Ser Val Asp Cys Arg Lys Val Val His Ser Leu His
                 85                  90                  95

Val Tyr Phe Leu Leu Val Gly Asp Phe Asn Ile Pro Ile Ile Tyr Gln
            100                 105                 110

Val Lys Arg Leu Arg Asp Gly Lys Ser Phe Ala Thr Arg Lys Val Asp
        115                 120                 125

Ala Ile Gln Lys Gly Asn Val Ile Phe Thr Leu Leu Ala Ser Xaa His
    130                 135                 140

Lys Gly Arg Ser Arg Val His His Xaa Glu Val Ser Xaa His
145                 150                 155


<210> SEQ ID NO 127
<211> LENGTH: 1663
<212> TYPE: DNA
<213> ORGANISM: Zea mays
<220> FEATURE:
<221> NAME/KEY: unsure
<222> LOCATION: (1623)..(1624)

<400> SEQUENCE: 127

gcacgaggca tgcaattgat ggtattccta agaactgcca gatattgcat gttgagcaag     60

aggtcgtggg tgacgatacg acagctttgc agtgtgttct gaacgccgat gtcgaacgag    120

ttcaactttt gcaggaagaa gctcgtcttg ttcaacaaca gaaagattta gagattgagg    180

ctgagtttgg gcagagctct gacaagggca aggatggttt tgacaaagat tctatcagca    240

agaggcttga ggagatatat aaacggcttg agctcattga tgcggatgca gcagaggctc    300

gcgcagcatc aattttggcg ggtcttagtt ttactccaga aatgcaacgc aagcgtacaa    360

aacaattttc tggtggatgg cgcatgagaa tagctctagc acgtgctctg ttcattgagc    420

ctgatttgct actacttgat gagccgacaa accatcttga tcttcatgct gtgttatggc    480

tagaaactta tctcctgaag tggccaaaga cattcattgt tgtatcacac gcaagggagt    540
```

-continued

```
ttttgaatac ggttgtcacc gatatccttc atctgcatgg tagaaaacta catgcttaca    600

aaggtgacta tgacacattt gagaggacaa gggaagagca ccttaagaat cagcagaaag    660

cctttgaaac aaatgagaag gccagacagc acatgcagac attcattgac aagtttcggt    720

acaatgcaaa gagagcatca cttgttcaat caagaatcaa ggcattggag cgaatggaac    780

atgttgatgc agttgtcagc gatccagact ataaatttga atttccaacc ccagatgacc    840

gccctgggcc accaatcatc agcttcagtg atgcctcatt tggttaccct ggagggccta    900

ccttgtttaa aaatttgaat tttggtatcg acctggacag ccgcatagca atggttggtc    960

ctaatggcat tggcaagtcc actatactga aactaatttc tggggatctg cagccaactt   1020

ctggaacagt atttcgctct cccaaggttc gcatggctgt attcaatcag catcatgttg   1080

atggccttga tttgacggtg aatccccttt tgtacatgat gaagtgctat ccgggtgtgc   1140

cggagcagaa gttgagggca catctgggtt cgtttggtgt ttcgggaagc cttgccctcc   1200

aatctatgta cactttatca ggtggtcaga agagtagggt tgcattcgcg aaaataacct   1260

tcaagaagcc gcacatcatt ctccttgacg agccttctaa ccatcttgat ctggacgctg   1320

ttgaggcgct catccagggt ttactcattt ttcagggagg ggtgctgatg gtgagtcacg   1380

atgagcatct tatcactgga agcgtggacg agctttgggt ggtgtcggaa ggcagggtga   1440

ccccgttctc gggcactttc aaggactaca agaagatgct caagtaacaa aaacatgtat   1500

tatcgaccat agcctatata tctatatgct tgctattatg ttgtattacc gtataaattt   1560

tgggagtaaa gcatcgaaat tattataaca catacctaat gccgaaagga gaagatttct   1620

cannaaaaaa aaaaaaaaaa taaaaaaaaa aaaaaaaaaa aaa                      1663
```

<210> SEQ ID NO 128
<211> LENGTH: 494
<212> TYPE: PRT
<213> ORGANISM: Zea mays

<400> SEQUENCE: 128

```
Thr Arg His Ala Ile Asp Gly Ile Pro Lys Asn Cys Gln Ile Leu His
  1               5                  10                  15

Val Glu Gln Glu Val Val Gly Asp Asp Thr Thr Ala Leu Gln Cys Val
             20                  25                  30

Leu Asn Ala Asp Val Glu Arg Val Gln Leu Leu Gln Glu Glu Ala Arg
         35                  40                  45

Leu Val Gln Gln Gln Lys Asp Leu Glu Ile Glu Ala Glu Phe Gly Gln
     50                  55                  60

Ser Ser Asp Lys Gly Lys Asp Gly Phe Asp Lys Asp Ser Ile Ser Lys
 65                  70                  75                  80

Arg Leu Glu Glu Ile Tyr Lys Arg Leu Glu Leu Ile Asp Ala Asp Ala
                 85                  90                  95

Ala Glu Ala Arg Ala Ala Ser Ile Leu Ala Gly Leu Ser Phe Thr Pro
            100                 105                 110

Glu Met Gln Arg Lys Arg Thr Lys Gln Phe Ser Gly Gly Trp Arg Met
        115                 120                 125

Arg Ile Ala Leu Ala Arg Ala Leu Phe Ile Glu Pro Asp Leu Leu Leu
    130                 135                 140

Leu Asp Glu Pro Thr Asn His Leu Asp Leu His Ala Val Leu Trp Leu
145                 150                 155                 160

Glu Thr Tyr Leu Leu Lys Trp Pro Lys Thr Phe Ile Val Val Ser His
                165                 170                 175
```

-continued

```
Ala Arg Glu Phe Leu Asn Thr Val Val Thr Asp Ile Leu His Leu His
            180                 185                 190

Gly Arg Lys Leu His Ala Tyr Lys Gly Asp Tyr Asp Thr Phe Glu Arg
        195                 200                 205

Thr Arg Glu Glu His Leu Lys Asn Gln Gln Lys Ala Phe Glu Thr Asn
    210                 215                 220

Glu Lys Ala Arg Gln His Met Gln Thr Phe Ile Asp Lys Phe Arg Tyr
225                 230                 235                 240

Asn Ala Lys Arg Ala Ser Leu Val Gln Ser Arg Ile Lys Ala Leu Glu
                245                 250                 255

Arg Met Glu His Val Asp Ala Val Val Ser Asp Pro Asp Tyr Lys Phe
            260                 265                 270

Glu Phe Pro Thr Pro Asp Asp Arg Pro Gly Pro Pro Ile Ile Ser Phe
        275                 280                 285

Ser Asp Ala Ser Phe Gly Tyr Pro Gly Gly Pro Thr Leu Phe Lys Asn
    290                 295                 300

Leu Asn Phe Gly Ile Asp Leu Asp Ser Arg Ile Ala Met Val Gly Pro
305                 310                 315                 320

Asn Gly Ile Gly Lys Ser Thr Ile Leu Lys Leu Ile Ser Gly Asp Leu
                325                 330                 335

Gln Pro Thr Ser Gly Thr Val Phe Arg Ser Pro Lys Val Arg Met Ala
            340                 345                 350

Val Phe Asn Gln His His Val Asp Gly Leu Asp Leu Thr Val Asn Pro
        355                 360                 365

Leu Leu Tyr Met Met Lys Cys Tyr Pro Gly Val Pro Glu Gln Lys Leu
    370                 375                 380

Arg Ala His Leu Gly Ser Phe Gly Val Ser Gly Ser Leu Ala Leu Gln
385                 390                 395                 400

Ser Met Tyr Thr Leu Ser Gly Gly Gln Lys Ser Arg Val Ala Phe Ala
                405                 410                 415

Lys Ile Thr Phe Lys Lys Pro His Ile Ile Leu Leu Asp Glu Pro Ser
            420                 425                 430

Asn His Leu Asp Leu Asp Ala Val Glu Ala Leu Ile Gln Gly Leu Leu
        435                 440                 445

Ile Phe Gln Gly Gly Val Leu Met Val Ser His Asp Glu His Leu Ile
    450                 455                 460

Thr Gly Ser Val Asp Glu Leu Trp Val Val Ser Glu Gly Arg Val Thr
465                 470                 475                 480

Pro Phe Ser Gly Thr Phe Lys Asp Tyr Lys Lys Met Leu Lys
                485                 490
```

<210> SEQ ID NO 129
<211> LENGTH: 1875
<212> TYPE: DNA
<213> ORGANISM: Oryza sativa

<400> SEQUENCE: 129

```
ctggaatgcc tccagtattt gtaaatcaca ataactctgg tgggccagct gttagggata      60

tccatatgga gaacttcagt gttactgttg gtggtcgtga tctcattcaa gattgcactg     120

taacacttgc ttttgggagg cactatggtc ttgttggaag aaatggtaca gggaaaacct     180

cttttctcag agctatggcg atgcatgcga ttgatgggat tcccaagaac tgccagatat     240

tgcatgttga gcaagaggtt gtgggcgatg acacaacagc tttgcagtgt gttctgaatg     300

ctgatattga acgggttcaa cttttgcaag aagaagctca tctggttcaa cggcagaaag     360
```

-continued

```
atctagagta tgaggctgag tttgagcaga gcgcgtccaa aagcaaggat ggtcttgaca    420

aagatgctat cagcaagagg cttgaggaga tatacaaacg ccttgagttt attgatgctg    480

atgctgcaga ggctcgtgca gcatcaattc tggcgggtct tagtttcact cctgaaatgc    540

aacgtaaacg cacaaaacag ttttctggtg gatggcgcat gagaattgct ctagcacgtg    600

ctctcttcat tgagcctgat ttgttgctac ttgatgagcc aacaaatcat cttgatctcc    660

atgctgtgtt atggttagaa acatatctcc tgaaatggcc aaagacattc attgttgtat    720

cacatgctag ggagtttctt aatacggtcg tcaccgacat tcttcatctg catggacaaa    780

agctacatgc ttacaaaggt gattatgaca cattcgagag gacaagggag gagcacctta    840

agaaccagca gaaagctttt gaaacaaatg agaaggccag atcccacatg caggcattca    900

ttgacaagtt ccgttacaat gcaaagagag catcacttgt tcaatcaaga atcaaggcat    960

tggagcgaat ggagcatgtt gatgcggtcg tcagtgatcc agactataaa ttcgaatttc   1020

caacaccaga tgaccgccct ggaccaccaa tcatcagctt cagtgacgca tcttttggtt   1080

atcctggagg ccccacctta tttaaaaact tgaattttgg tattgacctg gacagccgca   1140

tagcaatggt tggtccaaat ggtattggca aatccactat acttaaacta atatctggag   1200

atcttcagcc aacttcaggg acagtgttcc gctctcccaa ggttcgcatg gctgtattca   1260

atcaacacca tgttgatggg cttgatttaa cagtgaaccc ccttttgtac atgatgagat   1320

gctaccctgg tgtacctgaa cagaaactga gggcacactt gggttctttc ggtgttacag   1380

gaaatcttgc cctccaacca atgtacactt tatcaggtgg tcagaaaagt agggttgcct   1440

ttgcaaagat caccttcaag aagccacaca ttattcttct cgatgagcct tctaaccatc   1500

ttgatctgga tgctgtggag gcgctgatcc agggtttact cgttttccag ggaggagtgc   1560

taatggtgag tcacgacgag cacctgataa cggggagcgt ggatgagctt tgggtggtgt   1620

cggaaggcag ggtgtcgcct ttcgcaggca cgttcaagga ctacaagaag atgctcaagt   1680

cttaatctag agccagtgat gatatatata cagagacagc gagtctacaa agaaagacac   1740

caacatatat atctgtatcg tgcagcaccg atgtaacatt taccggcctg aggccaaatc   1800

atcatttatg tttatttcat gtggatttac tggggaaaaa aaaaaaaaaa aaaaaaaaaa   1860

aaaaaaaaaa aaaaa                                                     1875


<210> SEQ ID NO 130
<211> LENGTH: 560
<212> TYPE: PRT
<213> ORGANISM: Oryza sativa

<400> SEQUENCE: 130

Gly Met Pro Pro Val Phe Val Asn His Asn Asn Ser Gly Gly Pro Ala
  1               5                  10                  15

Val Arg Asp Ile His Met Glu Asn Phe Ser Val Thr Val Gly Gly Arg
             20                  25                  30

Asp Leu Ile Gln Asp Cys Thr Val Thr Leu Ala Phe Gly Arg His Tyr
         35                  40                  45

Gly Leu Val Gly Arg Asn Gly Thr Gly Lys Thr Ser Phe Leu Arg Ala
     50                  55                  60

Met Ala Met His Ala Ile Asp Gly Ile Pro Lys Asn Cys Gln Ile Leu
 65                  70                  75                  80

His Val Glu Gln Glu Val Val Gly Asp Asp Thr Thr Ala Leu Gln Cys
                 85                  90                  95
```

-continued

```
Val Leu Asn Ala Asp Ile Glu Arg Val Gln Leu Leu Gln Glu Glu Ala
            100                 105                 110

His Leu Val Gln Arg Gln Lys Asp Leu Glu Tyr Glu Ala Glu Phe Glu
        115                 120                 125

Gln Ser Ala Ser Lys Ser Lys Asp Gly Leu Asp Lys Asp Ala Ile Ser
    130                 135                 140

Lys Arg Leu Glu Glu Ile Tyr Lys Arg Leu Glu Phe Ile Asp Ala Asp
145                 150                 155                 160

Ala Ala Glu Ala Arg Ala Ala Ser Ile Leu Ala Gly Leu Ser Phe Thr
                165                 170                 175

Pro Glu Met Gln Arg Lys Arg Thr Lys Gln Phe Ser Gly Gly Trp Arg
            180                 185                 190

Met Arg Ile Ala Leu Ala Arg Ala Leu Phe Ile Glu Pro Asp Leu Leu
        195                 200                 205

Leu Leu Asp Glu Pro Thr Asn His Leu Asp Leu His Ala Val Leu Trp
    210                 215                 220

Leu Glu Thr Tyr Leu Leu Lys Trp Pro Lys Thr Phe Ile Val Val Ser
225                 230                 235                 240

His Ala Arg Glu Phe Leu Asn Thr Val Val Thr Asp Ile Leu His Leu
                245                 250                 255

His Gly Gln Lys Leu His Ala Tyr Lys Gly Asp Tyr Asp Thr Phe Glu
            260                 265                 270

Arg Thr Arg Glu Glu His Leu Lys Asn Gln Gln Lys Ala Phe Glu Thr
        275                 280                 285

Asn Glu Lys Ala Arg Ser His Met Gln Ala Phe Ile Asp Lys Phe Arg
    290                 295                 300

Tyr Asn Ala Lys Arg Ala Ser Leu Val Gln Ser Arg Ile Lys Ala Leu
305                 310                 315                 320

Glu Arg Met Glu His Val Asp Ala Val Val Ser Asp Pro Asp Tyr Lys
                325                 330                 335

Phe Glu Phe Pro Thr Pro Asp Asp Arg Pro Gly Pro Pro Ile Ile Ser
            340                 345                 350

Phe Ser Asp Ala Ser Phe Gly Tyr Pro Gly Gly Pro Thr Leu Phe Lys
        355                 360                 365

Asn Leu Asn Phe Gly Ile Asp Leu Asp Ser Arg Ile Ala Met Val Gly
    370                 375                 380

Pro Asn Gly Ile Gly Lys Ser Thr Ile Leu Lys Leu Ile Ser Gly Asp
385                 390                 395                 400

Leu Gln Pro Thr Ser Gly Thr Val Phe Arg Ser Pro Lys Val Arg Met
                405                 410                 415

Ala Val Phe Asn Gln His His Val Asp Gly Leu Asp Leu Thr Val Asn
            420                 425                 430

Pro Leu Leu Tyr Met Met Arg Cys Tyr Pro Gly Val Pro Glu Gln Lys
        435                 440                 445

Leu Arg Ala His Leu Gly Ser Phe Gly Val Thr Gly Asn Leu Ala Leu
    450                 455                 460

Gln Pro Met Tyr Thr Leu Ser Gly Gly Gln Lys Ser Arg Val Ala Phe
465                 470                 475                 480

Ala Lys Ile Thr Phe Lys Lys Pro His Ile Ile Leu Leu Asp Glu Pro
                485                 490                 495

Ser Asn His Leu Asp Leu Asp Ala Val Glu Ala Leu Ile Gln Gly Leu
            500                 505                 510
```

```
Leu Val Phe Gln Gly Gly Val Leu Met Val Ser His Asp Glu His Leu
        515                 520                 525

Ile Thr Gly Ser Val Asp Glu Leu Trp Val Val Ser Glu Gly Arg Val
    530                 535                 540

Ser Pro Phe Ala Gly Thr Phe Lys Asp Tyr Lys Lys Met Leu Lys Ser
545                 550                 555                 560


<210> SEQ ID NO 131
<211> LENGTH: 704
<212> TYPE: DNA
<213> ORGANISM: Glycine max

<400> SEQUENCE: 131

gcacgagctt ccgatctgct aaggttcgta tagcagtgtt cagtcagcac catgttgatg     60

gactcgactt atcctcaaat cctcttctgt atatgatgcg ctgctatcct ggagttccag    120

aacagaagct tcgagctcac ttaggttctt ttggtgtaac cggaaatctt gcgctgcagc    180

caatgtatac tttgtcaggt ggtcagaaaa gcagggttgc ctttgcaaag ataactttta    240

agaagccaca cataatattg cttgatgagc catccaatca tctggatttg gatgctgttg    300

aggcgcttat tcaaggtctt gtgctgttcc aaggaggcat tctcatggtg agtcacgatg    360

agcacctcat ctctggaagc gtggaggaac tatgggttgt atccgaagga agagtggcac    420

cattccatgg cacattccaa gattataaga agatactcca atcatcctag aaatgtcaaa    480

ttttgtggat gtatactgga aagacccctg gatcacattt tttttgctgt tcctctcagc    540

tgtcatacaa ttttgcaatt tatccaaacc tatgtatttc aaggcaattt tatgatttta    600

tgaacacgag gttaaattaa ctattaaata attttgtaat aaccttataa ttataagatg    660

tataatttat actttcacta cttttcaaaa aaaaaaaaaa aaaa                     704


<210> SEQ ID NO 132
<211> LENGTH: 155
<212> TYPE: PRT
<213> ORGANISM: Glycine max

<400> SEQUENCE: 132

Thr Ser Phe Arg Ser Ala Lys Val Arg Ile Ala Val Phe Ser Gln His
  1               5                  10                  15

His Val Asp Gly Leu Asp Leu Ser Ser Asn Pro Leu Leu Tyr Met Met
             20                  25                  30

Arg Cys Tyr Pro Gly Val Pro Glu Gln Lys Leu Arg Ala His Leu Gly
         35                  40                  45

Ser Phe Gly Val Thr Gly Asn Leu Ala Leu Gln Pro Met Tyr Thr Leu
     50                  55                  60

Ser Gly Gly Gln Lys Ser Arg Val Ala Phe Ala Lys Ile Thr Phe Lys
 65                  70                  75                  80

Lys Pro His Ile Ile Leu Leu Asp Glu Pro Ser Asn His Leu Asp Leu
                 85                  90                  95

Asp Ala Val Glu Ala Leu Ile Gln Gly Leu Val Leu Phe Gln Gly Gly
            100                 105                 110

Ile Leu Met Val Ser His Asp Glu His Leu Ile Ser Gly Ser Val Glu
        115                 120                 125

Glu Leu Trp Val Val Ser Glu Gly Arg Val Ala Pro Phe His Gly Thr
    130                 135                 140

Phe Gln Asp Tyr Lys Lys Ile Leu Gln Ser Ser
145                 150                 155
```

<210> SEQ ID NO 133
<211> LENGTH: 767
<212> TYPE: DNA
<213> ORGANISM: Triticum aestivum

<400> SEQUENCE: 133

```
gcacgagggg aagtccacta tactgaaatt aatatctgga gacctgcagc caacttcggg     60
aacagtgttt cgctccccca aggtccgcat ggctgtattc agtcagcatc atgttgatgg    120
acttgatctg acggtgaacc cccttctgta catgatgaga tgcttcccgg gtgtacctga    180
acagaaactg aggtcacatt tgggttcctt cggtgttaca ggaaatcttg ccctccaatc    240
tatgtacact ttatcaggtg gtcagaagag tagggtcgcg tttgcgaaga tcaccttcaa    300
gaagccgcac attatccttc ttgatgagcc ttctaaccat cttgatctcg acgcagtgga    360
ggcgctcatc cagggtctgc tcatattcca gggaggagtg ctgatggtga gtcacgacga    420
gcatctgatc acggggagtg tggacgagct ctgggcggtg acggacggca aggtcgcccc    480
gttcccgggc acgttcaagg agtacaagaa gatgctcacg acatgaacct ggaaaaagga    540
cgggacatag gggaagatgc ccacacagac ataaagaaac tatatgtatg atatgtacgc    600
cctggcatgg gaaactgatg taatcttatg cttgtcacct acctgaggtt tgaaagtttg    660
agtagaacta tgctactaca tacagtagta caattttgtt tgttccagcc tgcctgacaa    720
tctgcatcga gcttgcgatt ttcttggaca aaaaaaaaaa aaaaaaa                  767
```

<210> SEQ ID NO 134
<211> LENGTH: 174
<212> TYPE: PRT
<213> ORGANISM: Triticum aestivum

<400> SEQUENCE: 134

```
His Glu Gly Lys Ser Thr Ile Leu Lys Leu Ile Ser Gly Asp Leu Gln
  1               5                  10                  15

Pro Thr Ser Gly Thr Val Phe Arg Ser Pro Lys Val Arg Met Ala Val
             20                  25                  30

Phe Ser Gln His His Val Asp Gly Leu Asp Leu Thr Val Asn Pro Leu
         35                  40                  45

Leu Tyr Met Met Arg Cys Phe Pro Gly Val Pro Glu Gln Lys Leu Arg
     50                  55                  60

Ser His Leu Gly Ser Phe Gly Val Thr Gly Asn Leu Ala Leu Gln Ser
 65                  70                  75                  80

Met Tyr Thr Leu Ser Gly Gly Gln Lys Ser Arg Val Ala Phe Ala Lys
                 85                  90                  95

Ile Thr Phe Lys Lys Pro His Ile Ile Leu Leu Asp Glu Pro Ser Asn
            100                 105                 110

His Leu Asp Leu Asp Ala Val Glu Ala Leu Ile Gln Gly Leu Leu Ile
        115                 120                 125

Phe Gln Gly Gly Val Leu Met Val Ser His Asp Glu His Leu Ile Thr
    130                 135                 140

Gly Ser Val Asp Glu Leu Trp Ala Val Thr Asp Gly Lys Val Ala Pro
145                 150                 155                 160

Phe Pro Gly Thr Phe Lys Glu Tyr Lys Lys Met Leu Thr Thr
                165                 170
```

<210> SEQ ID NO 135
<211> LENGTH: 646
<212> TYPE: DNA
<213> ORGANISM: Zea mays

<400> SEQUENCE: 135

```
gcacgagcat cacccatcgt gcgtcgatag acgatgatgc cggagtcgca tccgcatccc     60

cacgcggggg cggtgctggc gtcgacgtct agccgtcgga gcctcagctt ggggtcctcc    120

atctcgcagt cgttccggca gatggacacg gaggacccct tcgcgcggtc gcagtcggag    180

catgagcacc gcgacgacga ggagaacctg cgctgggccg cgctcgagaa gctgcccacc    240

tacgaccgca tgcgccaggg tatcctacgc cgggcgctcg accaacaaca agagagcggc    300

ggcggcggcg tcgagatcgt cgacatccac aagctggccg ccggcgacgg gggccgtgcg    360

ctcctggagc gcctcttcca ggacgacagc gagcgattcc tgcgccggct cagggaccga    420

atcgacatgg ttggcatcga gctccccaca gtggaagttc ggtacgagca gttgacggtg    480

gaggctgacg tgattaccgc cgggagggcc ctcccgacgc tgtggaacgc cgccaccaat    540

tttcttcagg tttatcatag taattaatta attaatctct tttctattcc tttaaagcat    600

caattttgac ggtcttgttt ccctcaaaaa aaaaaaaaaa aaaaaa                   646
```

<210> SEQ ID NO 136
<211> LENGTH: 177
<212> TYPE: PRT
<213> ORGANISM: Zea mays

<400> SEQUENCE: 136

```
Met Met Pro Glu Ser His Pro His Pro His Ala Gly Ala Val Leu Ala
  1               5                  10                  15

Ser Thr Ser Ser Arg Arg Ser Leu Ser Leu Gly Ser Ser Ile Ser Gln
             20                  25                  30

Ser Phe Arg Gln Met Asp Thr Glu Asp Pro Phe Ala Arg Ser Gln Ser
         35                  40                  45

Glu His Glu His Arg Asp Asp Glu Glu Asn Leu Arg Trp Ala Ala Leu
     50                  55                  60

Glu Lys Leu Pro Thr Tyr Asp Arg Met Arg Gln Gly Ile Leu Arg Arg
 65                  70                  75                  80

Ala Leu Asp Gln Gln Gln Glu Ser Gly Gly Gly Gly Val Glu Ile Val
                 85                  90                  95

Asp Ile His Lys Leu Ala Ala Gly Asp Gly Gly Arg Ala Leu Leu Glu
            100                 105                 110

Arg Leu Phe Gln Asp Asp Ser Glu Arg Phe Leu Arg Arg Leu Arg Asp
        115                 120                 125

Arg Ile Asp Met Val Gly Ile Glu Leu Pro Thr Val Glu Val Arg Tyr
    130                 135                 140

Glu Gln Leu Thr Val Glu Ala Asp Val Ile Thr Ala Gly Arg Ala Leu
145                 150                 155                 160

Pro Thr Leu Trp Asn Ala Ala Thr Asn Phe Leu Gln Val Tyr His Ser
                165                 170                 175

Asn
```

<210> SEQ ID NO 137
<211> LENGTH: 2031
<212> TYPE: DNA
<213> ORGANISM: Zea mays

<400> SEQUENCE: 137

```
gcacgagggt tcttccattc aaccctcttg ctatgtcttt tgataatgtg aactactatg     60

ttgacatgcc tgcggaaatg aaacatcaag gagtgcagga tgacagactc caattgttgc    120
```

-continued

```
gtgaggttac aggatcattc aggcctggag tgctgacagc acttatgggt gtcagtggag    180

ctggaaagac tactcttatg gatgttttgg ctggaagaaa gactgggggg tatattgaag    240

gagacatcag aattgcaggc tatcccaaga accaagcaac attcgcaagg atttctggat    300

actgcgagca aaatgatata cattctcctc aggtcacagt aagggagtct ttgatatact    360

ctgccttttt gcgccttcct ggaaaaattg gagatcaaga aataactgat gacataaaga    420

tgcaatttgt ggatgaagtt atggaactag tggagctcga caatctgagg gatgccttag    480

ttgggctacc aggaatcaca gggctttcga cagagcaaag aaaaaggttg acaatagccg    540

tggagctcgt tgccaatcca tcaatcatat ttatggatga accaacatca gggcttgatg    600

caagagctgc agcaattgtc atgagaactg tgcggaacac agttgacact ggacggacag    660

ttgtttgcac aatccatcag ccaagcatcg acatctttga atcttttgat gagttgctat    720

tgttgaaaag aggaggccag gtgatctact ctgggaaatt gggtcgcaac tcccagaaaa    780

tggtggagta ttttgaggca attcctggag tgcctaaaat aaaagataag tacaatcctg    840

caacgtggat gctcgaggtc agttcagttg caactgaagt gcgactaaag atggattttg    900

ctaagtacta tgaaacatca gatctgtata agcaaaacaa ggtactggtg aaccagctga    960

gtcaaccaga gccaggaaca tcagatcttt atttccctac agagtactcg caatccacaa   1020

taggacagtt caaagcctgt ctctggaagc aatggctgac ttattggcgc agcccggatt   1080

acaaccttgt tagatattcc ttcactctgt tagttgcctt gcttctcggc tccattttct   1140

ggaggatagg caccaacatg gaagatgcaa ccactctcgg tatggttatt ggagcaatgt   1200

acactgctgt tatgtttatc ggcatcaaca attgttcaac tgtgcagcca gttgtttcaa   1260

ttgaaagaac ggtcttctac agagagaggg ctgctgggat gtactctgct atgccatatg   1320

ccattgctca ggttgttata gagataccat atgtatttgt gcaaacaacg tactacaccc   1380

tcattgtata cgccatgatg agcttccaat ggacagctgt caagttcttc tggttcttct   1440

tcatttccta cttctccttc ctctacttca cctactatgg catgatggct gtctcaatct   1500

ccccaaacca tgaggttgca tccatcttcg cagcagcttt cttttctctc ttcaatctct   1560

tctcaggctt cttcattccg agaccgagaa ttcctggatg gtggatctgg tactactgga   1620

tttgcccact ggcatggaca gtgtatgggc tcatcgtgac acaatacgga gacctggaag   1680

acctcatctc agtccctgga gaaagtgagc agacgataag ctactatgta acacatcatt   1740

ttggatacca cagggatttt ctgccggtca ttgcgccggt tctggtactc tttgcagtat   1800

tcttcgcgtt cttgtacgca gtctgcatca agaaactgaa cttccagcaa cgataagaac   1860

aagatatggc agcaaaagct cttgagagtt tttttggaac attgccgtgt atatagggta   1920

ttttgcacat cgcgttctcc tttcattttt tgagtccctt taatacattg tcgtgtatat   1980

agggtattct gcacatcgcc aaatgtggtg aggtcttata cagatttcta g            2031
```

<210> SEQ ID NO 138
<211> LENGTH: 617
<212> TYPE: PRT
<213> ORGANISM: Zea mays

<400> SEQUENCE: 138

```
Thr Arg Val Leu Pro Phe Asn Pro Leu Ala Met Ser Phe Asp Asn Val
  1               5                  10                  15

Asn Tyr Tyr Val Asp Met Pro Ala Glu Met Lys His Gln Gly Val Gln
             20                  25                  30
```

-continued

```
Asp Asp Arg Leu Gln Leu Leu Arg Glu Val Thr Gly Ser Phe Arg Pro
        35                  40                  45

Gly Val Leu Thr Ala Leu Met Gly Val Ser Gly Ala Gly Lys Thr Thr
    50                  55                  60

Leu Met Asp Val Leu Ala Gly Arg Lys Thr Gly Gly Tyr Ile Glu Gly
65                  70                  75                  80

Asp Ile Arg Ile Ala Gly Tyr Pro Lys Asn Gln Ala Thr Phe Ala Arg
                85                  90                  95

Ile Ser Gly Tyr Cys Glu Gln Asn Asp Ile His Ser Pro Gln Val Thr
            100                 105                 110

Val Arg Glu Ser Leu Ile Tyr Ser Ala Phe Leu Arg Leu Pro Gly Lys
        115                 120                 125

Ile Gly Asp Gln Glu Ile Thr Asp Asp Ile Lys Met Gln Phe Val Asp
    130                 135                 140

Glu Val Met Glu Leu Val Glu Leu Asp Asn Leu Arg Asp Ala Leu Val
145                 150                 155                 160

Gly Leu Pro Gly Ile Thr Gly Leu Ser Thr Glu Gln Arg Lys Arg Leu
                165                 170                 175

Thr Ile Ala Val Glu Leu Val Ala Asn Pro Ser Ile Ile Phe Met Asp
            180                 185                 190

Glu Pro Thr Ser Gly Leu Asp Ala Arg Ala Ala Ala Ile Val Met Arg
        195                 200                 205

Thr Val Arg Asn Thr Val Asp Thr Gly Arg Thr Val Val Cys Thr Ile
    210                 215                 220

His Gln Pro Ser Ile Asp Ile Phe Glu Ser Phe Asp Glu Leu Leu Leu
225                 230                 235                 240

Leu Lys Arg Gly Gly Gln Val Ile Tyr Ser Gly Lys Leu Gly Arg Asn
                245                 250                 255

Ser Gln Lys Met Val Glu Tyr Phe Glu Ala Ile Pro Gly Val Pro Lys
            260                 265                 270

Ile Lys Asp Lys Tyr Asn Pro Ala Thr Trp Met Leu Glu Val Ser Ser
        275                 280                 285

Val Ala Thr Glu Val Arg Leu Lys Met Asp Phe Ala Lys Tyr Tyr Glu
    290                 295                 300

Thr Ser Asp Leu Tyr Lys Gln Asn Lys Val Leu Val Asn Gln Leu Ser
305                 310                 315                 320

Gln Pro Glu Pro Gly Thr Ser Asp Leu Tyr Phe Pro Thr Glu Tyr Ser
                325                 330                 335

Gln Ser Thr Ile Gly Gln Phe Lys Ala Cys Leu Trp Lys Gln Trp Leu
            340                 345                 350

Thr Tyr Trp Arg Ser Pro Asp Tyr Asn Leu Val Arg Tyr Ser Phe Thr
        355                 360                 365

Leu Leu Val Ala Leu Leu Leu Gly Ser Ile Phe Trp Arg Ile Gly Thr
    370                 375                 380

Asn Met Glu Asp Ala Thr Thr Leu Gly Met Val Ile Gly Ala Met Tyr
385                 390                 395                 400

Thr Ala Val Met Phe Ile Gly Ile Asn Asn Cys Ser Thr Val Gln Pro
                405                 410                 415

Val Val Ser Ile Glu Arg Thr Val Phe Tyr Arg Glu Arg Ala Ala Gly
            420                 425                 430

Met Tyr Ser Ala Met Pro Tyr Ala Ile Ala Gln Val Val Ile Glu Ile
        435                 440                 445
```

-continued

```
Pro Tyr Val Phe Val Gln Thr Thr Tyr Tyr Thr Leu Ile Val Tyr Ala
    450                 455                 460

Met Met Ser Phe Gln Trp Thr Ala Val Lys Phe Phe Trp Phe Phe Phe
465                 470                 475                 480

Ile Ser Tyr Phe Ser Phe Leu Tyr Phe Thr Tyr Tyr Gly Met Met Ala
                485                 490                 495

Val Ser Ile Ser Pro Asn His Glu Val Ala Ser Ile Phe Ala Ala Ala
            500                 505                 510

Phe Phe Ser Leu Phe Asn Leu Phe Ser Gly Phe Phe Ile Pro Arg Pro
        515                 520                 525

Arg Ile Pro Gly Trp Trp Ile Trp Tyr Tyr Trp Ile Cys Pro Leu Ala
    530                 535                 540

Trp Thr Val Tyr Gly Leu Ile Val Thr Gln Tyr Gly Asp Leu Glu Asp
545                 550                 555                 560

Leu Ile Ser Val Pro Gly Glu Ser Glu Gln Thr Ile Ser Tyr Tyr Val
                565                 570                 575

Thr His His Phe Gly Tyr His Arg Asp Phe Leu Pro Val Ile Ala Pro
            580                 585                 590

Val Leu Val Leu Phe Ala Val Phe Phe Ala Phe Leu Tyr Ala Val Cys
        595                 600                 605

Ile Lys Lys Leu Asn Phe Gln Gln Arg
    610                 615
```

<210> SEQ ID NO 139
<211> LENGTH: 4159
<212> TYPE: DNA
<213> ORGANISM: Oryza sativa

<400> SEQUENCE: 139

```
gcacgagtgt atcccggatg acgctgctgc tgggcccgcc gtcgtcgggg aagacgaccc      60

tcctcctggc cctcgccggg aagctggacc cgtcgctccg gcgcggcggc gaggtgacgt     120

acaacgggtt cgagctggag gagttcgtgg cgcagaagac ggcggcgtac atcagccaga     180

cggacgtgca cgtcggcgag atgaccgtca aggagacgct cgacttctcg gccaggtgcc     240

agggcgtcgg caccaagtac gatcttctga cagagctggc aaggagggag aaggaggccg     300

gcatccggcc ggagcccgag gtcgacctct tcatgaaggc tacttcgatg gaaggagtcg     360

agagcagcct tcagacagat tacaccctca gaatactggg attggatata tgcgcggaca     420

cgatcgtcgg cgaccagatg cagaggggga tctccggtgg tcagaagaaa cgcgtcacca     480

ccggtgagat gattgtcggt ccaacaaagg ttctattcat ggatgagata tcaactggat     540

tggacagctc caccacattc cagattgtca aatgccttca gcaaatcgtg cacttgggcg     600

aggcaaccat cctcatgtca ctcctacaac cagcccctga gacttttgag ctattcgatg     660

acattatcct actgtcagaa ggccagattg tttatcaggg accccgcgaa tacgtccttg     720

agttctttga gtcatgcgga ttccgctgcc cagagcgtaa gggtactgca gactttcttc     780

aggaggtgac atcaaagaag gatcaggagc agtattgggc cgacaagcat aggccataca     840

gatacatttc agtctcagaa tttgcacaga gatttaaaag gttccatgtt gggctccaac     900

ttgagaatca tctctcagtc ccatttgata aaactcgtag ccatcaggct gctcttgtct     960

tctcgaagca atcggtgtca acaacagagc tcctcaaggc atcctttgcc aaggagtggc    1020

tcctcattaa gcgcaactca tttgtgtaca tcttcaagac catacagctc atcattgtag    1080

cccttgtcgc gtcgacagtg tttcttagga cccagatgca cacaaggaat ttagatgatg    1140
```

-continued

```
gctttgtgta cattggagca ctacttttca gtctgattgt gaacatgttc aatggtttcg   1200
ctgagctctc tttgaccatc acaaggttgc cagtgttctt caagcaccgg gacctcctct   1260
tctaccctgc ttggatcttc actctaccga atgttattct gagaatccca ttttccatca   1320
tcgaatctat agtctgggtg attgttacat actacactat aggatttgcc ccagaggctg   1380
acagattttt caagcagttg ctgctagtgt tcttgatcca gcagatggca ggtggccttt   1440
tcagagcaac tgctggtctg tgcagatcca tgatcattgc tcaaactgga ggagccctgg   1500
cccttctcat atttttcgtt cttggaggat ttcttctgcc aaaagcattc atcccaaaat   1560
ggtggatctg ggttactgg gtttcaccac tgatgtacgg gtataatgct ctagcagtca   1620
atgaattcta ctctcctcgg tggatgaaca agtttgtact ggataacaat ggcgttccta   1680
aaagactagg aatagctctg atggaaggtg ccaacatctt cactgacaaa aattggttct   1740
ggattggagc agcagggctc ctgggtttca ccatgttttt caatgtgctt ttcactctgt   1800
cactcgttta tctgaatcct ctgggcaaac cacaagctgt catatctgaa gaaactgcga   1860
aggaagcgga aggcaatggg gatgcaagac atacagtaag aaatggcagc acaaaatcaa   1920
atggtggaaa tcacaaagaa atgagggaga tgagattgag tgctcgtctg agcaatagtt   1980
catcgaatgg agtttcacga ctgatgtcca ttggtagcaa tgaagctggt ccaagaagag   2040
gaatggttct tccatttact cctctatcca tgtcttttga tgatgtgaac tactatgtcg   2100
acatgcctgc agaaatgaag cagcaaggag tggtggatga taggctccaa ttgttacgtg   2160
acgttactgg atcatttagg cctgcagtgc tgacagcact catgggagtc agtggagccg   2220
gaaagacaac tcttatggat gttttggcag gaagaaagac tggtggttac attgaaggag   2280
atatgagaat ttctggttat cctaagaacc aagaaacatt tgcaagaatt tctggctact   2340
gtgagcaaaa cgatatccat tcacctcagg tcacagttag ggagtctttg atatactctg   2400
ctttcctgcg ccttccagaa aaaataggag atcaagaaat cactgatgat atcaagattc   2460
aatttgttga tgaagttatg gaactagtgg agctcgacaa tctgaaggat gcgttagttg   2520
gcctgcctgg aatcacaggg ctttcaacag agcaaaggaa gagattgaca atagcagtgg   2580
agcttgttgc aaatccctcg atcatcttca tggatgaacc gacttcaggt cttgatgcaa   2640
gagcagcagc cattgttatg agaacagtga ggaacacagt tgacactgga cggacagtgg   2700
tttgcacaat tcaccagcca agcattgaca tatttgaggc ttttgatgag ctgctactac   2760
tgaaaagagg agggcaggtg atatactctg ggcaattggg tcgtaattcc cagaaaatga   2820
ttgaatattt cgaggcaatt cctggtgtgc ctaaaatcaa agataagtac aatccagcta   2880
catggatgct tgaggtcagt tcagttgctg cggaagtacg cttaaatatg gactttgctg   2940
agtactataa gacatcagac ctgtacaagc aaaacaaggt attggtgaat cagctaagtc   3000
aaccagagcc aggaacatca gatctgcatt ttcctacaaa atactctcaa tccaccatag   3060
ggcaatttag ggcctgcctc tggaagcaat ggctgaccta ttggcgcagc ccagattaca   3120
atcttgttag attttccttc actctgttca cagccttgct actcggcacc atcttttgga   3180
agatcggcac caagatggga aatgccaatt ctcttagaat ggtcattgga gcaatgtata   3240
cagcagtgat gtttatcggt atcaacaatt gtgcgactgt gcagccaatc gtgtcgattg   3300
agagaacagt tttctaccga gagagggctg ctgggatgta ctctgctatg ccctatgcca   3360
ttgctcaggt tgtcatggag ataccctatg tgttcgtcca aactgcatat tataccctca   3420
ttgtttatgc catgatgagc ttccagtgga cagcagccaa gttcttctgg ttcttcttcg   3480
tctcctactt ctcatttctc tacttcacct actatggtat gatgacggtg gcaatctcac   3540
```

-continued

```
caaaccatga ggttgcagcc atctttgccg cggcgttcta ttccttgttc aacctattct   3600

caagattctt cattccgaga ccaaggattc ccaaatggtg gatctggtac tactggcttt   3660

gcccattggc atggacagtg tatgggctca tagtgacaca gtatggagac ctagaacaaa   3720

tcatctcagt ccctggccaa tccaaccaga caatcagcta ctatgttact catcattttg   3780

gatatcacag gaaatttatg ccagttgttg cgccggtgct cgtgctcttc gctgtgtttt   3840

tcgcgttcat gtatgccatt tgcatcaaga agttgaactt ccaacatcga taggggcatt   3900

gaaacaacag gcaaaatctg gttggaaact ttttttggt tttgaaccaa atcttctttt   3960

gtcctttccc cacagataat atcttctttt atcctcacat tttgtggtc tatatatgcc   4020

atgtaaatat gctggtaggt tttctgtatt ccatacatcg ccaaatgtgg cgaggtttca   4080

tatgaccttt tagctttgga aatgtaaact ttataagagc attgttgtca gaaattttgt   4140

taaaaaaaaa aaaaaaaaa                                               4159
```

<210> SEQ ID NO 140
<211> LENGTH: 1296
<212> TYPE: PRT
<213> ORGANISM: Oryza sativa

<400> SEQUENCE: 140

```
Thr Ser Val Ser Arg Met Thr Leu Leu Leu Gly Pro Pro Ser Ser Gly
  1               5                  10                  15

Lys Thr Thr Leu Leu Leu Ala Leu Ala Gly Lys Leu Asp Pro Ser Leu
             20                  25                  30

Arg Arg Gly Gly Glu Val Thr Tyr Asn Gly Phe Glu Leu Glu Glu Phe
         35                  40                  45

Val Ala Gln Lys Thr Ala Ala Tyr Ile Ser Gln Thr Asp Val His Val
     50                  55                  60

Gly Glu Met Thr Val Lys Glu Thr Leu Asp Phe Ser Ala Arg Cys Gln
 65                  70                  75                  80

Gly Val Gly Thr Lys Tyr Asp Leu Leu Thr Glu Leu Ala Arg Arg Glu
                 85                  90                  95

Lys Glu Ala Gly Ile Arg Pro Glu Pro Glu Val Asp Leu Phe Met Lys
            100                 105                 110

Ala Thr Ser Met Glu Gly Val Glu Ser Ser Leu Gln Thr Asp Tyr Thr
        115                 120                 125

Leu Arg Ile Leu Gly Leu Asp Ile Cys Ala Asp Thr Ile Val Gly Asp
    130                 135                 140

Gln Met Gln Arg Gly Ile Ser Gly Gly Gln Lys Lys Arg Val Thr Thr
145                 150                 155                 160

Gly Glu Met Ile Val Gly Pro Thr Lys Val Leu Phe Met Asp Glu Ile
                165                 170                 175

Ser Thr Gly Leu Asp Ser Ser Thr Thr Phe Gln Ile Val Lys Cys Leu
            180                 185                 190

Gln Gln Ile Val His Leu Gly Glu Ala Thr Ile Leu Met Ser Leu Leu
        195                 200                 205

Gln Pro Ala Pro Glu Thr Phe Glu Leu Phe Asp Asp Ile Ile Leu Leu
    210                 215                 220

Ser Glu Gly Gln Ile Val Tyr Gln Gly Pro Arg Glu Tyr Val Leu Glu
225                 230                 235                 240

Phe Phe Glu Ser Cys Gly Phe Arg Cys Pro Glu Arg Lys Gly Thr Ala
                245                 250                 255
```

-continued

```
Asp Phe Leu Gln Glu Val Thr Ser Lys Lys Asp Gln Glu Gln Tyr Trp
        260                 265                 270

Ala Asp Lys His Arg Pro Tyr Arg Tyr Ile Ser Val Ser Glu Phe Ala
        275                 280                 285

Gln Arg Phe Lys Arg Phe His Val Gly Leu Gln Leu Glu Asn His Leu
    290                 295                 300

Ser Val Pro Phe Asp Lys Thr Arg Ser His Gln Ala Ala Leu Val Phe
305                 310                 315                 320

Ser Lys Gln Ser Val Ser Thr Thr Glu Leu Leu Lys Ala Ser Phe Ala
                325                 330                 335

Lys Glu Trp Leu Leu Ile Lys Arg Asn Ser Phe Val Tyr Ile Phe Lys
            340                 345                 350

Thr Ile Gln Leu Ile Ile Val Ala Leu Val Ala Ser Thr Val Phe Leu
        355                 360                 365

Arg Thr Gln Met His Thr Arg Asn Leu Asp Asp Gly Phe Val Tyr Ile
    370                 375                 380

Gly Ala Leu Leu Phe Ser Leu Ile Val Asn Met Phe Asn Gly Phe Ala
385                 390                 395                 400

Glu Leu Ser Leu Thr Ile Thr Arg Leu Pro Val Phe Phe Lys His Arg
                405                 410                 415

Asp Leu Leu Phe Tyr Pro Ala Trp Ile Phe Thr Leu Pro Asn Val Ile
            420                 425                 430

Leu Arg Ile Pro Phe Ser Ile Ile Glu Ser Ile Val Trp Val Ile Val
        435                 440                 445

Thr Tyr Tyr Thr Ile Gly Phe Ala Pro Glu Ala Asp Arg Phe Phe Lys
    450                 455                 460

Gln Leu Leu Leu Val Phe Leu Ile Gln Gln Met Ala Gly Gly Leu Phe
465                 470                 475                 480

Arg Ala Thr Ala Gly Leu Cys Arg Ser Met Ile Ile Ala Gln Thr Gly
                485                 490                 495

Gly Ala Leu Ala Leu Leu Ile Phe Phe Val Leu Gly Gly Phe Leu Leu
            500                 505                 510

Pro Lys Ala Phe Ile Pro Lys Trp Trp Ile Trp Gly Tyr Trp Val Ser
        515                 520                 525

Pro Leu Met Tyr Gly Tyr Asn Ala Leu Ala Val Asn Glu Phe Tyr Ser
    530                 535                 540

Pro Arg Trp Met Asn Lys Phe Val Leu Asp Asn Asn Gly Val Pro Lys
545                 550                 555                 560

Arg Leu Gly Ile Ala Leu Met Glu Gly Ala Asn Ile Phe Thr Asp Lys
                565                 570                 575

Asn Trp Phe Trp Ile Gly Ala Ala Gly Leu Leu Gly Phe Thr Met Phe
            580                 585                 590

Phe Asn Val Leu Phe Thr Leu Ser Leu Val Tyr Leu Asn Pro Leu Gly
        595                 600                 605

Lys Pro Gln Ala Val Ile Ser Glu Glu Thr Ala Lys Glu Ala Glu Gly
    610                 615                 620

Asn Gly Asp Ala Arg His Thr Val Arg Asn Gly Ser Thr Lys Ser Asn
625                 630                 635                 640

Gly Gly Asn His Lys Glu Met Arg Glu Met Arg Leu Ser Ala Arg Leu
                645                 650                 655

Ser Asn Ser Ser Ser Asn Gly Val Ser Arg Leu Met Ser Ile Gly Ser
            660                 665                 670
```

-continued

```
Asn Glu Ala Gly Pro Arg Arg Gly Met Val Leu Pro Phe Thr Pro Leu
        675                 680                 685

Ser Met Ser Phe Asp Asp Val Asn Tyr Tyr Val Asp Met Pro Ala Glu
    690                 695                 700

Met Lys Gln Gln Gly Val Val Asp Asp Arg Leu Gln Leu Leu Arg Asp
705                 710                 715                 720

Val Thr Gly Ser Phe Arg Pro Ala Val Leu Thr Ala Leu Met Gly Val
                725                 730                 735

Ser Gly Ala Gly Lys Thr Thr Leu Met Asp Val Leu Ala Gly Arg Lys
            740                 745                 750

Thr Gly Gly Tyr Ile Glu Gly Asp Met Arg Ile Ser Gly Tyr Pro Lys
        755                 760                 765

Asn Gln Glu Thr Phe Ala Arg Ile Ser Gly Tyr Cys Glu Gln Asn Asp
    770                 775                 780

Ile His Ser Pro Gln Val Thr Val Arg Glu Ser Leu Ile Tyr Ser Ala
785                 790                 795                 800

Phe Leu Arg Leu Pro Glu Lys Ile Gly Asp Gln Glu Ile Thr Asp Asp
                805                 810                 815

Ile Lys Ile Gln Phe Val Asp Glu Val Met Glu Leu Val Glu Leu Asp
            820                 825                 830

Asn Leu Lys Asp Ala Leu Val Gly Leu Pro Gly Ile Thr Gly Leu Ser
        835                 840                 845

Thr Glu Gln Arg Lys Arg Leu Thr Ile Ala Val Glu Leu Val Ala Asn
    850                 855                 860

Pro Ser Ile Ile Phe Met Asp Glu Pro Thr Ser Gly Leu Asp Ala Arg
865                 870                 875                 880

Ala Ala Ala Ile Val Met Arg Thr Val Arg Asn Thr Val Asp Thr Gly
                885                 890                 895

Arg Thr Val Val Cys Thr Ile His Gln Pro Ser Ile Asp Ile Phe Glu
            900                 905                 910

Ala Phe Asp Glu Leu Leu Leu Leu Lys Arg Gly Gly Gln Val Ile Tyr
        915                 920                 925

Ser Gly Gln Leu Gly Arg Asn Ser Gln Lys Met Ile Glu Tyr Phe Glu
    930                 935                 940

Ala Ile Pro Gly Val Pro Lys Ile Lys Asp Lys Tyr Asn Pro Ala Thr
945                 950                 955                 960

Trp Met Leu Glu Val Ser Ser Val Ala Ala Glu Val Arg Leu Asn Met
                965                 970                 975

Asp Phe Ala Glu Tyr Tyr Lys Thr Ser Asp Leu Tyr Lys Gln Asn Lys
            980                 985                 990

Val Leu Val Asn Gln Leu Ser Gln Pro Glu Pro Gly Thr Ser Asp Leu
        995                 1000                1005

His Phe Pro Thr Lys Tyr Ser Gln Ser Thr Ile Gly Gln Phe Arg Ala
    1010                1015                1020

Cys Leu Trp Lys Gln Trp Leu Thr Tyr Trp Arg Ser Pro Asp Tyr Asn
1025                1030                1035                1040

Leu Val Arg Phe Ser Phe Thr Leu Phe Thr Ala Leu Leu Leu Gly Thr
                1045                1050                1055

Ile Phe Trp Lys Ile Gly Thr Lys Met Gly Asn Ala Asn Ser Leu Arg
            1060                1065                1070

Met Val Ile Gly Ala Met Tyr Thr Ala Val Met Phe Ile Gly Ile Asn
        1075                1080                1085
```

-continued

```
Asn Cys Ala Thr Val Gln Pro Ile Val Ser Ile Glu Arg Thr Val Phe
   1090                1095                1100

Tyr Arg Glu Arg Ala Ala Gly Met Tyr Ser Ala Met Pro Tyr Ala Ile
1105                1110                1115                1120

Ala Gln Val Val Met Glu Ile Pro Tyr Val Phe Val Gln Thr Ala Tyr
               1125                1130                1135

Tyr Thr Leu Ile Val Tyr Ala Met Met Ser Phe Gln Trp Thr Ala Ala
           1140                1145                1150

Lys Phe Phe Trp Phe Phe Phe Val Ser Tyr Phe Ser Phe Leu Tyr Phe
       1155                1160                1165

Thr Tyr Tyr Gly Met Met Thr Val Ala Ile Ser Pro Asn His Glu Val
   1170                1175                1180

Ala Ala Ile Phe Ala Ala Ala Phe Tyr Ser Leu Phe Asn Leu Phe Ser
1185                1190                1195                1200

Arg Phe Phe Ile Pro Arg Pro Arg Ile Pro Lys Trp Trp Ile Trp Tyr
               1205                1210                1215

Tyr Trp Leu Cys Pro Leu Ala Trp Thr Val Tyr Gly Leu Ile Val Thr
           1220                1225                1230

Gln Tyr Gly Asp Leu Glu Gln Ile Ile Ser Val Pro Gly Gln Ser Asn
       1235                1240                1245

Gln Thr Ile Ser Tyr Tyr Val Thr His His Phe Gly Tyr His Arg Lys
   1250                1255                1260

Phe Met Pro Val Val Ala Pro Val Leu Val Leu Phe Ala Val Phe Phe
1265                1270                1275                1280

Ala Phe Met Tyr Ala Ile Cys Ile Lys Lys Leu Asn Phe Gln His Arg
               1285                1290                1295
```

<210> SEQ ID NO 141
<211> LENGTH: 509
<212> TYPE: DNA
<213> ORGANISM: Glycine max

<400> SEQUENCE: 141

```
gcacgaggaa acaaggtgga tctgaatgga gggaagtgat atatacagag caagtaacag     60

tttacgaaga agttccacgg tttggagaaa cagtggtgtg gaggtattct caaggtcttc    120

tcgcgaagag gatgacgaag aagctctgaa atgggctgca cttgagaagc tccctaccta    180

caaccgtctc aggaaaggct tgctcacagc ttcccatggc gtcgccaacg aaatcgacgt    240

ctctgatctc ggcatccaag agagacagaa acttctcgag aggttggtca aagtagctga    300

agaggacaat gagaggttcc tgttgaagct caaggaacgt attgatagag ttggacttga    360

tattccaaca attgaagttc gatatgagca ccttaatatt gaggcagagg cctttgtggg    420

aagtagagct ttgccctctt tcatcaactc tgttactaat gtcgtagagg gatttttcaa    480

tcttctccac attagcacaa gcaaaaaaa                                      509
```

<210> SEQ ID NO 142
<211> LENGTH: 161
<212> TYPE: PRT
<213> ORGANISM: Glycine max

<400> SEQUENCE: 142

```
Met Glu Gly Ser Asp Ile Tyr Arg Ala Ser Asn Ser Leu Arg Arg Ser
  1               5                  10                  15

Ser Thr Val Trp Arg Asn Ser Gly Val Glu Val Phe Ser Arg Ser Ser
             20                  25                  30
```

-continued

```
Arg Glu Glu Asp Asp Glu Glu Ala Leu Lys Trp Ala Ala Leu Glu Lys
         35                  40                  45

Leu Pro Thr Tyr Asn Arg Leu Arg Lys Gly Leu Leu Thr Ala Ser His
     50                  55                  60

Gly Val Ala Asn Glu Ile Asp Val Ser Asp Leu Gly Ile Gln Glu Arg
 65                  70                  75                  80

Gln Lys Leu Leu Glu Arg Leu Val Lys Val Ala Glu Glu Asp Asn Glu
                 85                  90                  95

Arg Phe Leu Leu Lys Leu Lys Glu Arg Ile Asp Arg Val Gly Leu Asp
            100                 105                 110

Ile Pro Thr Ile Glu Val Arg Tyr Glu His Leu Asn Ile Glu Ala Glu
        115                 120                 125

Ala Phe Val Gly Ser Arg Ala Leu Pro Ser Phe Ile Asn Ser Val Thr
    130                 135                 140

Asn Val Val Glu Gly Phe Phe Asn Leu Leu His Ile Ser Thr Ser Lys
145                 150                 155                 160

Lys
```

<210> SEQ ID NO 143
<211> LENGTH: 1977
<212> TYPE: DNA
<213> ORGANISM: Triticum aestivum

<400> SEQUENCE: 143

```
gcacgaggga ggatacatag aggggggaaat caccgtatca ggctatccaa agaagcaaga     60

gacctttgca cgtatatcgg gatactgtga gcaaaatgat attcattctc cacatgtgac    120

aatatatgaa tcactcgtat tttctgcatg gctgcggctt cctgcagagg ttgactcaga    180

aagaagaaag atgttcatcg aggagatcat ggatcttgta gagctcacat cattgagggg    240

ggcacttgtt gggctccctg gagtgaatgg tctatcaact gagcaacgca agaggcttac    300

aattgccgtg gagcttgttg ctaacccgtc gatcattttt atggatgagc caacatctgg    360

tcttgatgct cgtgcagctg caattgtgat gaggactgtt aggaacactg ttaacactgg    420

caggaccgtt gtttgcacca tccaccagcc aagtattgac atatttgaag catttgatga    480

gcttttcttg atgaagagag ggggagaaga aatttatgtt ggtcctgttg gccaaaattc    540

agcaaatttg attgagtatt ttgaggaaat tgaaggcatt agtaagataa aagatggata    600

taacccagcg acatggatgt tggaagtgtc ctctagtgcg caggaggaaa tgcttggtat    660

tgatttcgct gaagtttaca gacaatcaga actatatcaa aggaacaagg aactcataaa    720

ggagctaagc atgccagctc ctggctctag tgatctcaac ttccctacac agtactctag    780

atcattcgtc acacagtgtc tagcttgctt gtggaagcaa agttgtcata ttggagaaac    840

ccatcctata cggcagtgag attactcttc accatcgtca ttgcgctaat gttcggaacg    900

atgttctggg accttggaag taaaactcga agatcacagg atctattcaa tgccatggga    960

tcaatgtatg ctgcagtact atacatcgga gtgcaaaatt ctggttctgt tcaaccagtt   1020

gtcgtggtgg agcgaacagt cttttaccgg gaaagagcag ctggcatgta ttcagctttt   1080

ccatatgcat ttggacaggt tgctatcgaa tttccgtacg tattggttca ggctttgata   1140

tatggcgggc tagtctattc catgattgga ttcgaatgga cagttgccaa gttcttgtgg   1200

tacttgttct tcatgtactt caccatgcta tatttcacgt tctatggaat gatggctgtt   1260

ggcttgacgc cgaatgagag catagcagct atcatctcat cagcattcta caacgtatgg   1320

aacctcttct caggatatct tatcccccga cctaaacttc ctatttggtg gaggtggtac   1380
```

```
tcatggattt gcccggtggc atggacgcta tacggactgg ttgcctccca gtttggtgat   1440

atccaacaac cgctcgatca gggagttcca ggcccacaga taactgtggc ccagtttgtc   1500

acggactact ttggtttcca tcatgacttc ttgtgggttg tggcgatggt gcacgttgct   1560

ttcaccgtgc tgttcgcctt cctgtttagt ttcgccatca tgaggttcaa cttccagaaa   1620

agatgaggag gatgacattc tttcagattc cttgtacgta gtgccatact gctgtccaac   1680

agccagtgcg gatggattga acaaagtata gttgtttctg tagatgatat agaggttatt   1740

ttgtatttca agcatgtaga aattccgcac aactatgctc tctactctct atgacttgta   1800

ggaaaggcta attagtcttg ttgagcctcc agcttcttta ccagctctag ctgagtaact   1860

gctacttact tttctcgtcg gagaatgtaa acccgaccag taatgttgtc atttctgacg   1920

agttaatgga ggcagaaaaa aaaaaaaaaa aaaaaaaaaa aaaaaaaaaa aaaaaaa      1977
```

```
<210> SEQ ID NO 144
<211> LENGTH: 539
<212> TYPE: PRT
<213> ORGANISM: Triticum aestivum
<220> FEATURE:
<221> NAME/KEY: UNSURE
<222> LOCATION: (272)..(273)

<400> SEQUENCE: 144

Gly Gly Tyr Ile Glu Gly Glu Ile Thr Val Ser Gly Tyr Pro Lys Lys
  1               5                  10                  15

Gln Glu Thr Phe Ala Arg Ile Ser Gly Tyr Cys Glu Gln Asn Asp Ile
             20                  25                  30

His Ser Pro His Val Thr Ile Tyr Glu Ser Leu Val Phe Ser Ala Trp
         35                  40                  45

Leu Arg Leu Pro Ala Glu Val Asp Ser Glu Arg Arg Lys Met Phe Ile
     50                  55                  60

Glu Glu Ile Met Asp Leu Val Glu Leu Thr Ser Leu Arg Gly Ala Leu
 65                  70                  75                  80

Val Gly Leu Pro Gly Val Asn Gly Leu Ser Thr Glu Gln Arg Lys Arg
                 85                  90                  95

Leu Thr Ile Ala Val Glu Leu Val Ala Asn Pro Ser Ile Ile Phe Met
            100                 105                 110

Asp Glu Pro Thr Ser Gly Leu Asp Ala Arg Ala Ala Ala Ile Val Met
        115                 120                 125

Arg Thr Val Arg Asn Thr Val Asn Thr Gly Arg Thr Val Val Cys Thr
    130                 135                 140

Ile His Gln Pro Ser Ile Asp Ile Phe Glu Ala Phe Asp Glu Leu Phe
145                 150                 155                 160

Leu Met Lys Arg Gly Gly Glu Glu Ile Tyr Val Gly Pro Val Gly Gln
                165                 170                 175

Asn Ser Ala Asn Leu Ile Glu Tyr Phe Glu Glu Ile Glu Gly Ile Ser
            180                 185                 190

Lys Ile Lys Asp Gly Tyr Asn Pro Ala Thr Trp Met Leu Glu Val Ser
        195                 200                 205

Ser Ser Ala Gln Glu Glu Met Leu Gly Ile Asp Phe Ala Glu Val Tyr
    210                 215                 220

Arg Gln Ser Glu Leu Tyr Gln Arg Asn Lys Glu Leu Ile Lys Glu Leu
225                 230                 235                 240

Ser Met Pro Ala Pro Gly Ser Ser Asp Leu Asn Phe Pro Thr Gln Tyr
                245                 250                 255
```

-continued

```
Ser Arg Ser Phe Val Thr Gln Cys Leu Ala Cys Leu Trp Lys Gln Xaa
            260                 265                 270

Xaa Ser Tyr Trp Arg Asn Pro Ser Tyr Thr Ala Val Arg Leu Leu Phe
        275                 280                 285

Thr Ile Val Ile Ala Leu Met Phe Gly Thr Met Phe Trp Asp Leu Gly
    290                 295                 300

Ser Lys Thr Arg Arg Ser Gln Asp Leu Phe Asn Ala Met Gly Ser Met
305                 310                 315                 320

Tyr Ala Ala Val Leu Tyr Ile Gly Val Gln Asn Ser Gly Ser Val Gln
                325                 330                 335

Pro Val Val Val Val Glu Arg Thr Val Phe Tyr Arg Glu Arg Ala Ala
            340                 345                 350

Gly Met Tyr Ser Ala Phe Pro Tyr Ala Phe Gly Gln Val Ala Ile Glu
        355                 360                 365

Phe Pro Tyr Val Leu Val Gln Ala Leu Ile Tyr Gly Gly Leu Val Tyr
    370                 375                 380

Ser Met Ile Gly Phe Glu Trp Thr Val Ala Lys Phe Leu Trp Tyr Leu
385                 390                 395                 400

Phe Phe Met Tyr Phe Thr Met Leu Tyr Phe Thr Phe Tyr Gly Met Met
                405                 410                 415

Ala Val Gly Leu Thr Pro Asn Glu Ser Ile Ala Ala Ile Ile Ser Ser
            420                 425                 430

Ala Phe Tyr Asn Val Trp Asn Leu Phe Ser Gly Tyr Leu Ile Pro Arg
        435                 440                 445

Pro Lys Leu Pro Ile Trp Trp Arg Trp Tyr Ser Trp Ile Cys Pro Val
    450                 455                 460

Ala Trp Thr Leu Tyr Gly Leu Val Ala Ser Gln Phe Gly Asp Ile Gln
465                 470                 475                 480

Gln Pro Leu Asp Gln Gly Val Pro Gly Pro Gln Ile Thr Val Ala Gln
                485                 490                 495

Phe Val Thr Asp Tyr Phe Gly Phe His His Asp Phe Leu Trp Val Val
            500                 505                 510

Ala Met Val His Val Ala Phe Thr Val Leu Phe Ala Phe Leu Phe Ser
        515                 520                 525

Phe Ala Ile Met Arg Phe Asn Phe Gln Lys Arg
    530                 535


<210> SEQ ID NO 145
<211> LENGTH: 549
<212> TYPE: DNA
<213> ORGANISM: Zea mays
<220> FEATURE:
<221> NAME/KEY: unsure
<222> LOCATION: (2)
<221> NAME/KEY: unsure
<222> LOCATION: (12)
<221> NAME/KEY: unsure
<222> LOCATION: (15)
<221> NAME/KEY: unsure
<222> LOCATION: (20)
<221> NAME/KEY: unsure
<222> LOCATION: (23)
<221> NAME/KEY: unsure
<222> LOCATION: (31)
<221> NAME/KEY: unsure
<222> LOCATION: (39)
<221> NAME/KEY: unsure
<222> LOCATION: (47)..(48)
<221> NAME/KEY: unsure
<222> LOCATION: (56)
```

<221> NAME/KEY: unsure
<222> LOCATION: (59)
<221> NAME/KEY: unsure
<222> LOCATION: (68)
<221> NAME/KEY: unsure
<222> LOCATION: (72)
<221> NAME/KEY: unsure
<222> LOCATION: (74)
<221> NAME/KEY: unsure
<222> LOCATION: (78)
<221> NAME/KEY: unsure
<222> LOCATION: (86)
<221> NAME/KEY: unsure
<222> LOCATION: (326)
<221> NAME/KEY: unsure
<222> LOCATION: (348)
<221> NAME/KEY: unsure
<222> LOCATION: (434)
<221> NAME/KEY: unsure
<222> LOCATION: (512)
<221> NAME/KEY: unsure
<222> LOCATION: (529)

<400> SEQUENCE: 145

```
tngatttcag gnacntcggn ttnaagtatc ngagtcgcnc agatatnnag atattnagng     60

atttcacntt gnanatcncc tccggnaaga ctgttgcact cgtgggagag agtggcagtg    120

gcaagtcaac ggtgatctct ttgctggaac ggttctacaa ccctgactct ggcaccatct    180

cactggatgg ggtcgagatc aagagcctga aagtcaattg gttgagggac cagatgggtc    240

tggtggggca agagccaatc ctcttcaacg acacgatccg tgccaacata gcctacggga    300

agcatgggga ggtaaccgag gagganttgt caaggtcgca agggcggnca acgcgcacga    360

gttcatatcg agcttcccca ggggtacgac accactgtcg gagagagaag ggtcagctat    420

ccggtggcca gaancagccg gtgccatagc gagagccata ctgaagacct agatttactc    480

ttgacgaggc aacgagcgcc tgacgccgaa tntagcgcat gtgcagatnc ctgacatgta    540

tgtcgcaga                                                            549
```

<210> SEQ ID NO 146
<211> LENGTH: 127
<212> TYPE: PRT
<213> ORGANISM: Zea mays
<220> FEATURE:
<221> NAME/KEY: UNSURE
<222> LOCATION: (82)
<221> NAME/KEY: UNSURE
<222> LOCATION: (84)
<221> NAME/KEY: UNSURE
<222> LOCATION: (90)
<221> NAME/KEY: UNSURE
<222> LOCATION: (98)
<221> NAME/KEY: UNSURE
<222> LOCATION: (117)
<221> NAME/KEY: UNSURE
<222> LOCATION: (119)

<400> SEQUENCE: 146

```
Ser Gly Lys Thr Val Ala Leu Val Gly Glu Ser Gly Ser Gly Lys Ser
  1               5                  10                  15

Thr Val Ile Ser Leu Leu Glu Arg Phe Tyr Asn Pro Asp Ser Gly Thr
             20                  25                  30

Ile Ser Leu Asp Gly Val Glu Ile Lys Ser Leu Lys Val Asn Trp Leu
         35                  40                  45

Arg Asp Gln Met Gly Leu Val Gly Gln Glu Pro Ile Leu Phe Asn Asp
     50                  55                  60
```

-continued

```
Thr Ile Arg Ala Asn Ile Ala Tyr Gly Lys His Gly Glu Val Thr Glu
 65                  70                  75                  80

Glu Xaa Leu Xaa Lys Val Ala Arg Ala Xaa Asn Ala His Glu Phe Ile
                 85                  90                  95

Ser Xaa Leu Pro Gln Gly Tyr Asp Thr Thr Val Gly Glu Arg Gln Leu
            100                 105                 110

Ser Gly Gly Gln Xaa Gln Xaa Ala Ile Ala Arg Ala Ile Leu Lys
        115                 120                 125


<210> SEQ ID NO 147
<211> LENGTH: 628
<212> TYPE: DNA
<213> ORGANISM: Zea mays
<220> FEATURE:
<221> NAME/KEY: unsure
<222> LOCATION: (218)
<221> NAME/KEY: unsure
<222> LOCATION: (232)
<221> NAME/KEY: unsure
<222> LOCATION: (288)
<221> NAME/KEY: unsure
<222> LOCATION: (341)
<221> NAME/KEY: unsure
<222> LOCATION: (347)
<221> NAME/KEY: unsure
<222> LOCATION: (351)
<221> NAME/KEY: unsure
<222> LOCATION: (359)
<221> NAME/KEY: unsure
<222> LOCATION: (376)
<221> NAME/KEY: unsure
<222> LOCATION: (385)
<221> NAME/KEY: unsure
<222> LOCATION: (389)
<221> NAME/KEY: unsure
<222> LOCATION: (403)
<221> NAME/KEY: unsure
<222> LOCATION: (407)
<221> NAME/KEY: unsure
<222> LOCATION: (419)
<221> NAME/KEY: unsure
<222> LOCATION: (476)
<221> NAME/KEY: unsure
<222> LOCATION: (487)
<221> NAME/KEY: unsure
<222> LOCATION: (489)
<221> NAME/KEY: unsure
<222> LOCATION: (493)
<221> NAME/KEY: unsure
<222> LOCATION: (499)
<221> NAME/KEY: unsure
<222> LOCATION: (513)
<221> NAME/KEY: unsure
<222> LOCATION: (530)
<221> NAME/KEY: unsure
<222> LOCATION: (554)
<221> NAME/KEY: unsure
<222> LOCATION: (579)
<221> NAME/KEY: unsure
<222> LOCATION: (590)
<221> NAME/KEY: unsure
<222> LOCATION: (600)
<221> NAME/KEY: unsure
<222> LOCATION: (606)
<221> NAME/KEY: unsure
<222> LOCATION: (609)
<221> NAME/KEY: unsure
<222> LOCATION: (611)

<400> SEQUENCE: 147

cgcagtcagg gttacgccca ggtgaagttc ttgaaggggt tcagccaaga tgctaaggag     60

atgtacgagg atgcaagcca agtggcgact gatgctgtcg gcagcatcag aaccgtggcg    120
```

-continued

```
tcgttctgcg cagagaaaag agtggtcgca gcgtacagcg acaagtgtga ggctctgagg    180

aaacagggca tcccgaagcg gatcctccgg agggcttngg tacggttctc cntccttgat    240

gctgtccttc aacttatggc ctttgcttct acttccgtgc gcattttntt gcgccaaggg    300

aaaacaactt tccaaaagtt ttcaagtttc cttcccgtta nttcctngca nctattgant    360

ccccccaagc aattcnctgg ttccngatnc aacaaagcaa ggntccncat tccaacttna    420

cgttcttgac aggaatccaa attaccccac aacggaacgg atacccggag gatcantgga    480

aatcatnanc aantaactna attccacgct ccnactcaaa ttcacgactn acttccatcc    540

ttcggaaaaa atgnctttcg aaaattgacg aattcacana cccttctacn ttcaacaatn    600

cggaanccng nggtttaata accaatcc                                       628
```

<210> SEQ ID NO 148
<211> LENGTH: 66
<212> TYPE: PRT
<213> ORGANISM: Zea mays

<400> SEQUENCE: 148

```
Gly Tyr Ala Gln Val Lys Phe Leu Lys Gly Phe Ser Gln Asp Ala Lys
  1               5                  10                  15

Glu Met Tyr Glu Asp Ala Ser Gln Val Ala Thr Asp Ala Val Gly Ser
             20                  25                  30

Ile Arg Thr Val Ala Ser Phe Cys Ala Glu Lys Arg Val Val Ala Ala
         35                  40                  45

Tyr Ser Asp Lys Cys Glu Ala Leu Arg Lys Gln Gly Ile Pro Lys Arg
     50                  55                  60

Ile Leu
 65
```

<210> SEQ ID NO 149
<211> LENGTH: 1016
<212> TYPE: DNA
<213> ORGANISM: Zea mays

<400> SEQUENCE: 149

```
gcacgagcca acttcgaaaa gattctcggt tttgggcact gacgtgcctt ctgtttgcag     60

tcattgccct gatttcaatc caactggaat actttctgtt tggggttgct ggtgggaaac    120

ttatacaacg tgtccgctct ttgtctttcc agagcatagt acatcaagaa gttgcttggt    180

ttgatgagcc ttcaaattct agtggggccc ttggcgcgag actctatatt gatgctttga    240

acatccgacg ccttgtcgga gataacttgg ccatactagt gcagtgtata gtaacaatag    300

cggctggttt ttccatagca tttgcttctg actggaaact cacgctgatc gtcatatgtg    360

tgattcccgt aatgggctca caaaattata ttcaagtgaa attcttgaaa gggttcagtg    420

aagatgctaa ggtgatgtat gaagatgcaa gtcaagtcgt aaccgaggca attggtagta    480

ttcaaacagt agcatctttc tgtgcagaga agagggtaat tacatcatac atccaaaaat    540

gccaagcttc aatgaaacat ggcattagaa gtggaatggt tggaggcctt ggtttcagtt    600

tatcaaactt aattatgtat ctcacatatg ctctttgttt ctatgttggt gcactgttcg    660

tacacgaagg aaaaacaact tttaaagacg tttttagggt ctattttgct ctgattttca    720

cagcttttgg agtttcccaa acaagtgcaa cggcaacaga ttcaacaaaa gcccaggaat    780

ccacaatttc aatactaact attatagaca ggagatctaa aatcaactcg actagtgatg    840

aaggcgtgat tatagaaaaa gttgatggca acatagattt caggcatgta agcttcaaat    900
```

-continued

```
acccatcccg cccagacgtc caagtgctca gcaactttac tttggccatt ccagcaagaa    960

agactgttgc acttgttgga gagagtggta gtggtaagtc aacaataatt tctttg       1016


<210> SEQ ID NO 150
<211> LENGTH: 338
<212> TYPE: PRT
<213> ORGANISM: Zea mays

<400> SEQUENCE: 150

Thr Ser Gln Leu Arg Lys Asp Ser Arg Phe Trp Ala Leu Thr Cys Leu
  1               5                  10                  15

Leu Phe Ala Val Ile Ala Leu Ile Ser Ile Gln Leu Glu Tyr Phe Leu
             20                  25                  30

Phe Gly Val Ala Gly Gly Lys Leu Ile Gln Arg Val Arg Ser Leu Ser
         35                  40                  45

Phe Gln Ser Ile Val His Gln Glu Val Ala Trp Phe Asp Glu Pro Ser
     50                  55                  60

Asn Ser Ser Gly Ala Leu Gly Ala Arg Leu Tyr Ile Asp Ala Leu Asn
 65                  70                  75                  80

Ile Arg Arg Leu Val Gly Asp Asn Leu Ala Ile Leu Val Gln Cys Ile
                 85                  90                  95

Val Thr Ile Ala Ala Gly Phe Ser Ile Ala Phe Ala Ser Asp Trp Lys
            100                 105                 110

Leu Thr Leu Ile Val Ile Cys Val Ile Pro Val Met Gly Ser Gln Asn
        115                 120                 125

Tyr Ile Gln Val Lys Phe Leu Lys Gly Phe Ser Glu Asp Ala Lys Val
    130                 135                 140

Met Tyr Glu Asp Ala Ser Gln Val Val Thr Glu Ala Ile Gly Ser Ile
145                 150                 155                 160

Gln Thr Val Ala Ser Phe Cys Ala Glu Lys Arg Val Ile Thr Ser Tyr
                165                 170                 175

Ile Gln Lys Cys Gln Ala Ser Met Lys His Gly Ile Arg Ser Gly Met
            180                 185                 190

Val Gly Gly Leu Gly Phe Ser Leu Ser Asn Leu Ile Met Tyr Leu Thr
        195                 200                 205

Tyr Ala Leu Cys Phe Tyr Val Gly Ala Leu Phe Val His Glu Gly Lys
    210                 215                 220

Thr Thr Phe Lys Asp Val Phe Arg Val Tyr Phe Ala Leu Ile Phe Thr
225                 230                 235                 240

Ala Phe Gly Val Ser Gln Thr Ser Ala Thr Ala Thr Asp Ser Thr Lys
                245                 250                 255

Ala Gln Glu Ser Thr Ile Ser Ile Leu Thr Ile Ile Asp Arg Arg Ser
            260                 265                 270

Lys Ile Asn Ser Thr Ser Asp Glu Gly Val Ile Ile Glu Lys Val Asp
        275                 280                 285

Gly Asn Ile Asp Phe Arg His Val Ser Phe Lys Tyr Pro Ser Arg Pro
    290                 295                 300

Asp Val Gln Val Leu Ser Asn Phe Thr Leu Ala Ile Pro Ala Arg Lys
305                 310                 315                 320

Thr Val Ala Leu Val Gly Glu Ser Gly Ser Gly Lys Ser Thr Ile Ile
                325                 330                 335

Ser Leu
```

-continued

<210> SEQ ID NO 151
<211> LENGTH: 314
<212> TYPE: DNA
<213> ORGANISM: Triticum aestivum

<400> SEQUENCE: 151

```
cttcatatgc agtttcccag accaatacaa gactgtcgtg ggagagcgag gcatcaggtt     60

atctgggcgg ggcagaagca gagggtcgcc attgcaagag ctttgcttat gaacccacga    120

gtgcttctct tagatgaagc taccagcgct ctggacgccg aaagcgagta ccttgttcag    180

gatgcaatgg actcgttgat gaaagggagg accgttcttg tgatagctca tcggctctcc    240

accgtgaaga gcgccgacac ggttgccgtc atctccgagg gccagattgt ggagagaggc    300

acacacgacg aact                                                      314
```

<210> SEQ ID NO 152
<211> LENGTH: 103
<212> TYPE: PRT
<213> ORGANISM: Triticum aestivum
<220> FEATURE:
<221> NAME/KEY: UNSURE
<222> LOCATION: (22)

<400> SEQUENCE: 152

```
Phe Ile Cys Ser Phe Pro Asp Gln Tyr Lys Thr Val Val Gly Glu Arg
  1               5                  10                  15

Gly Ile Arg Leu Ser Xaa Gly Gln Lys Gln Arg Val Ala Ile Ala Arg
             20                  25                  30

Ala Leu Leu Met Asn Pro Arg Val Leu Leu Leu Asp Glu Ala Thr Ser
         35                  40                  45

Ala Leu Asp Ala Glu Ser Glu Tyr Leu Val Gln Asp Ala Met Asp Ser
     50                  55                  60

Leu Met Lys Gly Arg Thr Val Leu Val Ile Ala His Arg Leu Ser Thr
 65                  70                  75                  80

Val Lys Ser Ala Asp Thr Val Ala Val Ile Ser Glu Gly Gln Ile Val
                 85                  90                  95

Glu Arg Gly Thr His Asp Glu
            100
```

<210> SEQ ID NO 153
<211> LENGTH: 942
<212> TYPE: DNA
<213> ORGANISM: Triticum aestivum

<400> SEQUENCE: 153

```
gcacgagtgc acattcccta tggaaagact attgcactcg ttggagagag tggttgtggc     60

aagtcaactg taatctctct gctggagaga ttctacaatc ctgattcagg taccatttta    120

ttggatggag tggaaatcaa gagcttgaac atcaactggt tgaggaagca aactggacta    180

gtgagccaag agcctgtact cttcaatgac acaattcgtg ccaacatagc ctacggaaag    240

gatgaggaag tcagtgagga ggagctcatt gcagcggcga aggcatccaa tgcgcacgag    300

ttcatatcaa gccttcctca aggatacgaa acatctgttg gggagagagg gatacaacta    360

tccggtggcc agaagcagcg ggtggctatc gcaagggcca tactgaaaga cccgaagata    420

ctactacttg acgaggcgac cagcgccctg gatgctgaat ctgagcggat cgtgcagaat    480

gccttggatc atgtgatggt tggcaggacc acggttgccg tggcgcaccg cctctcgacg    540

atcaaaggcg ccgatgtcat tgcagtcctc aaggatggtg caattgtgga gaaaggggga    600
```

-continued

```
cacgagtccc tgatgaacat caaagatggg gtgtacgctt cactagttga acttcgctcg    660

gctcaccatg aaaatgccta gtagacgtac gcggtacacc atgcccaatt tgctgtatct    720

agcagtctaa gtctatttga tgtaagtttg ctcgcattta aaaggagatt ctgcttctgc    780

tttagatttt gattctggtt ctgaaacgta catttcctgc tatgtgtaga gcagtgtagt    840

tttgtgctgt aataactata gaaataattg aagatcgccc cttcagaaat tattgtatgg    900

agatgtctgt agctcttgtt tttcaaaaaa aaaaaaaaaa aa                       942
```

```
<210> SEQ ID NO 154
<211> LENGTH: 226
<212> TYPE: PRT
<213> ORGANISM: Triticum aestivum

<400> SEQUENCE: 154

Ala Arg Val His Ile Pro Tyr Gly Lys Thr Ile Ala Leu Val Gly Glu
  1               5                  10                  15

Ser Gly Cys Gly Lys Ser Thr Val Ile Ser Leu Leu Glu Arg Phe Tyr
             20                  25                  30

Asn Pro Asp Ser Gly Thr Ile Leu Leu Asp Gly Val Glu Ile Lys Ser
         35                  40                  45

Leu Asn Ile Asn Trp Leu Arg Lys Gln Thr Gly Leu Val Ser Gln Glu
     50                  55                  60

Pro Val Leu Phe Asn Asp Thr Ile Arg Ala Asn Ile Ala Tyr Gly Lys
 65                  70                  75                  80

Asp Glu Glu Val Ser Glu Glu Glu Leu Ile Ala Ala Ala Lys Ala Ser
                 85                  90                  95

Asn Ala His Glu Phe Ile Ser Ser Leu Pro Gln Gly Tyr Glu Thr Ser
            100                 105                 110

Val Gly Glu Arg Gly Ile Gln Leu Ser Gly Gly Gln Lys Gln Arg Val
        115                 120                 125

Ala Ile Ala Arg Ala Ile Leu Lys Asp Pro Lys Ile Leu Leu Leu Asp
    130                 135                 140

Glu Ala Thr Ser Ala Leu Asp Ala Glu Ser Glu Arg Ile Val Gln Asn
145                 150                 155                 160

Ala Leu Asp His Val Met Val Gly Arg Thr Thr Val Ala Val Ala His
                165                 170                 175

Arg Leu Ser Thr Ile Lys Gly Ala Asp Val Ile Ala Val Leu Lys Asp
            180                 185                 190

Gly Ala Ile Val Glu Lys Gly Gly His Glu Ser Leu Met Asn Ile Lys
        195                 200                 205

Asp Gly Val Tyr Ala Ser Leu Val Glu Leu Arg Ser Ala His His Glu
    210                 215                 220

Asn Ala
225
```

```
<210> SEQ ID NO 155
<211> LENGTH: 821
<212> TYPE: DNA
<213> ORGANISM: Zea mays

<400> SEQUENCE: 155

attctggtac aatctcactg gatggaacag aacttaaaaa actaaagctg agttggttaa     60

gagaccaaac gggcttagtg agccaagaac ctgtactttt caacaacaca attcgcacaa    120

acatagcata tggaaaacaa ggagaagtaa gagaggatga gatcgttgct gcggccaagg    180
```

-continued

```
cagcaaatgc tcatgagttc atatctagct tgcctcaggg atatagcact attgtcggcg    240

agaggggaac acagctctct ggaggacaaa aacaacgggt tgctattgca agggccatct    300

tgaaggaccc aaaaatactt ctactcgacg aggcaacaag tgctctggat gctgaaggag    360

agcacattgt tcaagatgca ctggaccaag tgatggttag caggaccacc attgttgtgg    420

cgcaccgact gtccacaatt aaaggggcag atatgatcgt agtcatgaaa gatggtgaag    480

ttgctgagaa ggggaagcat gaataccttg tgggaaaggg tggagtttat gcatcgctgg    540

tagaactaca ctccaagtca gcataaggat atatgggaac ttcgatggat tatttggtat    600

tacaaggaga gcatttgcag taggaggtag tcatgcaacg aaaacaaatc catgtgaaac    660

ttgtcaattc atacttctgg tttgttatta tagggcagtg agtcttatcc taaactcaat    720

gcagacaaag atagmattgg catcaccgta tttcatatgc tgcagtgcac ttgattatca    780

ataaattaat ggtaaaaagg agaaaaaaaa aaaaaaaaaa a                        821


<210> SEQ ID NO 156
<211> LENGTH: 187
<212> TYPE: PRT
<213> ORGANISM: Zea mays

<400> SEQUENCE: 156

Ser Gly Thr Ile Ser Leu Asp Gly Thr Glu Leu Lys Lys Leu Lys Leu
  1               5                  10                  15

Ser Trp Leu Arg Asp Gln Thr Gly Leu Val Ser Gln Glu Pro Val Leu
             20                  25                  30

Phe Asn Asn Thr Ile Arg Thr Asn Ile Ala Tyr Gly Lys Gln Gly Glu
         35                  40                  45

Val Arg Glu Asp Glu Ile Val Ala Ala Ala Lys Ala Ala Asn Ala His
     50                  55                  60

Glu Phe Ile Ser Ser Leu Pro Gln Gly Tyr Ser Thr Ile Val Gly Glu
 65                  70                  75                  80

Arg Gly Thr Gln Leu Ser Gly Gly Gln Lys Gln Arg Val Ala Ile Ala
                 85                  90                  95

Arg Ala Ile Leu Lys Asp Pro Lys Ile Leu Leu Leu Asp Glu Ala Thr
            100                 105                 110

Ser Ala Leu Asp Ala Glu Gly Glu His Ile Val Gln Asp Ala Leu Asp
        115                 120                 125

Gln Val Met Val Ser Arg Thr Thr Ile Val Val Ala His Arg Leu Ser
    130                 135                 140

Thr Ile Lys Gly Ala Asp Met Ile Val Val Met Lys Asp Gly Glu Val
145                 150                 155                 160

Ala Glu Lys Gly Lys His Glu Tyr Leu Val Gly Lys Gly Gly Val Tyr
                165                 170                 175

Ala Ser Leu Val Glu Leu His Ser Lys Ser Ala
            180                 185


<210> SEQ ID NO 157
<211> LENGTH: 688
<212> TYPE: DNA
<213> ORGANISM: Zea mays

<400> SEQUENCE: 157

gcacgagccg ctccgctccg ctcgtgctct gctcctgctc tctctctctc tcggcgtcga     60

ttgggcgacc gccgccgcct tccccaggtc ttcgctgggc ccgtcgccgg cgccgagcac    120

ccaccagggc aagttttact tgataatgtg gacatcaaga cgttgcaatt aaagcgactt    180
```

-continued

```
agagaccaga tcggattggt gaatcaggaa cctactcttt ttgcaactac aattcttgag    240

aatattcttt ttggcaaacc tgaggcgaca aaggcagagg ttgggtctac gactacttcc    300

gcagtagatt aaaggagccc tagctttcgg aggacaaccc agatgccttc aaagttcaaa    360

atgacggtga tgaaggtgga caagaaacaa aattttggat ggttcaaaat tttgctatag    420

gtcctagcaa cgcttatgtg ttgctatagg ggggttattt tgtagtgaac tcccaggcca    480

tatgctagct tactttgagg agtgcccact atttgtgcat gctacaggcg ctatcattac    540

atttccatga cctgtaaagt ggtgacatct ttaaatacag aatggccaca ttagcgaacc    600

agaggtttca cacgagtatt cccttgtgat gagaaagtcc catgtcaata atgtgacttc    660

ttttgttgat taaaaaaaaa aaaaaaaa                                       688
```

```
<210> SEQ ID NO 158
<211> LENGTH: 103
<212> TYPE: PRT
<213> ORGANISM: Zea mays

<400> SEQUENCE: 158

Ala Arg Ala Ala Pro Leu Arg Ser Cys Ser Ala Pro Ala Leu Ser Leu
  1               5                  10                  15

Ser Arg Arg Arg Leu Gly Asp Arg Arg Arg Leu Pro Gln Val Phe Ala
             20                  25                  30

Gly Pro Val Ala Gly Ala Glu His Pro Pro Gly Gln Val Leu Leu Asp
         35                  40                  45

Asn Val Asp Ile Lys Thr Leu Gln Leu Lys Arg Leu Arg Asp Gln Ile
     50                  55                  60

Gly Leu Val Asn Gln Glu Pro Thr Leu Phe Ala Thr Thr Ile Leu Glu
 65                  70                  75                  80

Asn Ile Leu Phe Gly Lys Pro Glu Ala Thr Lys Ala Glu Val Gly Ser
                 85                  90                  95

Thr Thr Thr Ser Ala Val Asp
            100
```

```
<210> SEQ ID NO 159
<211> LENGTH: 1123
<212> TYPE: DNA
<213> ORGANISM: Zea mays

<400> SEQUENCE: 159

gcacgagata tttgcaattg tagatcgaaa atcaaggata gacccaagtg aggatgcagg     60

ggtaactgtt gaggcactac aaggaaacat cgtattccag catgttagct tcaagtatcc    120

taccaggcca gatgttcaga tattccggga cctttgcttg acaattcatg ctggaaagac    180

tgttgcactc gttggagaga gtggtagtgg caaatcaacg gcaatttcat tgctccagag    240

gttctatgac ccagatgtag gccatatact actagatggc gtggacatac agaagttcca    300

gcttaggtgg ttaaggcaac aaatgggcct ggttagtcaa gaaccagctt tgtttaatga    360

cacaataagg gcaaacattg cctatggaaa agatggacaa gcaacagaat ctgagatcat    420

atctgctgca gaattggcaa atgctcacaa gtttatcagt tcggcgctgc agggatatga    480

cacagtggtt ggagagcgtg gagcccagtt gtcaggaggg cagaagcagc gagtggcgat    540

cgcccgtgca attgtgaagg accctaggat cctgcttctg gacgaagcga ctagtgcgct    600

ggatgctgag tccgagcgga tcgtccagga cgcactggac agggtgatgg tgaaccggac    660

aacagtgatc gtcgctcacc gtctgtcaac aatacaaaat gcagatttga ttgcggtcgt    720
```

```
gaggaatggg gttatcatcg agaagggaaa gcacgatgcc ttgatcaaca tcaaggatgg    780

cgcctatgcg tccctcgtcg cccttcactc ggcagcctct tcatagcagg tgatggtatg    840

ggatcgtgca tacgtctgct aagacatata tgaacagagt gagctggcac aacctgtgta    900

gcaatgcagg tgttagtctc tgttcctcta tttgatggca tacataattg cttataccta    960

agcggagaaa tgttacaaat agcaaggacc agatgtaaat gcaaggagct ggtccttaag   1020

ataacttttt ataatctata aatcttaata tgtatatgta gcttcgaaca tagaaaccaa   1080

atagatgatg gttatgctat aaaaaaaaaa aaaaaaaaaa aaa                     1123
```

<210> SEQ ID NO 160
<211> LENGTH: 274
<212> TYPE: PRT
<213> ORGANISM: Zea mays

<400> SEQUENCE: 160

```
His Glu Ile Phe Ala Ile Val Asp Arg Lys Ser Arg Ile Asp Pro Ser
  1               5                  10                  15

Glu Asp Ala Gly Val Thr Val Glu Ala Leu Gln Gly Asn Ile Val Phe
             20                  25                  30

Gln His Val Ser Phe Lys Tyr Pro Thr Arg Pro Asp Val Gln Ile Phe
         35                  40                  45

Arg Asp Leu Cys Leu Thr Ile His Ala Gly Lys Thr Val Ala Leu Val
     50                  55                  60

Gly Glu Ser Gly Ser Gly Lys Ser Thr Ala Ile Ser Leu Leu Gln Arg
 65                  70                  75                  80

Phe Tyr Asp Pro Asp Val Gly His Ile Leu Leu Asp Gly Val Asp Ile
                 85                  90                  95

Gln Lys Phe Gln Leu Arg Trp Leu Arg Gln Gln Met Gly Leu Val Ser
            100                 105                 110

Gln Glu Pro Ala Leu Phe Asn Asp Thr Ile Arg Ala Asn Ile Ala Tyr
        115                 120                 125

Gly Lys Asp Gly Gln Ala Thr Glu Ser Glu Ile Ile Ser Ala Ala Glu
    130                 135                 140

Leu Ala Asn Ala His Lys Phe Ile Ser Ser Ala Leu Gln Gly Tyr Asp
145                 150                 155                 160

Thr Val Val Gly Glu Arg Gly Ala Gln Leu Ser Gly Gly Gln Lys Gln
                165                 170                 175

Arg Val Ala Ile Ala Arg Ala Ile Val Lys Asp Pro Arg Ile Leu Leu
            180                 185                 190

Leu Asp Glu Ala Thr Ser Ala Leu Asp Ala Glu Ser Glu Arg Ile Val
        195                 200                 205

Gln Asp Ala Leu Asp Arg Val Met Val Asn Arg Thr Thr Val Ile Val
    210                 215                 220

Ala His Arg Leu Ser Thr Ile Gln Asn Ala Asp Leu Ile Ala Val Val
225                 230                 235                 240

Arg Asn Gly Val Ile Ile Glu Lys Gly Lys His Asp Ala Leu Ile Asn
                245                 250                 255

Ile Lys Asp Gly Ala Tyr Ala Ser Leu Val Ala Leu His Ser Ala Ala
            260                 265                 270

Ser Ser
```

<210> SEQ ID NO 161
<211> LENGTH: 1185

-continued

<212> TYPE: DNA
<213> ORGANISM: Glycine max

<400> SEQUENCE: 161

```
gcacgaggtt agcttcaagt accctatgag acctgatatc accatatttc agaacttaaa     60
cctcatagtc ccagcaggta agagtctggc agtagtgggg caaagtggtt cagggaaaag    120
cacagtgatt tctttggtaa tgagatttta cgaccccgat ttggggtcag tcctaataga    180
tgaatgtgat atcaaaagcc taaaccttag atccttaagg ctgagaatag gattggttca    240
gcaagaacct gctttgttct caaccacagt ttatgaaaac atcaagtatg gaaaagagga    300
ggcatcagaa atagaggtaa tgaaggcagc caaagcagca aatgctcatg aattcattag    360
cagaatgcca gaagggtaca aaactgaggt tggtgagaga ggggcgcagt tgtcaggagg    420
acaaaaacaa agagtggcaa ttgctagagc tattctgaaa gatccatcca ttcttttgtt    480
ggatgaagca acaagtgcac tagacacagt atcagagagg ctggtccaag aggctcttga    540
taagcttatg gaaggtagaa caactatttt agtagctcac aggctatcaa ctgttcgcga    600
tgccgacagc attgcagtgc ttcaaaatgg cagggttgct gaaatgggaa gccatgagag    660
gctgatggcc aaacctgcaa gcatctacaa gcaattggtt agtctacagc atgaaacacg    720
tgaccaacaa gaccattgat gaattattca tttgcagctt cacaattgta gaaattcaaa    780
gcgtacttgc aatttacaac ttgaattgag gcaaggccta gtttattctc aaaagcatgc    840
ctgaaatatg tttttttca taccacaatc atttttctgt ttatatacac gagtactatg    900
ataaaattca aagcctatgg ttggctgttt gttgtagaat gctacaactt ttgtaatttc    960
tttttgaatt ttacaagatc tttggacaat caaaatttgt tcttttctca ttttcactcc   1020
atcctccttc aaatctcatg aaactttttt tttagttaca agatctttga tccttccttt   1080
tcactaaatg gtagcttttc atggtttcac cttcttcatt tatgtttgtc atcatcaata   1140
aaagtactac gtgccaaccg ttttgacaaa aaaaaaaaaa aaaaa                  1185
```

<210> SEQ ID NO 162
<211> LENGTH: 245
<212> TYPE: PRT
<213> ORGANISM: Glycine max

<400> SEQUENCE: 162

```
His Glu Val Ser Phe Lys Tyr Pro Met Arg Pro Asp Ile Thr Ile Phe
  1               5                  10                  15

Gln Asn Leu Asn Leu Ile Val Pro Ala Gly Lys Ser Leu Ala Val Val
             20                  25                  30

Gly Gln Ser Gly Ser Gly Lys Ser Thr Val Ile Ser Leu Val Met Arg
         35                  40                  45

Phe Tyr Asp Pro Asp Leu Gly Ser Val Leu Ile Asp Glu Cys Asp Ile
     50                  55                  60

Lys Ser Leu Asn Leu Arg Ser Leu Arg Leu Arg Ile Gly Leu Val Gln
 65                  70                  75                  80

Gln Glu Pro Ala Leu Phe Ser Thr Thr Val Tyr Glu Asn Ile Lys Tyr
                 85                  90                  95

Gly Lys Glu Glu Ala Ser Glu Ile Glu Val Met Lys Ala Ala Lys Ala
            100                 105                 110

Ala Asn Ala His Glu Phe Ile Ser Arg Met Pro Glu Gly Tyr Lys Thr
        115                 120                 125

Glu Val Gly Glu Arg Gly Ala Gln Leu Ser Gly Gly Gln Lys Gln Arg
    130                 135                 140
```

-continued

```
Val Ala Ile Ala Arg Ala Ile Leu Lys Asp Pro Ser Ile Leu Leu Leu
145                 150                 155                 160

Asp Glu Ala Thr Ser Ala Leu Asp Thr Val Ser Glu Arg Leu Val Gln
                165                 170                 175

Glu Ala Leu Asp Lys Leu Met Glu Gly Arg Thr Thr Ile Leu Val Ala
            180                 185                 190

His Arg Leu Ser Thr Val Arg Asp Ala Asp Ser Ile Ala Val Leu Gln
        195                 200                 205

Asn Gly Arg Val Ala Glu Met Gly Ser His Glu Arg Leu Met Ala Lys
    210                 215                 220

Pro Ala Ser Ile Tyr Lys Gln Leu Val Ser Leu Gln His Glu Thr Arg
225                 230                 235                 240

Asp Gln Gln Asp His
                245


<210> SEQ ID NO 163
<211> LENGTH: 918
<212> TYPE: DNA
<213> ORGANISM: Glycine max

<400> SEQUENCE: 163

agaacttaaa cctcagagtc ccagcaggca agagtctggc agtagtgggg caaagtggtt      60

caggaaaaag cacagtgatt tctttggtaa tgagatttta tgaccccgat tcggggttag     120

tcctggtaga tgaatgtgat atcaaaaacc taaacctgag atccttaagg ctgagaatag     180

gattggttca gcaagaacct gctttgttct ctaccacagt ttatgaaaac atcaagtatg     240

gaaaagagga ggcatcagaa atagaggtaa tgaaggcagc caaagcagca aatgctcatg     300

aattcatcag cagaatgcca gaagggtaca aaaccgaggt tggtgagaga ggggtgcagt     360

tgtcaggagg acaaaaacaa agagtggcaa ttgctagagc tatcctgaaa gatccatcca     420

ttcttttgtt ggacgaagca acaagtgcac ttgacacagt atcagagagg ctagtccaag     480

aggctcttga taaacttatg gaaggtagaa caactatttt ggtagctcac aggttatcaa     540

ctgttcgcga tgccaacagc attgcagtgc ttcaaaatgg cagggttgct gaaatgggga     600

gccatgagag gctgatggcc aaatccggaa gcatctacaa gcaattggtt agtctacagc     660

atgaaacacg cgaccaagaa gatcattgat gaattattca ttcgcaattt cccaagtaat     720

tgtagaaatt cgaagtgtac ttgcaattcg caacttgaat tgaggcaagg cctagttcat     780

tctcaagaac atgcctgaaa gatgtttttt tttccttctt cataggacag ttgttttctg     840

tttatataca cgagtcctat gataaaattc aaagcctatg attgtttgtt tgttgtaaaa     900

aaaaaaaaaa aaaaaaaa                                                   918


<210> SEQ ID NO 164
<211> LENGTH: 228
<212> TYPE: PRT
<213> ORGANISM: Glycine max

<400> SEQUENCE: 164

Asn Leu Asn Leu Arg Val Pro Ala Gly Lys Ser Leu Ala Val Val Gly
  1               5                  10                  15

Gln Ser Gly Ser Gly Lys Ser Thr Val Ile Ser Leu Val Met Arg Phe
             20                  25                  30

Tyr Asp Pro Asp Ser Gly Leu Val Leu Val Asp Glu Cys Asp Ile Lys
         35                  40                  45
```

-continued

```
Asn Leu Asn Leu Arg Ser Leu Arg Leu Arg Ile Gly Leu Val Gln Gln
     50                  55                  60

Glu Pro Ala Leu Phe Ser Thr Thr Val Tyr Glu Asn Ile Lys Tyr Gly
 65                  70                  75                  80

Lys Glu Glu Ala Ser Glu Ile Glu Val Met Lys Ala Ala Lys Ala Ala
                 85                  90                  95

Asn Ala His Glu Phe Ile Ser Arg Met Pro Glu Gly Tyr Lys Thr Glu
            100                 105                 110

Val Gly Glu Arg Gly Val Gln Leu Ser Gly Gly Gln Lys Gln Arg Val
        115                 120                 125

Ala Ile Ala Arg Ala Ile Leu Lys Asp Pro Ser Ile Leu Leu Leu Asp
    130                 135                 140

Glu Ala Thr Ser Ala Leu Asp Thr Val Ser Glu Arg Leu Val Gln Glu
145                 150                 155                 160

Ala Leu Asp Lys Leu Met Glu Gly Arg Thr Thr Ile Leu Val Ala His
                165                 170                 175

Arg Leu Ser Thr Val Arg Asp Ala Asn Ser Ile Ala Val Leu Gln Asn
            180                 185                 190

Gly Arg Val Ala Glu Met Gly Ser His Glu Arg Leu Met Ala Lys Ser
        195                 200                 205

Gly Ser Ile Tyr Lys Gln Leu Val Ser Leu Gln His Glu Thr Arg Asp
    210                 215                 220

Gln Glu Asp His
225


<210> SEQ ID NO 165
<211> LENGTH: 578
<212> TYPE: DNA
<213> ORGANISM: Oryza sativa
<220> FEATURE:
<221> NAME/KEY: unsure
<222> LOCATION: (390)
<221> NAME/KEY: unsure
<222> LOCATION: (500)
<221> NAME/KEY: unsure
<222> LOCATION: (508)
<221> NAME/KEY: unsure
<222> LOCATION: (516)
<221> NAME/KEY: unsure
<222> LOCATION: (529)
<221> NAME/KEY: unsure
<222> LOCATION: (543)
<221> NAME/KEY: unsure
<222> LOCATION: (557)
<221> NAME/KEY: unsure
<222> LOCATION: (575)

<400> SEQUENCE: 165

cttacacggc acgagcttac agccaatgct catgaattca ttgtctctct tccacagggc     60

tatgacacac ttgttggtga acgtggcagc ctcctaagtg ggggacagag acagagaatt    120

gctattgctc gtgctcttct gaaaaactct cctattctaa tacttgatga ggctaccagt    180

gcacttgata cgaccagtga acggcttgta caggaagctc tcaatcactt gatgaaggga    240

aggacttctc tggtgatcgc gcacagattg agcaccgtgc aaaatgcgca tcaaatcgct    300

gtctgctcag atggcaagat agcagaactt gggactcatg tgaactggtt ctagcggtgg    360

ccgtatgcgt cacttgttgg tacacagagn tcgcatttga gtaagcaact tcagaaaatt    420

ctgttccgaa agacgttccg acgagttctc gacatattta catcatctga catatatacg    480
```

-continued ggatggttac gaacacatgn catgaatnac gaaacncatg ttcaagttnc actcaaaacg 540
agnctcatag tgtgccnaaa aaagtgtttt gaccnatt 578

<210> SEQ ID NO 166
<211> LENGTH: 106
<212> TYPE: PRT
<213> ORGANISM: Oryza sativa

<400> SEQUENCE: 166

```
Ala Asn Ala His Glu Phe Ile Val Ser Leu Pro Gln Gly Tyr Asp Thr
  1               5                  10                  15

Leu Val Gly Glu Arg Gly Ser Leu Leu Ser Gly Gly Gln Arg Gln Arg
             20                  25                  30

Ile Ala Ile Ala Arg Ala Leu Leu Lys Asn Ser Pro Ile Leu Ile Leu
         35                  40                  45

Asp Glu Ala Thr Ser Ala Leu Asp Thr Thr Ser Glu Arg Leu Val Gln
     50                  55                  60

Glu Ala Leu Asn His Leu Met Lys Gly Arg Thr Ser Leu Val Ile Ala
 65                  70                  75                  80

His Arg Leu Ser Thr Val Gln Asn Ala His Gln Ile Ala Val Cys Ser
                 85                  90                  95

Asp Gly Lys Ile Ala Glu Leu Gly Thr His
            100                 105
```

<210> SEQ ID NO 167
<211> LENGTH: 1428
<212> TYPE: DNA
<213> ORGANISM: Glycine max

<400> SEQUENCE: 167
gcacgagatt ttgtgatgca gaatgccgtg gttttgttat atttggctgg tgggtctttc 60
attgcttgtt tcctagaggg ttattgttgg acaagaacag gagaaaggca agctgcaaga 120
atgagagtta ggtaccttaa agcagttctc aggcaagaag tagcatactt tgatttgcat 180
gtcacaagca catcggaggt catcaccagc gtctctaatg atagcctcgt aattcaagat 240
tgtcttagtg aaaaggtccc aaactttttg atgaatgcgt ccatgtttgt tgggagctac 300
atagtggctt ttgcattatt gtggagattg gccattgtgg ggttcccttt tgtggcccta 360
cttgtgatcc ccggtttcat gtatgggagg acattaatgg ggttggctag caagataaga 420
gaagagtaca ataaagcagg cacaatagca gaacaagcaa tatcctccat cagaaccgtt 480
tattcttttg tgggggaaag caagactatt gatgctttct ctgaagccct acaagggtct 540
gttgagttgg gactgagaca aggcttagca aaaggtttag ctattggaag caatggtgtt 600
gtctttgcta tatgggcatt catgtcctat tatggtagca gattggtcat gtaccatgga 660
gctaaaggtg ggactgtatt tgcagttgga gcagccatag ctcttggagg attggcacta 720
ggtgctggtt tgtcgaacgt gaagtacttc tcagaagcaa gtaccgcagg agaacgcata 780
atggaagtga taaaaagggt tccaaagatt gattctgata gcatggctga ggagattctg 840
gagaacgttt caggggaagt tgaattcaac catgtggact ttgtgtaccc atcaaggcca 900
gacagtgtta ttctgaatga tttctgccta aagattccag cagggaaaac agtggctttg 960
gttggaggga gtggctctgg aaaatccact gtgatatcac ttttgcagag gttttatgac 1020
ccaattgagg gagagatatt tcttgatggt gtggccattc acaagttgca actcaagtgg 1080
ttgaggtctc aaatgggttt ggtcagccaa gagcctgcac tgtttgcaac tagcattaaa 1140

-continued

```
gagaatatac tttttggaag agaagatgcc actcaagaag aggttgtgga ggcagcaaaa   1200

gcttccaatg ctcataattt catttcacag ttgccacaag gatatgatac tcaggtgagt   1260

gctacttcat tagtcatttg tcaaaccaac ccaatatgtt agtagttagg ttaggatgtt   1320

tgtttgtgga gtgtgtgtca cggcatgcaa gttttaccct tggtggttgt taggatgaaa   1380

aaagaagtaa aaaaattcaa attaaactat aaaaaaaaaa aaaaaaa                 1428
```

<210> SEQ ID NO 168
<211> LENGTH: 433
<212> TYPE: PRT
<213> ORGANISM: Glycine max

<400> SEQUENCE: 168

```
Ala Arg Asp Phe Val Met Gln Asn Ala Val Val Leu Leu Tyr Leu Ala
  1               5                  10                  15

Gly Gly Ser Phe Ile Ala Cys Phe Leu Glu Gly Tyr Cys Trp Thr Arg
             20                  25                  30

Thr Gly Glu Arg Gln Ala Ala Arg Met Arg Val Arg Tyr Leu Lys Ala
         35                  40                  45

Val Leu Arg Gln Glu Val Ala Tyr Phe Asp Leu His Val Thr Ser Thr
     50                  55                  60

Ser Glu Val Ile Thr Ser Val Ser Asn Asp Ser Leu Val Ile Gln Asp
 65                  70                  75                  80

Cys Leu Ser Glu Lys Val Pro Asn Phe Leu Met Asn Ala Ser Met Phe
                 85                  90                  95

Val Gly Ser Tyr Ile Val Ala Phe Ala Leu Leu Trp Arg Leu Ala Ile
            100                 105                 110

Val Gly Phe Pro Phe Val Ala Leu Leu Val Ile Pro Gly Phe Met Tyr
        115                 120                 125

Gly Arg Thr Leu Met Gly Leu Ala Ser Lys Ile Arg Glu Glu Tyr Asn
    130                 135                 140

Lys Ala Gly Thr Ile Ala Glu Gln Ala Ile Ser Ser Ile Arg Thr Val
145                 150                 155                 160

Tyr Ser Phe Val Gly Glu Ser Lys Thr Ile Asp Ala Phe Ser Glu Ala
                165                 170                 175

Leu Gln Gly Ser Val Glu Leu Gly Leu Arg Gln Gly Leu Ala Lys Gly
            180                 185                 190

Leu Ala Ile Gly Ser Asn Gly Val Val Phe Ala Ile Trp Ala Phe Met
        195                 200                 205

Ser Tyr Tyr Gly Ser Arg Leu Val Met Tyr His Gly Ala Lys Gly Gly
    210                 215                 220

Thr Val Phe Ala Val Gly Ala Ala Ile Ala Leu Gly Gly Leu Ala Leu
225                 230                 235                 240

Gly Ala Gly Leu Ser Asn Val Lys Tyr Phe Ser Glu Ala Ser Thr Ala
                245                 250                 255

Gly Glu Arg Ile Met Glu Val Ile Lys Arg Val Pro Lys Ile Asp Ser
            260                 265                 270

Asp Ser Met Ala Glu Glu Ile Leu Glu Asn Val Ser Gly Glu Val Glu
        275                 280                 285

Phe Asn His Val Asp Phe Val Tyr Pro Ser Arg Pro Asp Ser Val Ile
    290                 295                 300

Leu Asn Asp Phe Cys Leu Lys Ile Pro Ala Gly Lys Thr Val Ala Leu
305                 310                 315                 320
```

-continued

```
Val Gly Gly Ser Gly Ser Gly Lys Ser Thr Val Ile Ser Leu Leu Gln
                325                 330                 335

Arg Phe Tyr Asp Pro Ile Glu Gly Glu Ile Phe Leu Asp Gly Val Ala
            340                 345                 350

Ile His Lys Leu Gln Leu Lys Trp Leu Arg Ser Gln Met Gly Leu Val
        355                 360                 365

Ser Gln Glu Pro Ala Leu Phe Ala Thr Ser Ile Lys Glu Asn Ile Leu
    370                 375                 380

Phe Gly Arg Glu Asp Ala Thr Gln Glu Glu Val Val Glu Ala Ala Lys
385                 390                 395                 400

Ala Ser Asn Ala His Asn Phe Ile Ser Gln Leu Pro Gln Gly Tyr Asp
                405                 410                 415

Thr Gln Val Ser Ala Thr Ser Leu Val Ile Cys Gln Thr Asn Pro Ile
            420                 425                 430

Cys


<210> SEQ ID NO 169
<211> LENGTH: 1995
<212> TYPE: DNA
<213> ORGANISM: Zea mays

<400> SEQUENCE: 169

agctcgggct ccctccccaa tccccatccc caaatcgctt tcgctccgcc ccggtcgccg     60

gaccatggcc gcctccgcct caaccacgct cttctcaccg tgcgccctca cctccaagct    120

cggggcagga cacgcgtcct atggctccgt acgccgcgct aacgtgcgcc ggcgcggccg    180

cctctcggtg gtggccgtac aaacgggccc gcagaagccg tcgccgttgt cgtcccaggc    240

cgccgcggcg gaggatgagg cggacgcgct gcagaagctt ctgaagaggg agtacaaata    300

cgggtttgtg tccgacttcg agtccttctc catccccaag gggctgtcgg aggccaccgt    360

ccgccgcatc tcggagctca aggcggagcc ggcgtggatg ctggacttcc gcctcgccgc    420

ctaccgccgc ttcctcacca tggtcgagcc cacctggagc gacaacgagt acgcgcccgt    480

ggacctgcag tctatctgct actactccgc gcccaaaacc aagcccaagc tcaatagcct    540

cgacgaggtc gacccggagc tgctcaatac cttcgaccgc ctcggcatcc cgctcagcga    600

gcagaagcgc ctcgccaacg tcgctgtcga cgccgtcatc gactccactt ccatcgccac    660

cacccaccgc gaggcgctca tggccaaggg cgtcatcttc tgctccatct ccgaggccat    720

ccgtgagtac ccggaccttg tcaggcgcta cctcggcagc atcgtaccgc cgggcgacaa    780

ctactatgcc gccctcaatt cagcggtgtt cagcgacgga tccttctgct acgtgcccaa    840

ggacacggtc tgccccatgg aaatttcgac ttacttcagg atcaacgaca aggagacagg    900

ccagtttgag aggactctga ttgtagccga tgagagaagc actgttagct atttggaagg    960

ctgcactgca ccagcatatg actcaaatca gctccatgct gcggttgtgg agcttgtgtg   1020

tgagaatggg gcagagatta agtactccac ggtgcagaat tggtactccg gtgatgagga   1080

ggggagagga ggcatttata actttgtgac aaagagggga aggtgcaaag ggcggggttc   1140

gaagatctca tggacacagg ttgagacagg atctgctatt acatggaagt acccaagcgt   1200

tgagctcgtc ggggatgaca gtgttggaga gttctactcg gttgcgctta caaaggattg   1260

ccagcaagca gacacaggga cgaaaatgat ccacaagggg aaaaattcac gcagccggat   1320

tatatccaag ggcatctctg cagggaagtc aaggaattgc taccgtggct tggtcctgat   1380

gaactctagt gcagagaatg cttataattc ttcacagtgt gactcattgt tgatcgggga   1440
```

-continued

```
taatgcggct gcgaacacct atcccaccat tcaggtgggg tgcactagtg gccgggttga   1500

gcatgaggca agcacttcca aaattggaga ggatcagcta ttttatttcc agcaaagagg   1560

ggtagatcat gaaaaggcag ttgccgccat gattggtgga ttctgcagat ctgttttcga   1620

gcaccttccc tatgaattcg cacaggaggt ggacgcactc atgaacctga aactcgaggg   1680

atcagttggc taatttgttg gctcagcgat ttcgtgtaat actccatgac agccagttag   1740

ctagaaaatc catgtgtaca gcagtacgag aagaataaat tacaggataa gtatacattt   1800

cctggctggt tgtaatactg aatgttgatg atgtctatgg caattggcaa cgaactatga   1860

agatgtagca gttgagcctg tttgtcttct gttgcccagt tttgctattt gctgtaagcg   1920

agctcacatg gctcacctat acaagaacgg aaatcaacgt gttggcgtta cagaaaaaaa   1980

aaaaaaaaaa aaaaa                                                     1995
```

<210> SEQ ID NO 170
<211> LENGTH: 563
<212> TYPE: PRT
<213> ORGANISM: Zea mays

<400> SEQUENCE: 170

```
Ala Arg Ala Pro Ser Pro Ile Pro Ile Pro Lys Ser Leu Ser Leu Arg
  1               5                  10                  15

Pro Gly Arg Arg Thr Met Ala Ala Ser Ala Ser Thr Thr Leu Phe Ser
             20                  25                  30

Pro Cys Ala Leu Thr Ser Lys Leu Gly Ala Gly His Ala Ser Tyr Gly
         35                  40                  45

Ser Val Arg Arg Ala Asn Val Arg Arg Arg Gly Arg Leu Ser Val Val
     50                  55                  60

Ala Val Gln Thr Gly Pro Gln Lys Pro Ser Pro Leu Ser Ser Gln Ala
 65                  70                  75                  80

Ala Ala Ala Glu Asp Glu Ala Asp Ala Leu Gln Lys Leu Leu Lys Arg
                 85                  90                  95

Glu Tyr Lys Tyr Gly Phe Val Ser Asp Phe Glu Ser Phe Ser Ile Pro
            100                 105                 110

Lys Gly Leu Ser Glu Ala Thr Val Arg Arg Ile Ser Glu Leu Lys Ala
        115                 120                 125

Glu Pro Ala Trp Met Leu Asp Phe Arg Leu Ala Ala Tyr Arg Arg Phe
    130                 135                 140

Leu Thr Met Val Glu Pro Thr Trp Ser Asp Asn Glu Tyr Ala Pro Val
145                 150                 155                 160

Asp Leu Gln Ser Ile Cys Tyr Tyr Ser Ala Pro Lys Thr Lys Pro Lys
                165                 170                 175

Leu Asn Ser Leu Asp Glu Val Asp Pro Glu Leu Leu Asn Thr Phe Asp
            180                 185                 190

Arg Leu Gly Ile Pro Leu Ser Glu Gln Lys Arg Leu Ala Asn Val Ala
        195                 200                 205

Val Asp Ala Val Ile Asp Ser Thr Ser Ile Ala Thr Thr His Arg Glu
    210                 215                 220

Ala Leu Met Ala Lys Gly Val Ile Phe Cys Ser Ile Ser Glu Ala Ile
225                 230                 235                 240

Arg Glu Tyr Pro Asp Leu Val Arg Arg Tyr Leu Gly Ser Ile Val Pro
                245                 250                 255

Pro Gly Asp Asn Tyr Tyr Ala Ala Leu Asn Ser Ala Val Phe Ser Asp
            260                 265                 270
```

-continued

```
Gly Ser Phe Cys Tyr Val Pro Lys Asp Thr Val Cys Pro Met Glu Ile
        275                 280                 285

Ser Thr Tyr Phe Arg Ile Asn Asp Lys Glu Thr Gly Gln Phe Glu Arg
    290                 295                 300

Thr Leu Ile Val Ala Asp Glu Arg Ser Thr Val Ser Tyr Leu Glu Gly
305                 310                 315                 320

Cys Thr Ala Pro Ala Tyr Asp Ser Asn Gln Leu His Ala Ala Val Val
                325                 330                 335

Glu Leu Val Cys Glu Asn Gly Ala Glu Ile Lys Tyr Ser Thr Val Gln
            340                 345                 350

Asn Trp Tyr Ser Gly Asp Glu Glu Gly Arg Gly Gly Ile Tyr Asn Phe
        355                 360                 365

Val Thr Lys Arg Gly Arg Cys Lys Gly Arg Gly Ser Lys Ile Ser Trp
    370                 375                 380

Thr Gln Val Glu Thr Gly Ser Ala Ile Thr Trp Lys Tyr Pro Ser Val
385                 390                 395                 400

Glu Leu Val Gly Asp Asp Ser Val Gly Glu Phe Tyr Ser Val Ala Leu
                405                 410                 415

Thr Lys Asp Cys Gln Gln Ala Asp Thr Gly Thr Lys Met Ile His Lys
            420                 425                 430

Gly Lys Asn Ser Arg Ser Arg Ile Ile Ser Lys Gly Ile Ser Ala Gly
        435                 440                 445

Lys Ser Arg Asn Cys Tyr Arg Gly Leu Val Leu Met Asn Ser Ser Ala
    450                 455                 460

Glu Asn Ala Tyr Asn Ser Ser Gln Cys Asp Ser Leu Leu Ile Gly Asp
465                 470                 475                 480

Asn Ala Ala Ala Asn Thr Tyr Pro Thr Ile Gln Val Gly Cys Thr Ser
                485                 490                 495

Gly Arg Val Glu His Glu Ala Ser Thr Ser Lys Ile Gly Glu Asp Gln
            500                 505                 510

Leu Phe Tyr Phe Gln Gln Arg Gly Val Asp His Glu Lys Ala Val Ala
        515                 520                 525

Ala Met Ile Gly Gly Phe Cys Arg Ser Val Phe Glu His Leu Pro Tyr
    530                 535                 540

Glu Phe Ala Gln Glu Val Asp Ala Leu Met Asn Leu Lys Leu Glu Gly
545                 550                 555                 560

Ser Val Gly


<210> SEQ ID NO 171
<211> LENGTH: 2043
<212> TYPE: DNA
<213> ORGANISM: Oryza sativa

<400> SEQUENCE: 171

gcacgagtac acacaacaac ccacccctcc tgcgctctcc atcccatccg catccctaat      60

ttcgcctcgg cctcgccacg ccgccgcacc atggccgcag ccgccgcgtc gtccacgccc     120

ctcttctcgc cctgctgcgc cgccgcgacc gccaagctcg gggcggcgtg cccgtcgtcg     180

tacggatccc ggcggaggcc gtgcacgcgc cgtggacgcc tctcggtggt ggccgtgcag     240

acgggcccgc agaagccatc gccgtcgtcg tcgtcccagg cggggacgga atcggagacg     300

ctgcagaacc tgctgaagag ggagtacaag tatgggttcg tgtctgattt cgagtccttc     360

tccatcccca aggggctctc cgaggccacg gtccgccgca tctcggagct caaggcggag     420

ccggcgtgga tgctcgactt ccgcctcgcc gcctaccgcc ggttcctgac catggtgcag     480
```

-continued

```
cccacctgga gcgacaacgt gtacgagccg gtggatctcc agtccatctg ctactactcc    540

gcgcccaaga ccaagcccaa gctcaacagc ctcgacgagg tcgacccgga gcttctcaac    600

accttcgatc gcctcgggat cccgctcagc gagcagaagc gcctcgccaa cgtcgccgtc    660

gatgccgtca tcgactccac ctccatcgcc accacccacc gggaggagct catgaagaag    720

ggcgtcatct tttgctccat ttccgaggcc atccgcgagt acccggacct tgtcaagcgc    780

taccttggca gcgtcgtgcc gccggcagat aactactatg ctgccctcaa ttcggccgtg    840

ttcagcgatg ggtcgttctg ctatgtgccc aaggatacgg tatgcccaat ggagatatcg    900

acatacttta ggatcaacga caaggagacc gggcaatttg agaggactct aattgtggct    960

gatgagagga gcacggttag ctatctggaa gggtgtactg ctccagctta tgactccaac   1020

cagctccatg cggcggttgt ggagcttgtg tgtgaggagc aggcagagat caagtactct   1080

acggtgcaga attggtactc tggtgatgag gaggggaagg ggggcattta caactttgtt   1140

actaagagag gacggtgcaa agggcggggc tctaagatct catggacaca ggttgagaca   1200

ggttcagcaa ttacatggaa gtacccaagt gtggagcttc ttggggatga tactgttgga   1260

gagttctact cagttgcact gacgaaggat taccagcagg cagacacagg gacaaaaatg   1320

atccacaagg gaaagaattc gcggagtcgg attatatcca aaggtatctc agctgggaag   1380

tcacggaatt gctaccgtgg gttggtccag ataaactcag gcgcagaaaa tgcttataat   1440

tcttcacagt gtgattcttt gctgattggg gataacgctg ctgccaacac ctatccgact   1500

attcaggtgg gttgcatttc tagtcgtgtt gagcatgagg caagcacttc aaaaataggg   1560

gaggaccagc tattttattt ccaacaaagg gggatagacc atgaaaaggc tgttgcagcg   1620

atgattggtg gattctgcag ggctgttttc gagaatcttc cttacgagtt tgcacatgag   1680

atggatgcac ttatgaacct gaagcttgag ggatcagttg gttaattaga tggagcaaaa   1740

tgtctttgca gtacaacaca acaattattt agatgtcctt tgtacagaag tatgagaaga   1800

ataaattgca tgagcaatgg acgttttcct agccttgtct accactaggg atgtccttgg   1860

caacaaagaa aattctgtta cttatctact gttttatccc tttttgtttc tgtttcttct   1920

gttgtaaaca aacccttatt agaatgcgta gccacactag aaatgtctcc aaaaaagcta   1980

cacaagaaat ggaatctgct tttttaaaaa aaaaaaaaaa aaaaaaaaaa aaaaaaaaaa   2040

aaa                                                                 2043
```

```
<210> SEQ ID NO 172
<211> LENGTH: 574
<212> TYPE: PRT
<213> ORGANISM: Oryza sativa

<400> SEQUENCE: 172

Ala Arg Val His Thr Thr Thr His Pro Ser Cys Ala Leu His Pro Ile
  1               5                  10                  15

Arg Ile Pro Asn Phe Ala Ser Ala Ser Pro Arg Arg Arg Thr Met Ala
             20                  25                  30

Ala Ala Ala Ala Ser Ser Thr Pro Leu Phe Ser Pro Cys Cys Ala Ala
         35                  40                  45

Ala Thr Ala Lys Leu Gly Ala Ala Cys Pro Ser Ser Tyr Gly Ser Arg
     50                  55                  60

Arg Arg Pro Cys Thr Arg Arg Gly Arg Leu Ser Val Val Ala Val Gln
 65                  70                  75                  80

Thr Gly Pro Gln Lys Pro Ser Pro Ser Ser Ser Ser Gln Ala Gly Thr
                 85                  90                  95
```

-continued

```
Glu Ser Glu Thr Leu Gln Asn Leu Leu Lys Arg Glu Tyr Lys Tyr Gly
            100                 105                 110

Phe Val Ser Asp Phe Glu Ser Phe Ser Ile Pro Lys Gly Leu Ser Glu
        115                 120                 125

Ala Thr Val Arg Arg Ile Ser Glu Leu Lys Ala Glu Pro Ala Trp Met
    130                 135                 140

Leu Asp Phe Arg Leu Ala Ala Tyr Arg Arg Phe Leu Thr Met Val Gln
145                 150                 155                 160

Pro Thr Trp Ser Asp Asn Val Tyr Glu Pro Val Asp Leu Gln Ser Ile
                165                 170                 175

Cys Tyr Tyr Ser Ala Pro Lys Thr Lys Pro Lys Leu Asn Ser Leu Asp
            180                 185                 190

Glu Val Asp Pro Glu Leu Leu Asn Thr Phe Asp Arg Leu Gly Ile Pro
        195                 200                 205

Leu Ser Glu Gln Lys Arg Leu Ala Asn Val Ala Val Asp Ala Val Ile
    210                 215                 220

Asp Ser Thr Ser Ile Ala Thr Thr His Arg Glu Glu Leu Met Lys Lys
225                 230                 235                 240

Gly Val Ile Phe Cys Ser Ile Ser Glu Ala Ile Arg Glu Tyr Pro Asp
                245                 250                 255

Leu Val Lys Arg Tyr Leu Gly Ser Val Val Pro Pro Ala Asp Asn Tyr
            260                 265                 270

Tyr Ala Ala Leu Asn Ser Ala Val Phe Ser Asp Gly Ser Phe Cys Tyr
        275                 280                 285

Val Pro Lys Asp Thr Val Cys Pro Met Glu Ile Ser Thr Tyr Phe Arg
    290                 295                 300

Ile Asn Asp Lys Glu Thr Gly Gln Phe Glu Arg Thr Leu Ile Val Ala
305                 310                 315                 320

Asp Glu Arg Ser Thr Val Ser Tyr Leu Glu Gly Cys Thr Ala Pro Ala
                325                 330                 335

Tyr Asp Ser Asn Gln Leu His Ala Ala Val Val Glu Leu Val Cys Glu
            340                 345                 350

Glu Gln Ala Glu Ile Lys Tyr Ser Thr Val Gln Asn Trp Tyr Ser Gly
        355                 360                 365

Asp Glu Glu Gly Lys Gly Gly Ile Tyr Asn Phe Val Thr Lys Arg Gly
    370                 375                 380

Arg Cys Lys Gly Arg Gly Ser Lys Ile Ser Trp Thr Gln Val Glu Thr
385                 390                 395                 400

Gly Ser Ala Ile Thr Trp Lys Tyr Pro Ser Val Glu Leu Leu Gly Asp
                405                 410                 415

Asp Thr Val Gly Glu Phe Tyr Ser Val Ala Leu Thr Lys Asp Tyr Gln
            420                 425                 430

Gln Ala Asp Thr Gly Thr Lys Met Ile His Lys Gly Lys Asn Ser Arg
        435                 440                 445

Ser Arg Ile Ile Ser Lys Gly Ile Ser Ala Gly Lys Ser Arg Asn Cys
    450                 455                 460

Tyr Arg Gly Leu Val Gln Ile Asn Ser Gly Ala Glu Asn Ala Tyr Asn
465                 470                 475                 480

Ser Ser Gln Cys Asp Ser Leu Leu Ile Gly Asp Asn Ala Ala Ala Asn
                485                 490                 495

Thr Tyr Pro Thr Ile Gln Val Gly Cys Ile Ser Ser Arg Val Glu His
            500                 505                 510
```

-continued

```
Glu Ala Ser Thr Ser Lys Ile Gly Glu Asp Gln Leu Phe Tyr Phe Gln
        515                 520                 525

Gln Arg Gly Ile Asp His Glu Lys Ala Val Ala Ala Met Ile Gly Gly
    530                 535                 540

Phe Cys Arg Ala Val Phe Glu Asn Leu Pro Tyr Glu Phe Ala His Glu
545                 550                 555                 560

Met Asp Ala Leu Met Asn Leu Lys Leu Glu Gly Ser Val Gly
                565                 570


<210> SEQ ID NO 173
<211> LENGTH: 1917
<212> TYPE: DNA
<213> ORGANISM: Glycine max

<400> SEQUENCE: 173

gcacgaggtt tttttttttt tttttttttt tttttttttt tttttttttg aggtggtaca     60

aaacctcatc catggcttct cttctccgct tcaacggcgt ctccctcttt cccttacctt    120

cccaacccac acgtgacccc atcctcccca aaccgtcacg cctcgtaacg gtgcgcgcgg    180

aggtgaaaga gacctccgca cccgccgccg ccacatcctc cgacgaaaag atccgcgaaa    240

tcctccgcaa ccgtgactac gacaagaaat tcgggttcag cgtggagatc gagtccttga    300

cgatcccaaa agggctctca aaagaaacca ttggtctgat ctcgtccctg aaggaggagc    360

cccactggat gctcgaattc cgcctgaagg ccttggataa attcctctcc atgaaggaac    420

ccacgtggtc tgacaacact taccctccca tcgacctcca gaatatctgc tactactccg    480

cccccaagaa taaaccctct cttcaatccc tcgacgacgc tgaccccgag cttctccgct    540

acttcgagaa gctcggcgtc cccctcaacg agcagaagcg cctcgccaac gtcgccgtcg    600

acgccgtcct cgacagcgtc tcaatcgcca caacgcaccg caaaacccta gaaaaggccg    660

gcgttatatt ctgctccatc tccgaggcca ttaaggaata tcctgatttg gtgaaaaagt    720

atttggggaa agttgtcccg tcagacgaca actactacgc cgcgttgaac gctgcggtct    780

tcagcgacgg gtcgttttgc tacattccta aagacaccaa gtgtcctatg cagatttcga    840

cttacttcag aatcaacgcg ttggagacag gacagtttga gaggactttg attgtcgccg    900

acgatcggag ctctgtggag tatttggaag gctgcaccgc gccttcctac gatcggaacc    960

agctccatgc cgcggtggtg gagttgtatt gcggcgaggg ggcggagatt aagtactcca   1020

cggtgcagaa ttggtacgct ggggacgaag aagggaaggg tggggtttac aatttcgtga   1080

ccaagagagg gttgtgtggt ggtgcaggtt cgaagatatc gtggacgcag gtggagacgg   1140

gttcggcgat cacgtggaag tacccgagtg ttgtgctgga aggagatggt agtgttgggg   1200

agttctattc tgtggctttg acgaataact atcagcaggc ggataccggg accaagatga   1260

tacacaaagg gaagaacacg aggagtagga ttatatccaa aggaatatcg gttgggcatt   1320

ccaggaactg ttatagaggg cttgttcagg ttctgtccaa ggctgacaat gcccgaaact   1380

cgtcacagtg tgattctatg cttattggtg acaatgctgc tgcaaatacc tatccttata   1440

tccaggtgaa aaatccaacc gcaagaattg aacatgaagc tagtacatcc aaaattggag   1500

aagatcaatt gttttatttt caacaaaggg gaatagacta tgaaaaggca atggctgcta   1560

tgatctctgg attttgccgt gatgtgttta atgagcttcc tgatgaattt ggttccgaag   1620

tgaaccaact catgagcttg aagcttgagg gatcagtagg ttaaacagca tatcactatt   1680

tggaatttac tcaggccatt tgttcttgaa attgtccaag tccttagagg tagtgtattc   1740

gaaaggatgt gtacatgttg tatatagata ctgtcttcaa ctgtaccgca aaagtggcct   1800
```

```
gaaacattac cagttttgaa tcttaataaa caatcaatgt catcctataa ttttgtttgt   1860

cgatttactc ttgatttata ttcatgtatc cctataaaaa aaaaaaaaaa aaaaaaa      1917


<210> SEQ ID NO 174
<211> LENGTH: 530
<212> TYPE: PRT
<213> ORGANISM: Glycine max

<400> SEQUENCE: 174

Met Ala Ser Leu Leu Arg Phe Asn Gly Val Ser Leu Phe Pro Leu Pro
  1               5                  10                  15

Ser Gln Pro Thr Arg Asp Pro Ile Leu Pro Lys Pro Ser Arg Leu Val
             20                  25                  30

Thr Val Arg Ala Glu Val Lys Glu Thr Ser Ala Pro Ala Ala Ala Thr
         35                  40                  45

Ser Ser Asp Glu Lys Ile Arg Glu Ile Leu Arg Asn Arg Asp Tyr Asp
     50                  55                  60

Lys Lys Phe Gly Phe Ser Val Glu Ile Glu Ser Leu Thr Ile Pro Lys
 65                  70                  75                  80

Gly Leu Ser Lys Glu Thr Ile Gly Leu Ile Ser Ser Leu Lys Glu Glu
                 85                  90                  95

Pro His Trp Met Leu Glu Phe Arg Leu Lys Ala Leu Asp Lys Phe Leu
            100                 105                 110

Ser Met Lys Glu Pro Thr Trp Ser Asp Asn Thr Tyr Pro Pro Ile Asp
        115                 120                 125

Leu Gln Asn Ile Cys Tyr Tyr Ser Ala Pro Lys Asn Lys Pro Ser Leu
    130                 135                 140

Gln Ser Leu Asp Asp Ala Asp Pro Glu Leu Leu Arg Tyr Phe Glu Lys
145                 150                 155                 160

Leu Gly Val Pro Leu Asn Glu Gln Lys Arg Leu Ala Asn Val Ala Val
                165                 170                 175

Asp Ala Val Leu Asp Ser Val Ser Ile Ala Thr Thr His Arg Lys Thr
            180                 185                 190

Leu Glu Lys Ala Gly Val Ile Phe Cys Ser Ile Ser Glu Ala Ile Lys
        195                 200                 205

Glu Tyr Pro Asp Leu Val Lys Lys Tyr Leu Gly Lys Val Val Pro Ser
    210                 215                 220

Asp Asp Asn Tyr Tyr Ala Ala Leu Asn Ala Ala Val Phe Ser Asp Gly
225                 230                 235                 240

Ser Phe Cys Tyr Ile Pro Lys Asp Thr Lys Cys Pro Met Gln Ile Ser
                245                 250                 255

Thr Tyr Phe Arg Ile Asn Ala Leu Glu Thr Gly Gln Phe Glu Arg Thr
            260                 265                 270

Leu Ile Val Ala Asp Asp Arg Ser Ser Val Glu Tyr Leu Glu Gly Cys
        275                 280                 285

Thr Ala Pro Ser Tyr Asp Arg Asn Gln Leu His Ala Ala Val Val Glu
    290                 295                 300

Leu Tyr Cys Gly Glu Gly Ala Glu Ile Lys Tyr Ser Thr Val Gln Asn
305                 310                 315                 320

Trp Tyr Ala Gly Asp Glu Glu Gly Lys Gly Gly Val Tyr Asn Phe Val
                325                 330                 335

Thr Lys Arg Gly Leu Cys Gly Gly Ala Gly Ser Lys Ile Ser Trp Thr
            340                 345                 350
```

-continued

```
Gln Val Glu Thr Gly Ser Ala Ile Thr Trp Lys Tyr Pro Ser Val Val
        355                 360                 365

Leu Glu Gly Asp Gly Ser Val Gly Glu Phe Tyr Ser Val Ala Leu Thr
    370                 375                 380

Asn Asn Tyr Gln Gln Ala Asp Thr Gly Thr Lys Met Ile His Lys Gly
385                 390                 395                 400

Lys Asn Thr Arg Ser Arg Ile Ile Ser Lys Gly Ile Ser Val Gly His
                405                 410                 415

Ser Arg Asn Cys Tyr Arg Gly Leu Val Gln Val Leu Ser Lys Ala Asp
            420                 425                 430

Asn Ala Arg Asn Ser Ser Gln Cys Asp Ser Met Leu Ile Gly Asp Asn
        435                 440                 445

Ala Ala Ala Asn Thr Tyr Pro Tyr Ile Gln Val Lys Asn Pro Thr Ala
    450                 455                 460

Arg Ile Glu His Glu Ala Ser Thr Ser Lys Ile Gly Glu Asp Gln Leu
465                 470                 475                 480

Phe Tyr Phe Gln Gln Arg Gly Ile Asp Tyr Glu Lys Ala Met Ala Ala
                485                 490                 495

Met Ile Ser Gly Phe Cys Arg Asp Val Phe Asn Glu Leu Pro Asp Glu
            500                 505                 510

Phe Gly Ser Glu Val Asn Gln Leu Met Ser Leu Lys Leu Glu Gly Ser
        515                 520                 525

Val Gly
    530
```

<210> SEQ ID NO 175
<211> LENGTH: 1919
<212> TYPE: DNA
<213> ORGANISM: Triticum aestivum

<400> SEQUENCE: 175

```
ttcgcctccg cctccgcctc gccggccgcg accgaccatg gcggcctccg cctccgcctc     60

cacgtccctc ttcgggccct gcgccctcac cgccaggctc ggggcggggc ggccgtccgg    120

ggggccacgc cggcgcgtcg acgcgcgcgg ccgcggccgc ctctcggtgg tggccgtgca    180

gacgggcccg cagaagccgt cgccgtcgcc ctcgccctcg tccccggcgg cggacgaggc    240

cgaggcgctg cagaacctgc tcaagcggga gtacaagtac ggcttcgtct ccgacttcga    300

gtccttctcc atccccaagg gcctctccga ggccaccgtc cgccgcatct cggagctcaa    360

ggcggagccg gcctggatgc tcgacttccg cctcgccgcc taccgccgct tcctcaccat    420

ggcggagccc acctggagcg acaacgtcta ctcgcccgtc gacctccagt ccctctgctt    480

ctactccgcg cccaagacca agcccaagct caacagcctc gacgaggtcg accccgagct    540

gctcaagacc ttcgaccgcc tcgggatccc tctcggcgag cagaagcgcc tctccaacgt    600

cgccgtcgac gccgtcatcg actccacctc catcgccacc acccaccggg aggcgctcat    660

ggccaagggc gtcatatttt gctccatctc cgaggccatc cgtgagtacc cggacctcat    720

caagcgctac atcgggagca tcgtgccgcc cggtgacaat tactatgccg cgctcaattc    780

agccgtgttc agtgacggat ccttctgcta cgtgcccaag gatacggtct gccccatgga    840

gatatcaacc tacttcagaa tcaacgacaa ggagaccggg cagtttgaga ggactctgat    900

tgtggctgat gagaggagca cggttagcta tttagaaggt tgtacagctc cagcatatga    960

ctccaaccag ctccacgccg cggtggtgga gcttgtgtgc gaagaagggg ccgagattaa   1020

gtactccacc gtgcagaatt ggtatgctgg cgatgaggag ggcaaagggg gcatttacaa   1080
```

-continued

```
ttttgtggcc aagagggggc ggtgcaaggg gcgtggctcg aaaatctcat ggacacaggt   1140

tgagacaggg tcagcaatca cctggaagta cccaagtgtg gagcttgttg gggacgacac   1200

tgttggagag ttctactccg tagcactgcc caaggattac cagcaggccg atacagggac   1260

aaagatgatc cataaggggga agaattcacg cagccggatt atatccaaag gtatctcggc   1320

aggaaagtca aggaattgct accgtgggct ggtccagatg aattcaggtg cagagaatgc   1380

ttataattct tcgcagtgtg attcattgct gattggggac aacgctgccg ccaacaccta   1440

tccgaccatt caggtgggtt gcactagtgg ccgtgttgag catgaggcaa gcacatccaa   1500

aattggcgag gatcagctat tctactttca gcaaagaggg attgatcatg aaaaggccgt   1560

tgcagccatg ataggtgggt tctgtagagc cgtctttgaa caccttcctt acgagtttgc   1620

ccaggaggtg gatgcactaa tgaacctgaa gctggaggga tcagttggct aagttattgg   1680

ttcaacaagt ctgcgaaata tcacccgata attatctgaa ataccatacg atggttatct   1740

aaggaagtcc atgtgaccat gtacagcagc agtatgagac tgagaagaat aagttacatg   1800

ataaaaggac gtttcatggc ttgtataatc gtccacgaca gcgaagagaa ccgcggcgct   1860

tctcttttgt tgtccatttt aaaaaaaaaa aaaaaaaaaa aaaaaaaaaa aaaaaaaaa    1919


<210> SEQ ID NO 176
<211> LENGTH: 544
<212> TYPE: PRT
<213> ORGANISM: Triticum aestivum

<400> SEQUENCE: 176

Met Ala Ala Ser Ala Ser Ala Ser Thr Ser Leu Phe Gly Pro Cys Ala
  1               5                  10                  15

Leu Thr Ala Arg Leu Gly Ala Gly Arg Pro Ser Gly Gly Pro Arg Arg
             20                  25                  30

Arg Val Asp Ala Arg Gly Arg Gly Arg Leu Ser Val Val Ala Val Gln
         35                  40                  45

Thr Gly Pro Gln Lys Pro Ser Pro Ser Pro Ser Pro Ser Ser Pro Ala
     50                  55                  60

Ala Asp Glu Ala Glu Ala Leu Gln Asn Leu Leu Lys Arg Glu Tyr Lys
 65                  70                  75                  80

Tyr Gly Phe Val Ser Asp Phe Glu Ser Phe Ser Ile Pro Lys Gly Leu
                 85                  90                  95

Ser Glu Ala Thr Val Arg Arg Ile Ser Glu Leu Lys Ala Glu Pro Ala
            100                 105                 110

Trp Met Leu Asp Phe Arg Leu Ala Ala Tyr Arg Arg Phe Leu Thr Met
        115                 120                 125

Ala Glu Pro Thr Trp Ser Asp Asn Val Tyr Ser Pro Val Asp Leu Gln
    130                 135                 140

Ser Leu Cys Phe Tyr Ser Ala Pro Lys Thr Lys Pro Lys Leu Asn Ser
145                 150                 155                 160

Leu Asp Glu Val Asp Pro Glu Leu Leu Lys Thr Phe Asp Arg Leu Gly
                165                 170                 175

Ile Pro Leu Gly Glu Gln Lys Arg Leu Ser Asn Val Ala Val Asp Ala
            180                 185                 190

Val Ile Asp Ser Thr Ser Ile Ala Thr Thr His Arg Glu Ala Leu Met
        195                 200                 205

Ala Lys Gly Val Ile Phe Cys Ser Ile Ser Glu Ala Ile Arg Glu Tyr
    210                 215                 220
```

-continued

```
Pro Asp Leu Ile Lys Arg Tyr Ile Gly Ser Ile Val Pro Pro Gly Asp
225                 230                 235                 240

Asn Tyr Tyr Ala Ala Leu Asn Ser Ala Val Phe Ser Asp Gly Ser Phe
                245                 250                 255

Cys Tyr Val Pro Lys Asp Thr Val Cys Pro Met Glu Ile Ser Thr Tyr
            260                 265                 270

Phe Arg Ile Asn Asp Lys Glu Thr Gly Gln Phe Glu Arg Thr Leu Ile
        275                 280                 285

Val Ala Asp Glu Arg Ser Thr Val Ser Tyr Leu Glu Gly Cys Thr Ala
    290                 295                 300

Pro Ala Tyr Asp Ser Asn Gln Leu His Ala Ala Val Val Glu Leu Val
305                 310                 315                 320

Cys Glu Glu Gly Ala Glu Ile Lys Tyr Ser Thr Val Gln Asn Trp Tyr
                325                 330                 335

Ala Gly Asp Glu Glu Gly Lys Gly Gly Ile Tyr Asn Phe Val Ala Lys
            340                 345                 350

Arg Gly Arg Cys Lys Gly Arg Gly Ser Lys Ile Ser Trp Thr Gln Val
        355                 360                 365

Glu Thr Gly Ser Ala Ile Thr Trp Lys Tyr Pro Ser Val Glu Leu Val
    370                 375                 380

Gly Asp Asp Thr Val Gly Glu Phe Tyr Ser Val Ala Leu Pro Lys Asp
385                 390                 395                 400

Tyr Gln Gln Ala Asp Thr Gly Thr Lys Met Ile His Lys Gly Lys Asn
                405                 410                 415

Ser Arg Ser Arg Ile Ile Ser Lys Gly Ile Ser Ala Gly Lys Ser Arg
            420                 425                 430

Asn Cys Tyr Arg Gly Leu Val Gln Met Asn Ser Gly Ala Glu Asn Ala
        435                 440                 445

Tyr Asn Ser Ser Gln Cys Asp Ser Leu Leu Ile Gly Asp Asn Ala Ala
    450                 455                 460

Ala Asn Thr Tyr Pro Thr Ile Gln Val Gly Cys Thr Ser Gly Arg Val
465                 470                 475                 480

Glu His Glu Ala Ser Thr Ser Lys Ile Gly Glu Asp Gln Leu Phe Tyr
                485                 490                 495

Phe Gln Gln Arg Gly Ile Asp His Glu Lys Ala Val Ala Ala Met Ile
            500                 505                 510

Gly Gly Phe Cys Arg Ala Val Phe Glu His Leu Pro Tyr Glu Phe Ala
        515                 520                 525

Gln Glu Val Asp Ala Leu Met Asn Leu Lys Leu Glu Gly Ser Val Gly
    530                 535                 540
```

<210> SEQ ID NO 177
<211> LENGTH: 1314
<212> TYPE: DNA
<213> ORGANISM: Zea mays

<400> SEQUENCE: 177

```
ggagaccgag ctttgacttc aactcaagga gagttggcac atgctctgag gttcttggca     60

tctgtggtgt cacaaagctt catagcgttt ggtgatattc ttgagttaca caagaagttc    120

cttgaactct ctggtggtat taacaggata tttgagcttg aggagcttct acaggcatca    180

caaagcaatc ctgtcatgcc ttctgatgcc acaaatgccg gttccgaaga aataatttcc    240

ttccgtggcg tgaacattgt gacaccatcg caaaagctat tggctagcca actgtcttgt    300

gatgtatctc aagggaaaag ccttcttgtg actggtccaa atggtagcgg aaagagttcc    360
```

-continued

```
atctttaggg tgcttcgagg cttgtggccc attgcttctg gtagtcttag caagccatct    420
gaaggaattt ttaatgttcc tcaacgtcca tatacttgtc ttggaacctt gagggatcag    480
atcatatacc ctctctctca cgaggaggca aagttgaaga tgctctcagg cgaaacaagt    540
gacaagtcta cagcttccga gctgttggat gatcacctga ggacgattct agagaatgtt    600
cgcttgctgt atcttctgga gagagaaggt tgggatgcta ccactaactg ggaagatact    660
ctatccttgg gagagcagca gaggctgggg atggctcgtc tgttctttca ctgtcccaag    720
tatggcatcc tcgacgagtg caccaatgcc acaagcgtgg acgttgagga gcatctgtac    780
aggctagcaa ccaacatggg cataacagtc atcacatcct cacaaaggcc tgctctgatt    840
cccttccatt cgttggaact gaaactcatt gacggcgaag gaaagtggga gctatgttcc    900
atccaccaat aaccgattga catcaaccag tttatttatg ttcatcggag tagggtattt    960
acaagttgca acgcacagag aaaaaaaaaa ctcgtccact cgggtgtaga gtgtgtgacg   1020
gagtcttttt tttttttggg tttccctttt ctttttctct cccctttgat ggaaatcttg   1080
cgatacggaa agggagggag gaaggaaata tacggcagga aaggaaagta ttaggagagg   1140
ttatagatgc aggcttcgtc atttgggata gcatagtaca tgttcctggc atgatatgcc   1200
agcctgattg atttttatac gagatacaga ataagttaaa ataaaaatgg atatggcaca   1260
aagtgtgccc ttgtaaatta aatgggaaac taatctatag gaaattcatc caaa         1314
```

```
<210> SEQ ID NO 178
<211> LENGTH: 303
<212> TYPE: PRT
<213> ORGANISM: Zea mays

<400> SEQUENCE: 178

Gly Asp Arg Ala Leu Thr Ser Thr Gln Gly Glu Leu Ala His Ala Leu
  1               5                  10                  15

Arg Phe Leu Ala Ser Val Val Ser Gln Ser Phe Ile Ala Phe Gly Asp
             20                  25                  30

Ile Leu Glu Leu His Lys Lys Phe Leu Glu Leu Ser Gly Gly Ile Asn
         35                  40                  45

Arg Ile Phe Glu Leu Glu Glu Leu Leu Gln Ala Ser Gln Ser Asn Pro
     50                  55                  60

Val Met Pro Ser Asp Ala Thr Asn Ala Gly Ser Glu Glu Ile Ile Ser
 65                  70                  75                  80

Phe Arg Gly Val Asn Ile Val Thr Pro Ser Gln Lys Leu Leu Ala Ser
                 85                  90                  95

Gln Leu Ser Cys Asp Val Ser Gln Gly Lys Ser Leu Leu Val Thr Gly
            100                 105                 110

Pro Asn Gly Ser Gly Lys Ser Ser Ile Phe Arg Val Leu Arg Gly Leu
        115                 120                 125

Trp Pro Ile Ala Ser Gly Ser Leu Ser Lys Pro Ser Glu Gly Ile Phe
    130                 135                 140

Asn Val Pro Gln Arg Pro Tyr Thr Cys Leu Gly Thr Leu Arg Asp Gln
145                 150                 155                 160

Ile Ile Tyr Pro Leu Ser His Glu Glu Ala Lys Leu Lys Met Leu Ser
                165                 170                 175

Gly Glu Thr Ser Asp Lys Ser Thr Ala Ser Glu Leu Leu Asp Asp His
            180                 185                 190

Leu Arg Thr Ile Leu Glu Asn Val Arg Leu Leu Tyr Leu Leu Glu Arg
        195                 200                 205
```

-continued

```
Glu Gly Trp Asp Ala Thr Thr Asn Trp Glu Asp Thr Leu Ser Leu Gly
    210                 215                 220

Glu Gln Gln Arg Leu Gly Met Ala Arg Leu Phe Phe His Cys Pro Lys
225                 230                 235                 240

Tyr Gly Ile Leu Asp Glu Cys Thr Asn Ala Thr Ser Val Asp Val Glu
                245                 250                 255

Glu His Leu Tyr Arg Leu Ala Thr Asn Met Gly Ile Thr Val Ile Thr
            260                 265                 270

Ser Ser Gln Arg Pro Ala Leu Ile Pro Phe His Ser Leu Glu Leu Lys
        275                 280                 285

Leu Ile Asp Gly Glu Gly Lys Trp Glu Leu Cys Ser Ile His Gln
    290                 295                 300


<210> SEQ ID NO 179
<211> LENGTH: 1126
<212> TYPE: DNA
<213> ORGANISM: Oryza sativa

<400> SEQUENCE: 179

gcacgagctt acacaaacat caaattcagg tcctgatgag ccatccaaca tacagtcaaa      60

cggtgaagaa ctgctacaaa gttcaaagca gagaagggat aatggtatat tctttgttcc     120

acagagacca tatatggttt tgggaaccct tcgtcagcaa ttgctctatc ctacatggac     180

tgaagatgtt tgtcattcat caaataatga tcctcaaagt acagaccctc ttacctttga     240

agtctccaca tcagatggag ttggttccaa gtctgagatg cccacaactg atgaactgat     300

cagagtactt gaggctgtta agttaggcta tatattgcct cgtttcaatg gtttggattc     360

tatgcatgat tgggccagcg ttctctctct gggggagcaa cagcgtcttg catttgctcg     420

gttgttactt gcaaaaccaa ctttagtcct ccttgatgag tccacaagtg cactagatga     480

tatgaatgag cgtcatctat acagtcagat tgaagctgca gggattactt acataagcat     540

tggtcaccgg aaaacactgc acaagttcca caacaaggtc ttgtacattt caaattccga     600

ttcaacggat agcaacccac gtaattggta cctaaagccc acagaacaga tgtcgattga     660

agagtcatcc tcatttgctt cataagaatt tcatgatttg agcaacattt gcccctgagc     720

agttttgtcg caagatttca cccatacgtg aagtgtatgg tgcccagcca agtacccaaa     780

atatgtcatg ctgattgttc taaagatgtg atgcttgagt agttgagttg tatgaccaaa     840

attgctagta tgctacaaac caactcgagg cgtggcacag attttagcac ctaaaggttg     900

aaagggaagc tcatctgttc ttggatcgtt ataccacgaa gttcagaatg aacatcatat     960

gtagatatgc agtcctctga tctttttgag tttcttttag aaatgacgac ggaatatctg    1020

aaactgtctc tttgttatta cgtgtgtggt gtgtccttgt aactatactg ggaattacag    1080

ctcttatata catgcagtgt gtgcaaaaaa aaaaaaaaaa aaaaaa                   1126


<210> SEQ ID NO 180
<211> LENGTH: 227
<212> TYPE: PRT
<213> ORGANISM: Oryza sativa

<400> SEQUENCE: 180

His Glu Leu Thr Gln Thr Ser Asn Ser Gly Pro Asp Glu Pro Ser Asn
  1               5                  10                  15

Ile Gln Ser Asn Gly Glu Glu Leu Leu Gln Ser Ser Lys Gln Arg Arg
             20                  25                  30
```

-continued

```
Asp Asn Gly Ile Phe Phe Val Pro Gln Arg Pro Tyr Met Val Leu Gly
        35                  40                  45

Thr Leu Arg Gln Gln Leu Leu Tyr Pro Thr Trp Thr Glu Asp Val Cys
    50                  55                  60

His Ser Ser Asn Asn Asp Pro Gln Ser Thr Asp Pro Leu Thr Phe Glu
65                  70                  75                  80

Val Ser Thr Ser Asp Gly Val Gly Ser Lys Ser Glu Met Pro Thr Thr
                85                  90                  95

Asp Glu Leu Ile Arg Val Leu Glu Ala Val Lys Leu Gly Tyr Ile Leu
            100                 105                 110

Pro Arg Phe Asn Gly Leu Asp Ser Met His Asp Trp Ala Ser Val Leu
        115                 120                 125

Ser Leu Gly Glu Gln Gln Arg Leu Ala Phe Ala Arg Leu Leu Leu Ala
    130                 135                 140

Lys Pro Thr Leu Val Leu Leu Asp Glu Ser Thr Ser Ala Leu Asp Asp
145                 150                 155                 160

Met Asn Glu Arg His Leu Tyr Ser Gln Ile Glu Ala Ala Gly Ile Thr
                165                 170                 175

Tyr Ile Ser Ile Gly His Arg Lys Thr Leu His Lys Phe His Asn Lys
            180                 185                 190

Val Leu Tyr Ile Ser Asn Ser Asp Ser Thr Asp Ser Asn Pro Arg Asn
        195                 200                 205

Trp Tyr Leu Lys Pro Thr Glu Gln Met Ser Ile Glu Glu Ser Ser Ser
    210                 215                 220

Phe Ala Ser
225
```

<210> SEQ ID NO 181
<211> LENGTH: 1118
<212> TYPE: DNA
<213> ORGANISM: Glycine max

<400> SEQUENCE: 181

```
tgacatgtga cattgagctt ggtaaaagcc tgcttgttac tggtccaaat ggaagtggaa      60

aaagttccat tttccgagtt cttagaggac tttggccaat tgcaagtgga agactctcta     120

gaccatctga ggatgtggat caagaggctg gatcaggttg tggcatcttc tatgttcctc     180

agcggcctta cacatgcttg ggaacattgc gggatcaaat tatataccca ttgtctcgtg     240

aagaggcaca gtttcgagca ctgaagatgc atggaaaagg tgaaaaacat cctgacccta     300

gaaaaatgtt ggacacacac ttgcaagtta tcctagagaa tgttcggttg aattatcttc     360

tagaaagaga caacaatggc tgggatgcaa atctaaactg ggaagacatt ctctctcttg     420

gagaacagca gagattaggc atggcacgct tgttcttcca taagcctaaa tttggtatcc     480

tggacgagtg taccaatgcc actagcgttg atgttgaaga acacctatat gggctagcga     540

acaaaatggg gatcactgtt gttacttcct cacaacgtcc tgctttaata ccatttcatt     600

ccatggaatt gcgtctgatt gatggtgagg gtaattggga acttcgttcg atcaagcaat     660

gactttcgca cctgcagatt ctcattgtta ctatttgaga tgttgctgag tcttcgaaca     720

tacagaatga ttgcaagcag atattaggct tgccatgatg gtcattcctt tatatttttt     780

tttcttcttt tttctttttt cattttgggt ttaccatatt ctccaagctt gctccgtcga     840

cttgtgggga caaacaaaca aaaacagcat cgatagccaa aatgattgat agtaagttgg     900

agtgcacaac cttttcatga tctctgcagt atataatcaa ttatgtacag ggttttcgct     960
```

-continued

```
tctattatta gttacttaga tatttattca cattttgtaa caattggatg taattattaa   1020

tgttatttta tcaataaaac ggcacgaaac aggagtagct tttagagatt aaaaaaaaaa   1080

aaaaaaaaaa aaaaaaaaaa aaaaaaaaaa aaaaaaa                            1118


<210> SEQ ID NO 182
<211> LENGTH: 219
<212> TYPE: PRT
<213> ORGANISM: Glycine max

<400> SEQUENCE: 182

Thr Cys Asp Ile Glu Leu Gly Lys Ser Leu Leu Val Thr Gly Pro Asn
  1               5                  10                  15

Gly Ser Gly Lys Ser Ser Ile Phe Arg Val Leu Arg Gly Leu Trp Pro
             20                  25                  30

Ile Ala Ser Gly Arg Leu Ser Arg Pro Ser Glu Asp Val Asp Gln Glu
         35                  40                  45

Ala Gly Ser Gly Cys Gly Ile Phe Tyr Val Pro Gln Arg Pro Tyr Thr
     50                  55                  60

Cys Leu Gly Thr Leu Arg Asp Gln Ile Ile Tyr Pro Leu Ser Arg Glu
 65                  70                  75                  80

Glu Ala Gln Phe Arg Ala Leu Lys Met His Gly Lys Gly Glu Lys His
                 85                  90                  95

Pro Asp Pro Arg Lys Met Leu Asp Thr His Leu Gln Val Ile Leu Glu
            100                 105                 110

Asn Val Arg Leu Asn Tyr Leu Leu Glu Arg Asp Asn Asn Gly Trp Asp
        115                 120                 125

Ala Asn Leu Asn Trp Glu Asp Ile Leu Ser Leu Gly Glu Gln Gln Arg
    130                 135                 140

Leu Gly Met Ala Arg Leu Phe Phe His Lys Pro Lys Phe Gly Ile Leu
145                 150                 155                 160

Asp Glu Cys Thr Asn Ala Thr Ser Val Asp Val Glu Glu His Leu Tyr
                165                 170                 175

Gly Leu Ala Asn Lys Met Gly Ile Thr Val Val Thr Ser Ser Gln Arg
            180                 185                 190

Pro Ala Leu Ile Pro Phe His Ser Met Glu Leu Arg Leu Ile Asp Gly
        195                 200                 205

Glu Gly Asn Trp Glu Leu Arg Ser Ile Lys Gln
    210                 215


<210> SEQ ID NO 183
<211> LENGTH: 788
<212> TYPE: DNA
<213> ORGANISM: Triticum aestivum

<400> SEQUENCE: 183

gcacgaggcc aagcctgaga tgccctcaac tgatgaactg atcagagtac ttgaggttgt     60

taggctgggc tacatattac cacgtttcaa tggcatggat tctgtccatg attgggctag    120

tgttctttcc ctaggggagc aacagcgtct tgcatttgct cggttgttac tcgcaaaacc    180

aactctggtc ctactggacg agtccacaag tgcactagat gatacaaatg aggttcatct    240

atacagtcag attgaagctg cagggattac atatataagt gtcggtcacc ggaagacact    300

tcacaggttc cacaacaagg ttttgtacat ttcaaagtcc gattcggcaa ctggcagcct    360

tcgtaattgg gagttaaagc ccacagacca gaaatcaatt gaagaatcat ccccatttgc    420

ttcataagaa cttcatgcga accagtttag gccccttcct caatattctt atcccacatt    480
```

-continued

```
taacccatta tggtaaatat tgttgcccta ccaaggatcc catctccacg agttcaacgt    540

tacaacttac aaactggagc tggactgttg gcgaggttga tcttacagct ggactgacaa    600

aattgtggca gtgctactaa ccaacctgat agcaggatac gttctaggac ttggaataat    660

ctcacctttt tgtttatgtt tatgcttcat tgtttagaat gaaatataac atatgtttat    720

gtacggttga tattgcgcgc tgttaccaac attttaattt ttattatctg aaaaaaaaaa    780

aaaaaaaa                                                             788
```

<210> SEQ ID NO 184
<211> LENGTH: 141
<212> TYPE: PRT
<213> ORGANISM: Triticum aestivum

<400> SEQUENCE: 184

```
His Glu Ala Lys Pro Glu Met Pro Ser Thr Asp Glu Leu Ile Arg Val
  1               5                  10                  15

Leu Glu Val Val Arg Leu Gly Tyr Ile Leu Pro Arg Phe Asn Gly Met
             20                  25                  30

Asp Ser Val His Asp Trp Ala Ser Val Leu Ser Leu Gly Glu Gln Gln
         35                  40                  45

Arg Leu Ala Phe Ala Arg Leu Leu Leu Ala Lys Pro Thr Leu Val Leu
     50                  55                  60

Leu Asp Glu Ser Thr Ser Ala Leu Asp Asp Thr Asn Glu Val His Leu
 65                  70                  75                  80

Tyr Ser Gln Ile Glu Ala Ala Gly Ile Thr Tyr Ile Ser Val Gly His
                 85                  90                  95

Arg Lys Thr Leu His Arg Phe His Asn Lys Val Leu Tyr Ile Ser Lys
            100                 105                 110

Ser Asp Ser Ala Thr Gly Ser Leu Arg Asn Trp Glu Leu Lys Pro Thr
        115                 120                 125

Asp Gln Lys Ser Ile Glu Glu Ser Ser Pro Phe Ala Ser
    130                 135                 140
```

<210> SEQ ID NO 185
<211> LENGTH: 705
<212> TYPE: DNA
<213> ORGANISM: Zea mays

<400> SEQUENCE: 185

```
gcacgagaaa cggggataac tggagcgtgg gacagcgcca acttattgca ctgggtaggg     60

cgctgctcaa gcaggcaaaa attttggtac tcgatgaggc gacagcatct gtcgacacag    120

caacagacaa tcttatccaa aagatcatcc gcagtgaatt caaggactgc acagtctgta    180

ccattgctca ccgtattccc accgttattg acagtgacct tgttctggtc cttagtgatg    240

gtaaaatcgc agagttcgac acgccccaga ggcttttaga ggacaagtca tctatgttca    300

tacagctagt atcggaatac tccactcggt cgagctgtat atagagaggc ttagcttaaa    360

accccgcccc aaacctggca acagaggctg ggaggcaaat agcccgtatc tgccatgctt    420

gcgccataga ggtccctgcg aacaccggag ggcggcgtag aagacgaggt gtacatgagt    480

gggaggaaca ctgggcgttc cctgacctga ataccgtgga atcggcgagg gagcgcggtt    540

ggtattggta ggcaccaggg gaggagttgg tgacactagt acattacccg aagctgatgc    600

ttcagtatgt atgtataaca acaatgcata ctgcttctcc ctttgcagag tggagaacca    660

agggaataac tcgtgcgtaa taagaggaga aatatttgtt ttttg                    705
```

<210> SEQ ID NO 186
<211> LENGTH: 113
<212> TYPE: PRT
<213> ORGANISM: Zea mays

<400> SEQUENCE: 186

Thr Arg Asn Gly Asp Asn Trp Ser Val Gly Gln Arg Gln Leu Ile Ala
1 5 10 15

Leu Gly Arg Ala Leu Leu Lys Gln Ala Lys Ile Leu Val Leu Asp Glu
20 25 30

Ala Thr Ala Ser Val Asp Thr Ala Thr Asp Asn Leu Ile Gln Lys Ile
35 40 45

Ile Arg Ser Glu Phe Lys Asp Cys Thr Val Cys Thr Ile Ala His Arg
50 55 60

Ile Pro Thr Val Ile Asp Ser Asp Leu Val Leu Val Leu Ser Asp Gly
65 70 75 80

Lys Ile Ala Glu Phe Asp Thr Pro Gln Arg Leu Leu Glu Asp Lys Ser
85 90 95

Ser Met Phe Ile Gln Leu Val Ser Glu Tyr Ser Thr Arg Ser Ser Cys
100 105 110

Ile

<210> SEQ ID NO 187
<211> LENGTH: 845
<212> TYPE: DNA
<213> ORGANISM: Zea mays

<400> SEQUENCE: 187
gcacgagtcg aactggagca tgggtcaaag gcagcttttt tgtttgggac gtgcacttct 60
aagaagatgc cgtatcttag ttcttgatga ggccacggca tctatagaca acgctactga 120
tgctatcctt cagaagacga tcaggacaga gtttagagat tgcactgtca tcactgtcgc 180
acaccgtata cccaccgtta tggactgcga tatggtactt gcaatgagtg acgggaaagt 240
agtggagtac gacaagccta caaagctcgt ggaaaccgaa ggatctctcg tccgtgatct 300
tgtcaaggag tactggtcat acacatcgaa ttgaaatatc taggagaaac tgtgacaatc 360
acatgtccac tcgttgcagt ctattaaaaa agagataaca ggagcctgtt ctcacacaca 420
tccgatgaac tattctatct caagtccgaa gtagaggtgt caggcattgt cgggaagtgc 480
ttttgttaac tagttgaaca gggggaaacc tgtcgtccct taaaaaaagg aaacctccag 540
cgtttttttg ctccgatatt gagcgaataa accgaaatat ctagtggaag gcgcatcaag 600
tatgcatcct tgatactgca tgttcacaga aatgcttgtg cggcaggctg ttccaaggct 660
ttaaacttta tggtgcttta cattcctaat aaaccgaatt gtgtatatga tgtttgggaa 720
aatggtgatt tttcaggttt cagctccctc tcttgctcac gtttaatgta ttatcagtgt 780
aaattcatcc gtgattggat ttaaggcaac caatttgttg gtacgtaaaa aaaaaaaaaa 840
aaaag 845

<210> SEQ ID NO 188
<211> LENGTH: 110
<212> TYPE: PRT
<213> ORGANISM: Zea mays

<400> SEQUENCE: 188

His Glu Ser Asn Trp Ser Met Gly Gln Arg Gln Leu Phe Cys Leu Gly
1 5 10 15

-continued

```
Arg Ala Leu Leu Arg Arg Cys Arg Ile Leu Val Leu Asp Glu Ala Thr
            20                  25                  30

Ala Ser Ile Asp Asn Ala Thr Asp Ala Ile Leu Gln Lys Thr Ile Arg
        35                  40                  45

Thr Glu Phe Arg Asp Cys Thr Val Ile Thr Val Ala His Arg Ile Pro
    50                  55                  60

Thr Val Met Asp Cys Asp Met Val Leu Ala Met Ser Asp Gly Lys Val
65                  70                  75                  80

Val Glu Tyr Asp Lys Pro Thr Lys Leu Val Glu Thr Glu Gly Ser Leu
                85                  90                  95

Val Arg Asp Leu Val Lys Glu Tyr Trp Ser Tyr Thr Ser Asn
            100                 105                 110


<210> SEQ ID NO 189
<211> LENGTH: 247
<212> TYPE: DNA
<213> ORGANISM: Zea mays

<400> SEQUENCE: 189

gcacgagctt cttcgacacc acgccgtccg gcaggatcct cagcagggcg tcgtcagatc      60

agacgaacgt cgatctcttc ctgccgttct tcgtctggat gagcgtatcc atgtacatca     120

ccgtgatcag tgtgctgatc gtcacgtgtc aggtggcgtg gccgtccgtc attgccataa     180

tccctctggt gatactgaac atctggtacc ggggctatta cttgtcgaca tcgagggagc     240

tgactcg                                                               247


<210> SEQ ID NO 190
<211> LENGTH: 81
<212> TYPE: PRT
<213> ORGANISM: Zea mays

<400> SEQUENCE: 190

Thr Ser Phe Phe Asp Thr Thr Pro Ser Gly Arg Ile Leu Ser Arg Ala
  1               5                  10                  15

Ser Ser Asp Gln Thr Asn Val Asp Leu Phe Leu Pro Phe Phe Val Trp
            20                  25                  30

Met Ser Val Ser Met Tyr Ile Thr Val Ile Ser Val Leu Ile Val Thr
        35                  40                  45

Cys Gln Val Ala Trp Pro Ser Val Ile Ala Ile Ile Pro Leu Val Ile
    50                  55                  60

Leu Asn Ile Trp Tyr Arg Gly Tyr Tyr Leu Ser Thr Ser Arg Glu Leu
65                  70                  75                  80

Thr


<210> SEQ ID NO 191
<211> LENGTH: 1518
<212> TYPE: DNA
<213> ORGANISM: Zea mays
<220> FEATURE:
<221> NAME/KEY: unsure
<222> LOCATION: (114)
<221> NAME/KEY: unsure
<222> LOCATION: (123)
<221> NAME/KEY: unsure
<222> LOCATION: (138)

<400> SEQUENCE: 191

acagatcaaa gcacagtgga tacaagaatt tttgacctga tgggctatct tctatttcct      60

gctattgaaa ttctaggaac agttattctg atgtcacatg ttgcatggca agtnttcata     120
```

-continued

```
gtnttaatcc ccattatnac tgcatcgctg tggtatcagc aatactacat agatgcagct    180

agagagttgc aaaggttggt tggagtttgc aggtcccccg tgcttcaaca tttttctgaa    240

tcaatggctg gctcaaatat aattagatgc tttcaaaagg aaagacaatt tatccgttat    300

attggatatt tggtggataa tttatctcga ccaagtttgt ataatgcagc cgcaatggaa    360

tggttgtgct ttcgtttgga tatgctttca tcctttgttt tttccttcac attgatactt    420

ctggtctctt caccatctgc tttaattgac ccaagtaaga ctgctggtct tgcggtcact    480

tatggactaa gcctcaatat gctacaaggg tgggctattg ctgtcctctg cagtttggaa    540

aatagaatga tatcagtgga aagaatgttg cagtatacga ctattccttc agaaccacca    600

cttacaatat cagaacgcca accaaataga cagtggccaa caaagggcga aattaagttt    660

cttaacctcc atgttcgata tgcaccgcag ctgccttttg ttctaaaagg cctgacgtgc    720

accttactcg gaggaaagaa gacaggtatt gttggtagaa caggtggtgg caaatcaacc    780

ttgattcagg cactatttcg cattgtggac ccatgtattg gccaagtgtt tatagatggc    840

actgacatct gcaccattgg actacatgac ctccggacaa gattgagcat cattccacaa    900

gatcctgtta tgtttgaggg gaccctgcga accaatattg accccttgg ggagtacagt    960

gacgagaaaa tctgggaggc attggattca tgtcatcttg gggatgaagt tagaaagaac   1020

gagcttaagc ttgactctac agtgacagaa aggggcaaaa actggagcac aggtcagcgt   1080

caacttgtgt gtctgggaag ggtgattctg aaacggagga agatcttggt tttggatgag   1140

gcaacttcat ccgtggatcc aattacagac agcttgattc aaaaaacctt aaagaacctt   1200

aaagtcttgc ttctggataa cggtgaaatt gcagagcatg acgccccagc aaaactgcta   1260

gaggacagtt catccctatt ctccaaactt gtatctgagt ataccatggg atctgataag   1320

tggcgaatgc aagaaagcag ctaaatcaat actctacaga taatacagga caaacgccct   1380

aggaagtgtg agtatctacg tgttaccaat tttatagctt aataaaaaga ttttttttta   1440

aaaaaaaaaa aaaaaaaaaa aaaaaaaaaa aaaagaaaaa aaaaagaaaa aaattaaaaa   1500

aaagaaaaaa aaaaaaaa                                                 1518
```

```
<210> SEQ ID NO 192
<211> LENGTH: 447
<212> TYPE: PRT
<213> ORGANISM: Zea mays
<220> FEATURE:
<221> NAME/KEY: UNSURE
<222> LOCATION: (46)

<400> SEQUENCE: 192

Thr Asp Gln Ser Thr Val Asp Thr Arg Ile Phe Asp Leu Met Gly Tyr
  1               5                  10                  15

Leu Leu Phe Pro Ala Ile Glu Ile Leu Gly Thr Val Ile Leu Met Ser
             20                  25                  30

His Val Ala Trp Gln Val Phe Ile Val Leu Ile Pro Ile Xaa Thr Ala
         35                  40                  45

Ser Leu Trp Tyr Gln Gln Tyr Tyr Ile Asp Ala Ala Arg Glu Leu Gln
     50                  55                  60

Arg Leu Val Gly Val Cys Arg Ser Pro Val Leu Gln His Phe Ser Glu
 65                  70                  75                  80

Ser Met Ala Gly Ser Asn Ile Ile Arg Cys Phe Gln Lys Glu Arg Gln
                 85                  90                  95

Phe Ile Arg Tyr Ile Gly Tyr Leu Val Asp Asn Leu Ser Arg Pro Ser
            100                 105                 110
```

-continued

```
Leu Tyr Asn Ala Ala Ala Met Glu Trp Leu Cys Phe Arg Leu Asp Met
        115                 120                 125

Leu Ser Ser Phe Val Phe Ser Phe Thr Leu Ile Leu Leu Val Ser Ser
    130                 135                 140

Pro Ser Ala Leu Ile Asp Pro Ser Lys Thr Ala Gly Leu Ala Val Thr
145                 150                 155                 160

Tyr Gly Leu Ser Leu Asn Met Leu Gln Gly Trp Ala Ile Ala Val Leu
                165                 170                 175

Cys Ser Leu Glu Asn Arg Met Ile Ser Val Glu Arg Met Leu Gln Tyr
            180                 185                 190

Thr Thr Ile Pro Ser Glu Pro Pro Leu Thr Ile Ser Glu Arg Gln Pro
        195                 200                 205

Asn Arg Gln Trp Pro Thr Lys Gly Glu Ile Lys Phe Leu Asn Leu His
    210                 215                 220

Val Arg Tyr Ala Pro Gln Leu Pro Phe Val Leu Lys Gly Leu Thr Cys
225                 230                 235                 240

Thr Leu Leu Gly Gly Lys Lys Thr Gly Ile Val Gly Arg Thr Gly Gly
                245                 250                 255

Gly Lys Ser Thr Leu Ile Gln Ala Leu Phe Arg Ile Val Asp Pro Cys
            260                 265                 270

Ile Gly Gln Val Phe Ile Asp Gly Thr Asp Ile Cys Thr Ile Gly Leu
        275                 280                 285

His Asp Leu Arg Thr Arg Leu Ser Ile Ile Pro Gln Asp Pro Val Met
    290                 295                 300

Phe Glu Gly Thr Leu Arg Thr Asn Ile Asp Pro Leu Gly Glu Tyr Ser
305                 310                 315                 320

Asp Glu Lys Ile Trp Glu Ala Leu Asp Ser Cys His Leu Gly Asp Glu
                325                 330                 335

Val Arg Lys Asn Glu Leu Lys Leu Asp Ser Thr Val Thr Glu Arg Gly
            340                 345                 350

Lys Asn Trp Ser Thr Gly Gln Arg Gln Leu Val Cys Leu Gly Arg Val
        355                 360                 365

Ile Leu Lys Arg Arg Lys Ile Leu Val Leu Asp Glu Ala Thr Ser Ser
    370                 375                 380

Val Asp Pro Ile Thr Asp Ser Leu Ile Gln Lys Thr Leu Lys Asn Leu
385                 390                 395                 400

Lys Val Leu Leu Leu Asp Asn Gly Glu Ile Ala Glu His Asp Ala Pro
                405                 410                 415

Ala Lys Leu Leu Glu Asp Ser Ser Ser Leu Phe Ser Lys Leu Val Ser
            420                 425                 430

Glu Tyr Thr Met Gly Ser Asp Lys Trp Arg Met Gln Glu Ser Ser
        435                 440                 445
```

<210> SEQ ID NO 193
<211> LENGTH: 2938
<212> TYPE: DNA
<213> ORGANISM: Oryza sativa

<400> SEQUENCE: 193

```
gcacgaggtt ctaacgatca aggtgtcgct ggaccgcatc ggcaagttcc tcatggagga     60

ggagttccgg gacgacgccg tcctgccatt accaatgcca agctccgaca tgatcaccat    120

ggccatcaac aatggcgtct tcagctggga gcctagcaag gccattgcaa cactgaaatc    180

catcagcatc gcagcaatgc agggcgagaa gatcgccgtc tgcggtccgg ttggcgcggg    240
```

-continued

```
gaaatcgtca ttgctctgcg caatgctcgg agaaatacca agaatgtctg gatcagtagc    300
tatgtccggc tcgatcgcct atgtcccgca gacgccatgg atccagagcg gcacggtgcg    360
cgacaacatc ctattcggga agccgatgaa caatgaggag tatgacaggg ccatcaggtg    420
ctgtgcattg gacaaggaca tggagaattt cccccatggc gacctgacgg agatcgggca    480
acgaggcctg aacatgagtg gagggcagaa gcagaggatt cagcttgcga gagccgtcta    540
caatggcgcc gacgtctacc tccttgacga tcctttcagc gccgtcgatg cgcataccgc    600
tgcgacactg ttcaatgatt gtgtcatggc agctcttgag aacaagacgg tcattcttgt    660
cacacatcaa gttgagttcc tctccaaggt tgacaagatc ctggtcatgg aaaatgggga    720
gataactcag gagggaactt acagtgagct tctgcaatcc ggcacggcat tcgaacagct    780
tgtgaatgcg cacaaggact caaaaacaat actagacacc gatgatcgcc gagaaggagc    840
aaaagaactc ggcgcgtttc agtaccaggt accactgata cagcagaaca gtgaggcaga    900
gatctcaacc ggtaacctga aatcagtcca gctgacagaa gaggagagga gggagctagg    960
agacattggg ctgaagccat acaaggatta tgtctcggta tccaagggct ggttcctcct   1020
ttccatgata ctagtcacgc agtgcgcgtt cttcggcctg caatgcctgg caacctactg   1080
gcttgcagta gcaattcaga accaacaatt cagtgctggg gttgtgattg gagtctatgc   1140
ggtgatggca actgtaagct gcttgtttgc atatgttagg agcctcattg ccgcgcattt   1200
tggactgaaa gcatcaaggg agttcttctc caggttcatg gattcggtgt ttaaggcacc   1260
catggtgttc tttgattcca ctcccacagg gagaatcatg accagggctt catcagattt   1320
gagcatctta gactttgaca tcccgtttgc aatgactttc gtgatctccg gctcgatcga   1380
aatagcaaca accatagcta tcatgatctt ggttacatgg cagcttgtac tggttgctat   1440
tcctgtcata gttgcacttc tgtacatcca gagatactac attgcctcag caagggagct   1500
ggtgaggatc aatggaacta caaaggcacc ggtcatgaac tacgcagcgg agtcgatgct   1560
gggagtgatc accataagag cctttgctga gacaaagagg tttattcaga caaatcttca   1620
gctcatcgac acagatgcga cactgttctt ctacacaaac gcagcactgg aatgggttct   1680
tttgcgcgtc gaggctctac agatcttggt tattgttgca tcatccatcc tcctcgtctt   1740
gcttccggag ggagcagttg ctccaggatt tcttggcctg tgtctctcgt atgcgttaat   1800
gctttcttca gcccaagtgt ttgtgacaag attttactca aacctggaaa actacatcat   1860
atctgtggag agaatcaaac agttcatgca tctgccagct gagcctcctg ctgttattac   1920
tgacagaagc cctcccctt catggccaac tgcaggaagg atagaattgg agaacttaag   1980
agtcaagtac ggcgaaatgc gcctacggta ttacgcggga ttacctgcac atttgcagca   2040
ggacataaga ttggagttgt tggaagaacc gggagcggga agacgactct tctgagcaca   2100
ttgttccgcc ttatcgaccc gtacagcggg agaattctca tcgatgatct tgacatttgc   2160
accatagggt tgaaagacct gaggatgaag ctcagcatca tccctcagga gccaacactt   2220
ttcagaggca gtgtaaggag caatgttgat cctctgggtc tgcacactga tgaagacatt   2280
tgggaggctt taaataagtg tcagttgaag aagacaatca gtgcccttcc tggccttctt   2340
gaatcaccag tgagcgacga cggcgagaac tggagcgccg gacaacggca gctcttctgc   2400
ctggcccggg tcctcctccg caggaacaag atcctggtcc tcgacgaggc gacggcgtcc   2460
atcgactcgg ccaccgacgc cgtcctgcag agagtcatca agcaggagtt ctcagggtgc   2520
actgtgatca ccatagctca cagggttccc actgtcactg acagtgacat ggtcatggtt   2580
ctttcatacg ggaaactcat agagtatgat aggccatcaa ggctgatgga gaatgaggac   2640
```

-continued

```
tctcccttct gtaagcttgt agctgagtac tggtccaact atagctgaat ctgccaagaa   2700

aaacggtcag gaacatcaaa tgcagaagac cttcactgct ttattcttca gtgaataagt   2760

ggaactggaa actgggacat tgcattgttg gccaatgatc atccagatgg acatatatga   2820

tgcactaatg atctggaaag tatgtatgag gggagctcat tcaaaaccag gggttcatgc   2880

aatgaaattg caagccttct cccaaaaaaa aaaaaaaaaa aaaaaaaaaa aaaaaaa      2938


<210> SEQ ID NO 194
<211> LENGTH: 895
<212> TYPE: PRT
<213> ORGANISM: Oryza sativa
<220> FEATURE:
<221> NAME/KEY: UNSURE
<222> LOCATION: (666)

<400> SEQUENCE: 194

His Glu Val Leu Thr Ile Lys Val Ser Leu Asp Arg Ile Gly Lys Phe
  1               5                  10                  15

Leu Met Glu Glu Glu Phe Arg Asp Asp Ala Val Leu Pro Leu Pro Met
             20                  25                  30

Pro Ser Ser Asp Met Ile Thr Met Ala Ile Asn Asn Gly Val Phe Ser
         35                  40                  45

Trp Glu Pro Ser Lys Ala Ile Ala Thr Leu Lys Ser Ile Ser Ile Ala
     50                  55                  60

Ala Met Gln Gly Glu Lys Ile Ala Val Cys Gly Pro Val Gly Ala Gly
 65                  70                  75                  80

Lys Ser Ser Leu Leu Cys Ala Met Leu Gly Glu Ile Pro Arg Met Ser
                 85                  90                  95

Gly Ser Val Ala Met Ser Gly Ser Ile Ala Tyr Val Pro Gln Thr Pro
            100                 105                 110

Trp Ile Gln Ser Gly Thr Val Arg Asp Asn Ile Leu Phe Gly Lys Pro
        115                 120                 125

Met Asn Asn Glu Glu Tyr Asp Arg Ala Ile Arg Cys Cys Ala Leu Asp
    130                 135                 140

Lys Asp Met Glu Asn Phe Pro His Gly Asp Leu Thr Glu Ile Gly Gln
145                 150                 155                 160

Arg Gly Leu Asn Met Ser Gly Gly Gln Lys Gln Arg Ile Gln Leu Ala
                165                 170                 175

Arg Ala Val Tyr Asn Gly Ala Asp Val Tyr Leu Leu Asp Asp Pro Phe
            180                 185                 190

Ser Ala Val Asp Ala His Thr Ala Ala Thr Leu Phe Asn Asp Cys Val
        195                 200                 205

Met Ala Ala Leu Glu Asn Lys Thr Val Ile Leu Val Thr His Gln Val
    210                 215                 220

Glu Phe Leu Ser Lys Val Asp Lys Ile Leu Val Met Glu Asn Gly Glu
225                 230                 235                 240

Ile Thr Gln Glu Gly Thr Tyr Ser Glu Leu Leu Gln Ser Gly Thr Ala
                245                 250                 255

Phe Glu Gln Leu Val Asn Ala His Lys Asp Ser Lys Thr Ile Leu Asp
            260                 265                 270

Thr Asp Asp Arg Arg Glu Gly Ala Lys Glu Leu Gly Ala Phe Gln Tyr
        275                 280                 285

Gln Val Pro Leu Ile Gln Gln Asn Ser Glu Ala Glu Ile Ser Thr Gly
    290                 295                 300
```

-continued

```
Asn Leu Lys Ser Val Gln Leu Thr Glu Glu Glu Arg Arg Glu Leu Gly
305                 310                 315                 320

Asp Ile Gly Leu Lys Pro Tyr Lys Asp Tyr Val Ser Val Ser Lys Gly
                325                 330                 335

Trp Phe Leu Leu Ser Met Ile Leu Val Thr Gln Cys Ala Phe Phe Gly
            340                 345                 350

Leu Gln Cys Leu Ala Thr Tyr Trp Leu Ala Val Ala Ile Gln Asn Gln
        355                 360                 365

Gln Phe Ser Ala Gly Val Val Ile Gly Val Tyr Ala Val Met Ala Thr
    370                 375                 380

Val Ser Cys Leu Phe Ala Tyr Val Arg Ser Leu Ile Ala Ala His Phe
385                 390                 395                 400

Gly Leu Lys Ala Ser Arg Glu Phe Phe Ser Arg Phe Met Asp Ser Val
                405                 410                 415

Phe Lys Ala Pro Met Val Phe Phe Asp Ser Thr Pro Thr Gly Arg Ile
            420                 425                 430

Met Thr Arg Ala Ser Ser Asp Leu Ser Ile Leu Asp Phe Asp Ile Pro
        435                 440                 445

Phe Ala Met Thr Phe Val Ile Ser Gly Ser Ile Glu Ile Ala Thr Thr
    450                 455                 460

Ile Ala Ile Met Ile Leu Val Thr Trp Gln Leu Val Leu Val Ala Ile
465                 470                 475                 480

Pro Val Ile Val Ala Leu Leu Tyr Ile Gln Arg Tyr Tyr Ile Ala Ser
                485                 490                 495

Ala Arg Glu Leu Val Arg Ile Asn Gly Thr Thr Lys Ala Pro Val Met
            500                 505                 510

Asn Tyr Ala Ala Glu Ser Met Leu Gly Val Ile Thr Ile Arg Ala Phe
        515                 520                 525

Ala Glu Thr Lys Arg Phe Ile Gln Thr Asn Leu Gln Leu Ile Asp Thr
    530                 535                 540

Asp Ala Thr Leu Phe Phe Tyr Thr Asn Ala Ala Leu Glu Trp Val Leu
545                 550                 555                 560

Leu Arg Val Glu Ala Leu Gln Ile Leu Val Ile Val Ala Ser Ser Ile
                565                 570                 575

Leu Leu Val Leu Leu Pro Glu Gly Ala Val Ala Pro Gly Phe Leu Gly
            580                 585                 590

Leu Cys Leu Ser Tyr Ala Leu Met Leu Ser Ser Ala Gln Val Phe Val
        595                 600                 605

Thr Arg Phe Tyr Ser Asn Leu Glu Asn Tyr Ile Ile Ser Val Glu Arg
    610                 615                 620

Ile Lys Gln Phe Met His Leu Pro Ala Glu Pro Pro Ala Val Ile Thr
625                 630                 635                 640

Asp Arg Ser Pro Pro Pro Ser Trp Pro Thr Ala Gly Arg Ile Glu Leu
                645                 650                 655

Glu Asn Leu Arg Val Lys Tyr Gly Glu Xaa Ala Pro Thr Val Leu Arg
            660                 665                 670

Gly Ile Thr Cys Thr Phe Ala Ala Gly His Lys Ile Gly Val Val Gly
        675                 680                 685

Arg Thr Gly Ser Gly Lys Thr Thr Leu Leu Ser Thr Leu Phe Arg Leu
    690                 695                 700

Ile Asp Pro Tyr Ser Gly Arg Ile Leu Ile Asp Asp Leu Asp Ile Cys
705                 710                 715                 720
```

-continued

```
Thr Ile Gly Leu Lys Asp Leu Arg Met Lys Leu Ser Ile Ile Pro Gln
                725                 730                 735

Glu Pro Thr Leu Phe Arg Gly Ser Val Arg Ser Asn Val Asp Pro Leu
            740                 745                 750

Gly Leu His Thr Asp Glu Asp Ile Trp Glu Ala Leu Asn Lys Cys Gln
        755                 760                 765

Leu Lys Lys Thr Ile Ser Ala Leu Pro Gly Leu Leu Glu Ser Pro Val
    770                 775                 780

Ser Asp Asp Gly Glu Asn Trp Ser Ala Gly Gln Arg Gln Leu Phe Cys
785                 790                 795                 800

Leu Ala Arg Val Leu Leu Arg Arg Asn Lys Ile Leu Val Leu Asp Glu
                805                 810                 815

Ala Thr Ala Ser Ile Asp Ser Ala Thr Asp Ala Val Leu Gln Arg Val
            820                 825                 830

Ile Lys Gln Glu Phe Ser Gly Cys Thr Val Ile Thr Ile Ala His Arg
        835                 840                 845

Val Pro Thr Val Thr Asp Ser Asp Met Val Met Val Leu Ser Tyr Gly
    850                 855                 860

Lys Leu Ile Glu Tyr Asp Arg Pro Ser Arg Leu Met Glu Asn Glu Asp
865                 870                 875                 880

Ser Pro Phe Cys Lys Leu Val Ala Glu Tyr Trp Ser Asn Tyr Ser
                885                 890                 895


<210> SEQ ID NO 195
<211> LENGTH: 1265
<212> TYPE: DNA
<213> ORGANISM: Glycine max

<400> SEQUENCE: 195

gcacgagccc atctcagagg atgtgcagcc acctgttgaa ggaacgactc ttatagcagt     60

ctatgttggt ttggccattg gaagttcttt ctgcatcctt gccagagcaa tacttcttgt    120

aacagctggt tataaaacag ctactatact cttcaataaa atgcacttct gcattttccg    180

tgctccaatg tcatttttcg attccactcc aagtggacga atccttaaca gagcttcgac    240

cgatcaaagt gcattggata cagacattcc ttatcaaatt gcatcatttg ccttcatttt    300

gatccagctt ctgggaatta tagcagtgat gtctcaagct gcatggcagg ttttcgttgt    360

ctttatacct gtgatagcaa tcagcgtctt gtatcagcaa tattatattc catcagcccg    420

agaactatca cgcttagttg gagtctgcaa agccccaatc attcaacact ttgctgaaac    480

aatttctggt actacaacta ttagaagctt tgatcagcag tcaagatttc aggaaacaaa    540

tatgaaactg actgatggat attctcggcc aatgttcaat attgctggtg ccgtggaatg    600

gttgtgtttc cgtttggata tgttgtcttc tatcacattt gccttttcct taatattctt    660

aatatctatt ccacagggat tcatagatcc aggccttgct ggtttagctg ttacatatgg    720

acttaatttg aacattgtac aaggttggat gatatggaat ctctgcaata tggagaacaa    780

aattatatca gtagaaagaa tacttcagta tacttgtatt ccttgtgagc cttcccttgt    840

tgtagacgat aatcggccag atccttcttg gccttcatat ggcgaggttg atatacaaga    900

tttgaaggtt cgttatgctc cacatctccc acttgtcttg cgcggtctta catgcaaatt    960

tcgtggagga ctgaaaactg gcattgttgg gagaacagga agtggtaaat ccactctcat   1020

acaaacactt ttccgaattg ttgagcctac tgccggccaa gttatgattg acagcatcaa   1080

catctcttca attggacttc atgatttgag gtctagacta agcatcattc ctcaagatcc   1140
```

-continued

```
aacaatgttt gaagggaccg tgagaaataa tttggacccc ctggaagaat acactgatga   1200

agaaatttgg gaggccttgg ataagtgtca acttggagat gaagttagaa aaaaaaaaaa   1260

aaaaa                                                               1265


<210> SEQ ID NO 196
<211> LENGTH: 418
<212> TYPE: PRT
<213> ORGANISM: Glycine max

<400> SEQUENCE: 196

His Glu Pro Ile Ser Glu Asp Val Gln Pro Pro Val Glu Gly Thr Thr
  1               5                  10                  15

Leu Ile Ala Val Tyr Val Gly Leu Ala Ile Gly Ser Ser Phe Cys Ile
             20                  25                  30

Leu Ala Arg Ala Ile Leu Leu Val Thr Ala Gly Tyr Lys Thr Ala Thr
         35                  40                  45

Ile Leu Phe Asn Lys Met His Phe Cys Ile Phe Arg Ala Pro Met Ser
     50                  55                  60

Phe Phe Asp Ser Thr Pro Ser Gly Arg Ile Leu Asn Arg Ala Ser Thr
 65                  70                  75                  80

Asp Gln Ser Ala Leu Asp Thr Asp Ile Pro Tyr Gln Ile Ala Ser Phe
                 85                  90                  95

Ala Phe Ile Leu Ile Gln Leu Leu Gly Ile Ile Ala Val Met Ser Gln
            100                 105                 110

Ala Ala Trp Gln Val Phe Val Val Phe Ile Pro Val Ile Ala Ile Ser
        115                 120                 125

Val Leu Tyr Gln Gln Tyr Tyr Ile Pro Ser Ala Arg Glu Leu Ser Arg
    130                 135                 140

Leu Val Gly Val Cys Lys Ala Pro Ile Ile Gln His Phe Ala Glu Thr
145                 150                 155                 160

Ile Ser Gly Thr Thr Thr Ile Arg Ser Phe Asp Gln Gln Ser Arg Phe
                165                 170                 175

Gln Glu Thr Asn Met Lys Leu Thr Asp Gly Tyr Ser Arg Pro Met Phe
            180                 185                 190

Asn Ile Ala Gly Ala Val Glu Trp Leu Cys Phe Arg Leu Asp Met Leu
        195                 200                 205

Ser Ser Ile Thr Phe Ala Phe Ser Leu Ile Phe Leu Ile Ser Ile Pro
    210                 215                 220

Gln Gly Phe Ile Asp Pro Gly Leu Ala Gly Leu Ala Val Thr Tyr Gly
225                 230                 235                 240

Leu Asn Leu Asn Ile Val Gln Gly Trp Met Ile Trp Asn Leu Cys Asn
                245                 250                 255

Met Glu Asn Lys Ile Ile Ser Val Glu Arg Ile Leu Gln Tyr Thr Cys
            260                 265                 270

Ile Pro Cys Glu Pro Ser Leu Val Val Asp Asp Asn Arg Pro Asp Pro
        275                 280                 285

Ser Trp Pro Ser Tyr Gly Glu Val Asp Ile Gln Asp Leu Lys Val Arg
    290                 295                 300

Tyr Ala Pro His Leu Pro Leu Val Leu Arg Gly Leu Thr Cys Lys Phe
305                 310                 315                 320

Arg Gly Gly Leu Lys Thr Gly Ile Val Gly Arg Thr Gly Ser Gly Lys
                325                 330                 335

Ser Thr Leu Ile Gln Thr Leu Phe Arg Ile Val Glu Pro Thr Ala Gly
            340                 345                 350
```

-continued

```
Gln Val Met Ile Asp Ser Ile Asn Ile Ser Ser Ile Gly Leu His Asp
        355                 360                 365

Leu Arg Ser Arg Leu Ser Ile Ile Pro Gln Asp Pro Thr Met Phe Glu
    370                 375                 380

Gly Thr Val Arg Asn Asn Leu Asp Pro Leu Glu Glu Tyr Thr Asp Glu
385                 390                 395                 400

Glu Ile Trp Glu Ala Leu Asp Lys Cys Gln Leu Gly Asp Glu Val Arg
                405                 410                 415

Lys Lys


<210> SEQ ID NO 197
<211> LENGTH: 1412
<212> TYPE: DNA
<213> ORGANISM: Glycine max

<400> SEQUENCE: 197

gcacgagtgg acttgctgtg acatatggcc tgaatttaaa tgcacgtcta tcacggtgga     60

tactcagctt ttgcaaactt gaaaataaaa ttatatctat tgagagaatt tatcagtaca    120

gccaaattcc tagtgaagca cccacagtta ttgaagatta tcgccctcca tcctcatggc    180

ctgaaaatgg gacaattgaa ataattgatt tgaagattcg ttacaaggag aatcttcctt    240

tggtgcttta tggagtaaca tgcacatttc ctggtggaaa gaagattgga atagtaggac    300

gtactggcag tggaaaatct actttaattc aggcgttatt tcgattgatt gaaccaacaa    360

gtgggagtat ccttatagac aacattaata tttcagagat tggccttcat gaccttcgaa    420

gccatctcag tatcatacca caagatccaa ccttatttga aggtaccatt cgaggcaatc    480

ttgatcctct ggatgagcac tcagataaag agatttggga ggcacttgat aagtctcagc    540

ttggagaggt tatccgtgag aaaggacaac agcttgatac gccagttcta gaaaatggag    600

ataattggag tgtaggacag cgacaacttg ttgctctggg ccgagctctg ctgcagcagt    660

caagaatact tgtactagat gaagcaacag catcagttga taccgccaca gataatctta    720

tacagaagat tatccgaagt gagttcaaag aatgcactgt ttgcaccatt gcacatcgaa    780

tacctactgt cattgacagt gatctagttc ttgtgctcag tgatggtcga gttgcagagt    840

tcaacactcc ttcaagacta ttagaggata agtcatccat gtttctgaag ctggtgactg    900

agtactcatc acgttcaagt ggcataccag acttttagaa caaatggaag gtgtgaatgc    960

tttcatagtg tggtggctgg agcttaagat agttcaaaag ttgaatcagg aagtgatgcc   1020

acccttgcat gtcactgctg cattcggggc atgcatagag acacgagatg gaaacaaaca   1080

aaataaaagg gagaggtttg tgcctcctca tgaatcaagc atcctactgg gggaaatttg   1140

tttgattatt ccccttaaag ttgagaaatt catgcaaggt tagcatgctt tgtaacacaa   1200

aataagatga tctgtgatta caggaaagta acgaaatagt ttgtagaatg aggcactagg   1260

attttgcttg gttagaaaaa gtgtagagtt taaactagtt ttgtgtattc cacaattttc   1320

ttgtagtgaa agtttagaat taagccaaaa aaaaaaaaaa aaaaaaaaaa aaaaaaaaaa   1380

aaaaaaaaaa aaaaaaaaaa aaaaaaaaaa aa                                 1412


<210> SEQ ID NO 198
<211> LENGTH: 311
<212> TYPE: PRT
<213> ORGANISM: Glycine max
```

-continued

<400> SEQUENCE: 198

```
Thr Ser Gly Leu Ala Val Thr Tyr Gly Leu Asn Leu Asn Ala Arg Leu
  1               5                  10                  15

Ser Arg Trp Ile Leu Ser Phe Cys Lys Leu Glu Asn Lys Ile Ile Ser
             20                  25                  30

Ile Glu Arg Ile Tyr Gln Tyr Ser Gln Ile Pro Ser Glu Ala Pro Thr
         35                  40                  45

Val Ile Glu Asp Tyr Arg Pro Pro Ser Ser Trp Pro Glu Asn Gly Thr
     50                  55                  60

Ile Glu Ile Ile Asp Leu Lys Ile Arg Tyr Lys Glu Asn Leu Pro Leu
 65                  70                  75                  80

Val Leu Tyr Gly Val Thr Cys Thr Phe Pro Gly Gly Lys Lys Ile Gly
                 85                  90                  95

Ile Val Gly Arg Thr Gly Ser Gly Lys Ser Thr Leu Ile Gln Ala Leu
            100                 105                 110

Phe Arg Leu Ile Glu Pro Thr Ser Gly Ser Ile Leu Ile Asp Asn Ile
        115                 120                 125

Asn Ile Ser Glu Ile Gly Leu His Asp Leu Arg Ser His Leu Ser Ile
    130                 135                 140

Ile Pro Gln Asp Pro Thr Leu Phe Glu Gly Thr Ile Arg Gly Asn Leu
145                 150                 155                 160

Asp Pro Leu Asp Glu His Ser Asp Lys Glu Ile Trp Glu Ala Leu Asp
                165                 170                 175

Lys Ser Gln Leu Gly Glu Val Ile Arg Glu Lys Gly Gln Gln Leu Asp
            180                 185                 190

Thr Pro Val Leu Glu Asn Gly Asp Asn Trp Ser Val Gly Gln Arg Gln
        195                 200                 205

Leu Val Ala Leu Gly Arg Ala Leu Leu Gln Gln Ser Arg Ile Leu Val
    210                 215                 220

Leu Asp Glu Ala Thr Ala Ser Val Asp Thr Ala Thr Asp Asn Leu Ile
225                 230                 235                 240

Gln Lys Ile Ile Arg Ser Glu Phe Lys Glu Cys Thr Val Cys Thr Ile
                245                 250                 255

Ala His Arg Ile Pro Thr Val Ile Asp Ser Asp Leu Val Leu Val Leu
            260                 265                 270

Ser Asp Gly Arg Val Ala Glu Phe Asn Thr Pro Ser Arg Leu Leu Glu
        275                 280                 285

Asp Lys Ser Ser Met Phe Leu Lys Leu Val Thr Glu Tyr Ser Ser Arg
    290                 295                 300

Ser Ser Gly Ile Pro Asp Phe
305                 310
```

<210> SEQ ID NO 199
<211> LENGTH: 1936
<212> TYPE: DNA
<213> ORGANISM: Glycine max

<400> SEQUENCE: 199

```
gcacgagcta gcatggattt tatccttctt ggctggtgac tactggctag caattggaac     60

tgcagaagat agtgcctttc ctccttctac attcatcatt gtctatgctt gcatagcagg    120

tcttgtatgt actgtggtga tgatcagatc agtcttattt acatattggg gtctaaagac    180

atctcaaagc ttcttcagtg gaatgcttga aagcatcttg catgcaccaa tgtcattctt    240

tgacacaact ccctctggca gaattttgag tcgtgtatct actgatatac tttgggttga    300
```

-continued

```
tatctcaatt ccaatgttgg tgaacttcgt catggttgct tacttctcag taaccagcat    360

cctcattgta acatgccaaa atgcttggga aacggtcttc ctcttaatcc cactgttctg    420

gctgaataac tggtatcgga aatattacct tgcatcttct cgggaattga ctcgccttga    480

ttccatcacc aaagctcctg tgattcacca tttttcagaa accattgctg gtgttatgac    540

catacgcggc ttcagaaagc agaacgcatt ttgtcaagaa aatattgaca aagtgaatgc    600

tagtctgaga atggatttcc acaacaacgg tgctaatgaa tggcttggtt ttcgcttgga    660

ctatatggga gtgattttcc tttgctttgc cactattttt atgatctttc tgccaagtgc    720

tattattaag ccagaatatg ttggtttgtc tttgtcctat ggcctggctc tcagtagtct    780

cttggcattt accataagca tgacttgttc tgttgagaac aaaatggttt cagttgagag    840

aataaagcag ttctccagcc ttccctcaga agctccatgg aaaattgctg acaaaactcc    900

tcctcagaat tggcccagtc aaggcattat tgagttaacc aatttgcagg ttcggtatcg    960

accaaatact cctctggttc tcaagggaat ctctctcacc attgaagcag gagaaaagat   1020

tggtgttgtt ggtcgtacag gaagtgggaa atcaaccctc attcaggtgt tatttaggtt   1080

gattgagcct tcagctggga aaataactgt tgatggaatc aacatttgca ccctgggcct   1140

tcatgatgtg aggtctagat ttggaattat tcctcaagag cctgtcctct ttcaaggaac   1200

agtacgaagc aacattgacc cccttggact gtattcagag gaagaaattt ggaagagtct   1260

tgagcgctgc caactgaaag atgtggtggc tgcaaagcca gagaaacttg aggctccagt   1320

ggttgatggt ggagacaatt ggagtgtggg gcaaagacag cttctttgct tgggaaggat   1380

catgctaaaa agcagcaaaa tattgttcat ggatgaggca acagcatccg ttgattcgca   1440

aactgacgct gtgatacaaa agatcatccg tgaggacttt gcggatcgta caattatcag   1500

cattgctcat agaataccaa cagtcatgga ttgtgacagg gttttagtca ttgatgcagg   1560

ctatgcaaag gaatatgaca agccatcgcg tttgctagaa aggcattcac tttttggagc   1620

attggttaag gagtactcta atagatcagc tgaactagag gtttagattc taacaaggac   1680

ccagttgatg cactcagttt ccatccaaca cacagcacca aagtcaaaag acatgagtcg   1740

atgggtctat tgagaaatca atatttttga gcattagttt tgatgtttta ctctttcagt   1800

agtttaataa ttagactagg acaataggaa ggaaatttta aaatttttta ctaataaaaa   1860

atcaagtttg ggtgcaattg ttactatttt ataaaaaaaa aaaaaaaatc tgtttgctaa   1920

aaaaaaaaaa aaaaaa                                                   1936
```

<210> SEQ ID NO 200
<211> LENGTH: 554
<212> TYPE: PRT
<213> ORGANISM: Glycine max

<400> SEQUENCE: 200

```
His Glu Leu Ala Trp Ile Leu Ser Phe Leu Ala Gly Asp Tyr Trp Leu
  1               5                  10                  15

Ala Ile Gly Thr Ala Glu Asp Ser Ala Phe Pro Pro Ser Thr Phe Ile
             20                  25                  30

Ile Val Tyr Ala Cys Ile Ala Gly Leu Val Cys Thr Val Val Met Ile
         35                  40                  45

Arg Ser Val Leu Phe Thr Tyr Trp Gly Leu Lys Thr Ser Gln Ser Phe
     50                  55                  60

Phe Ser Gly Met Leu Glu Ser Ile Leu His Ala Pro Met Ser Phe Phe
 65                  70                  75                  80
```

-continued

```
Asp Thr Thr Pro Ser Gly Arg Ile Leu Ser Arg Val Ser Thr Asp Ile
                85                  90                  95

Leu Trp Val Asp Ile Ser Ile Pro Met Leu Val Asn Phe Val Met Val
            100                 105                 110

Ala Tyr Phe Ser Val Thr Ser Ile Leu Ile Val Thr Cys Gln Asn Ala
        115                 120                 125

Trp Glu Thr Val Phe Leu Leu Ile Pro Leu Phe Trp Leu Asn Asn Trp
    130                 135                 140

Tyr Arg Lys Tyr Tyr Leu Ala Ser Ser Arg Glu Leu Thr Arg Leu Asp
145                 150                 155                 160

Ser Ile Thr Lys Ala Pro Val Ile His His Phe Ser Glu Thr Ile Ala
                165                 170                 175

Gly Val Met Thr Ile Arg Gly Phe Arg Lys Gln Asn Ala Phe Cys Gln
            180                 185                 190

Glu Asn Ile Asp Lys Val Asn Ala Ser Leu Arg Met Asp Phe His Asn
        195                 200                 205

Asn Gly Ala Asn Glu Trp Leu Gly Phe Arg Leu Asp Tyr Met Gly Val
    210                 215                 220

Ile Phe Leu Cys Phe Ala Thr Ile Phe Met Ile Phe Leu Pro Ser Ala
225                 230                 235                 240

Ile Ile Lys Pro Glu Tyr Val Gly Leu Ser Leu Ser Tyr Gly Leu Ala
                245                 250                 255

Leu Ser Ser Leu Leu Ala Phe Thr Ile Ser Met Thr Cys Ser Val Glu
            260                 265                 270

Asn Lys Met Val Ser Val Glu Arg Ile Lys Gln Phe Ser Ser Leu Pro
        275                 280                 285

Ser Glu Ala Pro Trp Lys Ile Ala Asp Lys Thr Pro Pro Gln Asn Trp
    290                 295                 300

Pro Ser Gln Gly Ile Ile Glu Leu Thr Asn Leu Gln Val Arg Tyr Arg
305                 310                 315                 320

Pro Asn Thr Pro Leu Val Leu Lys Gly Ile Ser Leu Thr Ile Glu Ala
                325                 330                 335

Gly Glu Lys Ile Gly Val Val Gly Arg Thr Gly Ser Gly Lys Ser Thr
            340                 345                 350

Leu Ile Gln Val Leu Phe Arg Leu Ile Glu Pro Ser Ala Gly Lys Ile
        355                 360                 365

Thr Val Asp Gly Ile Asn Ile Cys Thr Leu Gly Leu His Asp Val Arg
    370                 375                 380

Ser Arg Phe Gly Ile Ile Pro Gln Glu Pro Val Leu Phe Gln Gly Thr
385                 390                 395                 400

Val Arg Ser Asn Ile Asp Pro Leu Gly Leu Tyr Ser Glu Glu Glu Ile
                405                 410                 415

Trp Lys Ser Leu Glu Arg Cys Gln Leu Lys Asp Val Val Ala Ala Lys
            420                 425                 430

Pro Glu Lys Leu Glu Ala Pro Val Val Asp Gly Gly Asp Asn Trp Ser
        435                 440                 445

Val Gly Gln Arg Gln Leu Leu Cys Leu Gly Arg Ile Met Leu Lys Ser
    450                 455                 460

Ser Lys Ile Leu Phe Met Asp Glu Ala Thr Ala Ser Val Asp Ser Gln
465                 470                 475                 480

Thr Asp Ala Val Ile Gln Lys Ile Ile Arg Glu Asp Phe Ala Asp Arg
                485                 490                 495
```

-continued

```
Thr Ile Ile Ser Ile Ala His Arg Ile Pro Thr Val Met Asp Cys Asp
            500                 505                 510

Arg Val Leu Val Ile Asp Ala Gly Tyr Ala Lys Glu Tyr Asp Lys Pro
        515                 520                 525

Ser Arg Leu Leu Glu Arg His Ser Leu Phe Gly Ala Leu Val Lys Glu
    530                 535                 540

Tyr Ser Asn Arg Ser Ala Glu Leu Glu Val
545                 550


<210> SEQ ID NO 201
<211> LENGTH: 1328
<212> TYPE: DNA
<213> ORGANISM: Triticum aestivum

<400> SEQUENCE: 201

ctcgtgccga attcggcacg aggtcacata tgggcttaac ttgaacatgc tgcaagcatg     60

ggttgtgtgg agcatgtgca atttggagaa caagatcata tcagtagaaa gaattctgca    120

atacataagc attcctgaag agccccccact ttcaatgtca gaagataagt tgccccataa    180

ctggccgtca cagggagaaa ttcagcttca tgacgtccat gtaagatatg ctccacaact    240

accatttgtt ctgaagggcc ttaacgtcac tttccctgga ggcatgaaga ctggtattgt    300

tggaagaaca ggcagtggta aatcaacact catacaggcc cttttccgta ttgtcgagcc    360

tactgtcggt cagatactgg tagatggtgt tgacatctgc accatcgggc tgcatgatct    420

gagatctaga cttagcatca ttccacaaga tccaacgatg tttgagggaa ctgtgaggag    480

caaccttgac cctcttaacg agtacaatga cgatcagatc tgggaggcct tggataactg    540

tcagctggga gatgaggtca ggaagaagga gctgaaactc gactcaccag tgatcgagaa    600

cggagagaac tggagcgtgg gccagcgcca gctagtctgt cttggaagag tgattctgaa    660

acggaccaag atactggttc tggacgaagc cactgcttca gtggataccg cgacagacaa    720

catgattcag aaaacactac gtgagaactt ctcggaggcg acggtcatca cgattgcgca    780

tcgaatcacc tcggtcctcg acagcgacat ggttctgctc ctcgacaacg gtgtggccgt    840

ggagcgtgac acgccggcca agctgctgga gaacaagtcg tctctgttct caaagcttgt    900

ggcggagtac acgatcagag cgacgcacgc gtagccaacg aatagatcct ccagcaaatt    960

cttccatgcc gttgaggctt cttgagtgag tctggccgtc gataatgccg aaaaattact   1020

ggtagatgtg atgtgaagtg ctctcggatc tgccacggtg ttggtgctac tgatacgcgc   1080

acggtaactt tacattttct gaaggaaaag gctgaaggtg gttaagagtc ggtcaaagtt   1140

tagtgtttga agaaagtagt tcgttaagga tagcaagacc tgaaccatgg tagtagtcac   1200

tcactttacg gcggaccata cacgccgaaa aagttttggg gcttagtaat ttgatgatgt   1260

actgtgtgat accgggataa ataaatgaag tggaagtggt tcagtttaaa aaaaaaaaaa   1320

aaaaaaaa                                                            1328


<210> SEQ ID NO 202
<211> LENGTH: 310
<212> TYPE: PRT
<213> ORGANISM: Triticum aestivum

<400> SEQUENCE: 202

Ser Cys Arg Ile Arg His Glu Val Thr Tyr Gly Leu Asn Leu Asn Met
  1               5                  10                  15

Leu Gln Ala Trp Val Val Trp Ser Met Cys Asn Leu Glu Asn Lys Ile
             20                  25                  30
```

-continued

```
Ile Ser Val Glu Arg Ile Leu Gln Tyr Ile Ser Ile Pro Glu Glu Pro
        35                  40                  45

Pro Leu Ser Met Ser Glu Asp Lys Leu Pro His Asn Trp Pro Ser Gln
    50                  55                  60

Gly Glu Ile Gln Leu His Asp Val His Val Arg Tyr Ala Pro Gln Leu
65                  70                  75                  80

Pro Phe Val Leu Lys Gly Leu Asn Val Thr Phe Pro Gly Gly Met Lys
                85                  90                  95

Thr Gly Ile Val Gly Arg Thr Gly Ser Gly Lys Ser Thr Leu Ile Gln
            100                 105                 110

Ala Leu Phe Arg Ile Val Glu Pro Thr Val Gly Gln Ile Leu Val Asp
        115                 120                 125

Gly Val Asp Ile Cys Thr Ile Gly Leu His Asp Leu Arg Ser Arg Leu
    130                 135                 140

Ser Ile Ile Pro Gln Asp Pro Thr Met Phe Glu Gly Thr Val Arg Ser
145                 150                 155                 160

Asn Leu Asp Pro Leu Asn Glu Tyr Asn Asp Asp Gln Ile Trp Glu Ala
                165                 170                 175

Leu Asp Asn Cys Gln Leu Gly Asp Glu Val Arg Lys Lys Glu Leu Lys
            180                 185                 190

Leu Asp Ser Pro Val Ile Glu Asn Gly Glu Asn Trp Ser Val Gly Gln
        195                 200                 205

Arg Gln Leu Val Cys Leu Gly Arg Val Ile Leu Lys Arg Thr Lys Ile
    210                 215                 220

Leu Val Leu Asp Glu Ala Thr Ala Ser Val Asp Thr Ala Thr Asp Asn
225                 230                 235                 240

Met Ile Gln Lys Thr Leu Arg Glu Asn Phe Ser Glu Ala Thr Val Ile
                245                 250                 255

Thr Ile Ala His Arg Ile Thr Ser Val Leu Asp Ser Asp Met Val Leu
            260                 265                 270

Leu Leu Asp Asn Gly Val Ala Val Glu Arg Asp Thr Pro Ala Lys Leu
        275                 280                 285

Leu Glu Asn Lys Ser Ser Leu Phe Ser Lys Leu Val Ala Glu Tyr Thr
    290                 295                 300

Ile Arg Ala Thr His Ala
305                 310
```

<210> SEQ ID NO 203
<211> LENGTH: 1069
<212> TYPE: DNA
<213> ORGANISM: Triticum aestivum

<400> SEQUENCE: 203

```
tggtttaggc acgtggattt ggtacgggca ccgcctcgag cggagagatg atcaatgtcg      60

tgagcctcga tgccgagtgt gtaggagatt tcagtcgatc catgcacgat ctttggcggc     120

ttcctgtgca aattgttcta gccatgctca tcttatactc gacacttggt tttgccctg     180

catttgctgc ccttcttgcc actgctttga caattggggg taataagcct ttagggagaa     240

tggagcaaaa ttatcaagag agaatgatga gcgccaagga cgtgagaatg agggctatgt     300

ctgagatctt acagagcatg cgcattctca agcttcaagg atgggaaatg atcttcttgt     360

ccaagatcat agagttgagg aaggtagaga tgaattggct aaagaagaac gtatacacct     420

cggcgatgct cctatccatc ttcttttctg ctcctgcttt tgttgctatg gtcactttcg     480

gtgtttgcgt gcttatgggc attccattag aaacaggtaa agtgctatgt gccctggcaa     540
```

-continued

```
catttagaca gctgcaaaca cctatccatg gtctaccaga cgcatactct atgatcattc    600

agacaaaagt atcgcttgac aggatatgct catttctctg tcttgaggaa ctccctagtg    660

atgttgtaac taagcttcct aggggtacca ccgatgtgtc gattgaggtg acgaacggtc    720

atttctcttg gaatacatct tctcaagtgc ctactctcca agacgtgaac ttccgtatac    780

gacagggaat gagggttgct gtctgtggaa cagttggatc tggcaaatca agtttattgt    840

cttgcatact cggtgagata ccaaaattat caggagaggt taaaacttgt ggcaggatct    900

cctatgttag ccaaacacct tggatacaga gtgggaaaat tgaagataat atacttttcg    960

gcacagaaat gaatagggag aggtatgaaa aggtccttga agcatgctca cttatcaagg   1020

acctggatat attaccattc ggtgaccaga cgattatagg agctcgtgc              1069


<210> SEQ ID NO 204
<211> LENGTH: 353
<212> TYPE: PRT
<213> ORGANISM: Triticum aestivum

<400> SEQUENCE: 204

Ala Arg Gly Phe Gly Thr Gly Thr Ala Ser Ser Gly Glu Met Ile Asn
  1               5                  10                  15

Val Val Ser Leu Asp Ala Glu Cys Val Gly Asp Phe Ser Arg Ser Met
             20                  25                  30

His Asp Leu Trp Arg Leu Pro Val Gln Ile Val Leu Ala Met Leu Ile
         35                  40                  45

Leu Tyr Ser Thr Leu Gly Phe Cys Pro Ala Phe Ala Ala Leu Leu Ala
     50                  55                  60

Thr Ala Leu Thr Ile Gly Gly Asn Lys Pro Leu Gly Arg Met Glu Gln
 65                  70                  75                  80

Asn Tyr Gln Glu Arg Met Met Ser Ala Lys Asp Val Arg Met Arg Ala
                 85                  90                  95

Met Ser Glu Ile Leu Gln Ser Met Arg Ile Leu Lys Leu Gln Gly Trp
            100                 105                 110

Glu Met Ile Phe Leu Ser Lys Ile Ile Glu Leu Arg Lys Val Glu Met
        115                 120                 125

Asn Trp Leu Lys Lys Asn Val Tyr Thr Ser Ala Met Leu Leu Ser Ile
    130                 135                 140

Phe Phe Ser Ala Pro Ala Phe Val Ala Met Val Thr Phe Gly Val Cys
145                 150                 155                 160

Val Leu Met Gly Ile Pro Leu Glu Thr Gly Lys Val Leu Cys Ala Leu
                165                 170                 175

Ala Thr Phe Arg Gln Leu Gln Thr Pro Ile His Gly Leu Pro Asp Ala
            180                 185                 190

Tyr Ser Met Ile Ile Gln Thr Lys Val Ser Leu Asp Arg Ile Cys Ser
        195                 200                 205

Phe Leu Cys Leu Glu Glu Leu Pro Ser Asp Val Val Thr Lys Leu Pro
    210                 215                 220

Arg Gly Thr Thr Asp Val Ser Ile Glu Val Thr Asn Gly His Phe Ser
225                 230                 235                 240

Trp Asn Thr Ser Ser Gln Val Pro Thr Leu Gln Asp Val Asn Phe Arg
                245                 250                 255

Ile Arg Gln Gly Met Arg Val Ala Val Cys Gly Thr Val Gly Ser Gly
            260                 265                 270

Lys Ser Ser Leu Leu Ser Cys Ile Leu Gly Glu Ile Pro Lys Leu Ser
        275                 280                 285
```

-continued

```
Gly Glu Val Lys Thr Cys Gly Arg Ile Ser Tyr Val Ser Gln Thr Pro
    290                 295                 300

Trp Ile Gln Ser Gly Lys Ile Glu Asp Asn Ile Leu Phe Gly Thr Glu
305                 310                 315                 320

Met Asn Arg Glu Arg Tyr Glu Lys Val Leu Glu Ala Cys Ser Leu Ile
                325                 330                 335

Lys Asp Leu Asp Ile Leu Pro Phe Gly Asp Gln Thr Ile Ile Gly Ala
            340                 345                 350

Arg
```

PLANT METABOLISM GENES

This application claims the benefit of U.S. Provisional Applications No. 60/143,401 filed Jul. 12, 1999; No. 60/143,412, filed Jul. 12, 1999; No. 60/146,650, filed Jul. 30, 1999; No. 60/170,906 filed Dec. 15, 1999; No. 60/172,959 filed Dec. 21, 1999; No. 60/172,946 filed Dec. 21, 1999.

FIELD OF THE INVENTION

This invention is in the field of plant molecular biology. More specifically, this invention pertains to nucleic acid fragments encoding metabolism proteins in plants and seeds.

BACKGROUND OF THE INVENTION

Gibberellic acid (GA) is an important regulator (phytohormone) of plant development. Gibberellic acid has been shown to stimulate elongation in the internodes of stems and to play roles in flower and fruit development. Identification and characterization of genes involved in GA biosynthesis will permit genetic engineering methods aimed at modulating levels of GA in plants which will in turn allow for better control of plant stature, fertility and plant development in general (see World Patent Publication No. WO 95/35383).

Gibberellic acid is synthesized from isoprenoid geranylgeranyl diphosphate (GGDP), beginning with the conversion of GGDP to copalyl diphosphate (CDP). Copalyl diphosphate is then converted to $GA_{12}$-aldehyde which in turn can be converted to a number of different gibberellins required for normal plant development. For example GA-20 oxidase catalizes the conversion of GA12 to GA9. A key enzyme in the synthesis of gibberellin is dioxygenase which appears to play a role in the conversion of $GA_{12}$-aldehyde to $GA_9$ and $GA_{25}$. Because $GA_{12}$-aldehyde dioxygenase appears to catalyze key steps in the synthesis of GA it is a target enzymes that may be manipulated to control GA levels. Ent-Kaurene synthase A (KSA) catalyzes the conversion of GGDP to CDP, which is subsequently converted to ent-kaurene by ent-kaurene synthase B (KSB) (Yamaguchi et al. (1996) *Plant J.* 10(2):203–213). Gibberillin 3-beta-hydroxylase catalizes the conversion of GA20 to GA1 a major gibberellin that is involved in controlling stem elongation. These enzymes catalyze key steps in the synthesis of GA and thus provide target enzymes that may be manipulated to control GA levels.

Thus there is a great deal of interest in identifying genes that encode proteins that may be used to control plant developmental. Accordingly, the availability of nucleic acid sequences encoding all or a substantial portion of a GA dioxygenase would facilitate studies to better understand plant development and provide tools to genetically engineer improved developmental properties in plants.

Riboflavin is the precursor to essential electron transport chain components and redox coenzymes such as flavin mononucleotide (FMN) and flavin adenine dinucleotide (FAD). Humans, unlike plants and bacteria, are incapable of synthesizing riboflavin (vitamin $B_2$) from GTP, and must obtain this compound through their diet. Thousands of tons of riboflavin are produced each year as additives for food and animal feed (Bacher et al. (1997) *Methods Enzymol* 280:382–389). Historically, riboflavin has been made via chemical synthesis, however recent advances in biotechnology have enabled industrial production using yeast and bacteria (Humbelin et al. (1999) *J Indust Micro & Biotech* 22:1–7). The biologically synthesized riboflavin is cheaper to produce, and the process is better for the environment.

Several enzymatic steps are required to take GTP to riboflavin. The first step in bacteria is catalyzed by a GTP cyclohydrolase II activity which takes GTP to 2,5-iamino-6-ribosylamino-4(3H)-pyrimidinone 5'-phosphate. The enzyme performing this step is encoded by the ribA gene. RibA has two enzymatic activities, the above mentioned cyclohydrolase and a 3,4-dihydroxy-2-butanone 4-phosphate synthase activity that takes ribulose 5-phosphate to L-3,4-dihydroxy-2-butanone-4-phosphate, which is combined to a pathway intermediate, to form 6,7-dimethyl-8-ribityllumazine, the penultimate intermediate to riboflavin. The second step in the pathway is encoded by ribG a riboflavin-specific deaminase.

Studies using riboflavin over-producing *Bacillus subtilis* strains, have led to the conclusion that the GTP cyclohydrolase II/3,4-dihydroxy-2-butanone 4-phosphate synthase enzyme is rate-limiting for high-level riboflavin accumulation (Humbelin et al. (1999) *J Indust Micro & Biotech* 22:1–7). Increasing the copy number of the ribA gene in these strains results in improved riboflavin productivity. The pathways leading to riboflavin biosynthesis are largely conserved between plants and bacteria. Therefore, the potential exists for improving the riboflavin content in crop plants, thus reducing the need for vitamin supplementation in food.

The present invention describes the identification and utility of GTP cyclohydrolase II/3,4-dihydroxy-2-butanone 4-phosphate synthase sequences from corn, rice, soybean, and wheat. Also disclosed are sequences from corn, rice, and wheat that encode riboflavin-specific deaminases. It is believed that modulation of these activities through over-expression, under-expression, or mutation will lead to altered levels of riboflavin in plants.

Hormones in animal systems and phytohormones in plants control many metabolic processes. Phytohormones differ in their structure and specific actions compared to animal hormones, though the signal transduction mechanisms involved may be similar in plants and animals. Phytohormones affect shoot elongation, stem elongation, root growth, seed dormancy, fruit ripening, leaf senescence and morphogenesis, disease resistance (Hoffman et al. (1999) *Plant Physiol* 119:935–949), to name a few.

Among the phytohormones that have been studied so far, ethylene is the simplest in terms of chemical structure. Its effects, however, are far-ranging, affecting seed dormancy, fruit ripening and abscission, flower development, leaf senescence, adventitious root formation, and shoot and root growth and differentiation. Ethylene is synthesized from methionine via three enzymatic steps. Methionine is converted to S-adenosyl-methionine (SAM) by SAM synthetase, which is then converted to 1-aminocyclopropane-1-carboxylic acid (ACC) by ACC synthase. Finally, ACC oxidase acts on ACC to yield ethylene. The genes encoding these enzymes have been cloned, and transgenic approaches based on these genes have been attempted to control ethylene levels, and consequently fruit ripening. Using antisense technology, ACC synthase or ACC oxidase activities have been reduced in transgenic plants leading to inhibition of fruit ripening (Hamilton et al. (1990) *Nature* 346:284–287; Oeller et al. (1991) *Science* 254:437–439).

The mechanisms by which ethylene regulates plant development however are yet to be clearly defined. Ethylene-insensitive mutants and constitutive ethylene response mutants, principally in Arabidopsis, have been valuable in outlining the ethylene response pathway (Kieber (1997) *Annu. Rev. Plant Physiol. Plant Mol. Biol.* 48:277–296). The isolation of the genes affected in these mutants indicates the involvement of a protein kinase cascade in ethylene signaling. CTR1, a negative regulator of the ethylene response encodes a serine/threonine kinase that is most similar to the Raf family of protein kinases (Kieber et al. (1993) *Cell* 72:427–441). ETR1 in which dominant mutations lead to defective ethylene responses encodes a protein that is similar to bacterial two-component histidine kinases (Chang et al. (1993) *Science* 262:539–544). It most probably serves as an ethylene receptor/ethylene response factor since etr1 mutant seedlings bind ethylene at reduced levels compared to wild-type (Bleecker et al. (1988) *Science* 241:1086–1089), the ETR1 protein has been shown to bind ethylene (Schaller and Bleeker (1995) *Science* 270:1809–1811), and genetic epistasis analysis puts ETR1 the start of the ethylene response pathway (Kieber et al. (1993)*Cell* 72:427–441). U.S. Pat. Nos. 5,689,055 and 5,824,868 describe the Arabidopsis ETR1 gene, its tomato homologs, and their use in generating transgenic plants with modified response to ethylene.

ETR1 belongs to a small gene family in Arabidopsis, and at least one ETR1 homolog in Arabidopsis, ERS, has already been cloned (Hua et al. (1995) *Science* 269:1712–1714). Homologs in other species like rice and tomato have been isolated as well (Wilkinson et al. (1995) *Science* 270:1807–1809; Yau and Yip (1997) *Plant Physiol* 115:315; Tieman and Klee (1999) *Plant Physiol* 120:165–172). Many questions however remain regarding ethylene response factor gene organization, evolution, structure and function. Accordingly, additional nucleic acid sequences encoding ethylene response factors are disclosed herein which would facilitate studies to better understand ethylene response factors and ethylene signaling in plants and could provide genetic tools to enhance or otherwise alter developmental and physiological processes regulated by ethylene.

Acyl-CoA thioesterases catalyze the hydrolysis of variable length acyl-CoAs to produce free fatty acids and CoASH. Acyl-CoA thioesterase activities are generally found in most organisms from prokaryotes to eukaryotes. Eukaryotic acyl-CoA thioesterase activities have been detected in various subcellular organelles including lysosomes, peroxisomes, and mitochondria, as well as in the cytosol. Long chain acyl-CoA esters are important intermediates in degradation and synthesis of fatty acids, and may have important roles in regulating intermediary metabolism and gene expression (Waku (1992) *Biochem Biophys Acta* 1124:101–111). In animal systems, free fatty acids and acyl-CoAs have been shown to be nuclear receptor ligands which regulate lipid homeostasis. Also, acyl-CoAs act as potent feedback inhibitors of fatty acid synthesis. Typically, fatty acids entering cells are rapidly esterified to their corresponding CoA-esters. These acyl-CoAs are then oxidized in mitochondria or peroxisomes, elongated, desaturated or esterified into complex lipids or transferred post-translationally to proteins. The precise role of acyl-CoA thioesterases, their substrates, and products is not yet fully understood. However it is clear that animal and yeast acyl-CoA thioesterase enzymes are involved in the regulation of lipid metabolism by modulation of cellular concentrations of acyl-CoAs and fatty acids. It is unclear at this time what role the acyl-CoA thioesterases play in plants although these enzymatic activities are well known in plants (Murphy et al. (1984) *Eur J Biochem* 142:43–48).

Previously, acyl-CoA thioesterases were thought to coordinate with the fatty acid synthases in the biosynthesis of fatty acids in the cytosol. Although this is true, recent findings of peroxisomal and mitochondrial forms of the enzyme implicate additional roles for the thioesterases since peroxisomes and mitochondria do not contain synthase activities (Hunt et al. (1999) *J Biol Chem* 274:34317–34326, Jones et al. (1999) *J Biol Chem* 274:9216–9223, and Liu et al. (1997) *J Biol Chem* 272:13779–13785). Many aspects of fatty acid utilization and regulation are tied into growth rates and the ability of plants to adapt to their environment. It is therefore likely that the acyl-CoA thioesterases will play some role in regulating plant metabolism, just as they do in animal systems.

Members of the superfamily of adenosine triphosphate (ATP)-binding-cassette (ABC) transport systems couple the hydrolysis of ATP to the translocation of solutes across a biological membrane. Recognized by their common modular organization and two sequence motifs that constitute a nucleotide binding fold, ABC transporters are widespread among all living organisms. They accomplish not only the uptake of nutrients in bacteria but are involved in diverse processes, such as signal transduction, protein secretion, drug and antibiotic resistance, antigen presentation, bacterial pathogenesis and sporulation. Moreover, some human inheritable diseases, like cystic fibrosis, adrenoleukodystrophy and Stargardt's disease are caused by defective ABC transport systems. Details of the molecular mechanism by which these systems exert their functions are still poorly understood (Schneider, E. and Hunke, S. (1998) *FEMS Microbiol Rev* 22:1–20).

The pleiotropic drug resistance gene PDR5 encodes a protein which is a member of the ABC-transport protein superfamily. This ABC transporter functions as a drug extrusion pump by being involved in the ATP-dependent efflux of a variety of structurally unrelated cytotoxic compounds. The transcription regulators PDR1, PDR3, PDR7, and PDR9 control the expression of the gene PDR5 (Balzi, E. and Goffeau, A. (1995) *J Bioenerg Biomembr* 27:71–76). PDR5 encodes a 160-kDa protein with a predicted duplicated six membrane-spanning domain and a repeated putative ATP-binding domain. PDR5 shares this structural feature with the mammalian multidrug resistance pumps as well as the functional capacity of conferring resistance to various inhibitors upon amplification (Leppert, G. et al. (1990) *Genetics* 125:13–20). PDR5 homologs are present in plants, may function during stress conditions in an analogous fashion to that described in yeast, and expression of such ABC transporters is subject to a complex hormonal and environmental regulation (Smart, C. C. and Fleming, A. J. (1996) *J Biol Chem* 271:19351–19357).

Also a member of the ABC-superfamily, GCN20 uptakes ions and amino acids. GCN20 is co-immunoprecipitated from cell extracts with GCN 1, another factor required to activate GCN2, and the two proteins interact in the yeast two-hybrid system. These two factors indicate that GCN1 and GCN20 are components of a protein complex that couples the kinase activity of GCN2 to the availability of amino acids. GCN20 is closely related to ABC proteins identified in *Caenorhabditis elegans,* rice and humans, suggesting that the function of GCN20 may be conserved among diverse eukaryotic organisms (Vazquez de Aldana, C. R. et al. (1995) *EMBO J* 14:3184–3199). As part of the GCN1/GCN20 complex, GCN20 may be involved in the modulation of the EF3-related function which facilitates the activation of GCN2 by uncharged tRNA on translating ribosomes (Marton, M. J. et al. (1997) *Mol Cell Biol* 17:4474–4489).

ABC transporters play a role in the protection of organisms against exogenous toxins by cellular detoxification processes. P-glycoprotein, the product of the multidrug resistance (MDR1) gene, is an ATP-driven transmembrane pump that increases the resistance of cells by actively exporting toxic chemicals. In addition to transporting anti-cancer drugs, P-glycoprotein also extrudes steroid hormones and a variety of lipophilic drugs, such as calcium channel blockers, phenothiazines, cyclosporines, etc.

The 70-kDa peroxisomal membrane protein (PMP70) is one of the major integral membrane proteins of rat liver peroxisomes. The carboxyl-terminal region of PMP70 has strong sequence similarities to a group of ATP-binding proteins such as MalK and MDR. These proteins form a superfamily and are involved in various biological processes including membrane transport. The PMP70 protein is a transmembrane protein possibly forming a channel, with its ATP-binding domain exposed to the cytosol. PMP70 is involved in active transport across the peroxisomal membrane. (Kamijo, K. et al. (1990) *J. Biol. Chem.* 265:4534–4540).

Immunoblot analysis shows that PMP70 is associated with the peroxisomal membrane in liver, renal cortex, and jejunal mucosa (Usuda, N. et al. (1991) *Cytochem* 39:1357–1366). cDNAs for human and rat PMP70 have been cloned and sequenced and the gene mapped to human chromosome 1p21–22. In humans, mutations in the PMP70 gene have been found in a subset of patients with Zellweger-syndrome, a lethal inborn error of peroxisome biogenesis (Gartner, J. and Valle, D. (1993) i Semin Cell Biol 4:45–52). Members of an MDR-like gene family, with no similarity to PMP70, have been identified from an *Arabidopsis thaliana* cDNA library (Dudler, R. and Hertig, C. (1991) *J. Biol. Chem.* 267:5882–5888). No other plant MDR-like genes have been identified to date, although identification of these genes in plants will be useful to understand the herbicide resistance.

Plants produce cytotoxic compounds to which they are susceptible, and are exposed to exogenous toxins (microbial products, allelochemicals, and agrochemicals) making cell survival contingent on mechanisms for detoxifying these agents. One detoxification mechanism is the glutathione S-transferase-catalyzed glutathionation of the toxin, or an activated derivative, and transport of the conjugate out of the cytosol. The glutathione S-conjugate (GS-X) pump family is a new class of ATP-binding cassette (ABC) transporters responsible for the elimination and/or sequestration of pharmacologically and agronomically important compounds in mammalian, yeast and plant cells. The molecular structure and function of GS-X pumps encoded by mammalian and plant MRP, cMOAT (canalicular multispecific anion transporter), and YCF1 (yeast cadmium factor) genes have been conserved throughout molecular evolution. The physiologic function of GS-X pumps is closely related to cellular detoxification, oxidative stress, inflammation, and cancer drug resistance. Coordinated expression of GS-X pump genes, such as MRP1 and YCF1, and gamma-glutamylcystaine synthetase, a rate-limiting enzyme of cellular glutathione biosynthesis, is frequently observed (Ishikawa T. et al. (1997) *Biosci. Rep.* 17:189–207).

Four expressed sequence tags identified from an Arabidopsis cDNA library have deduced amino acid sequences which are highly similar to MRP and YCF1. These genes are differentially expressed in response to treatments of Arabidopsis with several herbicides, heavy metals and other toxic compounds indicating the involvement of different ABC transporters in different-detoxification mechanisms. The full-length cDNA from one of these ESTs (named AtMRP) has been sequenced and this information is present in GenBank (Accession No. U92650). At the amino acid level AtMRP is 34% identical to both MRP and YCF1 but its biochemical function has not been demonstrated (Tommasini, R. et al. (1997) *FEBS Lett.* 411:206–210).

An AtMRP1 gene which encodes a transporter responsible for the removal of glutathione S-conjugates from the cytosol has been isolated and sequenced. The AtMRP1 gene encodes an ABC transporter competent in the transport of glutathione S-conjugates of xenobiotics and endogenous substances, including herbicides and anthocyanins (Lu, Y. P. et al. (1997) *Proc Natl Acad Sci USA* 94:8243–8248). AtMRP1 possesses the same overall domain organization as HmMRP1 and ScYCF1. These three ABC transporters catalyze Mg-ATP-energized, vanadate-inhibitable transport of GS conjugates. A cDNA encoding a putative ABC transporter from Arabidopsis, AtMRP1 (not necessarily the same one as above), was identified based on sequence similarities to mammalian MRP1 (Marin, E. et al. (1998) *Biochim Biophys Acta* 1369:7–13).

Another gene, AtMRP2, from Arabidopsis has been isolated which is 87% identical at the amino acid level to AtMRP1 described by Lu et al. (1997) *Proc Natl Acad Sci USA* 94:8243–8248. This gene belongs to the same subclass of ABC transporter genes as AtMRP1, and its heterologous expression in yeast also confers Mg-ATP-energized GS conjugate transport. Besides transporting glutathione conjugates, AtMRP2 transports at high capacity Bn-NCC-1, a malonyl ester of the predominant nonfluorescent chlorophyll catabolite from *Brassica napus.* AtMRP2 simultaneously transports Bn-NCC-1 and GS conjugates without either substrate interfering with the transport of the other suggesting that the same pump may have both functions (Lu, Y. P. (1998) *Plant Cell* 10:267–282).

AtMRP3, another ABC-transporter from *Arabidopsis thaliana* exhibits high sequence similarity to the human (MRP1) and yeast (YCF1) glutathione-conjugate transporters and complements a cadmium-sensitive yeast mutant that also lacks glutathione-conjugate transport activity. The kinetic properties of AtMRP3 are very similar to those described for the vacuolar glutathione-conjugate transporter of barley and mung bean. AtMRP3 also is involved in the uptake of the chlorophyll catabolite Bn-NCC-1 (Tommasini, R. et al. (1998) *Plant J.* 13:773–780).

Also forming part of the *Arabidopsis thaliana* MRP gene family, encoding a putative GS-X pump, is AtMRP4. The derived amino acid sequence from AtMRP4 shares high levels of similarity (55–63%) with human, yeast, and other Arabidopsis homologues. Expression of the different members of the AtMRP gene family in Arabidopsis cell suspensions after treatment with chemicals that modify glutathione metabolism (compounds that induce different types of stress and that act as herbicide antidotes- safenus- in monocotyledonous species) reveals that the members of this gene family are differentially regulated (Sanchez-Fernandez, R. (1998) *Mol. Gen. Genet:* 258:655–662).

SUMMARY OF THE INVENTION

An isolated polynucleotide comprising a first nucleotide sequence selected from the group consisting of: (a) first nucleotide sequence encoding a polypeptide of at least 30 amino acids that has at least 80% identity based on the Clustal method of alignment when compared to a polypeptide selected from the group consisting of SEQ ID NOs:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202 and 204; or (b) a second nucleotide sequence comprising a complement of the first nucleotide sequence.

The present invention concerns an isolated polynucleotide comprising a nucleotide sequence selected from the group consisting of: (a) a first nucleotide sequence encoding a polypeptide of at least 351 amino acids having at least 80% identity based on the Clustal method of alignment when compared to a polypeptide selected from the group consisting of SEQ ID NOs:2, 4, 6, and 8, 50, 82, 100 and (b) a second nucleotide sequence comprising the complement of the first nucleotide sequence.

The present invention also concerns an isolated polynucleotide comprising a nucleotide sequence selected from the group consisting of: (a) a first nucleotide sequence encoding a polypeptide of at least 72 amino acids having at least 80% identity based on the Clustal method of alignment when compared to a polypeptide selected from the group consisting of SEQ ID NOs:12, 16, 18, 20, 22, 24, 26 and 28, and (b) a second nucleotide sequence comprising the complement of the first nucleotide sequence.

The present invention also concerns an isolated polynucleotide comprising a nucleotide sequence selected from the group consisting of: (a) a first nucleotide sequence encoding a polypeptide of at least 110 amino acids having at least 80% identity based on the Clustal method of alignment when compared to a polypeptide selected from the group consisting of SEQ ID NOs:10, 32, 36, 38, 40, 42, 44, 46, 48, 52, 60, 102, 104, 124 and (b) a second nucleotide sequence comprising the complement of the first nucleotide sequence.

The present invention also concerns an isolated polynucleotide comprising a nucleotide sequence selected from the group consisting of: (a) a first nucleotide sequence encoding a polypeptide of at least 189 amino acids having at least 80% identity based on the Clustal method of alignment when compared to a polypeptide selected from the group consisting of SEQ ID NOs:14, 34, 62, 64, 66, 68, 70, 72, 74, 76, 78, 80, 120, 122 and (b) a second nucleotide sequence comprising the complement of the first nucleotide sequence.

The present invention also concerns an isolated polynucleotide comprising a nucleotide sequence selected from the group consisting of: (a) a first nucleotide sequence encoding a polypeptide of at least 67 amino acids having at least 80% identity based on the Clustal method of alignment when compared to a polypeptide selected from the group consisting of SEQ ID NOs:84, 86, 88, 90, 92, 94 and 96, and (b) a second nucleotide sequence comprising the complement of the first nucleotide sequence.

The present invention also concerns an isolated polynucleotide comprising a nucleotide sequence selected from the group consisting of: (a) a first nucleotide sequence encoding a polypeptide of at least 87 amino acids having at least 80% identity based on the Clustal method of alignment when compared to a polypeptide selected from the group consisting of SEQ ID NOs:98, 110, 112, 114, 116 and 118, and (b) a second nucleotide sequence comprising the complement of the first nucleotide sequence.

The present invention also concerns an isolated polynucleotide comprising a nucleotide sequence selected from the group consisting of: (a) a first nucleotide sequence encoding a polypeptide of at least 155 amino acids having at least 80% identity based on the Clustal method of alignment when compared to a polypeptide selected from the group consisting of SEQ ID NOs:128, 130, 132, 134, and (b) a second nucleotide sequence comprising the complement of the first nucleotide sequence.

The present invention also concerns an isolated polynucleotide comprising a nucleotide sequence selected from the group consisting of: (a) a first nucleotide sequence encoding a polypeptide of at least 161 amino acids having at least 80% identity based on the Clustal method of alignment when compared to a polypeptide selected from the group consisting of SEQ ID NOs:54, 136, 138, 140, 142 144, and (b) a second nucleotide sequence comprising the complement of the first nucleotide sequence.

The present invention also concerns an isolated polynucleotide comprising a nucleotide sequence selected from the group consisting of: (a) a first nucleotide sequence encoding a polypeptide of at least 66 amino acids having at least 80% identity based on the Clustal method of alignment when compared to a polypeptide selected from the group consisting of SEQ ID NOs:146, 148, 150, 152, 154, 156, 158, 160, 162, 164, 166 168 and (b) a second nucleotide sequence comprising the complement of the first nucleotide sequence.

The present invention also concerns an isolated polynucleotide comprising a nucleotide sequence selected from the group consisting of: (a) a first nucleotide sequence encoding a polypeptide of at least 141 amino acids having at least 80% identity based on the Clustal method of alignment when compared to a polypeptide selected from the group consisting of SEQ ID NOs:58, 106, 170, 172, 174, 176, 178, 180, 182 and 184 or (b) a second nucleotide sequence comprising the complement of the first nucleotide sequence.

The present invention also concerns an isolated polynucleotide comprising a nucleotide sequence selected from the group consisting of: (a) a first nucleotide sequence encoding a polypeptide of at least 81 amino acids having at least 80% identity based on the Clustal method of alignment when compared to a polypeptide selected from the group consisting of SEQ ID NOs:186, 188, 190, 192, 194, 196, 198, 200, 202, 204 and (b) a second nucleotide sequence comprising the complement of the first nucleotide sequence.

The present invention also concerns an isolated polynucleotide comprising a nucleotide sequence selected from the group consisting of (a) a first nucleotide sequence encoding a polypeptide of at least 48 amino acids having at least 80% identity based on the Clustal method of alignment when compared to a polypeptide selected from the group consisting of SEQ ID NOs:30, 56, 108, and (b) a second nucleotide sequence comprising the complement of the first nucleotide sequence.

In a second embodiment, it is preferred that the isolated polynucleotide of the claimed invention comprises a nucleotide sequence which comprises a nucleic acid sequence selected from the group consisting of SEQ ID NOs:1, 3, 5, 7, 49, 81 and 99 that codes for the polypeptide selected from the group consisting of SEQ ID NOs:2, 4, 6, 8, 50, 82 and 100.

Also in a second embodiment, it is preferred that the isolated polynucleotide of the claimed invention comprises a first nucleotide sequence which comprises a nucleic acid sequence selected from the group consisting of SEQ ID NOs:11, 15, 17, 19, 21, 23, 25 and 27 that codes for the polypeptide selected from the group consisting of SEQ ID NOs:12, 16, 18, 20, 22, 24, 26 and 28.

Also in a second embodiment, it is preferred that the isolated polynucleotide of the claimed invention comprises a nucleotide sequence which comprises a nucleic acid sequence selected from the group consisting of SEQ ID NOs:9, 31, 35, 37, 39, 41, 43, 45, 47, 51, 59, 101, 103 and 123 that codes for the polypeptide selected from the group consisting of SEQ ID NOs:10, 32, 36, 38, 40, 42, 44, 46, 48, 52, 60, 102, 104, and 124.

Also in a second embodiment, it is preferred that the isolated polynucleotide of the claimed invention comprises a nucleotide sequence which comprises a nucleic acid sequence selected from the group consisting of SEQ ID NOs:13, 33, 61, 63, 65, 67, 69, 71, 73, 75, 77, 79, 119 and 121 that codes for the polypeptide selected from the group consisting of SEQ ID NOs:14, 34, 62, 64, 66, 68, 70, 72, 74, 76, 78, 80, 120 and 122.

Also in a second embodiment, it is preferred that the isolated polynucleotide of the claimed invention comprises a nucleotide sequence which comprises a nucleic acid sequence selected from the group consisting of SEQ ID NOs:83, 85, 87, 89, 91, 93 and 95 that codes for the polypeptide selected from the group consisting of SEQ ID NOs:84, 86, 88, 90, 92, 94 and 96.

Also in a second embodiment, it is preferred that the isolated polynucleotide of the claimed invention comprises a nucleotide sequence which comprises a nucleic acid sequence selected from the group consisting of SEQ ID NOs:97, 109, 111, 113, 115 and 117 that codes for the polypeptide selected from the group consisting of SEQ ID NOs:98, 110, 112, 114, 116 and 118.

Also in a second embodiment, it is preferred that the isolated polynucleotide of the claimed invention comprises a nucleotide sequence which comprises a nucleic acid sequence selected from the group consisting of SEQ ID NOs:127, 129, 131 and 133 that codes for the polypeptide selected from the group consisting of SEQ ID NOs: 128, 130, 132 and 134.

Also in a second embodiment, it is preferred that the isolated polynucleotide of the claimed invention comprises a nucleotide sequence which comprises a nucleic acid sequence selected from the group consisting of SEQ ID NOs:53, 135, 137, 139, 141 and 143 that codes for the polypeptide selected from the group consisting of SEQ ID NOs:54, 136, 138, 140, 142 and 144.

Also in a second embodiment, it is preferred that the isolated polynucleotide of the claimed invention comprises a nucleotide sequence which comprises a nucleic acid sequence selected from the group consisting of SEQ ID NOs:145, 147, 149, 151, 153, 155, 157, 159, 161, 163, 165 and 167 that codes for the polypeptide selected from the group consisting of SEQ ID NOs:146, 148, 150, 152, 154, 156, 158, 160, 162, 164, 166 and 168.

Also in a second embodiment, it is preferred that the isolated polynucleotide of the claimed invention comprises a nucleotide sequence which comprises a nucleic acid sequence selected from the group consisting of SEQ ID NOs:57, 105, 169, 171, 173, 175, 177, 179, 181 and 183 that codes for the polypeptide selected from the group consisting of SEQ ID NOs:58, 106, 170, 172, 174, 176, 178, 180, 182 and 184.

Also in a second embodiment, it is preferred that the isolated polynucleotide of the claimed invention comprises a nucleotide sequence which comprises a nucleic acid sequence selected from the group consisting of SEQ ID NOs:185, 187, 189, 191, 193, 195, 197, 199, 201 and 203 that codes for the polypeptide selected from the group consisting of SEQ ID NOs:186, 188, 190, 192, 194, 196, 198, 200, 202 and 204.

Also in a second embodiment, it is preferred that the isolated polynucleotide of the invention comprises a first nucleotide sequence which comprises a nucleic acid sequence selected from the group consisting of SEQ ID NOs:29, 55 and 107, that codes for the polypeptide selected from the group consisting of SEQ ID NOs:30, 56 and 108.

In a third embodiment, this invention concerns an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183 185, 187, 189, 191, 193, 195, 197, 199, 201 and 203 and the complement of such nucleotide sequences.

In a fourth embodiment, this invention relates to a chimeric gene comprising an isolated polynucleotide of the present invention operably linked to at least one suitable regulatory sequence.

In a fifth embodiment, the present invention concerns a host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

In a sixth embodiment, the invention also relates to a process for producing a host cell comprising a chimeric gene of the present invention or an isolated polynucleotide of the present invention, the process comprising either transforming or transfecting a compatible host cell with a chimeric gene or isolated polynucleotide of the present invention.

In a seventh embodiment, the invention concerns a polypeptide of at least 351 amino acids comprising at least 80% identity based on the Clustal method of alignment compared to a polypeptide selected from the group consisting of SEQ ID NOs:2, 4, 6, 8, 50, 82, and 100.

Also in a seventh embodiment, the invention concerns a polypeptide of at least 72 amino acids comprising at least 80% identity based on the Clustal method of alignment compared to a polypeptide selected from the group consisting of SEQ ID NOs:12, 16, 18, 20, 22, 24, 26 and 28.

Also in a seventh embodiment, the invention concerns a polypeptide of at least 110 amino acids comprising at least 80% identity based on the Clustal method of alignment compared to a polypeptide selected from the group consisting of SEQ ID NOs:10, 32, 36, 38, 40, 42, 44, 46, 48, 52, 60, 102, 104 and 124.

Also in a seventh embodiment, the invention concerns a polypeptide of at least 189 amino acids comprising at least 80% identity based on the Clustal method of alignment compared to a polypeptide selected from the group consisting of SEQ ID NOs:14, 34, 62, 64, 66, 68, 70, 72, 74, 76, 78, 80, 120 and 122.

Also in a seventh embodiment, the invention concerns a polypeptide of at least 67 amino acids comprising at least 80% identity based on the Clustal method of alignment compared to a polypeptide selected from the group consisting of SEQ ID NOs:84, 86, 88, 90, 92, 94 and 96.

Also in a seventh embodiment, the invention concerns a polypeptide of at least 87 amino acids comprising at least 80% identity based on the Clustal method of alignment compared to a polypeptide selected from the group consisting of SEQ ID NOs:98, 110, 112, 114, 116 and 118.

Also in a seventh embodiment, the invention concerns a polypeptide of at least 155 amino acids comprising at least 80% identity based on the Clustal method of alignment compared to a polypeptide selected from the group consisting of SEQ ID NOs: 128, 130, 132 and 134.

Also in a seventh embodiment, the invention concerns a polypeptide of at least 161 amino acids comprising at least 80% identity based on the Clustal method of alignment compared to a polypeptide selected from the group consisting of SEQ ID NOs:54, 136, 138, 140, 142 and 144.

Also in a seventh embodiment, the invention concerns a polypeptide of at least 66 amino acids comprising at least 80% identity based on the Clustal method of alignment compared to a polypeptide selected from the group consisting of SEQ ID NOs:146, 148, 150, 152, 154, 156, 158, 160, 162, 164, 166 and 168.

Also in a seventh embodiment, the invention concerns a polypeptide of at least 141 amino acids comprising at least 80% identity based on the Clustal method of alignment compared to a polypeptide selected from the group consisting of SEQ ID NOs:58, 106, 170, 172, 174, 176, 178, 180, 182 and 184.

Also in a seventh embodiment, the invention concerns a polypeptide of at least 81 amino acids comprising at least 80% identity based on the Clustal method of alignment compared to a polypeptide selected from the group consisting of SEQ ID NOs:186, 188, 190, 192, 194, 196, 198, 200, 202 and 204.

Also in a seventh embodiment, the invention concerns a polypeptide of at least 48 amino acids comprising at least 80% identity based on the Clustal method of alignment compared to a polypeptide selected from the group consisting of SEQ ID NOs:30, 56 and 108.

In an eighth embodiment, the invention relates to a method of selecting an isolated polynucleotide that affects the level of expression of a dioxygenase, Ent-kaurene synthase A, Ent-Kaurene synthase B, GA-20 or Gibberellin 3-beta Hydroxylase, GTP cyclohydrolase II/3,4-dihydroxy-2-butanone-4-phosphate, riboflavin specific deaminase, ethylene response factor, acyl-CoA thioesterase, GCN20-like ABC transporter, PDR5-like ABC transporter, P-glycoprotein, ABC transporter or MRP4 ABC transporter polypeptide or enzyme activity in a host cell, preferably a plant cell, the method comprising the steps of: (a) constructing an isolated polynucleotide of the present invention or a chimeric gene of the present invention; (b) introducing the isolated polynucleotide or the chimeric gene into a host cell; (c) measuring the level of the dioxygenase, Ent-kaurene synthase A, Ent-Kaurene synthase B, GA-20 or Gibberellin 3-beta Hydroxylase, GTP cyclohydrolase II/3,4-dihydroxy-2-butanone-4-phosphate, riboflavin specific deaminase, ethylene response factor, acyl-CoA thioesterase, GCN20-like ABC transporter, PDR5-like ABC transporter, P-glycoprotein, ABC transporter or MRP4 ABC transporter polypeptide or enzyme activity in the host cell containing the isolated polynucleotide; and (d) comparing the level of the dioxygenase, Ent-kaurene synthase A, Ent-Kaurene synthase B, GA-20 or Gibberellin 3-beta Hydroxylase, GTP cyclohydrolase II/3,4-dihydroxy-2-butanone-4-phosphate, riboflavin specific deaminase, ethylene response factor, acyl-CoA thioesterase, GCN20-like ABC transporter, PDR5-like ABC transporter, P-glycoprotein, ABC transporter or MRP4 ABC transporter polypeptide or enzyme activity in the host cell containing the isolated polynucleotide with the level of the dioxygenase, Ent-kaurene synthase A, Ent-Kaurene synthase B, GA-20 or Gibberellin 3-beta Hydroxylase, GTP cyclohydrolase II/3,4-dihydroxy-2-butanone-4-phosphate, riboflavin specific deaminase, ethylene response factor, acyl-CoA thioesterase, GCN20-like ABC transporter, PDR5-like ABC transporter, P-glycoprotein, ABC transporter or MRP4 ABC transporter polypeptide or enzyme activity in the host cell that does not contain the isolated polynucleotide.

In a ninth embodiment, the invention concerns a method of obtaining a nucleic acid fragment encoding a substantial portion of a dioxygenase, Ent-kaurene synthase A, Ent-Kaurene synthase B, GA-20 or Gibberellin 3-beta Hydroxylase, GTP cyclohydrolase II/3,4-dihydroxy-2-butanone-4-phosphate, riboflavin specific deaminase, ethylene response factor, acyl-CoA thioesterase, GCN20-like ABC transporter, PDR5-like ABC transporter, P-glycoprotein, ABC transporter or MRP4 ABC transporter polypeptide, preferably a plant dioxygenase, Ent-kaurene synthase A, Ent-Kaurene synthase B, GA-20 or Gibberellin 3-beta Hydroxylase, GTP cyclohydrolase II/3,4-dihydroxy-2-butanone-4-phosphate, riboflavin specific deaminase, ethylene response factor, acyl-CoA thioesterase, GCN20-like ABC transporter, PDR5-like ABC transporter, P-glycoprotein, ABC transporter or MRP4 ABC transporter polypeptide, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID: NOs: dioxygenase, Ent-kaurene synthase A, Ent-Kaurene synthase B, GA-20 or Gibberellin 3-beta Hydroxylase, GTP cyclohydrolase II/3,4-dihydroxy-2-butanone-4-phosphate, riboflavin specific deaminase, ethylene response factor, acyl-CoA thioesterase, GCN20-like ABC transporter, PDR5-like ABC transporter, P-glycoprotein, ABC transporter or MRP4 ABC transporter, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a dioxygenase, Ent-kaurene synthase A, Ent-Kaurene synthase B, GA-20 or Gibberellin 3-beta Hydroxylase, GTP cyclohydrolase II/3,4-dihydroxy-2-butanone-4-phosphate, riboflavin specific deaminase, ethylene response factor, acyl-CoA thioesterase, GCN20-like ABC transporter, PDR5-like ABC transporter, P-glycoprotein, ABC transporter or MRP4 ABC transporter amino acid sequence.

In a tenth embodiment, this invention relates to a method of obtaining a nucleic acid fragment encoding all or a substantial portion of the amino acid sequence encoding a dioxygenase, Ent-kaurene synthase A, Ent-Kaurene synthase B, GA-20 or Gibberellin 3-beta Hydroxylase, GTP cyclohydrolase II/3,4-dihydroxy-2-butanone-4-phosphate, riboflavin specific deaminase, ethylene response factor, acyl-CoA thioesterase, GCN20-like ABC transporter, PDR5-like ABC transporter, P-glycoprotein, ABC transporter or MRP4 ABC transporter polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In an eleventh embodiment, this invention concerns a composition, such as a hybridization mixture, comprising an isolated polynucleotide or polypeptide of the present invention.

In a twelfth embodiment, this invention concerns a method for positive selection of a transformed cell comprising: (a) transforming a host cell with the chimeric gene of the present invention or a construct of the present invention; and (b) growing the transformed host cell, preferably a plant cell, such as a monocot or a dicot, under conditions which allow expression of the dioxygenase, Ent-kaurene synthase A, Ent-Kaurene synthase B, GA-20 or Gibberellin 3-beta Hydroxylase, GTP cyclohydrolase II/3,4-dihydroxy-2-butanone-4-phosphate, riboflavin specific deaminase, ethylene response factor, acyl-CoA thioesterase, GCN20-like ABC transporter, PDR5-like ABC transporter, P-glycoprotein, ABC transporter or MRP4 ABC transporter polynucleotide in an amount sufficient to complement a null mutant to provide a positive selection means.

In a thirteenth embodiment, this invention relates to a method of altering the level of expression of a metabolism protein in a host cell comprising: (a) transforming a host cell with a chimeric gene of the present invention; and (b) growing the transformed host cell under conditions that are suitable for expression of the chimeric gene wherein expression of the chimeric gene results in production of altered levels of the metabolism proteins in the transformed host cell.

BRIEF DESCRIPTION OF THE SEQUENCE LISTINGS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS").

Nucleotide sequences, SEQ ID NOs:1, 3, 5 and 7 and amino acid sequences SEQ ID NOs:2, 4, 6 and 8 were determined by further sequence analysis of cDNA clones encoding the amino acid sequences set forth in SEQ ID NOs:10, 12, 14 and 16. Nucleotide SEQ ID NOs:9, 11, 13 and 15 amino acid SEQ ID NOs:10, 12, 14 and 16 were presented in a U.S. Provisional Application No. 60/143,401, filed Jul. 12, 1999.

Nucleotide sequences, SEQ ID NOs:17, 21 and 23 and amino acid sequences SEQ ID NOs:18, 20 and 24 were determined by further sequence analysis of cDNA clones encoding the amino acid sequences set forth in SEQ ID NOs:30, 32 and 34. Nucleotide SEQ ID NOs:25, 27, 29, 31 and 33 amino acid SEQ ID NOs:26, 28, 30, 32 and 34 were presented in a U.S. Provisional Application No. 60/143,412, filed Jul. 12, 1999.

Nucleotide sequences, SEQ ID NOs:35, 37, 39, 41, 43 and 45 and amino acid sequences SEQ ID NOs:36, 38, 40, 42, 44 and 46 were determined by further sequence analysis of cDNA clones encoding the amino acid sequences set forth in SEQ ID NOs:50, 52, 54, 56, 58 and 60. Nucleotide SEQ ID NOs:47, 49, 51. 53. 55, 57 and 59 amino acid SEQ ID NOs:48, 50, 52, 54, 56, 58 and 60 were presented in a U.S. Provisional Application No. 60/146,650 filed Jul. 30, 1999.

Nucleotide sequence, SEQ ID NO:69 and amino acid sequence SEQ ID NO:70, were determined by further sequence analysis of cDNA clones encoding the amino acid sequence set forth in SEQ ID NO:82. Nucleotide SEQ ID NOs:65, 73 and 81 amino acid SEQ ID NOs:66, 74 and 82 were presented in a U.S. Provisional Application No. 60/170,906 filed Dec. 14, 1999.

Nucleotide sequences, SEQ ID NOs:85, 87, 89, 91, 93 and 95 and amino acid sequences SEQ ID NOs:84, 86, 88, 90, 92, 94 and 96, were determined by further sequence analysis of cDNA clones encoding the amino acid sequences set forth in SEQ ID NOs:100, 102, 104, 106, 108 and 110. Nucleotide SEQ ID NOs:97, 99, 101, 103, 105, 107 and 109 and amino acid SEQ ID NOs:98, 100, 102, 104, 106, 108 and 110 were presented in a U.S. Provisional Application No. 60/172,959 filed Dec. 21, 1999.

Nucleotide sequences, SEQ ID NOs:109, 111, 115 and 117 and amino acid sequences SEQ ID NOs:110, 112, 116 and 118, were determined by further sequence analysis of cDNA clones encoding the amino acid sequences set forth in SEQ ID NO:120, 122, 124 and 126. Nucleotide SEQ ID NOs:113, 119, 121, 123 and 125 amino acid SEQ ID NOs:114, 120, 122, 124 and 126 were presented in a U.S. Provisional Application No. 60/172,946 filed Dec. 21, 1999.

TABLE 1

Metabolism Proteins

| Protein | Clone Designation | SEQ ID NO: (Nucleotide) | SEQ ID NO: (Amino Acid) |
|---|---|---|---|
| Dioxygenase | p0128.cpiac95r (CGS) | 1 | 2 |
| Dioxygenase | rr1.pk0049.e8 (CGS) | 3 | 4 |
| Dioxygenase | src3c.pk010.b10 (CGS) | 5 | 6 |
| Dioxygenase | w1e1n.pk0078.d6 (CGS) | 7 | 8 |
| Dioxygenase | p0128.cpiac95r (EST) | 9 | 10 |
| Dioxygenase | rr1.pk0049.e8 (EST) | 11 | 12 |
| | Contig composed of:<br>se3.pk0036.f9<br>src2c.pk003.h10<br>src2c.pk003.17<br>src2c.pk011.f20 | 13 | 14 |

TABLE 1-continued

Metabolism Proteins

| Protein | Clone Designation | SEQ ID NO: (Nucleotide) | SEQ ID NO: (Amino Acid) |
|---|---|---|---|
| | src2c.pk016.g24 | | |
| | src2c.pk021.120 | | |
| | src2c.pk029.g20 | | |
| | src3c.pk001.k23 | | |
| | src3c.pk007.p21 | | |
| | src3c.pk010.b10 | | |
| | src3c.pk016.g17 | | |
| | src3c.pk021.i7 | | |
| | src3c.pk023.j17 | | |
| | srr1c.pk001.o3 | | |
| | srr2c.pk001.b6 | | |
| | ss1.pk0002.e3 | | |
| Dioxygenase | w1e1n.pk0078.d6 (EST) | 15 | 16 |
| Ent-Kaurene Synthase A | r10n.pk111.f7 (FIS) | 17 | 18 |
| Ent-Kaurene Synthase A | ytc055c.pk001.j11.f (EST) | 19 | 20 |
| Ent-Kaurene Synthase A | sf11.pk135.m11 (CGS) | 21 | 22 |
| Ent-Kaurene Synthase B | Contig composed of: p0014.ctutf13r p0014.ctutf13rb p0083.cldec87r p0117.chclk47ra p0121.cfrmf53r | 23 | 24 |
| Ent-Kaurene Synthase B | rs11n.pk010.m8 (EST) | 25 | 26 |
| Ent-Kaurene Synthase B | wre1n.pk0102.e7 (EST) | 27 | 28 |
| Ent-Kaurene Synthase A | r10n.pk111.f7 (EST) | 29 | 30 |
| Ent-Kaurene Synthase A | sf11.pk135.m11 (EST) | 31 | 32 |
| Ent-Kaurene Synthase B | Contig composed of: p0014.ctutf13rb p0083.cldec87r p0117.chclk47ra p0121.cfrmf53r | 33 | 34 |
| GA-20 Oxidase | p0128.cpide86r (CGS) | 35 | 36 |
| | rds2c.pk010.n9 (CGS) | 37 | 38 |
| | se2.pk0011.a6 (FIS) | 39 | 40 |
| Gibberellin 3-beta Hydroxylase | cen3n.pk0019.d10 (FIS) | 41 | 42 |
| Gibberellin 3-beta Hydroxylase | se4.pk0034.g5 (CGS) | 43 | 44 |
| Gibberellin 3-beta Hydroxylase | wdk1c.pk0004.f8 (FIS) | 45 | 46 |
| Gibberellin 3-beta Hydroxylase | wlm96.pk043.m13 (EST) | 47 | 48 |
| GA-20 Oxidase | Contig composd of: cbn10.pk0055.e7 cbn10.pk0061.a4 cco1n.pk084.i6 cen3n.pk0196.g3 cen3n.pk0211.h10 cr1n.pk0018.e6 p0044.cjrai81r p0085.cscag24r p0119.cmtoh11r p0128.cpide86r | 49 | 50 |
| GA-20 Oxidase | rds2c.pk010.n9 (EST) | 51 | 52 |
| GA-20 Oxidase | se2.pk0011.a6 (EST) | 53 | 54 |
| Gibberellin 3-beta Hydroxylase | cen3n.pk0019.d10 (EST) | 55 | 56 |
| Gibberellin 3-beta Hydroxylase | se5.pk0039.b1 (EST) | 57 | 58 |
| Gibberellin 3-beta Hydroxylase | wdk1c.pk0004.f8 (EST) | 59 | 60 |
| GTP Cyclohydrolase II/3,4-dihydroxy-2-butanone-4-phosphate synthase | cp1c.pk004.k22 (CGS) | 61 | 62 |
| GTP Cyclohydrolase II/3,4-dihydroxy-2-butanone-4-phosphate synthase | cta1.pk0006.g8 (FIS) | 63 | 64 |
| GTP Cyclohydrolase II/3,4-dihydroxy-2-butanone-4-phosphate synthase | p0126.cnlbv55r (CGS) | 65 | 66 |
| GTP Cyclohydrolase II/3,4-dihydroxy-2-butanone-4-phosphate synthase | r10n.pk0033.e3 (FIS) | 67 | 68 |

TABLE 1-continued

Metabolism Proteins

| Protein | Clone Designation | SEQ ID NO: (Nucleotide) | SEQ ID NO: (Amino Acid) |
|---|---|---|---|
| GTP Cyclohydrolase II/3,4-dihydroxy-2-butanone-4-phosphate synthase | Contig (CGS) composed of: r10n.pk0061.b10 rtc1c.pk005.k11.f | 69 | 70 |
| GTP Cyclohydrolase II/3,4-dihydroxy-2-butanone-4-phosphate synthase | sre.pk0017.d6 (CGS) | 71 | 72 |
| GTP Cyclohydrolase II/3,4-dihydroxy-2-butanone-4-phosphate synthase | wle1n.pk0091.e7 (FIS) | 73 | 74 |
| Riboflavin specific deaminase | cs1.pk0038.d1 (FIS) | 75 | 76 |
| Riboflavin specific deaminase | rls6.pk0005.a8 (FIS) | 77 | 78 |
| Riboflavin Specific Deaminase | wdk1c.pk008.d16 (FIS) | 79 | 80 |
| GTP Cyclohydrolase II/3,4-dihydroxy-2-butanone-4-phosphate synthase | r10n.pk0061.b10 (FIS) | 81 | 82 |
| Ethylene Response Factor/ Ethylene Receptor Gene | cep7.pk0016.h9 (EST) | 83 | 84 |
| Ethylene Response Factor/ Ethylene Receptor Gene | p0119.cmtnf84r (CGS) | 85 | 86 |
| Ethylene Response Factor/ Ethylene Receptor Gene | p0128.cpiar27r (CGS) | 87 | 88 |
| Ethylene Response Factor/ Ethylene Receptor Gene | r10n.pk114.d10 (CGS) | 89 | 90 |
| Ethylene Response Factor/ Ethylene Receptor Gene | scb1c.pk004.g21 (CGS) | 91 | 92 |
| Ethylene Response Factor/ Ethylene Receptor Gene | sdp2c.pk003.a21 (FIS) | 93 | 94 |
| Ethylene Response Factor/ Ethylene Receptor Gene | wdk3c.pk023.i19 (CGS) | 95 | 96 |
| Ethylene Response Factor/ Ethylene Receptor Gene | p0119.cmtnf84r (EST) | 97 | 98 |
| Ethylene Response Factor/ Ethylene Receptor Gene | Contig (CGS) of: cbn10.pk0015.b5 cco1.pk0035.d12 p0031.ccmar94r p0031.ccmar94rx p0059.cmsba25r p0072.comgu73rb p0107.cbcas83r p0110.cgsmr50r p0110.cgsnq75r p0110.cgsnq76r p0125.czaab26r p0128.cpiar27r | 99 | 100 |
| Ethylene Response Factor/ Ethylene Receptor Gene | r10n.pk114.d10 (EST) | 101 | 102 |
| Ethylene Response Factor/ Ethylene Receptor Gene | scb1c.pk004.g21 (EST) | 103 | 104 |
| Ethylene Response Factor/ Ethylene Receptor Gene | sdp2c.pk003.a21 (EST) | 105 | 106 |
| Ethylene Response Factor/ Ethylene Receptor Gene | wdk3c.pk023.i19 (EST) | 107 | 108 |
| Acyl-CoA Thioesterase II | Contig composed of: cbn10.pk0023.h4 (FIS) cpi1c.pk014.m16 (EST) | 109 | 110 |
| Acyl-CoA Thioesterase II | r1r48.pk0025.c4 (CGS) | 111 | 112 |
| Acyl-CoA Thioesterase II | sgs4c.pk004.e3 (EST) | 113 | 114 |
| Acyl-CoA Thioesterase II | src2c.pk001.c19 (CGS) | 115 | 116 |
| Acyl-CoA Thioesterase II | Contig (CGS) composed of: ses8w.pk0009.g12 src2c.pk001.g10 | 117 | 118 |
| Acyl-CoA Thioesterase II | Contig of: cbn10.pk0023.h4 (FIS) cpi1c.pk014.m16 (EST) | 119 | 120 |
| Acyl-CoA Thioesterase II | r1r48.pk0025.c4 (FIS) | 121 | 122 |
| Acyl-CoA Thioesterase II | Contig of: ses8w.pk0009.g12, src2c.pk001.g10 (FIS) | 123 | 124 |

TABLE 1-continued

Metabolism Proteins

| Protein | Clone Designation | SEQ ID NO: (Nucleotide) | SEQ ID NO: (Amino Acid) |
|---|---|---|---|
| Acyl-CoA Thioesterase II | Contig of: src2c.pk001.c19, src2c.pk006.p3 | 125 | 126 |
| ABC Transporter GCN20-like | ccase-b.pk0001.a3 (FIS) | 127 | 128 |
| ABC Transporter GCN20-like | rr1.pk0051.a2 (FIS) | 129 | 130 |
| ABC Transporter GCN20-like | ssm.pk0059.d10 (FIS) | 131 | 132 |
| ABC Transporter GCN20-like | wre1n.pk0104.f8 (FIS) | 133 | 134 |
| ABC Transporter PDR5-like | cr1n.pk0147.b9 (FIS) | 135 | 136 |
| ABC Transporter PDR5-like | cs1.pk0080.b11 (FIS) | 137 | 138 |
| ABC Transporter PDR5-like | rls48.pk0025.d10 (FIS) | 139 | 140 |
| ABC Transporter PDR5-like | srr2c.pk003.j11 (FIS) | 141 | 142 |
| ABC Transporter PDR5-like | wr1.pk0083.d6 (FIS) | 143 | 144 |
| P-glycoprotein I | cen3n.pk0005.f9 (EST) | 145 | 146 |
| P-glycoprotein I | chpc24.pk0004.b2 (EST) | 147 | 148 |
| P-glycoprotein I | cs1.pk0051.e12 (FIS) | 149 | 150 |
| P-glycoprotein 1 | wle1n.pk0068.c6 (EST) | 151 | 152 |
| P-glycoprotein I | wr1.pk0099.h10 (FIS) | 153 | 154 |
| P-glycoprotein 3 | cs1.pk0067.d8 (EST) | 155 | 156 |
| P-glycoprotein ATPGP | cr1n.pk0002.a6 (FIS) | 157 | 158 |
| P-glycoprotein ATPGP | cr1n.pk0195.h6 (FIS) | 159 | 160 |
| P-glycoprotein ATPGP | sfl1.pk0062.d9 (FIS) | 161 | 162 |
| P-glycoprotein ATPGP | ssm.pk0028.g8 (EST) | 163 | 164 |
| P-glycoprotein HVMDR2 | r10n.pk0010.g12 (EST) | 165 | 166 |
| P-glycoprotein HVMDR2 | srr1c.pk001.d13 (FIS) | 167 | 168 |
| ABC Transporter | Contig (CGS) composed of: cco1.pk0025.b9 cpf1c.pk003.15 | 169 | 170 |
| ABC Transporter | rlr72.pk0008.e6 (CGS) | 171 | 172 |
| ABC Transporter | srr1c.pk001.a24 (CGS) | 173 | 174 |
| ABC Transporter | wlk8.pk0002.f4 (CGS) | 175 | 176 |
| PMP70 ABC Transporter | cco1.pk0004.f8 (FIS) | 177 | 178 |
| PMP70 ABC Transporter | r10n.pk093.h6 (FIS) | 179 | 180 |
| PMP70 ABC Transporter | ses4d.pk0035.h2 (FIS) | 181 | 182 |
| PMP70 ABC Transporter | wle1n.pk0074.a9 (FIS) | 183 | 184 |
| MRP4 ABC Transporter | cen3n.pk0045.f5 (FIS) | 185 | 186 |
| MRP4 ABC Transporter | cr1n.pk0020.f7 (FIS) | 187 | 188 |
| MRP4 ABC Transporter | cr1n.pk0176.b9 (FIS) | 189 | 190 |
| MRP4 ABC Transporter | Contig composed of: ccase-b.pk0009.c11 p0080.cgabm66r | 191 | 192 |
| MRP4 ABC Transporter | rls6.pk0054.e10 (FIS) | 193 | 194 |
| MRP4 ABC Transporter | sdp3c.pk005.c8 (FIS) | 195 | 196 |
| MRP4 ABC Transporter | se5.pk0050.h4 (FIS) | 197 | 198 |
| MRP4 ABC Transporter | sre.pk0009.g6 (FIS) | 199 | 200 |
| MRP4 ABC Transporter | wlm96.pk028.e8 (FIS) | 201 | 202 |
| MRP4 ABC Transporter | wre1n.pk0015.d11 (FIS) | 203 | 204 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOs:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183 185, 187, 189, 191, 193, 195, 197, 199, 201 and 203, or the complement of such sequences.

The term "isolated polynucleotide" refers to a polynucleotide that is substantially free from other nucleic acid sequences, such as and not limited to other chromosomal and extrachromosomal DNA and RNA, that normally accompany or interact with it as found in its naturally occuring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183 185, 187, 189, 191, 193, 195, 197, 199, 201 and 203, and the complement of such nucleotide sequences may be used in methods of selecting an isolated polynucleotide that affects the expression of a dioxygenase, Ent-kaurene synthase A, Ent-Kaurene synthase B, GA-20 or Gibberellin 3-beta Hydroxylase, GTP cyclohydrolase II/3, 4-dihydroxy-2-butanone-4-phosphate, riboflavin specific deaminase, ethylene response factor, acyl-CoA thioesterase, GCN20-like ABC transporter, PDR5-like ABC transporter, P-glycoprotein, ABC transporter or MRP4 ABC transporter polypeptide in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or a chimeric gene of the present invention; introducing the isolated polynucleotide or the chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA- DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS which was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotide, may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' Non-coding sequences" refers to nucleotide sequences located downstream of a coding sequence and includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3 non-coding sequences is exemplified by Ingelbrecht et al. (1989)*Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense RNA" refers to an RNA transcript that includes the mRNA and can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. "Expression" may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Null mutant" refers to a host cell which either lacks the expression of a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual;* Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence selected from the group consisting of: (a) first nucleotide sequence encoding a polypeptide of at least 351 amino acids having at least 80% identity based on the Clustal method of alignment when compared to a polypeptide selected from the group consisting of SEQ ID NOs:2, 4, 6, 8, 50, 82 and 100 and (b) a second nucleotide sequence comprising the complement of the first nucleotide sequence.

The present invention also concerns an isolated polynucleotide comprising a nucleotide sequence selected from the group consisting of: (a) first nucleotide sequence encoding a polypeptide of at least 72 amino acids having at least 80% identity based on the Clustal method of alignment when compared to a polypeptide selected from the group consisting of SEQ ID NOs:12, 16, 18, 20, 22, 24, 26 and 28, and (b) a second nucleotide sequence comprising the complement of the first nucleotide sequence.

The present invention also concerns an isolated polynucleotide comprising a nucleotide sequence selected from the group consisting of: (a) first nucleotide sequence encoding a polypeptide of at least 110 amino acids having at least 80% identity based on the Clustal method of alignment when compared to a polypeptide selected from the group consisting of SEQ ID NOs:10, 32, 36, 38, 40, 42, 44, 46, 48, 52, 60, 102, 104, 124or (b) a second nucleotide sequence comprising the complement of the first nucleotide sequence.

The present invention also concerns an isolated polynucleotide comprising a nucleotide sequence selected from the group consisting of: (a) a first nucleotide sequence encoding a polypeptide of at least 189 amino acids having at least 80% identity based on the Clustal method of alignment when compared to a polypeptide selected from the group consisting of SEQ ID NOs:14, 34, 62, 64, 66, 68, 70, 72, 74, 76, 78, 80, 120, 122 and (b) a second nucleotide sequence comprising the complement of the first nucleotide sequence.

The present invention also concerns an isolated polynucleotide comprising a nucleotide sequence selected from the group consisting of: (a) a first nucleotide sequence encoding a polypeptide of at least 67 amino acids having at least 80% identity based on the Clustal method of alignment when compared to a polypeptide selected from the group consisting of SEQ ID NOs:84, 86, 88, 90, 92, 94 and 96, and (b) a second nucleotide sequence comprising the complement of the first nucleotide sequence.

The present invention also concerns an isolated polynucleotide comprising a nucleotide sequence selected from the group consisting of: (a) a first nucleotide sequence encoding a polypeptide of at least 87 amino acids having at least 80% identity based on the Clustal method of alignment when compared to a polypeptide selected from the group consisting of SEQ ID NOs:98, 110, 112, 114, 116 and 118, and (b) a second nucleotide sequence comprising the complement of the first nucleotide sequence.

The present invention also concerns an isolated polynucleotide comprising a nucleotide sequence selected from the group consisting of: (a) a first nucleotide sequence encoding a polypeptide of at least 155 amino acids having at least 80% identity based on the Clustal method of alignment when compared to a polypeptide selected from the group consisting of SEQ ID NOs:128, 130, 132, and 134 and (b) a second nucleotide sequence comprising the complement of the first nucleotide sequence.

The present invention also concerns an isolated polynucleotide comprising a nucleotide sequence selected from the group consisting of: (a) a first nucleotide sequence encoding a polypeptide of at least 161 amino acids having at least 80% identity based on the Clustal method of alignment when compared to a polypeptide selected from the group consisting of SEQ ID NOs:54, 136, 138, 140, 142 and 144 and (b) a second nucleotide sequence comprising the complement of the first nucleotide sequence.

The present invention also concerns an isolated polynucleotide comprising a nucleotide sequence selected from the group consisting of: (a) a first nucleotide sequence encoding a polypeptide of at least 66 amino acids having at least 80% identity based on the Clustal method of alignment when compared to a polypeptide selected from the group consisting of SEQ ID NOs: 146, 148, 150, 152, 154, 156, 158, 160, 162, 164, 166 and 168 and (b) a second nucleotide sequence comprising the complement of the first nucleotide sequence.

The present invention also concerns an isolated polynucleotide comprising a nucleotide sequence selected from the group consisting of: (a) a first nucleotide sequence encoding a polypeptide of at least 141 amino acids having at least 80% identity based on the Clustal method of alignment when compared to a polypeptide selected from the group consisting of SEQ ID NOs:58, 106, 170, 172, 174, 176, 178, 180, 182 and 184, and (b) a second nucleotide sequence comprising the complement of the first nucleotide sequence.

The present invention also concerns an isolated polynucleotide comprising a nucleotide sequence selected from the group consisting of: (a) a first nucleotide sequence encoding a polypeptide of at least 81 amino acids having at least 80% identity based on the Clustal method of alignment when compared to a polypeptide selected from the group consisting of SEQ ID NOs:186, 188, 190, 192, 194, 196, 198, 200, 202 and 204, and (b) a second nucleotide sequence comprising the complement of the first nucleotide sequence.

The present invention also concerns an isolated polynucleotide comprising a nucleotide sequence selected from the group consisting of: (a) a first nucleotide sequence encoding a polypeptide of at least 48 amino acids having at least 80% identity based on the Clustal method of alignment when compared to a polypeptide selected from the group consisting of SEQ ID NOs:30, 56 and 108, and (b) a second nucleotide sequence comprising the complement of the first nucleotide sequence.

Preferably, the first nucleotide sequence comprises a nucleic acid sequence selected from the group consisting of SEQ ID NOs:1, 3, 5, 7, 49, 81 and 99 that codes for the polypeptide selected from the group consisting of SEQ ID NOs:2, 4, 6, 8, 50, 82 and 100.

Also preferably, the first nucleotide sequence comprises a nucleic acid sequence selected from the group consisting of SEQ ID NOs:11, 15, 17, 19, 21, 23, 25 and 27, that codes for the polypeptide selected from the group consisting of SEQ ID NOs:12, 16, 18, 20, 22, 24, 26 and 28.

Also preferably, the first nucleotide sequence comprises a nucleic acid sequence selected from the group consisting of SEQ ID NOs:9, 31, 35, 37, 39, 41, 43, 45, 47, 51, 59, 101, 103 and 123 that codes for the polypeptide selected from the group consisting of SEQ ID NOs:10, 32, 36, 38, 40, 42, 44, 46, 48, 52, 60, 102, 104 and 124.

Also preferably, the first nucleotide sequence comprises a nucleic acid sequence selected from the group consisting of SEQ ID NOs:13, 33, 61, 63, 65, 67, 69, 71, 73, 75, 77, 79, 119, 121 that codes for the polypeptide selected from the group consisting of SEQ ID NOs:14, 34, 62, 64, 66, 68, 70, 72, 74, 76, 78, 80, 120 and 122.

Also preferably, the first nucleotide sequence comprises a nucleic acid sequence selected from the group consisting of SEQ ID NOs:83, 85, 87, 89, 91, 93 and 95, that codes for the polypeptide selected from the group consisting of SEQ ID NOs:84, 86, 88, 90, 92, 94 and 96.

Also preferably, the first nucleotide sequence comprises a nucleic acid sequence selected from the group consisting of SEQ ID NOs:97, 109, 111, 113, 115 and 117, that codes for the polypeptide selected from the group consisting of SEQ ID NOs:98, 110, 112, 114, 116 and 118.

Also preferably, the first nucleotide sequence comprises a nucleic acid sequence selected from the group consisting of SEQ ID NOs:127, 129, 131 and 133, that codes for the polypeptide selected from the group consisting of SEQ ID NOs:128, 130, 132 and 134.

Also preferably, the first nucleotide sequence comprises a nucleic acid sequence selected from the group consisting of SEQ ID NOs:53, 135, 137, 139, 141 and 143, that codes for the polypeptide selected from the group consisting of SEQ ID NOs:54, 136, 138, 140, 142 and 144.

Also preferably, the first nucleotide sequence comprises a nucleic acid sequence selected from the group consisting of SEQ ID NOs:145, 147, 149, 151, 153, 155, 157, 159, 161, 163, 165 and 167, that codes for the polypeptide selected from the group consisting of SEQ ID NOs:146, 148, 150, 152, 154, 156, 158, 160, 162, 164, 166 and 168.

Also preferably, the first nucleotide sequence comprises a nucleic acid sequence selected from the group consisting of SEQ ID NOs:57, 105, 169, 171, 173, 175, 177, 179, 181 and 183, that codes for the polypeptide selected from the group consisting of SEQ ID NOs:58, 106, 170, 172, 174, 176, 178, 180, 182 and 184.

Also preferably, the first nucleotide sequence comprises a nucleic acid sequence selected from the group consisting of SEQ ID NOs:185, 187, 189, 191, 193, 195, 197, 199, 201 and 203, that codes for the polypeptide selected from the group consisting of SEQ ID NOs:186, 188, 190, 192, 194, 196, 198, 200, 202 and 204.

Also preferably, the first nucleotide sequence comprises a nucleic acid sequence selected from the group consisting of SEQ ID NOs:29, 55 and 107, that codes for the polypeptide selected from the group consisting of SEQ ID NOs:30, 56 and 108.

Nucleic acid fragments encoding at least a substantial portion of several metabolism proteins have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other dioxygenase, Ent-kaurene synthase A, Ent-Kaurene synthase B, GA-20 or Gibberellin 3-beta Hydroxylase, GTP cyclohydrolase II/3, 4-dihydroxy-2-butanone-4-phosphate, riboflavin specific deaminase, ethylene response factor, acyl-CoA thioesterase, GCN20-like ABC transporter, PDR5-like ABC transporter, P-glycoprotein, ABC transporter or MRP4 ABC transporter proteins, either as cDNAs or genomic DNAs, could be isolated directly by using all or a substantial portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence(s) can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183 185, 187, 189, 191, 193, 195, 197, 199, 201 and 203 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a dioxygenase, Ent-kaurene synthase A, Ent-Kaurene synthase B, GA-20 or Gibberellin 3-beta Hydroxylase, GTP cyclohydrolase II/3,4-dihydroxy-2-butanone-4-phosphate, riboflavin specific deaminase, ethylene response factor, acyl-CoA thioesterase, GCN20-like ABC transporter, PDR5-like ABC transporter, P-glycoprotein, ABC transporter or MRP4 ABC transporter polypeptide, preferably a substantial portion of a plant dioxygenase, Ent-kaurene synthase A, Ent-Kaurene synthase B, GA-20 or Gibberellin 3-beta Hydroxylase, GTP cyclohydrolase II/3,4-dihydroxy-2-butanone-4-phosphate, riboflavin specific deaminase, ethylene response factor, acyl-CoA thioesterase, GCN20-like ABC transporter, PDR5-like ABC transporter, P-glycoprotein, ABC transporter or MRP4 ABC transporter polypeptide, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183 185, 187, 189, 191, 193, 195, 197, 199, 201 and 203, and the complement of such nucleotide sequences; and amplifying a nucleic acid fragment (preferably a cDNA inserted in a cloning vector) using the oligonucleotide primer. The amplified nucleic acid fragment preferably will encode a portion of a dioxygenase, Ent-kaurene synthase A, Ent-Kaurene synthase B, GA-20 or Gibberellin 3-beta Hydroxylase, GTP cyclohydrolase II/3, 4-dihydroxy-2-butanone-4-phosphate, riboflavin specific deaminase, ethylene response factor, acyl-CoA thioesterase, GCN20-like ABC transporter, PDR5-like ABC transporter, P-glycoprotein, ABC transporter or MRP4 ABC transporter polypeptide.

Availability of the instant nucleotide and deduced amino acid sequences facilitates immunological screening of cDNA expression libraries. Synthetic peptides representing substantial portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of activity of those proteins and subsequently modifying specific metabolic steps in those cells.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate their secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express anti sense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen bn practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a polypeptide of at least 351 amino acids that has at least 80% identity-based on the Clustal method of alignment when compared to a polypeptide selected from the group consisting of SEQ ID NOs:2, 4, 6, 8, 50, 82 and 100.

In another embodiment, the present invention concerns a polypeptide of at least 72 amino acids that has at least 80% identity based on the Clustal method of alignment when compared to a polypeptide selected from the group consisting of SEQ ID NOs:12, 16, 18, 20, 22, 24, 26 and 28.

In another embodiment, the present invention concerns a polypeptide of at least 110 amino acids that has at least 80% identity based on the Clustal method of alignment when compared to a polypeptide selected from the group consisting of SEQ ID NOs:10, 32, 36, 38, 40, 42, 44, 46, 48, 52, 60, 102, 104 and 124.

In another embodiment, the present invention concerns a polypeptide of at least 189 amino acids that has at least 80% identity based on the Clustal method of alignment when compared to a polypeptide selected from the group consisting of SEQ ID NOs:14, 34, 62, 64, 68, 70, 72, 74, 76, 78, 80, 120 and 122.

In another embodiment, the present invention concerns a polypeptide of at least 67 amino acids that has at least 80% identity based on the Clustal method of alignment when compared to a polypeptide selected from the group consisting of SEQ ID NOs:84, 86, 88, 90, 92, 94 and 96.

In another embodiment, the present invention concerns a polypeptide of at least 87 amino acids that has at least 80% identity based on the Clustal method of alignment when compared to a polypeptide selected from the group consisting of SEQ ID NOs:98, 110, 112, 114, 116 and 118.

In another embodiment, the present invention concerns a polypeptide of at least 155 amino acids that has at least 80% identity based on the Clustal method of alignment when compared to a polypeptide selected from the group consisting of SEQ ID NOs:128, 130, 132 and 134.

In another embodiment, the present invention concerns a polypeptide of at least 161 amino acids that has at least 80% identity based on the Clustal method of alignment when compared to a polypeptide selected from the group consisting of SEQ ID NOs:54, 136, 138, 140, 142 and 144.

In another embodiment, the present invention concerns a polypeptide of at least 66 amino acids that has at least 80% identity based on the Clustal method of alignment when compared to a polypeptide selected from the group consisting of SEQ ID NOs:146, 148, 150, 152, 154, 156, 158, 160, 162, 164, 166 and 168.

In another embodiment, the present invention concerns a polypeptide of at least 141 amino acids that has at least 80% identity based on the Clustal method of alignment when compared to a polypeptide selected from the group consisting of SEQ ID NOs:58, 106, 170, 172, 174, 176, 178, 180, 182 and 184.

In another embodiment, the present invention concerns a polypeptide of at least 81 amino acids that has at least 80% identity based on the Clustal method of alignment when compared to a polypeptide selected from the group consisting of SEQ ID:186, 188, 190, 192, 194, 196, 198, 200, 202 and 204.

In another embodiment, the present invention concerns a polypeptide of at least 48 amino acids that has at least 80% identity based on the Clustal method of alignment when compared to a polypeptide selected from the group consisting of SEQ ID:30, 56 and 108.

The instant polypeptides (or substantial portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded metabolism protein. An example of a vector for high level expression of the instant polypeptides in a bacterial host is provided (Example 6).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries, Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| cbn10 | Corn developing kernel (embryo and endosperm); 10 days after pollination | cbn10.pk0055.e7<br>cbn10.pk0023.h4<br>cbn10.pk0061.a4<br>cbn10.pk0015.b5 |
| ccase-b | Corn callus type II tissue, somatic embryo formed, highly transformable | ccase-b.pk0001.a3<br>ccase-b.pk0009.c11 |
| cco1n | Corn cob of 67 day old plants grown in green house* | cco1n.pk084.i6<br>cco1.pk0035.d12<br>cco1.pk0004.f8<br>cco1.pk0025.b9 |
| cen3n | Corn endosperm 20 days after pollination* | cen3n.pk0005.f9<br>cen3n.pk0045.f5<br>cen3n.pk0019.d10<br>cen3n.pk0196.g3<br>cen3n.pk0211.h10 |
| cep7 | Corn 7 day old epicotyl; grown in light | cep7.pk0016.h9 |
| chpc24 | Corn 8 day old shoot treated 24 hours with herbicide**** | chpc24.pk0004.b2 |
| cpf1c | Corn pooled BMS treated with chemicals related to protein synthesis****** | cpf1c.pk003.15 |
| cpi1c | Corn pooled BMS treated with chemicals related to biochemical compound synthesis***** | cpi1c.pk014.m16 |
| cpl1c | Corn Pooled BMS Treated With Chemical Chelators*** | cpl1c.pk004.k22 |
| cr1n | Corn root from 7 day old seedlings* | cr1n.pk0018.e6<br>cr1n.pk0147.b9<br>cr1n.pk0002.f7<br>cr1n.pk0002.a6<br>cr1n.pk0195.h6<br>cr1n.pk0176.b9 |
| cs1 | Corn leaf sheath from 5 week old plant | cs1.pk0038.d1<br>cs1.pk0080.b11<br>cs1.pk0051.e12<br>cs1.pk0067.d8 |
| cta1 | Corn tassel | cta1.pk0006.g8<br>cta1.pk0006.g8 |
| p0014 | | p0014.ctutf13r<br>p0014.ctutf13rb |
| p0031 | Corn shoot culture | p0031.ccmar94r<br>p0031.ccmar94rx |
| p0044 | Corn pedicel 20 days after pollination | p0044.cjrai81r |
| p0059 | Corn scutelar node from seeds two and three days after germination | p0059.cmsba25r |
| p0072 | Corn coleoptile 14 days after planting etiolated seedling | p0072.comgu73rb |
| p0080 | Corn pedical 10 days after pollination | p0080.cgabm66r |
| p0083 | Corn whole kernels 7 days after pollination | p0083.cldec87r |
| p0085 | Corn shoot culture | p0085.cscag24r |
| p107 | Corn whole kernels 7 days after pollination* | p0107.cbcas83r |
| p0110 | Corn (stages V3/V4)** leaf tissue minus midrib harvested 4 hours, 24 hours and 7 days after infiltration with salicylic acid, pooled* | p0110.cgsmr50r<br>p0110.cgsnq75r<br>p0110.cgsnq76r |
| p0117 | Expanding internode: plants sampled @ the V10 stage**. Internodes 5–9 (the upper 4–5 expanding internodes) | p0117.chclk47ra |
| p0119 | Corn V12-stage** ear shoot with husk, night harvested* | p0119.cmtoh11r<br>p0119.cmtnf84r |
| p0121 | Corn shank ear tissue collected 5 days after pollination* | p0121.cfrmf53r |
| p0125 | Corn anther prophase I* | p0125.czaab26r |
| p0126 | Corn leaf tissue From V8–V10 stages, pooled, night-harvested | p0126.cnlbv55r |
| p0128 | Corn primary and secondary immature ear | p0128.cpiac95r<br>p0128.cpide86r<br>p0128.cpiar27r |
| rds2c | Rice developing seeds from middle of the plant | rds2c.pk010.n9 |
| r10n | Rice 15 day old leaf* | r10n.pk0033.e3<br>r10n.pk0061.b10<br>r10n.pk111.f7<br>r10n.pk114.d10<br>r10n.pk0010.g 12<br>r10n.pk093.h6 |
| rlr48 | Rice leaf 15 days after germination, 48 hours after infection of strain *Magaporthe grisea* 4360-R-62 (AVR2-YAMO) | rlr48.pk0025.c4<br>rls48.pk0025.d10 |
| rlr72 | Rice leaf 15 days after germination, 72 hours after infection of strain *Magaporthe grisea* 4360-R-62 (AVR2-YAMO) | rlr72.pk0008.e6 |
| rls6 | Rice leaf 15 days after germination, 6 hours after infection of strain *Magaporthe grisea* 4360-R-67 (AVR2-YAMO) | rls6.pk0005.a8<br>rls6.pk0054.e10 |
| rr1 | Rice root of two week old developing seedling | rr1.pk0049.e8<br>rrl1pk0051.a2 |

TABLE 2-continued cDNA Libraries from Corn, Rice, Soybean and Wheat

| Library | Tissue | Clone |
|---|---|---|
| rsl1n | Rice 15-day-old seedling* | rsl1n.pk010.m8 |
| rtc1c | Rice leaf inoculated with *Magaporthe griseastrain* 0184 at 4, 8 and 24 hours | rtc1c.pk005.k11.f |
| scb1c | Soybean embryogenic suspension culture | scb1c.pk004.g21 |
| sdp2c | Soybean developing pods (6–7 mm) | sdp2c.pk003.a21 |
| sdp3c | Soybean developing pods (8–9 mm) | sdp3c.pk005.c8 |
| se2 | Soybean embryo, 13 days after flowering | se2.pk0011.a6 |
| se3 | Soybean embryo, 17 days after flowering | se3.pk0036.f9 |
| se4 | Soybean embryo, 19 days after flowering | se4.pk0034.g5 |
| se5 | Soybean embryo, 21 days after flowering | se5.pk0039.b1 |
| | | se5.pk0050.h4 |
| ses4d | Soybean embryogenic suspension 4 days after subculture | ses4d.pk0035.h2 |
| ses8w | Soybean mature embryo 8 weeks after subculture | ses8w.pk0009.g12 |
| sfl1 | Soybean immature flower | sfl1.pk135.m11 |
| | | sfl1.pk0062.d9 |
| sgs4c | Soybean seeds 2 days after germination | sgs4c.pk004.e3 |
| src2c | Soybean 8 day old root inoculated with eggs of cyst nematode *Heterodera glycines* (Race 1) for 4 days. | src2c.pk003.h10 |
| | | src2c.pk006.p3 |
| | | src2c.pk003.17 |
| | | src2c.pk001.c19 |
| | | src2c.pk001.g10 |
| | | src2c.pk011.f20 |
| | | src2c.pk016.g24 |
| | | src2c.pk021.120 |
| | | src2c.pk029.g20 |
| src3c | Soybean 8 day old root infected with cyst nematode *Heterodera glycines* | src3c.pk001.k23 |
| | | src3c.pk007.p21 |
| | | src3c.pk010.b10 |
| | | src3c.pk016.g17 |
| | | src3c.pk021.i7 |
| | | src3c.pk023.j17 |
| sre | Soybean root elongation zone 4 to 5 days after germination | sre.pk0017.d6 |
| | | sre.pk0009.g6 |
| srr1c | Soybean control for src1c (8 day old root inoculated with eggs of cyst nematode, *Heterodera glycines* (Race 1) for 4 days). | srr1c.pk001.o3 |
| | | srr1c.pk001.d13 |
| | | srr1c.pk001.a24 |
| srr2c | Soybean control for src2c (8 day old root inoculated with eggs of cyst nematode *Heterodera glycines* (Race 1) for 4 days) | srr2c.pk001.b6 |
| | | srr2c.pk003.j11 |
| ss1 | Soybean seedling 5–10 days after germination | ss1.pk0002.e3 |
| ssm | Soybean shoot meristem | ssm.pk0059.d10 |
| | | ssm.pk0028.g8 |
| wdk1c | Wheat developing kernel, 3 days after anthesis | wdk1c.pk0004.f8 |
| | | wdk1c.pk008.d16 |
| wdk3c | Wheat developing kernel, 14 days after anthesis | wdk3c.pk023.i19 |
| wle1n | Wheat leaf from 7 day old etiolated seedling* | wle1n.pk0078.d6 |
| | | wle1n.pk0091.e7 |
| | | wle1n.pk0068.c6 |
| | | wle1n.pk0074.a9 |
| wlk8 | Wheat seedlings 8 hours after treatment with herbicide***** | wlk8.pk0002.f4 |
| wlm96 | Wheat seedlings 96 hr after inoculation w/*E. graminis* | wlm96.pk043.m13 |
| | | wlm96.pk028.e8 |
| wr1 | Wheat root from 7 day old seedling | wr1.pk0083.d6 |
| | | wr1.pk0099.h10 |
| wre1n | Wheat root from 7 day old etiolated seedling* | wre1n.pk0102.e7 |
| | | wre1n.pk0104.f8 |
| | | wre1n.pk0015.d11 |

TABLE 2-continued cDNA Libraries from Corn, Rice, Soybean and Wheat

| Library | Tissue | Clone |
|---|---|---|
| ytc055c | Rice yeast two-hybrid library constructed with, rtc1c (rice leaf inoculated with *M. grisea* strain 0184 at 4, 8 and 24 hours) | ytc055c.pk001.j11.f |

*These libraries were normalized essentially as described in U.S. Pat. No. 5,482,845, incorporated herein by reference.
**Corn developmental stages are explained in the publication "How a corn plant develops" from the Iowa State University Coop. Ext. Service Special Report No. 48 reprinted June 1993.
***Chemicals used included nitrilotriacetic acid, mercaptobenzothiazole, diethyldithiocarbamate
****Application of 2-[(2,4-dihydro-2,6,9-trimethyl[1]benzothiopyrano[4,3-c]pyrazol-8-yl)carbonyl]-1, 3-cyclohexanedione S,S-dioxide; synthesis and methods of using this compound are described in WO 97/19087, incorporated herein by reference. Chemicals used in tissue treatments were: chloramphenicol, cyclohexamide, sorbitol, egosterol, taxifolin, caffeine, trigonelline, diphenylene iodonium Cl, methotrexate, BHQ, cyclopiazonic acid, nifedipine, verapamil, fluphenizine-N-2-chloroethane, neomycin sulfate, LY 294002, suramin, aurintricarboxylic acid, wortmannin, MAS 7, dipyridamole, zarinast, 8 bromo cGMP, a 23187, calmidazoilum chloride, compound 48/80, 1,2, Didecanoyl rac glycerol, staurosporine, trequinsin HCl, FTS, hydroxyurea, aphidicolin, tunicamycin, brefeldin A, Valinomycin, D-Mannose, Hydrogen peroxide, D-galactose, bafilomycin A1, Oligomycin, lonomycin, paraquat, glutathione, N acetyl-L-cysteine, nitrilotriacetic acid, mercaptobenzothiazole, diethyldithiocarbamate, aminotriazole, alpha-amino adipic acid, ancymidol, HC-toxin, okadaic acid, K-252a, A3, H-7, olomoucine, rapamycin, cyclosporin A, calyculin A, cypermethrin, actinomysin D, cytochalsain B, all of which are commercially available from Calbiochem-Novabiochem Corp.
*****Application of 6-iodo-2-propoxy-3-propyl-4(3H)-quinazolinone; synthesis and methods of using this compound are described in USSN 08/545,827, incorporated herein by reference.
******Chemicals used included chloramphenicol, cyclohexamide, aurintricarboylic acid cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding transcription factors were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Plant Metabolism Proteins

The BLASTX search using the EST sequences from clones listed in Table 3 revealed similarity of the polypeptides encoded by the cDNAs to the following proteins.

Dioxygenase from *Marah macrocarpus* (NCBI General Identifier No. gi 1666096).

Ent-Kaurene synthase A from *Cucurbita maxima* (NCBI General Identifer No. gi 4151195), *Zea mays* (NCBI General Identifer No. gi 7489781), *Stevia rebaudiana* (NCBI General Identifer No. gi 2642661) and *Pisum sativum* (NCBI General Identifer No. gi 2160544).

Ent-Kaurene synthase B from *Cucurbita maxima* (NCBI General Identifer No. gi 74847663), *Cucurbita maxima* (NCBI General Identifer No. gi 1431870) and *Arabidopsis thaliana* (NCBI General Identifer No. gi 3056725).

GA-20 oxidase from *Triticum aestivum* (NCBI Identification No. gi 2222798) and *Pisum sativum* (NCBI Identification No. gi 1381673).

Gibberellin 3-beta hydroxylase from *Lycopersicon esculentum* (NCBI Identifier No. gi 3834350), *Lactuca sativa* (NCBI Identifier No. gi 4164145) and *Pisum sativum* (NCBI Identifier No. gi 2316102).

GTP cyclohydrolase II/3,4-dihydroxy-2-butanone-4-phosphate synthase from *Arabidopsis thaliana* (NCBI General Identifer No. gi 2462925).

Riboflavin specific deaminase from *Arabidopsis thaliana* (NCBI General Identifer No. gi 5262786) and *Arabidopsis thaliana* (NCBI General Identifer No. gi 5541706).

Ethylene response factor from Phalaenopsis sp. (NCBI General Identifier No. gi 4650821), *Oryza sativa* (NCBI General Identifier No. gi 2281705), *Vigna radiata* (NCBI General Identifier No. gi 4138853), *Lycopersicon esculentum* (NCBI General Identifier No. gi 4877653) and *Nicotiana tabacum* (NCBI General dentifier No. gi 5733831).

Acyl-CoA thioesterase from *Arabidopsis thaliana* (NCBI General Identifier No. gi 3047124), *Homo sapiens* (NCBI General Identifier No. gi 4885565), *Caenorhabditis elegans* (NCBI General Identifier No. gi 1213545).

ABC transporter GCN20-like from *Arabidopsis thaliana* (NCBI General Identifier No. gi 6633814).

ABC transporter PDR5-like from *Arabidopsis thaliana* (NCBI General Identifier No. gi 4581139), *Arabidopsis thaliana* (NCBI General Identifier No. gi 2062169), *Arabidopsis thaliana* (NCBI General Identifier No. gi 8072390) and *Spirodela polyrrhiza* (NCBI General Identifier No. gi 4581139).

P-glycoproteins (1, 3, ATPGP and HVMDR2) from *Arabidopsis thaliana* (NCBI General Identifier No. gi 7268557), *Arabidopsis thaliana* (NCBI General Identifier No. gi 4558552), *Arabidopsis thaliana* (NCBI General Identifier No. gi 3522943), *Mus musculus* (NCBI General Identifier No. gi 8571454), *Arabidopsis thaliana* (NCBI General Identifier No. gi 2739309), *Oryza sativa* (NCBI General Identifier No. gi 8468012), *Arabidopsis thaliana* (NCBI General Identifier No. gi 6573748), *Arabidopsis thaliana* (NCBI General Identifier No. gi 7486813) and *Hordeum vulgare* (NCBI General Identifier No. gi 3047124), *Arabadopsis thaliana* (NCBI General Indentifier No. gi 7442648) and *Hordeum vulgare* (NCBI General Identifier No. gi 7442649).

ABC transporter proteins from *Arabidopsis thaliana* (NCBI General Identifier No. gi 4115931), *Arabidopsis thaliana* (NCBI General Identifier No. gi 7487703) and *Arabidopsis thaliana* (NCBI General Identifier No. gi 4585979).

MRP4 ABC transproter proteins from *Arabidopsis thaliana* (NCBI General Identifier No. gi 7485868), *Arabidopsis thaliana* (NCBI General Identifier No. gi 2980641) and *Arabidopsis thaliana* (NCBI General Identifier No. gi 7362750), *Arabidopsis thaliana* (NCBI General Identifier No. gi 2316016), *Arabidopsis thaliana* (NCBI General Identifier No. gi 2959767) and *Arabidopsis thaliana* (NCBI General Identifier No. gi 7076769).

Shown in Table 3 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 3

BLAST Results for Sequences Encoding Polypeptides Homologous to Various Plant Metabolism Proteins

| Clone | Status | BLAST pLog Score (NCBI General Identifier No.) |
|---|---|---|
| Dioxygenase | | |
| p0128.cpiac95r | EST | 27.30 (gi 1666096) |
| rr1.pk0049.e8 | EST | 14.20 (gi 1666096) |
| Contig composed of: | Contig | 150.00 (gi 1666096) |
| se3.pk0036.f9 | | |
| src2c.pk003.h10 | | |
| src2c.pk003.17 | | |
| src2c.pk011.f20 | | |
| src2c.pk016.g24 | | |
| src2c.pk021.120 | | |
| src2c.pk029.g20 | | |
| src3c.pk001.k23 | | |
| src3c.pk007.p21 | | |
| src3c.pk010.b10 | | |
| src3c.pk016.g17 | | |
| src3c.pk021.i7 | | |
| src3c.pk023.j17 | | |
| srr1c.pk001.o3 | | |
| srr2c.pk001.b6 | | |
| ss1.pk0002.e3 | | |
| wle1n.pk0078.d6 | EST | 7.00 (gi 1666096) |
| Ent-Kaurene Synthase A | | |
| rl0n.pk111.f7 | EST | 13.70 (gi 2642661) |
| sfl1.pk135.m11 | EST | 25.70 (gi 2160544) |
| Ent-Kaurene Synthase B | | |
| Contig composed of: | Contig | 71.70 (gi 1431870) |
| p0014.ctutf13rb | | |
| p0083.cldec87r | | |
| p0117.chclk47ra | | |
| p0121.cfrmf53r | | |
| rsl1n.pk010.m8 | EST | 31.30 (gi 3056725) |
| wre1n.pk0102.e7 | EST | 39.00 (gi 3056725) |
| GA-20 Oxidase | | |
| Contig composd of: | Contig | 172.00 (gi 2222798) |
| cbn10.pk0055.e7 | | |
| cbn10.pk0061.a4 | | |
| cco1n.pk084.i6 | | |
| cen3n.pk0196.g3 | | |
| cen3n.pk0211.h10 | | |
| cr1n.pk0018.e6 | | |
| p0044.cjrai81r | | |
| p0085.cscag24r | | |
| p0119.cmtoh11r | | |
| p0128.cpide86r | | |
| rds2c.pk010.n9 | EST | 36.00 (gi 2222798) |
| se2.pk0011.a6 | EST | 97.70 (gi 1381673) |
| Gibberellin 3-beta Hydroxylase | | |
| cen3n.pk0019.d10 | | 14.00 (gi 3834350) |
| se5.pk0039.b1 | | 28.00 (gi 4164145) |
| wdk1c.pk0004.f8 | | 12.20 (gi 2316102) |
| wlm96.pk043.m13 | | 23.30 (gi 3834350) |
| GTP cyclohydrolase II/3,4-dihydroxy-2-butanone-4-phosphate synthase | | |
| p0126.cnlbv55r | FIS | 166.00 (gi 2462925) |
| rl0n.pk0061.b10 | FIS | 141.00 (gi 2462925) |
| wle1n.pk0091.e7 | FIS | 104.00 (gi 2462925) |
| Riboflavin specfic deaminase | | |
| cs1.pk0038.d1 | FIS | 45.00 (gi 5262786) |
| rls6.pk0005.a8 | FIS | 98.00 (gi 5262786) |
| wdk1c.pk008.d16 | FIS | 117.00 (gi 5541706) |

TABLE 3-continued

BLAST Results for Sequences Encoding Polypeptides Homologous to Various Plant Metabolism Proteins

| Clone | Status | BLAST pLog Score (NCBI General Identifier No.) |
|---|---|---|
| Ethylene Response Factor/Ethylene Receptor Gene | | |
| cep7.pk0016.h9 | EST | 10.20 (gi 4650821) |
| p0119.cmtnf84r | EST | 8.00 (gi 5733831) |
| Contig of: | CGS | >254.00 (gi 2281705) |
| cbn10.pk0015.b5 | | |
| cco1.pk0035.d12 | | |
| p0031.ccmar94r | | |
| p0031.ccmar94rx | | |
| p0059.cmsba25r | | |
| p0072.comgu73rb | | |
| p0107.cbcas83r | | |
| p0110.cgsmr50r | | |
| p0110.cgsnq75r | | |
| p0110.cgsnq76r | | |
| p0125.czaab26r | | |
| p0128.cpiar27r | | |
| rl0n.pk114.d10 | EST | 55.20 (gi 2281705) |
| scb1c.pk004.g21 | EST | 71.20 (gi 4138853) |
| sdp2c.pk003.a21 | EST | 67.70 (gi 4877653) |
| wdk3c.pk023.i19 | EST | 7.40 (gi 4650821) |
| Acyl-Coa thioesterase II | | |
| Contig composed of: | Contig | 51.70 (gi 3047124) |
| cbn10.pk0023.h4 | | |
| cpi1c.pk014.m16 | | |
| rlr48.pk0025.c4 | FIS | 54.70 (gi 4885565) |
| sgs4c.pk004.e3 | EST | 7.70 (gi 1213545) |
| Contig composed of: | Contig | 21.70 (gi 3047124) |
| src2c.pk001.c19 | | |
| src2c.pk006.p3 | | |
| ABC transporter GCN20-like | | |
| ccase-b.pk0001.a3 | FIS | >254.00 (gi 6633814) |
| rr1.pk0051.a2 | FIS | >254.00 (gi 6633814) |
| ssm.pk0059.d10 | FIS | 80.10 (gi 6633814) |
| wre1n.pk0104.f8 | FIS | 83.00 (gi 6633814) |
| ABC transporter PDR5-like | | |
| cr1n.pk0147.b9 | FIS | 28.00 (gi 4581139) |
| cs1.pk0080.b11 | FIS | >254.00 (gi 2062169) |
| rls48.pk0025.d10 | FIS | >254.00 (gi 2062169) |
| srr2c.pk003.j11 | FIS | 54.30 (gi 8072390) |
| wr1.pk0083.d6 | FIS | >254.00 (gi 1514643) |
| P-glycoprotein 1 | | |
| cen3n.pk0005.f9 | EST | 48.50 (gi 7268557) |
| chpc24.pk0004.b2 | EST | 21.40 (gi 4558552) |
| cs1.pk0051.e12 | FIS | 101.00 (gi 4558552) |
| wle1n.pk0068.c6 | EST | 38.10 (gi 8571454) |
| wr1.pk0099.h10 | FIS | 89.70 (gi 3522943) |
| P-glycoprotein 3 | | |
| cs1.pk0067.d8 | EST | 69.20 (gi 2739309) |
| P-glycoprotein ATPGP | | |
| cr1n.pk0002.a6 | FIS | 12.30 (gi 7268557) |
| cr1n.pk0195.h6 | FIS | 139.00 (gi 8468012) |
| sfl1.pk0062.d9 | FIS | 86.70 (gi 6573748) |
| ssm.pk0028.g8 | EST | 76.00 (gi 7442648) |
| P-glycoprotein HVMDR2 | | |
| rl0n.pk0010.g12 | EST | 53.70 (gi 7486813) |
| srr1c.pk001.d13 | FIS | 125.00 (gi 7442649) |
| ABC Transporter | | |
| Contig composed of: | CGS | >254.00 (gi 4115931) |
| cco1.pk0025.b9 | | |
| cpf1c.pk003.15 | | |
| rlr72.pk0008.e6 | CGS | >254.00 (gi 4115931) |
| srr1c.pk001.a24 | CGS | >254.00 (gi 4115931) |
| wlk8.pk0002.f4 | CGS | >254.00 (gi 4115931) |
| PMP70 ABC Transporter | | |
| cco1.pk0004.f8 | FIS | 84.10 (gi 7487703) |
| rl0n.pk093.h6 | FIS | 40.70 (gi 4585979) |
| ses4d.pk0035.h2 | FIS | 54.00 (gi 7487703) |
| wle1n.pk0074.a9 | FIS | 40.00 (gi 4585979) |
| MRP4 ABC Transporter | | |
| cen3n.pk0045.f5 | FIS | 50.30 (gi 7485868) |
| cr1n.pk0020.f7 | FIS | 32.40 (gi 2980641) |
| cr1n.pk0176.b9 | FIS | 28.40 (gi 7362750) |
| Contig composed of: | Contig | 172.00 (gi 2316016) |
| ccase-b.pk0009.c11 | | |
| p0080.cgabm66r | | |
| rls6.pk0054.e10 | FIS | >254.00 (gi 7076769) |
| sdp3c.pk005.c8 | FIS | 178.00 (gi 2316016) |
| se5.pk0050.h4 | FIS | 152.00 (gi 7485868) |
| sre.pk0009.g6 | FIS | >254.00 (gi 2959767) |
| wlm96.pk028.e8 | FIS | 133.00 (gi 2316016) |
| wre1n.pk0015.d11 | FIS | 121.00 (gi 2316016) |

The sequence of the entire cDNA insert in the clones listed in Table 3 was determined. Further sequencing and searching of the DuPont proprietary database allowed the identification of other corn, rice, soybean and/or wheat clones encoding dioxygenase, Ent-kaurene synthase A, Ent-kaurene synthase B, GA-20 oxidase, gibberellin 3-beta hydroxylase, GTP cyclohydrolase II/3,4-dihydroxy-2-butanone-4-phosphate synthase, riboflavin specific deaminase, ethylene response factor, acyl-CoA thioesterase.

The BLASTX search using the EST sequences from clones listed in Table 4 revealed similarity of the polypeptides encoded by the cDNAs to the following proteins.

Dioxygenase from *Marah macrocarpus* (NCBI General Identifier No. gi 1666096) and *Phaseolus coccineus* (NCBI General Identifier No. gi 4678586).

Ent-kaurene synthase A from *Cucurbita maxima* (NCBI General Identifer No. gi 4151195), *Zea mays* (NCBI General Identifer No. gi 7489781), and *Pisum sativum* (NCBI General Identifer No. gi 2160544).

Ent-kaurene synthase B from *Cucurbita maxima* (NCBI General Identifer No. gi 7484763), and *Arabidopsis thaliana* (NCBI General Identifer No. gi 3056725).

GA-20 oxidase from *Triticum aestivum* (NCBI General Identifer No. gi 7433220), *Triticum aestivum* (NCBI General Identifer No. gi 2222798) and *Pisum sativum* (NCBI General Identifer No. gi 1381673).

Gibberellin 3-beta hydroxylase from *Pisum sativum* (NCBI General Identifer No. gi 5813796), *Lactuca sativa* (NCBI General Identifer No. gi 4164145), *Arabdopsis thaliana* (NCBI General Identifer No. gi 3924597) and *Lycoperscon esculentum* (NCBI General Identifer No. gi 3834350).

GTP cyclohydrolase II/3,4-dihydroxy-2-butanone-4-phosphate synthase from *Arabidopsis thaliana* (NCBI General Identifer No. gi 2462925) and *Arabidopsis thaliana* (NCBI General Identifer No. gi 1346113).

Riboflavin specific deaminase from *Arabidopsis thaliana* (NCBI General Identifer No. gi 5262786) and *Arabidopsis thaliana* (NCBI General Identifer No. gi 5541706).

Ethylene response factor from Phalaenopsis sp. (NCBI General Identifier No. gi 4650821), Phalaenopsis sp. (NCBI General Identifier No. gi 4154359), *Cucumis sativus* (NCBI General Identifier No. gi 6136818), *Oryza sativa* (NCBI General dentifier No. gi 7489538), *Oryza sativa* (NCBI General dentifier No. gi 2281705), *Vigna radiata* (NCBI General dentifier No. gi 4138853), and *Lycopersicon esculentum* (NCBI General dentifier No. gi 4877653).

Acyl-CoA thioesterase from *Arabidopsis thaliana* (NCBI General Identifier No. gi 3047124), *Homo sapiens* (NCBI General Identifier No. gi 4885565), *Caenorhabditis elegans* (NCBI General Identifier No. gi 1213545).

Shown in Table 4 are the BLAST results for individual ESTs ("EST"), the sequences of the entire cDNA inserts comprising the indicated cDNA clones ("FIS"), sequences of contigs assembled from two or more ESTs ("Contig"), sequences of contigs assembled from an FIS and one or more ESTs ("Contig*"), or sequences encoding the entire protein derived from an FIS, a contig, or an FIS and PCR ("CGS"):

TABLE 4

BLAST Results for Sequences Encoding Polypeptides Homologous to Plant Metabolism Proteins

| Clone | Status | BLAST pLog Score (NCBI General Identifier) |
|---|---|---|
| Dioxygenase | | |
| p0128.cpiac95r | CGS | 103.00 (gi 4678586) |
| rr1.pk0049.e8 | CGS | 104.00 (gi 4678586) |
| src3c.pk010.b10 | CGS | 150.00 (gi 1666096) |
| wle1n.pk0078.d6 | CGS | 105.00 (gi 4678586) |
| Ent-Kaurene Synthase A | | |
| rl0n.pk111.f7 | FIS | 22.30 (gi 4151195) |
| ytc055c.pk001.j11.f | EST | 47.00 (gi 7489781) |
| sfl1.pk135.m11 | CGS | >254.00 (gi 2160544) |
| Ent-Kaurene Synthase B | | |
| Contig composed of: p0014.ctutf13r p0014.ctutf13rb p0083.cldec87r p0117.chclk47ra p0121.cfrmf53r | Contig | >254.00 (gi 7484763) |
| rsl1n.pk010.m8 | EST | 31.30 (gi 3056725) |
| wre1n.pk0102.e7 | EST | 39.00 (gi 3056725) |
| GA-20 Oxidase | | |
| p0128.cpide86r | CGS | 153.00 (gi 743320) |
| rds2c.pk010.n9 | CGS | 125.00 (gi 2222798) |
| se2.pk0011.a6 | FIS | 142.00 (gi 1381673) |
| Gibberellin 3-beta Hydroxylase | | |
| cen3n.pk0019.d10 | FIS | 19.10 (gi 5813796) |
| se4.pk0034.g5 | CGS | 96.00 (gi 4164145) |
| wdk1c.pk0004.f8 | FIS | 25.50 (gi 3924597) |
| wlm96.pk043.m13 | EST | 23.30 (gi 3834350) |
| GTP cyclohydrolase II/3,4-dihydroxy-2-butanone-4-phosphate synthase | | |
| cp1c.pk004.k22 | CGS | 109.00 (gi 2462925) |
| cta1.pk0006.g8 | FIS | 68.40 (gi 1346113) |
| p0126.cnlbv55r | CGS | 166.00 (gi 2462925) |
| rl0n.pk0033.e3 | FIS | 143.00 (gi 2462925) |
| Contig composed of: rl0n.pk0061.b10 rtc1c.pk005.k11.f | CGS | 168.00 (gi 2462925) |
| sre.pk0017.d6 (CGS) | CGS | >254.00 (gi 2462925) |
| wle1n.pk0091.e7 | FIS | 104.00 (gi 2462925) |

TABLE 4-continued

BLAST Results for Sequences Encoding Polypeptides Homologous to Plant Metabolism Proteins

| Clone | Status | BLAST pLog Score (NCBI General Identifier) |
|---|---|---|
| Riboflavin specfic deaminase | | |
| cs1.pk0038.d1 | FIS | 45.00 (gi 5262786) |
| rls6.pk0005.a8 | FIS | 98.00 (gi 5262786) |
| wdk1c.pk008.d16 | FIS | 117.00 (gi 5541706) |
| Ethylene response factor | | |
| cep7.pk0016.h9 | EST | 10.20 (gi 4650821) |
| p0119.cmtnf84r | CGS | >254.00 (gi 6136818) |
| p0128.cpiar27r | CGS | >254.00 (gi 7489538) |
| rl0n.pk114.d10 | CGS | >254.00 (gi 4154359) |
| scb1c.pk004.g21 | CGS | >254.00 (gi 4138853) |
| sdp2c.pk003.a21 | FIS | 93.70 (gi 4877653) |
| wdk3c.pk023.i19 | CGS | 159.00 (gi 2281705) |
| Acyl-CoA thioesterase | | |
| Contig composed of: cbn10.pk0023.h4 cpi1c.pk014.m16 | Contig | 51.70 (gi 3047124) |
| rlr48.pk0025.c4 | CGS | 54.70 (gi 4885565) |
| sgs4c.pk004.e3 | EST | 7.70 (gi 1213545) |
| src2c.pk001.c19 | CGS | 53.50 (gi 3047124) |
| Contig composed of: ses8w.pk0009.g12 src2c.pk001.g10 | CGS | 60.20 (gi 3047124) |

The data in Table 5 represents a calculation of the percent identity of the amino acid sequences set forth in SEQ ID NOs:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 68, 70, 72, 74, 76, 78, 80, 82, 84, 86, 88, 90, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202 and 204 and the homologous sequence from the above identified species.

TABLE 5

Percent Identity of Amino Acid Sequences Deduced From the Nucleotide Sequences of cDNA Clones Encoding Polypeptides Homologous to Plant Metabolism Proteins

| SEQ ID NO. | Percent Identity to (NCBI General Identifier) |
|---|---|
| Dioxygenase | |
| 2 | 47% (gi 4678586) |
| 4 | 38% (gi 4678586) |
| 6 | 70% (gi 1666096) |
| 8 | 40% (gi 4678586) |
| Ent-Kaurene Synthase A | |
| 18 | 60% (gi 4151195) |
| 20 | 55% (gi 7489781) |
| 22 | 71% (gi 2160544) |
| Ent-Kaurene Synthase B | |
| 24 | 41% (gi 7484763) |
| 26 | 54% (gi 3056725) |
| 28 | 43% (gi 3056725) |
| GA-20 Oxidase | |
| 36 | 50% (gi 7433220) |
| 38 | 56% (gi 2222798) |

TABLE 5-continued

Percent Identity of Amino Acid Sequences Deduced From the Nucleotide Sequences of cDNA Clones Encoding Polypeptides Homologous to Plant Metabolism Proteins

| SEQ ID NO. | Percent Identity to (NCBI General Identifier) |
|---|---|
| 40 | 77% (gi 1381673) |
| Gibberellin 3-beta Hydroxylase | |
| 42 | 32% (gi 5813796) |
| 44 | 49% (gi 4164145) |
| 46 | 29% (gi 3924597) |
| 48 | 46% (gi 3834350) |
| GTP cyclohydrolase II/3,4-dihydroxy-2-butanone-4-phosphate. synthase | |
| 62 | 67% (gi 2462925) |
| 64 | 66% (gi 1346113) |
| 66 | 55% (gi 2462925) |
| 68 | 79% (gi 2462925) |
| 70 | 59% (gi 2462925) |
| 72 | 71% (gi 2462925) |
| 74 | 68% (gi 2462925) |
| Riboflavin specific deaminase | |
| 76 | 57% (gi 5262786) |
| 78 | 79% (gi 5262786) |
| 80 | 26% (gi 5262786) |
| Ethylene response factor | |
| 84 | 43% (gi 4650821) |
| 86 | 49% (gi 6136818) |
| 88 | 92% (gi 7489538) |
| 90 | 69% (gi 4154359) |
| 92 | 97% (gi 4138853) |
| 94 | 74% (gi 4877653) |
| 96 | 76% (gi 2281705) |
| Acyl-CoA thioesterase | |
| 110 | 45% (gi 3047124) |
| 112 | 35% (gi 4885565) |
| 114 | 32% (gi 1213545) |
| 116 | 48% (gi 3047124) |
| 118 | 55% (gi 3047124) |
| ABC transporters GCN20-like | |
| 128 | 78% (gi 6633814) |
| 130 | 80 (gi 6633814) |
| 132 | 92% (gi 6633814) |
| 134 | 85% (gi 6633814) |
| ABC transporters PDR5-like | |
| 136 | 36% (gi 4581139) |
| 138 | 63% (gi 2062169) |
| 140 | 70% (gi 2062169) |
| 142 | 60% (gi 8072390) |
| 144 | 73% (gi 1514643) |
| P-glycoprotein 1 | |
| 146 | 72% (gi 7268557) |
| 148 | 62% (gi 4558552) |
| 150 | 51% (gi 4558552) |
| 152 | 71% (gi 8571454) |
| 154 | 74% (gi 3522943) |
| P-glycoprotein 3 | |
| 156 | 70% (gi 2739309) |
| P-glycoprotein ATPGP | |
| 158 | 37% (gi 7268557) |
| 160 | 70% (gi 8468012) |
| 162 | 64% (gi 6573748) |
| 164 | 61% (gi 7442648) |
| P-glycoprotein HVMDR2 | |
| 166 | 86% (gi 7486813) |
| 168 | 51% (gi 7442649) |
| ABC Transporter | |
| 170 | 66% (gi 4115931) |
| 172 | 67% (gi 4115931) |
| 174 | 77% (gi 4115931) |
| 176 | 68% (gi 4115931) |
| PMP70 ABC Transporter | |
| 178 | 50% (gi 7487703) |
| 180 | 41% (gi 4585979) |
| 182 | 46% (gi 7487703) |
| 184 | 55% (gi 4585979) |
| MRP4 ABC Transporter | |
| 186 | 87% (gi 7485868) |
| 188 | 60% (gi 2980641) |
| 190 | 70% (gi 7362750) |
| 192 | 58% (gi 2316016) |
| 194 | 43% (gi 7076769) |
| 196 | 72% (gi 2316016) |
| 198 | 84% (gi 7485868) |
| 200 | 70% (gi 2959767) |
| 202 | 73% (gi 2316016) |
| 204 | 59% (gi 2316016) |

Sequence alignments and percent identity calculations were performed using the Megalign program of the LASERGENE bioinformatics computing suite (DNASTAR Inc., Madison, Wis. ). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments, BLAST scores and probabilities indicate that the nucleic acid fragments comprising the instant cDNA clones encode a substantial portion of various plant metabolism proteins.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML 103. Plasmid pML 103 has been deposited under the terms of the Budapest Treaty at ATCC (American Type Culture Collection, 10801 University Blvd., Manassas, Va. 20110–2209), and bears accession number ATCC 97366. The DNA segment from pML 103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens.*

The particle bombardment method (Klein et al. (1987) *Nature* 327:70–73) may be used .to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of mercury (Hg). The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific construct composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin construct includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire construct is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed construct.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed construct comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches of mercury (Hg). The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 μg/mL ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 μL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μ/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25° C. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the-protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:

(a) a nucleotide sequence encoding a polypeptide having GTP cyclohydrolase II/3,4-dihydroxy-2-butanone-4-phosphate synthase activity, wherein the amino acid sequence of the polypeptide and the amino acid sequence of SEQ ID NO:66 have at least 80% sequence identity, or (b) the complement of the nucleotide sequence, wherein the complement and the nucleotide sequence contain the same number of nucleotides and are 100% complementary.

2. The polynucleotide of claim 1, wherein the amino acid sequence of the polypeptide and the amino acid sequence of SEQ ID NO:66 have at least 85% sequence identity.

3. The polynucleotide of claim 1, wherein the amino acid sequence of the polypeptide and the amino acid sequence of SEQ ID NO:66 have at least 90% sequence identity.

4. The polynucleotide of claim 1, wherein the amino acid sequence of the polypeptide and the amino acid sequence of SEQ ID NO:66 have at least 95% sequence identity.

5. The polynucleotide of claim 1, wherein the polypeptide comprises the amino acid sequence of SEQ ID NO:66.

6. The polynucleotide of claim 1, wherein the nucleotide sequence comprises the nucleotide sequence of SEQ ID NO:65.

7. A vector comprising the polynucleotide of claim 1.

8. A recombinant DNA construct comprising the polynucleotide of claim 1 operably linked to at least one regulatory sequence.

9. A method for transforming a cell comprising transforming a cell with the polynucleotide of claim 1.

10. A cell comprising the recombinant DNA construct of claim 8.

11. A method for producing a plant comprising transforming a plant cell with the polynucleotide of claim 1 and regenerating a plant from the transformed plant cell.

12. A plant comprising the recombinant DNA construct of claim 1.

13. A seed comprising the recombinant DNA construct of claim 1.

* * * * *

UNITED STATES PATENT AND TRADEMARK OFFICE

CERTIFICATE OF CORRECTION

PATENT NO. : 6,677,502 B1
DATED : January 13, 2004
INVENTOR(S) : Miao Guo-Hua and Weng Zude It is certified that error appears in the above-identified patent and that said Letters Patent is hereby corrected as shown below:

Title page,
Item [75], Inventors, delete
"Stephen M. Allen, Wilmington, DE (US);
Anthony J. Kinney, Wilmington, DE (US);
J. Antoni Rafalski, Wilmington, DE (US);
Emil M. Orozco, Jr., West Grove, PA (US);
Omolayo O. Famodu, Newark, DE (US);
Jian-Ming Lee, West Caldwell, NJ (US);
Karin N. Lohman, Newark, DE (US);
Alan R. Rendina, Wilmington, DE (US);
Hajime Sakai, Wilmington, DE (US);
Perry G. Caimi, Kennet Square, PA (US);
Yiwen Fang, Los Angeles, CA (US);
Jennie Bih-Jien Shen, Wilmington, DE (US);
Ilham L. Zoughi, Wilmington, DE (US);
Shawn L. Anderson, West Grove, PA (US);
Jinrui Shi, Johnston, IA (US);
Guihua Lu, Urbandale, IA (US);
Timothy G. Helentjaris, Ankeny, IA (US);
Chun Ping Li, Johnston, IA (US)"

Signed and Sealed this

Twenty-sixth Day of October, 2004

JON W. DUDAS
*Director of the United States Patent and Trademark Office*